US012612395B2

(12) United States Patent
Porco, Jr. et al.

(10) Patent No.: US 12,612,395 B2
(45) Date of Patent: Apr. 28, 2026

(54) ROCAGLATE DERIVATIVES AND USES THEREOF

(71) Applicants: TRUSTEES OF BOSTON UNIVERSITY, Boston, MA (US); University of Massachusetts, Boston, MA (US)

(72) Inventors: John A. Porco, Jr., Brookline, MA (US); Zihao Wang, Winchester, MA (US); Lauren E. Brown, Waltham, MA (US); Stanley I. Goldstein, Brighton, MA (US); Sunil K. Malonia, Boston, MA (US); Ritesh P. Thakare, Boston, MA (US); Alok K. Mishra, Boston, MA (US); Michael R. Green, Boston, MA (US)

(73) Assignees: TRUSTEES OF BOSTON UNIVERSITY, Boston, MA (US); UNIVERSITY OF MASSACHUSETTS, Boston, MA (US)

( * ) Notice: Subject to any disclaimer, the term of this patent is extended or adjusted under 35 U.S.C. 154(b) by 0 days.

(21) Appl. No.: 18/904,487

(22) Filed: Oct. 2, 2024

(65) Prior Publication Data

US 2025/0115593 A1 Apr. 10, 2025

Related U.S. Application Data

(60) Provisional application No. 63/541,979, filed on Oct. 2, 2023.

(51) Int. Cl.

| | |
|---|---|
| ***C07D 413/12*** | (2006.01) |
| ***A61K 31/343*** | (2006.01) |
| ***A61K 31/397*** | (2006.01) |
| ***A61K 31/4025*** | (2006.01) |
| ***A61K 31/4184*** | (2006.01) |
| ***A61K 31/4525*** | (2006.01) |
| ***A61K 31/5377*** | (2006.01) |
| ***A61P 35/00*** | (2006.01) |
| ***C07D 307/93*** | (2006.01) |
| ***C07D 405/04*** | (2006.01) |
| ***C07D 405/10*** | (2006.01) |
| ***C07D 405/12*** | (2006.01) |

(52) U.S. Cl.

CPC .......... *C07D 413/12* (2013.01); *A61K 31/343* (2013.01); *A61K 31/397* (2013.01); *A61K 31/4025* (2013.01); *A61K 31/4184* (2013.01); *A61K 31/4525* (2013.01); *A61K 31/5377* (2013.01); *A61P 35/00* (2018.01); *C07D 307/93* (2013.01); *C07D 405/04* (2013.01); *C07D 405/10* (2013.01); *C07D 405/12* (2013.01)

(58) Field of Classification Search

None

See application file for complete search history.

(56) References Cited

FOREIGN PATENT DOCUMENTS

| | | | |
|---|---|---|---|
| CN | 116077483 A | * | 5/2023 |
| WO | 2010060891 A1 | | 6/2010 |

OTHER PUBLICATIONS

McLlwain et al. "Caspase functions in cell death and disease." Cold Spring Harbor perspectives in biology 5.4: a008656 (2013).

Mo et al. "DDX3X: structure, physiologic functions and cancer." Molecular cancer 20.1: 38 (2021).

Moggridge et al. "Extending the compatibility of the SP3 paramagnetic bead processing approach for proteomics." Journal of proteome research 17.4: 1730-1740 (2018).

Molina et al. "Monitoring drug target engagement in cells and tissues using the cellular thermal shift assay." Science 341.6141: 84-87 (2013).

Molina et al. "The cellular thermal shift assay: a novel biophysical assay for in situ drug target engagement and mechanistic biomarker studies." Annual review of pharmacology and toxicology 56.1: 141-161 (2016).

Müller et al. "Bidirectional crosstalk between cancer stem cells and immune cell subsets." Frontiers in immunology 11: 140 (2020).

Naineni et al. "Exploring the targeting spectrum of rocaglates among eIF4A homologs." RNA 29.6: 826-835 (2023).

Nalli et al. "Sensitization of renal carcinoma cells to TRAIL-induced apoptosis by rocaglamide and analogs." Scientific Reports 8.1: 17519 (2018).

Norouzi et al. "Crosstalk in cancer resistance and metastasis." Critical Reviews in Oncology/Hematology 132: 145-153 (2018).

Novac et al. "Inhibitors of protein synthesis identified by a high throughput multiplexed translation screen." Nucleic acids research 32.3: 902-915 (2004).

Oeckinghaus et al. "The NF-κB family of transcription factors and its regulation." Cold Spring Harbor perspectives in biology 1.4: a000034 (2009).

Park et al. "The translational landscape as regulated by the RNA helicase DDX3." BMB reports 55.3: 125-135 (2022).

Radin et al. "Lucanthone, a potential PPT1 inhibitor, perturbs stemness, reduces tumor microtube formation, and slows the growth of temozolomide-resistant gliomas in vivo." Journal of Pharmacology and Experimental Therapeutics 389.1, 2023-002021: 51-60 (2024).

Roche et al. "Biomimetic photocycloaddition of 3-hydroxyflavones: synthesis and evaluation of rocaglate derivatives as inhibitors of eukaryotic translation." Angewandte Chemie (International ed. in English) 49.37: 6533-6538 (2010).

Rodrigo et al. "Synthesis of rocaglamide hydroxamates and related compounds as eukaryotic translation inhibitors: synthetic and biological studies." Journal of medicinal chemistry 55.1: 558-562 (2012).

(Continued)

*Primary Examiner* — Joseph K McKane

*Assistant Examiner* — Quincy McKoy

(74) *Attorney, Agent, or Firm* — Nixon Peabody LLP; Ronald I. Eisenstein; Ravinderjit Braich

(57) ABSTRACT

The disclosure provides rocaglate acyl sulfamides (Roc ASFs), compositions and kits comprising same, and methods for their use.

45 Claims, 27 Drawing Sheets

Specification includes a Sequence Listing.

(56) References Cited

OTHER PUBLICATIONS

Rubio et al. "Transcriptome-wide characterization of the eIF4A signature highlights plasticity in translation regulation." Genome biology 15(10), 476: 1-19 (2014).
Savitski et al. "Tracking cancer drugs in living cells by thermal profiling of the proteome." Science 346.6205: 1255784 (2014).
Schulz et al. "Rocaglamide and silvestrol: a long story from anti-tumor to anti-coronavirus compounds." Natural Product Reports 38.1: 18-23 2021).
Sharma et al. "The Ded1/DDX3 subfamily of DEAD-box RNA helicases." Critical reviews in biochemistry and molecular biology 49.4: 343-360 (2014).
Shriwas et al. "DDX3 modulates cisplatin resistance in OSCC through ALKBH5-mediated m 6 A-demethylation of FOXM1 and NANOG." Apoptosis 25: 233-246 (2020).
Song et al. "The mechanism of RNA duplex recognition and unwinding by DEAD-box helicase DDX3X." Nature communications 10.1: 3085 (2019).
Stephens. "False discovery rates: a new deal." Biostatistics 18.2: 275-294 (2017).
Stone et al. "Biomimetic kinetic resolution: highly enantio-and diastereoselective transfer hydrogenation of aglain ketones to access flavagline natural products." Journal of the American Chemical Society 137.1: 525-530 (2015).
Subramanian et al. "Gene set enrichment analysis: a knowledge-based approach for interpreting genome-wide expression profiles." Proceedings of the National Academy of Sciences 102.43: 15545-15550 (2005).
Sun et al. "The role of DDX3 in regulating Snail." Biochimica et Biophysica Acta (BBA)-Molecular Cell Research 1813.3: 438-447 (2011).
Turdo et al. "Meeting the challenge of targeting cancer stem cells." Frontiers in cell and developmental biology 7: 16 (2019).
Van Vranken et al. "Large-scale characterization of drug mechanism of action using proteome-wide thermal shift assays." bioRxiv (2024).
Volegova et al. "The MYCN 5' UTR as a therapeutic target in neuroblastoma." Cell Reports 43.5: 114134 (2024).
Wang et al. "Synthesis of aza-rocaglates via ESIPT-mediated (3+2) photocycloaddition." Chemistry—A European Journal 22.34: 12006-12010 (2016).
Wang et al. "TNF-α induces two distinct caspase-8 activation pathways." Cell 133.4: 693-703 (2008).
Webster et al. "The balance of TNF mediated pathways regulates inflammatory cell death signaling in healthy and diseased tissues." Frontiers in cell and developmental biology 8: 365 (2020).
Wolfe et al. "RNA G-quadruplexes cause eIF4A-dependent oncogene translation in cancer." Nature 513.7516: 65-70 (2014).
Wu et al. "Cross-talk between cancer stem cells and immune cells: potential therapeutic targets in the tumor immune microenvironment." Molecular Cancer 22.1: 38 (2023).
Xiang et al. "The DEAD-box RNA helicase DDX3 interacts with NF-κB subunit p65 and suppresses p65-mediated transcription." PloS one 11.10: e0164471 (2016).
Greger. "Comparative phytochemistry of flavaglines (= rocaglamides), a group of highly bioactive flavolignans from *Aglaia* species (Meliaceae)." Phytochemistry Reviews 21.3: 725-764 (2022).
Agliano et al. "The challenge of targeting cancer stem cells to halt metastasis." Seminars in Cancer Biology. vol. 44. Academic Press: 25-42, (2017).
Alvarez et al. "TNF-α contributes to caspase-3 independent apoptosis in neuroblastoma cells: role of NFAT." PloS one 6.1: e16100 (2011).
Alves et al. "Role of glioblastoma stem cells in cancer therapeutic resistance: A perspective on antineoplastic agents from natural sources and chemical derivatives." Stem Cell Research & Therapy 12,206: 1-22 (2021).
Araki et al. "Antiproliferative Activities of Cynaropicrin and Related Compounds against Cancer Stem Cells." Chemical and Pharmaceutical Bulletin 72.2: 200-208 (2024).
Atashzar et al. "Cancer stem cells: A review from origin to therapeutic implications." Journal of cellular physiology 235.2: 790-803 (2019).
Blum et al. "Omics Notebook: robust, reproducible and flexible automated multiomics exploratory analysis and reporting." Bioinformatics Advances 1.1: vbab024 (2021).
Bol et al. "Targeting DDX 3 with a small molecule inhibitor for lung cancer therapy." EMBO molecular medicine 7.5: 648-669 (2015).
Brai et al. "Targeting DDX3X helicase activity with BA103 shows promising therapeutic effects in preclinical glioblastoma models." Cancers 13.21: 5569 (2021).
Calviello et al. "DDX3 depletion represses translation of mRNAs with complex 5' UTRs." Nucleic acids research 49.9: 5336-5350 (2021).
Chan et al. "eIF4A supports an oncogenic translation program in pancreatic ductal adenocarcinoma." Nature communications 10.1: 5151 (2019).
Chen et al. "Dual targeting of DDX3 and eIF4A by the translation inhibitor rocaglamide A." Cell chemical biology 28.4: 475-486.e8 (2021).
Chu et al. "Amidino-rocaglates: a potent class of eIF4A inhibitors." Cell chemical biology 26.11: 1586-1593.e3 (2019).
Chu et al. "Rocaglates induce gain-of-function alterations to eIF4A and eIIF4F." Cell reports 30.8: 2481-2488.e5 (2020).
Chu et al. "Translation inhibition by rocaglates is independent of eIF4E phosphorylation status." Molecular cancer therapeutics 15.1: 136-141 (2016).
Chudnovsky et al. "ZFHX4 interacts with the NuRD core member CHD4 and regulates the glioblastoma tumor-initiating cell state." Cell reports 6.2: 313-324 (2014).
Cox et al. "Andromeda: a peptide search engine integrated into the MaxQuant environment." Journal of proteome research 10.4: 1794-1805 (2011).
Cox et al. "MaxQuant enables high peptide identification rates, individualized ppb-range mass accuracies and proteome-wide protein quantification." Nature biotechnology 26.12: 1367-1372 (2008).
Dart et al. "Homogeneous assay for target engagement utilizing bioluminescent thermal shift." ACS medicinal chemistry letters 9.6: 546-551 (2018).
Desai et al. "Concise reviews: cancer stem cell targeted therapies: toward clinical success." Stem cells translational medicine 8.1: 75-81 (2019).
Dobin et al. "STAR: ultrafast universal RNA-seq aligner." Bioinformatics 29.1: 15-21 (2012).
Elias et al. "Target-decoy search strategy for increased confidence in large-scale protein identifications by mass spectrometry." Nature methods 4.3: 207-214 (2007).
Gaetani et al. Proteome Integral Solubility Alteration: A High-Throughput Proteomics Assay for Target Deconvolution. J. Proteome Res. 18 (11), 4027-4037 (2019).
Gaudreault et al. "Side-chain rotamer changes upon ligand binding: common, crucial, correlate with entropy and rearrange hydrogen bonding." Bioinformatics 28.18: 1423-i430 (2012).
Gerard et al. "Enantioselective photocycloaddition mediated by chiral Brønsted acids: Asymmetric synthesis of the rocaglamides." Journal of the American Chemical Society 128.24: 7754-7755 (2006).
Gerard et al. "Enantioselective Synthesis of the Complex Rocaglate (−)-Silvestrol." Angewandte Chemie 119.41: 7977-7980 (2007).
Golstein et al. "Proteomic Discovery of RNA-Protein Molecular Clamps Using a Thermal Shift Assay with ATP and RNA (TSAR)." bioRxiv (2024).
Grootjans et al "Initiation and execution mechanisms of necroptosis: an overview." Cell Death & Differentiation 24.7: 1184-1195 (2017).
Harrow et al. "Gencode: the reference human genome annotation for the Encode Project." Genome research 22.9: 1760-1774 (2012).
Hueng et al. "DDX3X biomarker correlates with poor survival in human gliomas." International journal of molecular sciences 16.7: 15578-15591 (2015).
Hughes et al. "Single-pot, solid-phase-enhanced sample preparation for proteomics experiments." Nature protocols 14.1: 68-85 (2019).

(56) References Cited

OTHER PUBLICATIONS

Iwasaki "Rocaglates convert DEAD-box protein eIF4A into a sequence-selective translational repressor." Nature 534.7608: 558-561 (2016).
Iwasaki et al. "The translation inhibitor rocaglamide targets a bimolecular cavity between eIF4A and polypurine RNA." Molecular cell 73.4: 738-748.e9 (2019).
Jordan et al. "A solvent-reagent selection guide for Steglich-type esterification of carboxylic acids." Green Chemistry 23.17: 6405-6413 (2021).
Kaboudin et al. "Resolution of enantiomers of novel C2-symmetric aminobisphosphinic acids via diastereomeric salt formation with quinine." Chirality 27.1: 71-74 (2015).
Kanellis et al. The exon-junction complex helicase eIF4A3 controls cell fate via coordinated regulation of ribosome biogenesis and translational output. Sci. Adv., 7 (32) (2021).
Kerr et al. "Targeting RNA helicase DDX3 in stem cell maintenance and teratoma formation." Genes & Cancer 10.1-2: 11-20 (2019).
Kessel et al. "Real-time viability and apoptosis kinetic detection method of 3D multicellular tumor spheroids using the Celigo Image Cytometer." Cytometry Part A 91.9: 883-892 (2017).
Kharkar. "Cancer stem cell (CSC) inhibitors in oncology—a promise for a better therapeutic outcome: state of the art and future perspectives." Journal of Medicinal Chemistry 63.24: 15279-15307 (2020).
Korentzelos et al. "A perspective on therapeutic pan-resistance in metastatic cancer." International Journal of Molecular Sciences 21.19: 7304 (2020).
Kortagere et al. "Halogenated ligands and their interactions with amino acids: Implications for structure-activity and structure-toxicity relationships." J. Mol. Graph. Model., 27 (2), 170-177 (2008).
Kuşoğlu et al. "Cancer stem cells: A brief review of the current status." Gene 681: 80-85 (2019).
Lajkiewicz et al. "Remodeling natural products: chemistry and serine hydrolase activity of a rocaglate-derived β-lactone." Journal of the American Chemical Society 136.6: 2659-2664 (2014).
Lassalas et al. "Structure property relationships of carboxylic acid isosteres." Journal of medicinal chemistry 59.7: 3183-3203 (2016).
Lee et al. "Tumor stem cells derived from glioblastomas cultured in bFGF and EGF more closely mirror the phenotype and genotype of primary tumors than do serum-cultured cell lines." Cancer cell 9.5: 391-403 (2006).
Li et al. "OneStopRNAseq: a web application for comprehensive and efficient analyses of RNA-Seq data." Genes 11.10: 1165 (2020).
Liao et al. "featureCounts: an efficient general purpose program for assigning sequence reads to genomic features." Bioinformatics 30.7: 923-930 (2014).
Lim et al. "An efficient proteome-wide strategy for discovery and characterization of cellular nucleotide-protein interactions." PLoS One 13.12: 1-30 e0208273 (2018).
Lo et al. "Evaluation of fluorescence-based thermal shift assays for hit identification in drug discovery." Analytical biochemistry 332.1: 153-159 (2004).
Love et al. "Moderated estimation of fold change and dispersion for RNA-seq data with DESeq2." Genome biology 15:550 1-21 (2014).
Lu et al. "X-ray crystal structure of rocaglamide, a novel antileulemic 1 H-cyclopenta [b] benzofuran from Aglaia elliptifolia." Journal of the Chemical Society, Chemical Communications 20: 1150-1151 (1982).

* cited by examiner

A

1
RocA 2
silvestrol

3: R = OMe
methyl rocaglate

9: R = Br 4
aglaroxin C

5
CR-1-31b

6
RHT

7
SDS-1-021

8
eFT226

B

| Condition | $EC_{50}$ |
|---|---|
| DMSO | nd |
| (-)-**5** (50 µM) | 263 nM |
| (-)-**7** (50 µM) | 207 nM |
| (-)-**20** (50 µM) | 296 nM |

| Condition | $EC_{50}$ |
|---|---|
| DMSO | nd |
| (-)-**5** (50 µM) | 5.7 µM |
| (-)-**7** (50 µM) | 2.6 µM |
| (-)-**20** (50 µM) | 2.8 µM |

A

B

BUCMD00747 (*rac*)

ZW-12-29

ZW-12-30

ZW-12-31

ZW-12-34

ZW-12-35

ZW-12-36

ZW-12-37

ZW-12-38

A ring variations $R^2$ variations $R^3$ variations (±)-10: $R^1$ = OMe (±)-11: $R^1$ = Br 22: $R^1$ = OMe
24: $R^1$ = Br 23: $R^1$ = OMe
25: $R^1$ = Br (+)-10: $R^1$ = OMe (≥ 98% ee)
(+)-11: $R^1$ = Br (≥ 98% ee)

(-)-10: $R^1$ = OMe (≥ 98% ee)
(-)-11: $R^1$ = Br (≥ 98% ee)

(+)-15: $R^1$ = OMe, $R^2$ = $SO_2CH_3$ (≥ 98% ee)

(+)-16: $R^1$ = OMe, Br, $R^2$ = $SO_2N(CH_3)_2$ (≥ 98% ee)

(-)-15: $R^1$ = OMe, $R^2$ = $SO_2CH_3$ (≥ 98% ee)

(-)-16: $R^1$ = OMe, Br, $R^2$ = $SO_2N(CH_3)_2$ (≥ 98% ee)

(-)-19: $R^1$ = Br, $R^2$ = $SO_2CH_3$ (≥ 93% ee)

(-)-20: $R^1$ = Br, $R^2$ = $SO_2N(CH_3)_2$ (≥ 93% ee)

(-)-HQ

24

X-ray crystal structure of (-)-quinine salt 24

24

ROCAGLATE DERIVATIVES AND USES THEREOF

RELATED APPLICATIONS

This application claims benefit under 35 U.S.C. § 119(e) of the U.S. Provisional Application No. 63/541,979 filed on Oct. 2, 2023, the content of which is incorporated herein by reference in its entirety.

GOVERNMENT SUPPORT

This invention was made with government support under grant Nos. TR002625, GM118173, and CA218008 awarded by the National Institutes of Health. The government has certain rights to the invention.

TECHNICAL FIELD

The disclosure relates, generally, to rocaglate (flavagline) derivatives. More particularly, the disclosure is directed to rocaglate acyl sulfamides (Roc ASFs), compositions comprising same and their uses.

SEQUENCE LISTING

The instant application contains a Sequence Listing which has been submitted in XML format via Patent Center and is hereby incorporated by reference in its entirety. Said XML copy, created on Oct. 1, 2024, is named 701586_000122WOPT_USPT_SL.xml and is 7,158 bytes in size.

BACKGROUND

Metastatic spread and development of therapeutic resistance pose major challenges for the treatment of cancer.[1,2] A large body of evidence suggests that tumor initiation, progression, metastasis, and recurrence are driven by a small subpopulation (1-5%) of cells within tumors called tumor-initiating cells or cancer stem cells (CSCs). CSCs are slow-dividing, undifferentiated, self-renewing cells, which give rise to the differentiated cells comprising the bulk of the tumor (non-stem cancer cells, hereafter termed "non-CSCs"). CSCs have been identified in various types of tumors such as leukemia, breast, brain, colon, and lung, although the markers and driver pathways vary among tumor types.[3,4] In addition, CSCs interact with multiple components of the tumor microenvironment (TME) and can modulate the immune response to tumors. CSCs possess a range of capabilities that confer resistance to chemo- and radiotherapies and therefore not only persist after treatment, but are often actually enriched, leading to tumor recurrence.[6,7] These capabilities include a robust DNA damage repair system, upregulated efflux pumps, activation of survival pathways, enhanced cellular plasticity, immune evasion, and the ability to adapt to hostile microenvironments.[8,9] Additionally, CSCs can undergo phenotypic changes such as epithelial-mesenchymal transition (EMT) which further enhance their resistance to treatment.[8] Thus, targeting of CSCs is crucial to prevent tumor recurrence and improve patient survival after chemotherapy. Of particular interest are compounds that specifically target and eliminate CSCs while minimizing impact on non-CSCs. Such compounds are more likely to demonstrate specific efficacy against cancers rather than acting as general cytotoxic agents.[10,11,12,13]

Glioblastoma (GBM) is the most common and aggressive malignant brain tumor in adults and generally has a poor prognosis. Irrespective of treatment, which includes surgical resection, radiotherapy, and chemotherapy, almost all patients experience tumor recurrence, leading to mortality and a median survival of <15 months. Thus, there is a need in the art for targeted prevention of tumor recurrence, such as by specifically eradicating GBM CSCs, as a potential therapeutic strategy for glioblastoma.

Rocaglates (also known as flavaglines) are a group of natural products containing a cyclopenta[b]tetrahydrobenzofuran skeleton originally isolated from plants of the genus *Aglaia*.[14] Since the first report of rocaglamide A (RocA, FIG. 1A, 1) as an antitumor agent, there have been extensive biological studies on rocaglates.[15] Beyond RocA, other nature-produced rocaglates (FIG. 1A) include silvestrol (2), methyl rocaglate/aglafoline (3), and aglaroxin C (4). In addition, many synthetic rocaglates have been developed as molecular probes and drug candidates, including the C2-hydroxamates CR-1-31b (5), rohinitib ("RHT," 6), and SDS-1-021 (7), as well as the C2-amine congener eFT226 (Zotatifin, 8), a compound currently in clinical development for breast and non-small cell lung cancers. In a comprehensive study of >200 natural and synthetic rocaglates, Pelletier and coworkers showed that most rocaglates preferentially repress translation of mRNAs containing purine-rich 5' leaders by stimulating the binding of DEAD-box helicase eIF4A to these sequences, and in some cases also exerting a trans-inhibitory effect on global translation by limiting the pool of eIF4A (and the parent complex eIF4F) available for ribosome recruitment.[16] Mechanistically, rocaglates bind a bimolecular cavity formed by the complexation of eIF4A onto polypurine RNA as shown in an X-ray co-crystal structure of a RocA-eIF4A1-r$(AG)_5$ complex reported by Iwasaki and coworkers.[17] The same group found that RocA could additionally clamp the related DEAD box helicase DDX3 to polypurine RNA in an ATP-independent manner, thereby expanding our understanding of the potential mechanisms underlying RocA's antiproliferative effects.[18]

Accordingly, there is a continuing need for development of new rocaglates and their uses as therapeutic agents. The present disclosure addresses this need.

SUMMARY

The present disclosure describes studies in which the inventors probe the activity of rocaglates against glioblastoma (GBM) CSCs. Using comparative dose-response assays, the inventors found that rocaglate translation inhibitors exhibit potent, dose-dependent cytotoxic effects against GBM CSCs at concentrations that are predominantly nonlethal to non-CSC populations, prompting further study of this chemotype and the underlying mechanism. The present disclosure describes the inventors' results, including identification of new rocaglate congeners for use as tool and therapeutic lead compounds to explore the mechanism of action for targeted and selective killing of GBM CSCs.

In one aspect provided herein is a compound of Formula (I):

(Formula I)

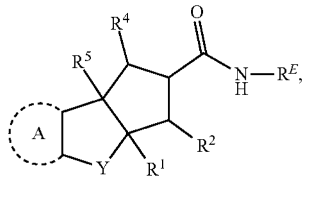

stereoisomers, tautomers, or a pharmaceutically acceptable salt or solvate thereof.

In compounds of Formula (I), $R^E$ can be —$SO_2$—$R^3$. Thus, in some embodiments, compound is of Formula (Ia):

(Formula Ia)

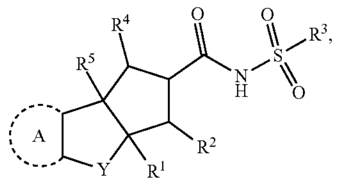

stereoisomers, tautomers, or a pharmaceutically acceptable salt or solvate thereof.

In compounds of Formula (Ia), $R^3$ can be $NR^{N1}R^{N2}$, alkyl, alkenyl, alkynyl, aryl, heteroaryl, cycloalkyl, heterocyclyl, H, halogen, CN, haloalkyl, $OR^A$, —$C(O)R^A$, $C(O)NHR^A$, $C(O)NR^AR^B$, $C(O)[alkylene]NHR^A$, $C(O)[alkylene]NR^AR^B$, $CO_2R^A$, $C(S)NHR^A$, $C(S)NR^AR^B$, $SR^A$, $S(O)R^A$, $SO_2R^A$, $SO_2NHR^A$, $SO_2NR^AR^B$, $NHC(O)R^A$, $NR^AC(O)R^B$, $NHC(O)NHR^A$, $NHC(O)NR^AR^B$, $NR^AC(O)NHR^B$, $NR^AC(O)NR^BR^C$, $P(O)(OH)(OR^A)$, or $P(O)(OR^A)(OR^B)$, where $R^{N1}$ and $R^{N2}$ are independently H, alkyl, alkenyl, cycloalkyl, heterocyclyl, H, halogen, CN, haloalkyl, $OR^A$, —$C(O)R^A$, $C(O)NHR^A$, $C(O)NR^AR^B$, $C(O)[alkylene]NHR^A$, $C(O)[alkylene]NR^AR^B$, $CO_2R^A$, $C(S)NHR^A$, $C(S)NR^AR^B$, $SR^A$, $S(O)R^A$, $SO_2R^A$, $SO_2NHR^A$, $SO_2NR^AR^B$, $NHC(O)R^A$, $NR^AC(O)R^B$, $NHC(O)NHR^A$, $NHC(O)NR^AR^B$, $NR^AC(O)NHR^B$, $NR^AC(O)NR^BR^C$, $P(O)(OH)(OR^A)$, or $P(O)(OR^A)(OR^B)$ or $R^{N1}$ and $R^{N2}$ together with the nitrogen they are attached to form a heterocyclyl or heteroaryl, and where any aryl, heteroaryl, cycloalkyl, heterocyclyl, alkyl, alkenyl, or alkynyl can be optionally substituted. In some embodiments, R3 is 2-propanamino, 2-propynylaminyl, 2-propynyl, methyl, dimethylamino, diethylamino, azetidinyl, pyrrolidinyl, morpholinyl, 3-methylazetinyl, 2-(trifluoromethyl)pyrrolidinyl, morpholinyl, or piperidinolyl. In some embodiments, $R^3$ is

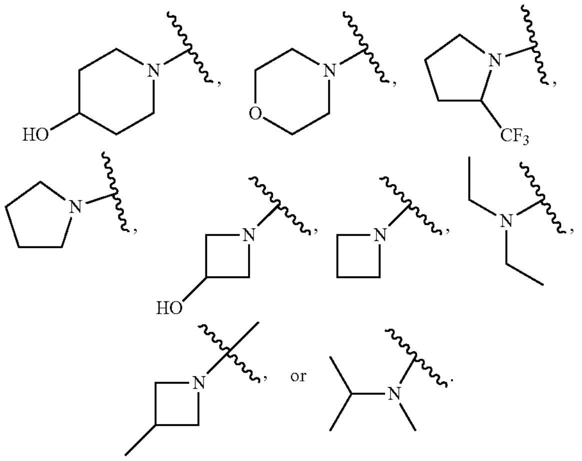

In compounds of Formula (I), e.g., Formula (Ia), Ring A can be an optionally substituted aryl, optionally substituted heteroaryl, optionally substituted cycloalkyl, or optionally substituted heterocycle, e.g., an optionally substituted aryl or heteroaryl. For example, Ring A can be an optionally substituted 3-12 membered aryl or optionally substituted 3-12 membered heteroaryl. In some embodiments, Ring A is an optionally substituted benzene. In some embodiments, Ring A is an optionally substituted pyridine or an optionally substituted pyrimidine. In some embodiments, Ring A is an optionally substituted thiazole. For example, Ring A can be

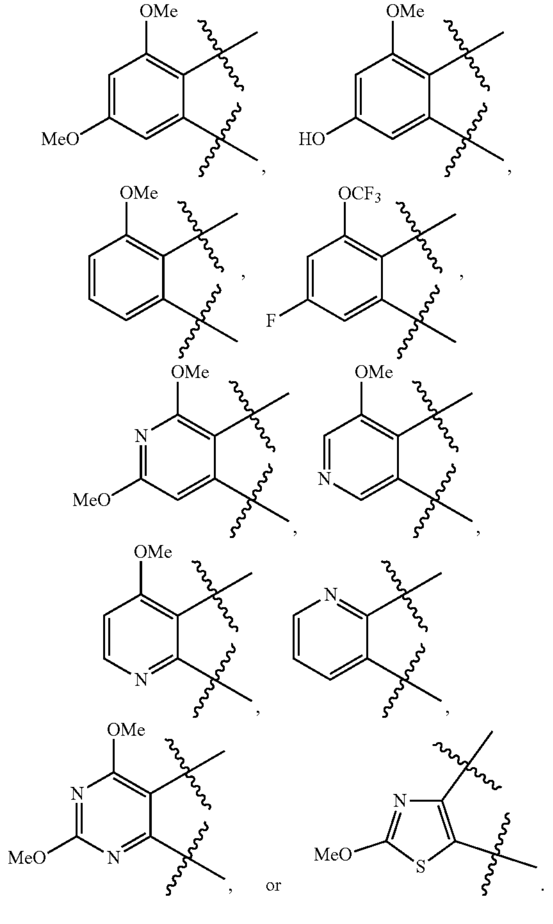

In compounds of Formula (I), e.g., Formula (Ia), Y can be O, S, $NR^{YA}$, $CR^{YA}R^{YB}$, C═$CR^{YA}R^{YB}$, SO or $SO_2$, where $R^{YA}$ and $R^{YB}$ are independently aryl, heteroaryl, cycloalkyl, heterocyclyl, H, halogen, CN, alkyl, haloalkyl, alkenyl, alkynyl, $OR^A$, $NR^AR^B$, —$C(O)R^A$, $C(O)NHR^A$, $C(O)NR^AR^B$, $C(O)[alkylene]NHR^A$, $C(O)[alkylene]NR^AR^B$, $CO_2R^A$, $C(S)NHR^A$, $C(S)NR^AR^B$, $SR^A$, $S(O)R^A$, $SO_2R^A$, $SO_2NHR^A$, $SO_2NR^AR^B$, $NHC(O)R^A$, $NR^AC(O)R^B$, $NHC(O)NHR^A$, $NHC(O)NR^AR^B$, $NR^AC(O)NHR^B$, $NR^AC(O)NR^BR^C$, $P(O)(OH)(OR^A)$, or $P(O)(OR^A)(OR^B)$. For example, Y can be O or S. In some embodiments, Y is O.

In embodiments of the various aspects described herein, $R^A$, $R^B$ and $R^C$ are independently H, alkyl, haloalkyl, alkenyl, alkynyl, aryl, heteroaryl, cycloalkyl, or heterocyclyl, each of which can be optionally substituted.

In compounds of Formula (I), e.g., Formula (Ia), $R^1$ can be aryl, heteroaryl, cycloalkyl, heterocyclyl, H, halogen, CN, alkyl, haloalkyl, alkenyl, alkynyl, $OR^A$, $NR^AR^B$, —$C(O)R^A$, $C(O)NHR^A$, $C(O)NR^AR^B$, $C(O)[alkylene]NHR^A$, $C(O)[alkylene]NR^AR^B$, $CO_2R^A$, $C(S)NHR^A$, $C(S)NR^AR^B$, $SR^A$, $S(O)R^A$, $SO_2R^A$, $SO_2NHR^A$, $SO_2NR^AR^B$, $NHC(O)R^A$, $NR^AC(O)R^B$, $NHC(O)NHR^A$, $NHC(O)NR^AR^B$, $NR^AC(O)NHR^B$, $NR^AC(O)NR^BR^C$, $P(O)(OH)(OR^A)$, or $P(O)(OR^A)(OR^B)$, where any aryl, heteroaryl, cycloalkyl, heterocyclyl, alkyl, alkenyl, or alkynyl can be optionally substituted. In some embodiments, $R^1$ is an optionally substituted aryl or optionally substituted heteroaryl. For example, R1 is an optionally substituted 3-12 membered aryl or an optionally substituted 3-12 membered heteroaryl comprising 1, 2 or 3 independently selected heteroatoms (e.g., independently selected from N, O, and S). In some embodiments, $R^1$ is phenyl, thiophenyl, or benzothiazolyl, each of which can be optionally substituted. For example, R1 can be 4-bromophenyl, 4-cyanophenyl, 4-methoxyphenyl, 4-fluorophenyl, 4-chlorophenyl, 4-iodophenyl, 4-trifluoromethylphenyl, 3-trifluoromethylphenyl, 4-trifluoromethylphenyl, 4-cyanophenyl, benzothiazol-6-yl, benzothiazole-5-yl, 2-benzoxazolinon-6-yl, 2-benzoxazolinon-5-yl, 4-ethynylphenyl, 3,4,5-trimethylphenyl, 5-carboxythiophen-2-yl, 5-carboxythiophen-3-yl, 5-carboxythiophen-4-yl, 4-difluoromethoxyphenyl, 4-(azetidin-3-yl) phenyl, 4-(2-hydroxymethylazetidin-3-yl)phenyl, 4-(2-(2-hydroxyethyl) azetidine-3-yl)phenyl, 4-(azetidine-3-ylmethyl)phenyl, 4-(azetidine-3-yl-hydroxy)phenyl, 4-(pyrrolidine-3-yl)phenyl, 4-piperidin-4-yl)phenyl, or benzimidazol-6-yl.

In some embodiments, $R^1$ is

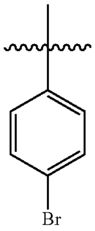 , 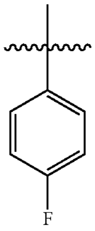 , 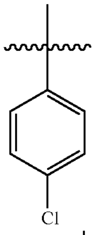 , 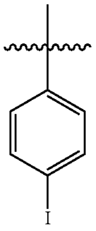 ,

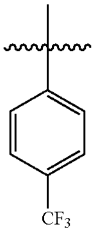 , 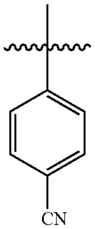 , 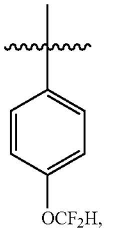 or

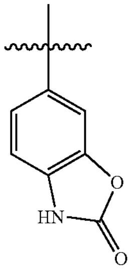 , 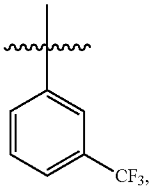 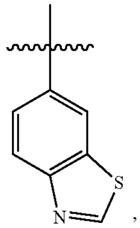 ,

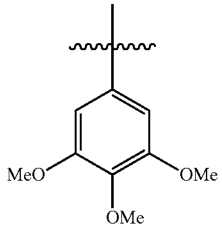 , 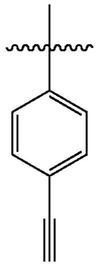 , 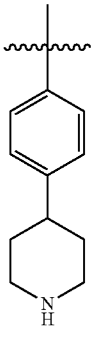 ,

-continued

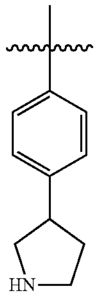 , 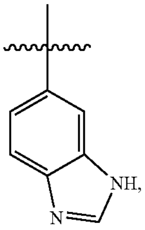

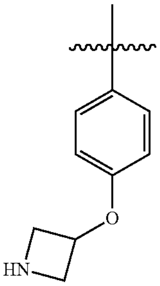 , 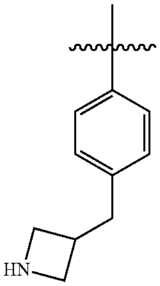 ,

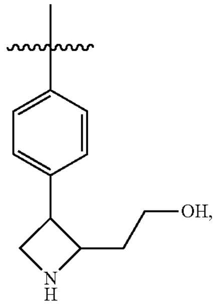 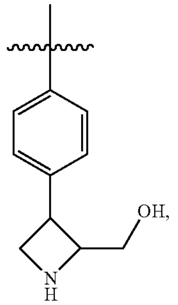 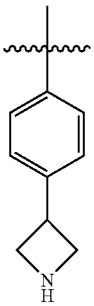 or

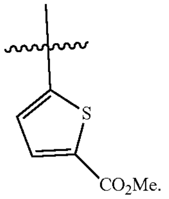

In some preferred embodiments, $R^1$ is 4-bromophenyl.

In compounds of Formula (I), e.g., Formula (Ia), $R^2$ can be aryl, heteroaryl, alkyl, alkenyl, alkynyl, cycloalkyl, heterocyclyl, H, halogen, CN, haloalkyl, $OR^A$, $NR^AR^B$, —C(O)$R^A$, C(O)$NHR^A$, C(O)$NR^AR^B$, C(O)[alkylene]$NHR^A$, C(O)[alkylene]$NR^AR^B$, $CO_2R^A$, C(S)$NHR^A$, C(S)$NR^AR^B$, $SR^A$, S(O)$R^A$, $SO_2R^A$, $SO_2NHR^A$, $SO_2NR^AR^B$, NHC(O)$R^A$, $NR^A$-C(O)$R^B$, NHC(O)$NHR^A$, NHC(O)$NR^AR^B$, $NR^A$C(O)$NHR^B$, $NR^A$C(O)$NR^BR^C$, P(O)(OH)($OR^A$), or P(O)($OR^A$)($OR^B$), where any aryl, heteroaryl, cycloalkyl, heterocyclyl, alkyl, alkenyl, or alkynyl can be optionally substituted. In some embodiments, $R^2$ is an optionally substituted aryl, an optionally substituted heterocyclyl or an optionally substituted heteroaryl. For example, $R^2$ is an optionally substituted 3-12 membered aryl or an optionally substituted 3-12 membered heteroaryl or an optionally substituted 3-12 membered heterocyclyl comprising 1, 2 or 3 independently selected heteroatoms (e.g., independently selected from N, O, and S). In some embodiments, $R^2$ is phenyl, pyridinyl, pyrimidinyl, or morpholinyl. For example, $R^2$ can be

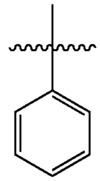,
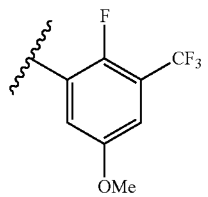,
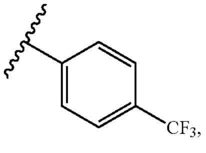
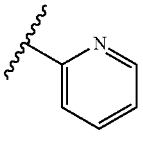,
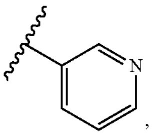,
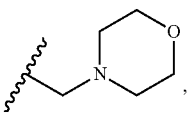,
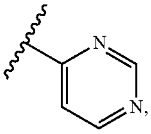
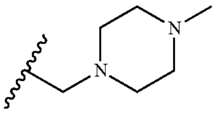,
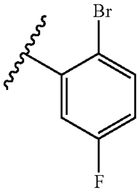,
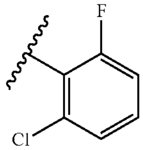,
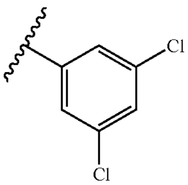, or
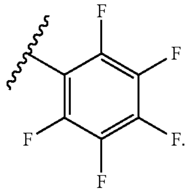

In some embodiments, $R^2$ is an optionally substituted alkyl, alkenyl, or alkynyl. For example, $R^2$ is methyl, ethyl, propyl, isopropyl, butyl, butan-2-yl, 2-methylpropyl, tert-butyl, pentyl, 2-methylbutan-2-yl, pentan-2-yl, pentan-3-yl, or 3-methylbutan-2-yl. In some embodiments, $R^2$ is

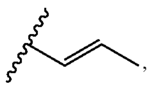,
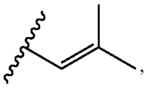,
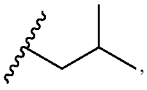, or
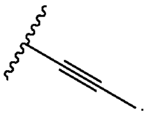

In some preferred embodiments, $R^2$ is phenyl.

In some compounds of Formula (I), RE can be CN.

In compounds of Formula (I), e.g., Formula (Ia), $R^4$ can be $OR^{4A}$, H, halogen, CN, alkyl, haloalkyl, alkenyl, alkynyl, aryl, heteroaryl, cycloalkyl, heterocylcyl, $NR^AR^B$, —C(O)$R^A$, C(O)$NHR^A$, C(O)$NR^AR^B$, C(O)[alkylene]$NHR^A$, C(O)[alkylene]$NR^AR^B$, $CO_2R^A$, C(S)$NHR^A$, C(S)$NR^AR^B$, $SR^A$, S(O)$R^A$, $SO_2R^A$, $SO_2NHR^A$, $SO_2NR^AR^B$, NHC(O)$R^A$, $NR^A$-C(O)$R^B$, NHC(O)$NHR^A$, NHC(O)$NR^AR^B$, $NR^A$C(O)$NHR^B$, $NR^A$C(O)$NR^BR^C$, P(O)(OH)($OR^A$), or P(O)($OR^A$)($OR^B$), where any aryl, heteroaryl, cycloalkyl, heterocyclyl, alkyl, alkenyl, or alkynyl can be optionally substituted. In some embodiments, $R^{4A}$ is H, alkyl, alkenyl, or alkynyl. In some preferred embodiments, $R^4$ is OH.

In compounds of Formula (I), e.g., Formula (Ia), $R^5$ can be $OR^{5A}$, H, halogen, CN, alkyl, haloalkyl, alkenyl, alkynyl, aryl, heteroaryl, cycloalkyl, heterocylcyl, $NR^AR^B$, —C(O)$R^A$, C(O)$NHR^A$, C(O)$NR^AR^B$, C(O)[alkylene]$NHR^A$, C(O)[alkylene]$NR^AR^B$, $CO_2R^A$, C(S)$NHR^A$, C(S)$NR^AR^B$, $SR^A$, S(O)$R^A$, $SO_2R^A$, $SO_2NHR^A$, $SO_2NR^AR^B$, NHC(O)$R^A$, $NR^A$-C(O)$R^B$, NHC(O)$NHR^A$, NHC(O)$NR^AR^B$, $NR^A$C(O)$NHR^B$, $NR^A$C(O)$NR^BR^C$, P(O)(OH)($OR^A$), or P(O)($OR^A$)($OR^B$), where any aryl, heteroaryl, cycloalkyl, heterocyclyl, alkyl, alkenyl, or alkynyl can be optionally substituted. In some embodiments, $R^{5A}$ is H, alkyl, alkenyl, or alkynyl. In some preferred embodiments, $R^5$ is OH.

In some compounds of Formula (I), e.g., Formula (Ia), $R^5$ together with the carbon $R^4$ is attached to forms a heterocyclyl. For example, $R^5$ together with the carbon $R^4$ is attached to forms an optionally substituted 3-12 membered heterocyclyl comprising 1, 2 or 3 independently selected heteroatoms (e.g., independently selected from N, O, and S).

It is noted that any alkyl, alkenyl, cycloalkyl, heterocyclyl, heteroaryl or aryl in compounds of Formula (I) can be optionally substituted with 1, 2, 3, 4 or more substituents selected independently from OH, oxo (=O), CN, SH, $SO_2NH_2$, $SO_2(C_1\text{-}C_4)$alkyl, $SO_2NH(C_1\text{-}C_4)$alkyl, halogen, $NH_2$, $NH(C_1\text{-}C_4)$alkyl, $N[(C_1\text{-}C_4)alkyl]_2$, $C(O)NH_2$, COOH, COOMe, acetyl, $(C_1\text{-}C_8)$alkyl, $O(C_1\text{-}C_8)$alkyl, $O(C_1\text{-}C_8)$haloalkyl, $(C_2\text{-}C_8)$alkenyl, $(C_2\text{-}C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy, where "m" and "p" are independently 1, 2, 3, 4, 5 or 6.

In embodiments, the compound of Formula (I), e.g., Formula (Ia), is of the structure:

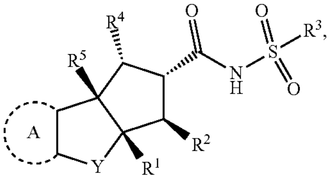

stereoisomers, tautomers, or a pharmaceutically acceptable salt or solvate thereof. In some embodiments, the compound of Formula (I), e.g., Formula (Ia), is of the structure:

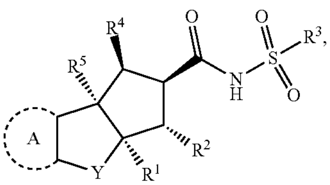

stereoisomers, tautomers, or a pharmaceutically acceptable salt or solvate thereof.

In some embodiments, the compound of Formula (I) is selected from the group consisting of:

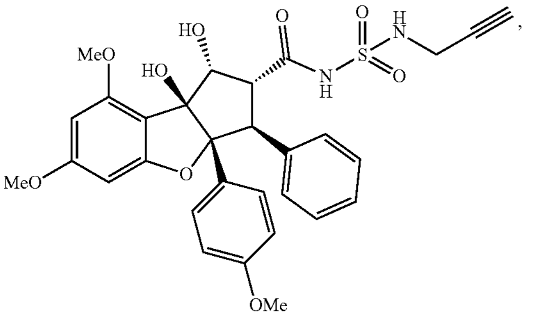
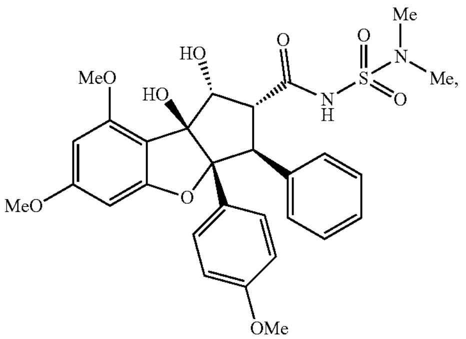
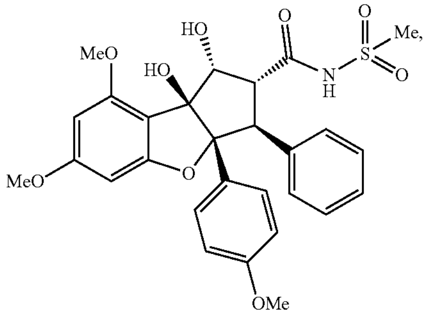
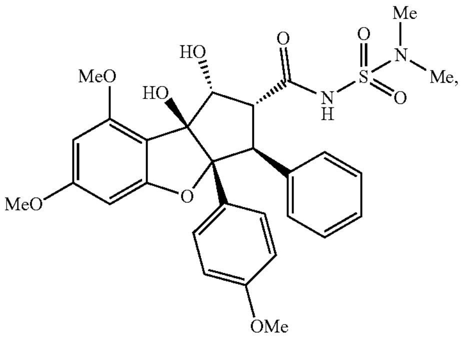
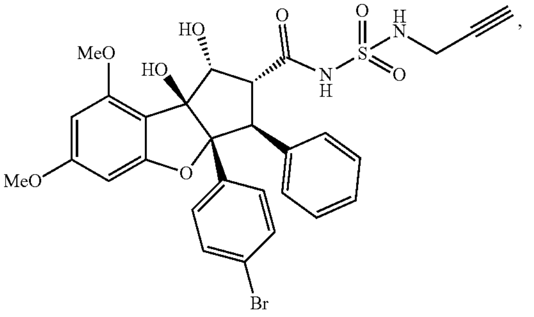
-continued
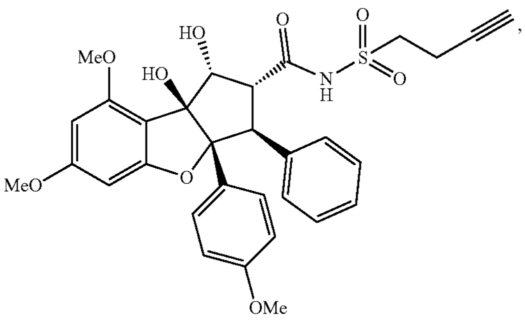
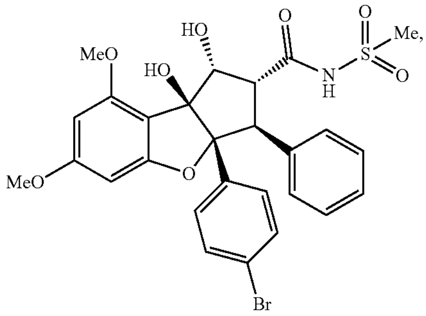
ZW-12-29
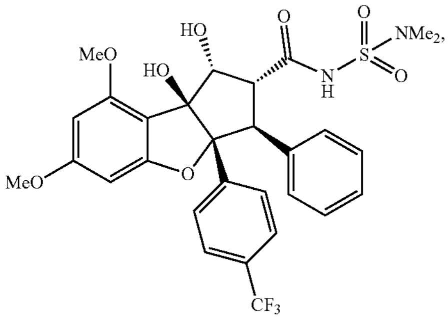
ZW-12-30
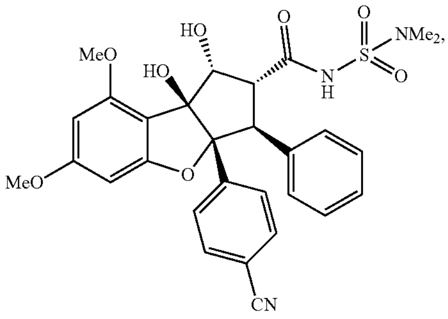
ZW-12-31
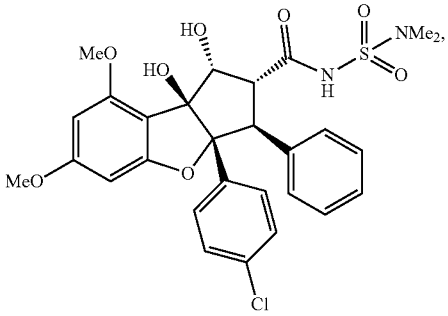

-continued
ZW-12-34
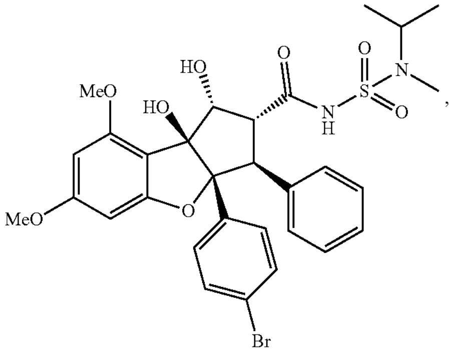
,
ZW-12-35
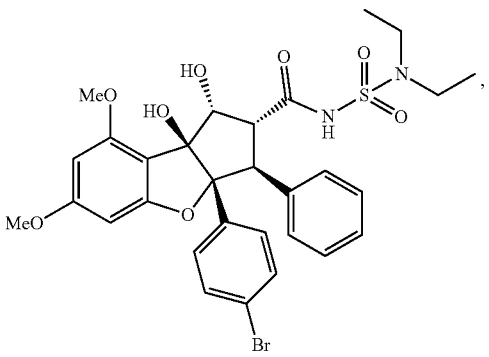
,
ZW-12-36
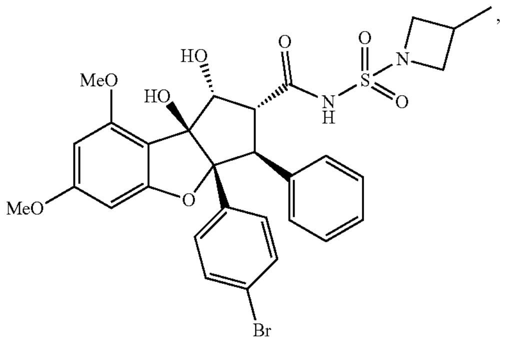
,
ZW-12-37
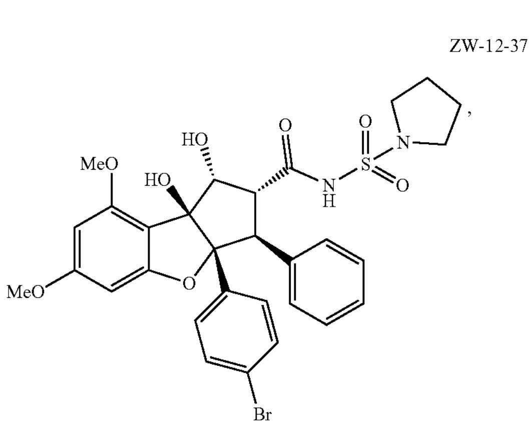
,
-continued
ZW-12-38
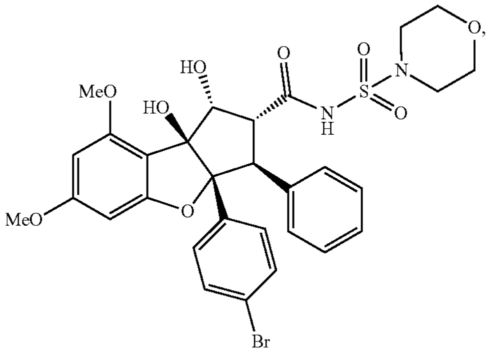
,
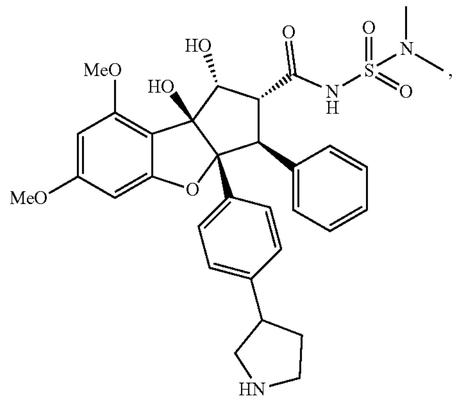
,
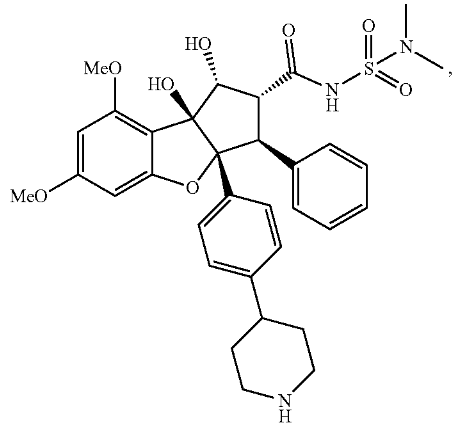
,
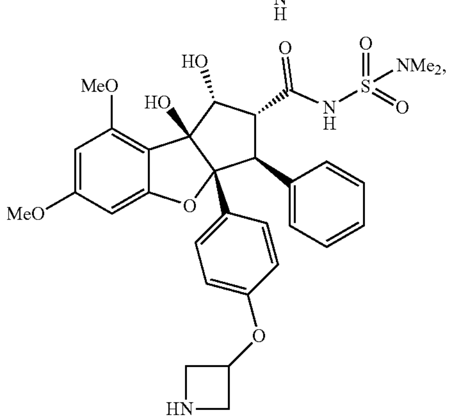
, -continued

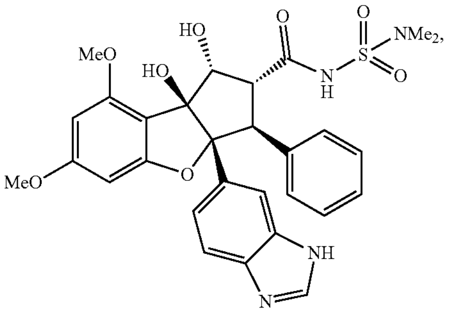

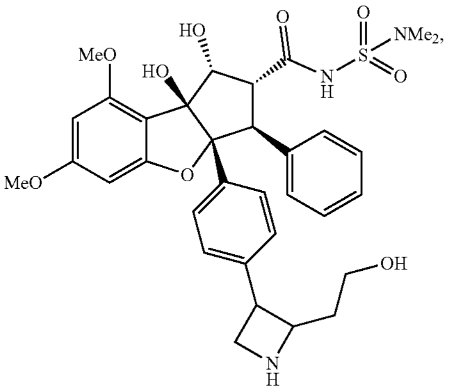

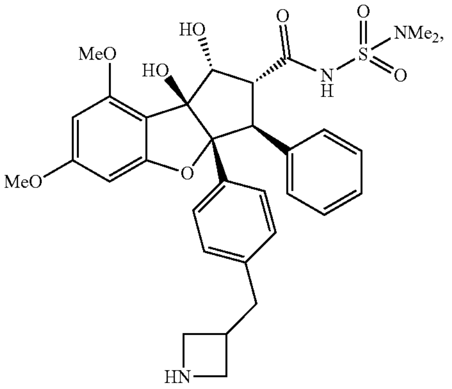

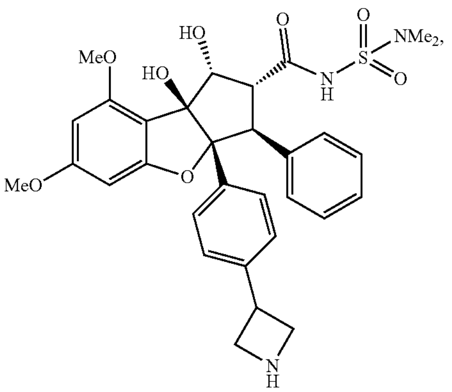

-continued

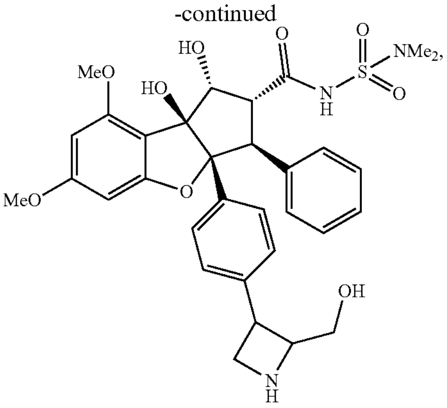

and stereoisomers, tautomers, and pharmaceutically acceptable salts or solvates thereof.

In another aspect provided herein is a pharmaceutical composition comprising a compound of Formula (I), e.g., Formula (Ia), and a pharmaceutically acceptable carrier, diluent, or excipient. In some embodiments, the composition further comprises a therapeutic agent. For example, the composition comprises, in addition to a compound of Formula (I), e.g., Formula (Ia), an anticancer agent, chemotherapeutic, antimicrobial agent, antifungal agent, antibacterial agent, antiprotozoal agent, antihelminthic agent, anti-inflammatory agent, anti-fibrotic agent, or antiviral agent.

Without wishing to be bound by a theory, inventors have discovered inter alia that compounds of Formula (I), e.g., Formula (Ia), are surprisingly and unexpectedly selective inhibitors of cancer stem cell propagation. This, in another aspect provided herein is a method for inhibiting cancer stem cell propagation. The method comprises administering a compound of Formula (I), e.g., Formula (Ia), to a cancer stem cell. Some exemplary cancer stem cells include, but are not limited to, glioblastoma (GBM), diffuse large B-cell lymphoma (DLBCL), hepatocellular cancer, acute myeloid leukemia, breast cancer, colorectal cancer, small cell lung cancer, or non-small cell lung cancer stem cells. In some preferred embodiments, the cancer stem cell is a GBM stem cell.

It is noted that administering to the cell can be in vitro, ex vivo, or in vivo. For example, when the administering to the cell is in vivo, the compound can be administered to a subject. The subject can be one having a eukaryotic initiation factor 4A (eIF4A)-dependent condition or in need of treatment for an eIF4A dependent condition. For example, the subject can be a subject having, diagnosed with or in need of treatment for cancer, e.g., GBM. In another example, the subject can be a subject having or in need of treatment for an infection, e.g., a fungal, bacterial, viral, or protozoal infection.

In yet another aspect provided herein is a method for treating a eukaryotic initiation factor 4A (eIF4A)-dependent condition. The method comprises administering a therapeutically effective amount of a compound of Formula (I) e.g., Formula (Ia), to a subject in need thereof. Some exemplary eIF4A-dependent conditions include, but are not limited to, a disease of uncontrolled cell growth, proliferation and/or survival, a disease of inappropriate cellular inflammatory responses, a disease caused by a parasite/pathogen or a neurodegenerative disease requiring neuroprotection. In some embodiments, the eIF4A dependent condition is cancer. For example, the eIF4A-dependent condition is glioblastoma. In some embodiments, the eIF4A-dependent condition is an infection, e.g., a viral, bacterial, fungal or protozoal infection.

In still another aspect provided herein is a method for treating a DEAD box helicase-dependent condition, e.g. a DDX3-, DDX21, DDX50, -or DDX41-dependent condition, such as a cancer, infection, fibrosis, or inflammatory disease. The method comprises administering a therapeutically effective amount of a compound of Formula (I), e.g., Formula (Ia), to a subject in need thereof.

In yet still another aspect provided herein is a method for treating a cancer. The method comprises administering a therapeutically effective amount of a compound of Formula (I), e.g., Formula (Ia), to a subject in need thereof. In some embodiments, the method for treating cancer further comprises co-administering at least one additional anti-cancer therapy to the subject. It is noted that the additional anti-cancer therapy can be an anticancer agent or chemotherapeutic, radiation therapy or surgery.

Another aspect provided herein is a method for treating an infection. The method comprises administering a therapeutically effective amount of a compound of Formula (I), e.g., Formula (Ia), to a subject in need thereof. Infection can be a bacterial, fungal, viral, helminth, or protozoal infection. In some embodiments, the method for treating an infection further comprises co-administering an antimicrobial agent, e.g., an antifungal agent, antibacterial agent, antiprotozoal agent, antihelminthic agent or antiviral agent to the subject Yet in another aspect provided herein is a method for treating an inflammatory disease or condition. The method comprises administering a therapeutically effective amount of a compound of Formula (I), e.g., Formula (Ia), to a subject in need thereof. In some embodiments, the method further comprises co-administering an anti-inflammatory agent to the subject.

Still in another aspect provided herein is a method for treating fibrosis. The method comprises administering a therapeutically effective amount of a compound of Formula (I), e.g., Formula (Ia), to a subject in need thereof. In some embodiments, the method further comprises co-administering an antifibrotic agent to the subject.

It is noted that a subject in need of treatment can be a mammal. For example, the subject can be a primate, a human, or a non-human primate. In some embodiments, the subject is having or diagnosed with cancer.

Figure 1A:
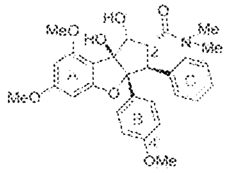
FIG. 1A shows nature-produced (1-4) and synthetic (5-9) rocaglates.
Figure 1A:
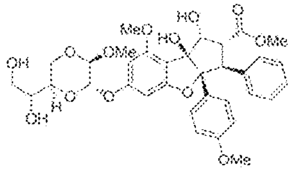
Figure 1A:
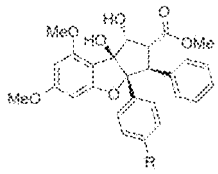
Figure 1A:
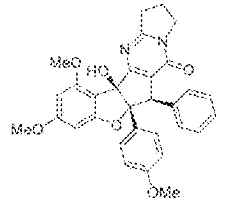
Figure 1A:
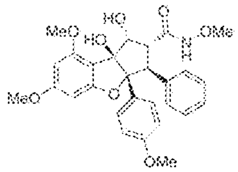
Figure 1A:
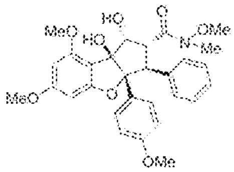
Figure 1A:
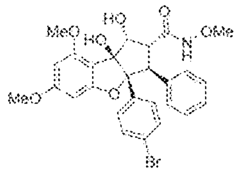
Figure 1A:
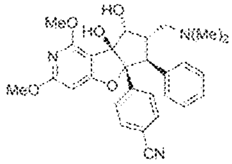
Figure 1B:
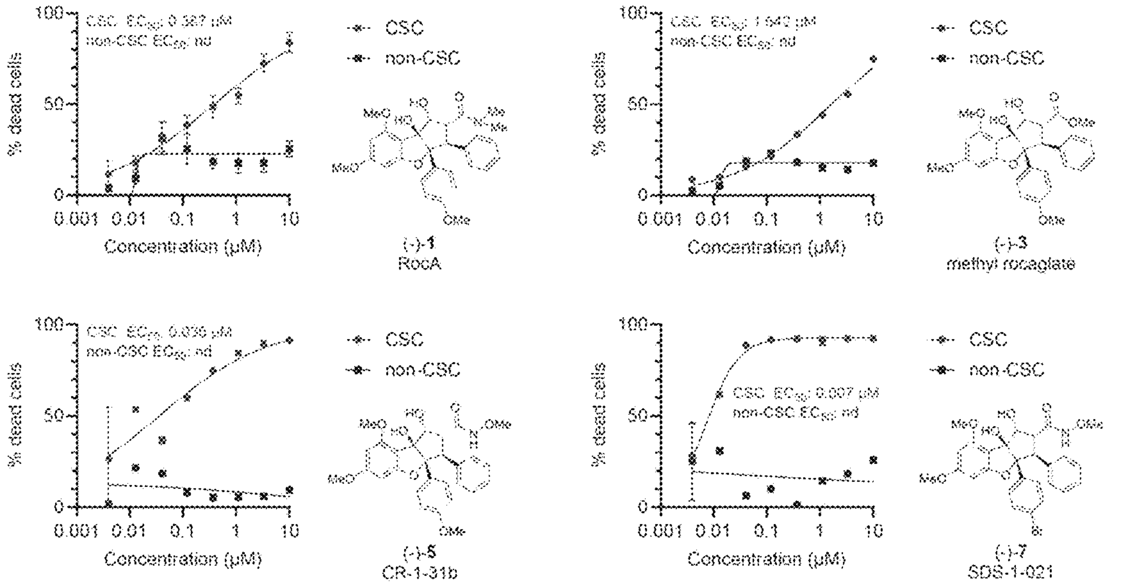
FIG. 1B shows a comparative dose-response for killing of CSC and non-CSC populations for select rocaglates.
Figure 2:
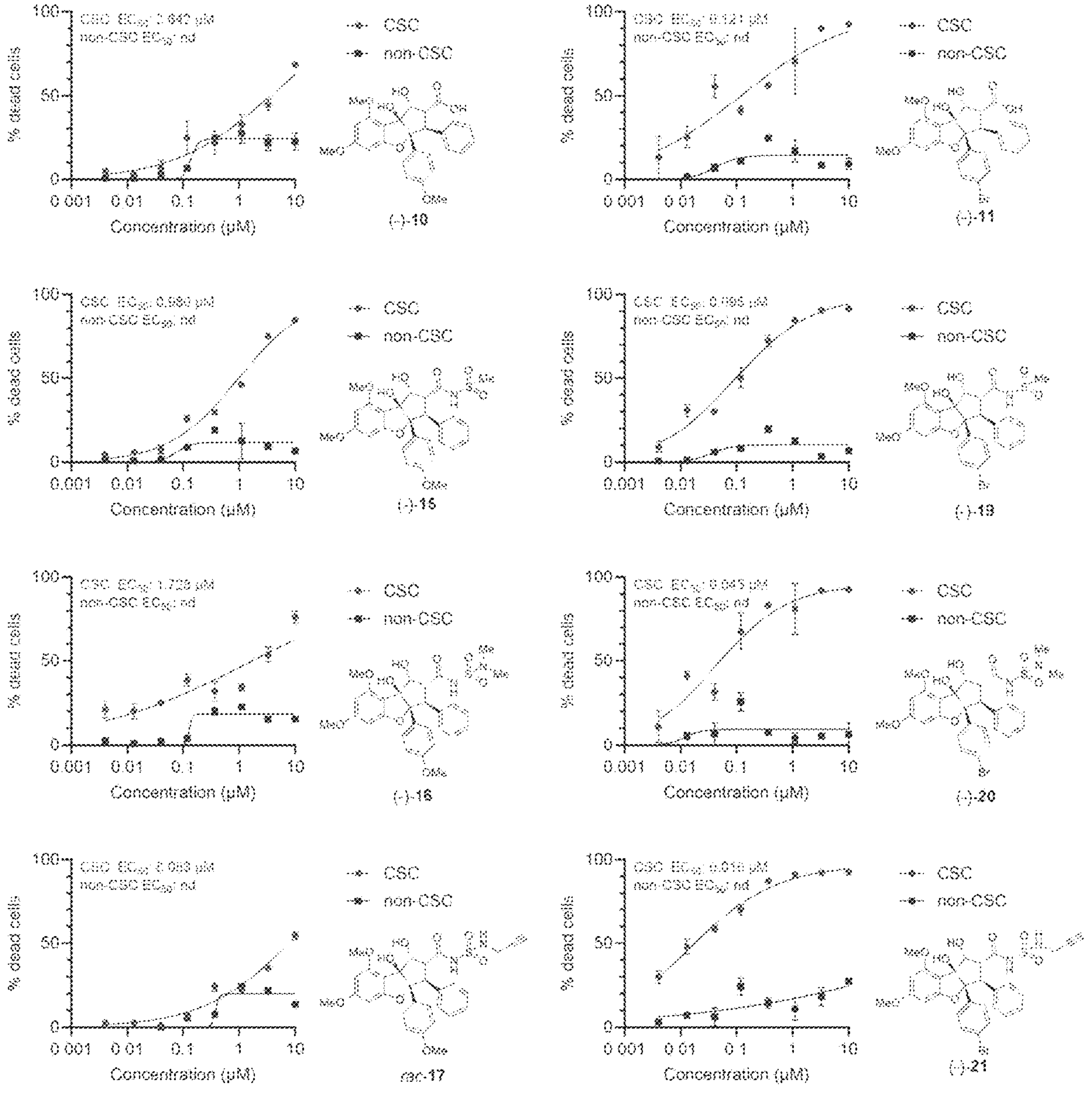
FIG. 2 shows a comparative dose-response for killing of CSC and non-CSC populations for select rocaglaic acid and N-acylated derivatives showing enhanced selective CSC-killing for C4'-brominated congeners (right column) over their C4'-methoxy substituted counterparts (left column).
Figure 6:
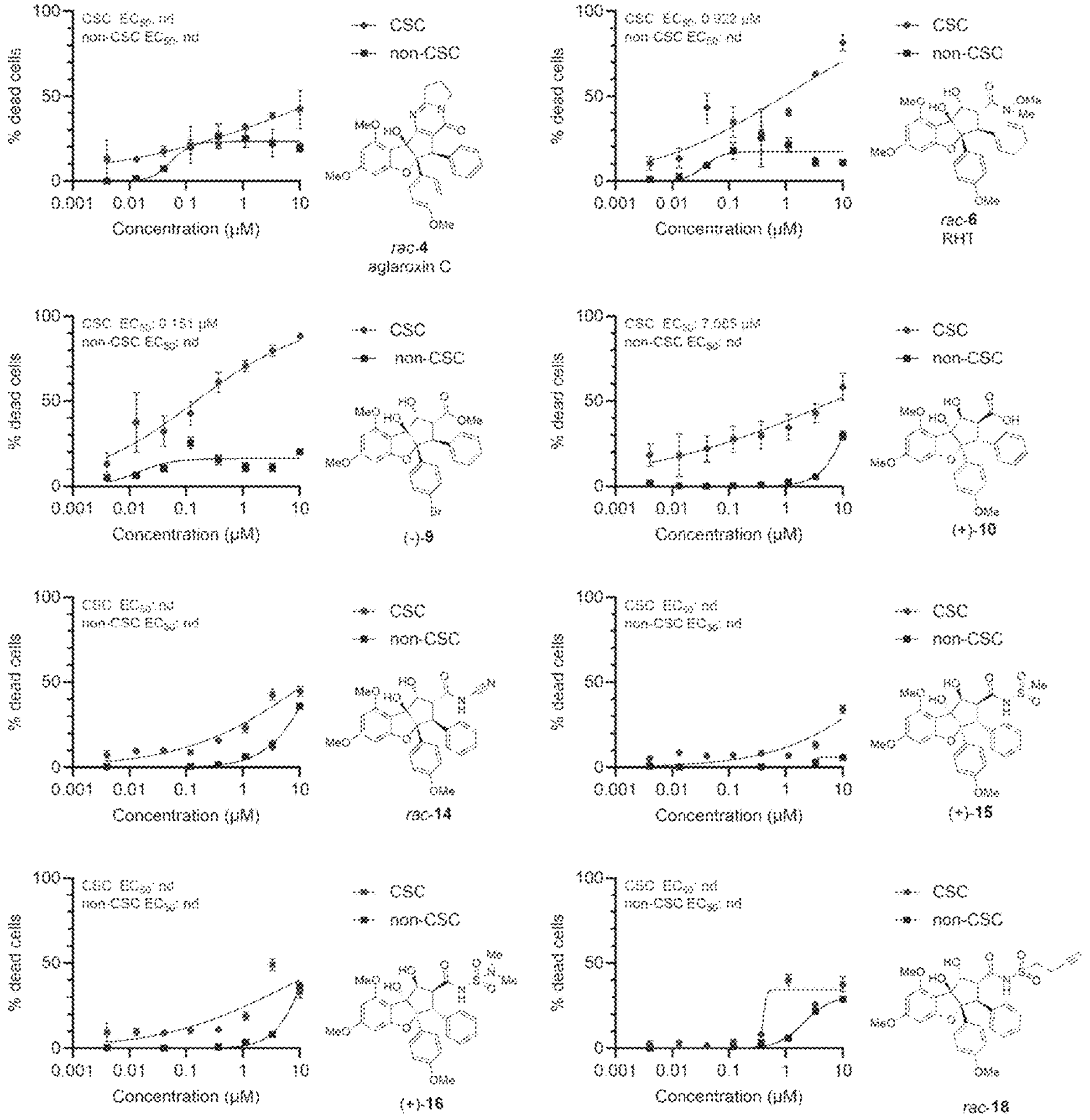

FIG. 6 shows the dose-response curves and chemical structures for all tested compounds (Table 1 and Table 2) not appearing in FIG. 1B and FIG. 2.

Figure 7A:
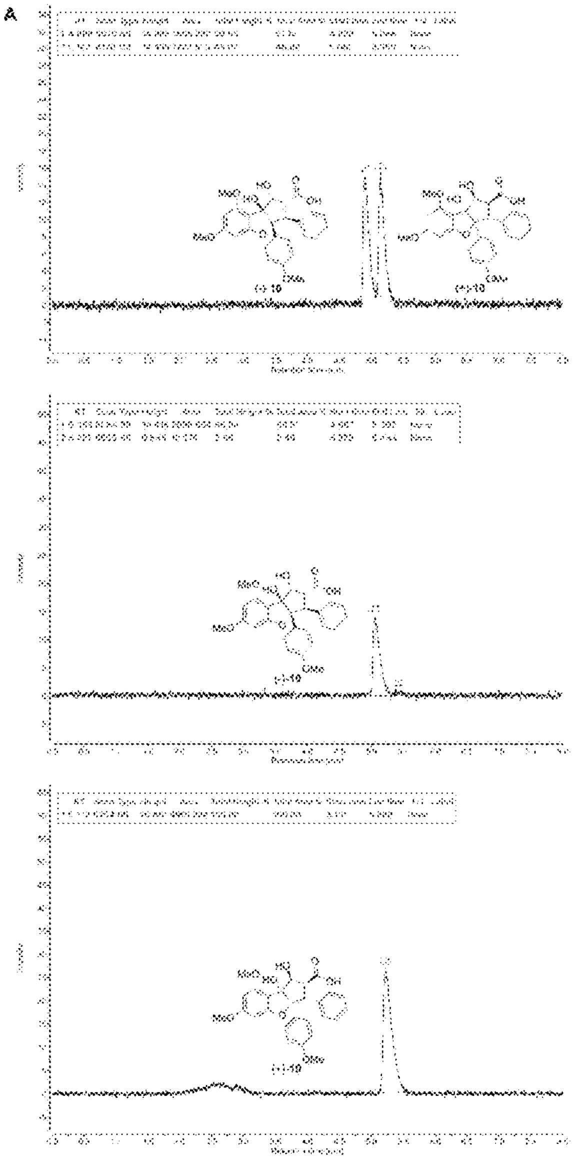
Figure 7B:
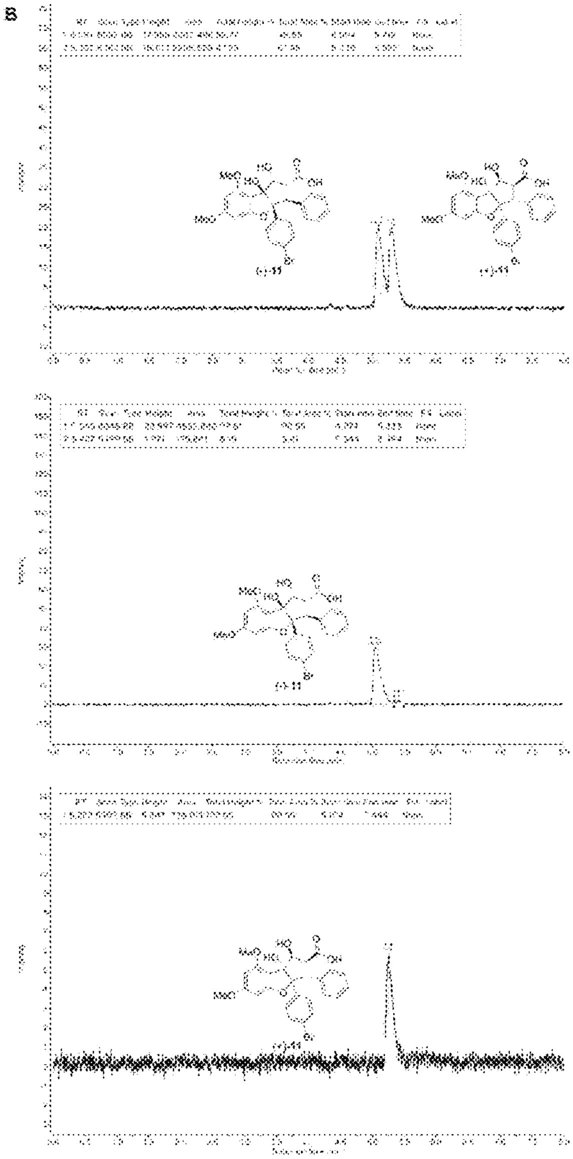

FIG. 7A and FIG. 7B show a chiral $UPC^2$ analysis for enantioenriched rocaglaic acid. Column: 2.5 μm Trefoil CEL2; Method: 5% to 40% MeOH in supercritical $CO_2$ over 4 minutes and 40% MeOH in supercritical $CO_2$ for 2 minutes. FIG. 7A: Compound 10. FIG. 7B: Compound 11.

Figure 8:
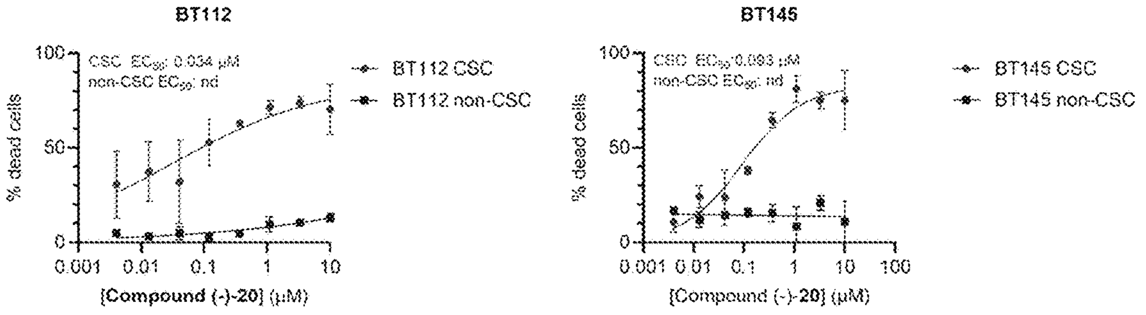

FIG. 8 shows dose-response curves comparing the killing of CSC and non-CSC populations using compound (−)-20 in BT112 (left) and BT145 (right) glioblastoma cell lines.

Figure 9:
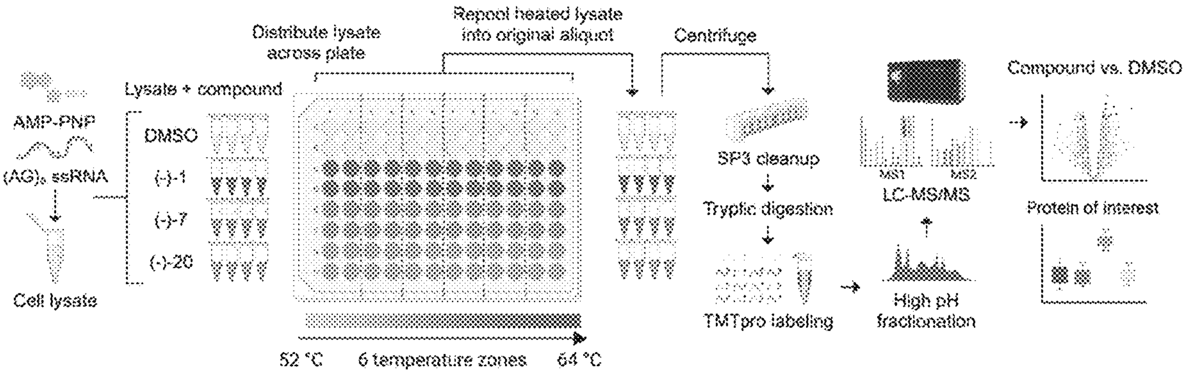

FIG. 9 shows a schematic of the PISA workflow employed in this study. Cell lysates were pre-loaded with AMP-PNP and (AG) 8 RNA, treated with test compounds, then aliquoted across a PCR plate and heated to one of six different temperatures. For each sample corresponding to a single TMTpro plex, the six individually heated lysate aliquots were then repooled back into a single "integral" tube. The 16 repooled samples were centrifuged to remove aggregates, subjected to an SP3-based cleanup, digested with trypsin, then labeled with TMTpro 16plex reagents and combined. Peptides were fractionated and analyzed via LC-MS/MS. Protein abundances were compared between DMSO and compound treated samples using a moderated t-test with a Benjamini-Hochberg correction.

Figure 10:
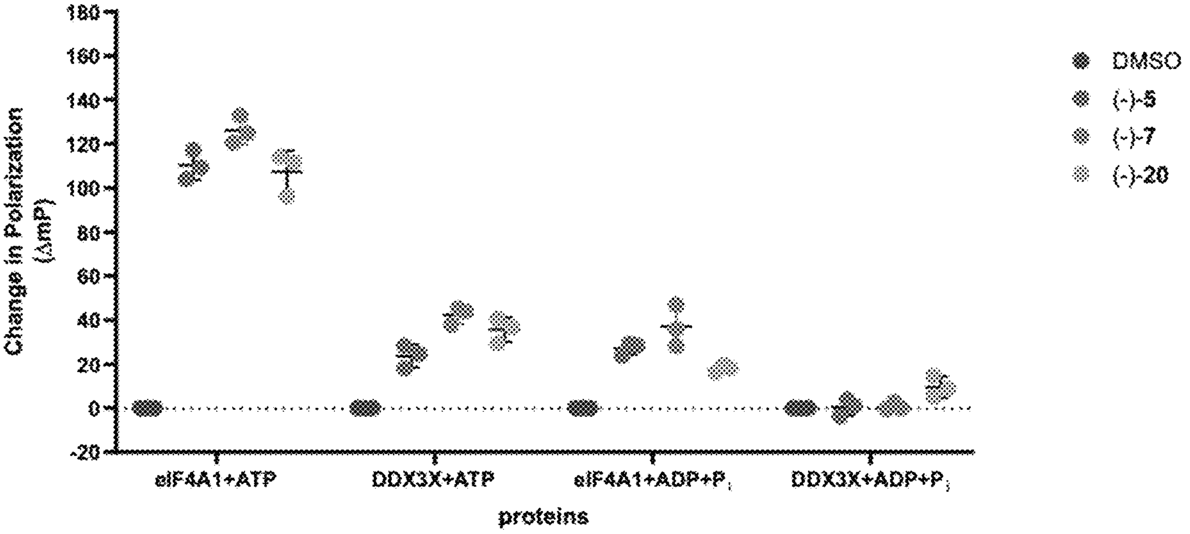

FIG. 10 shows data from ATP independent clamping of eIF4A1 and DDX3X. Fluorescence polarization assay was performed to assess change in polarization (ΔmP) obtained with eIF4A1: FAM-labeled poly $r(AG)_8$ and DDX3X:FAM-labeled poly $r(AG)_8$ in the presence of (−)-5, (−)-7, or (−)-20 (10 μM) and either 1 mM ATP or 1 mM ADP+$P_i$. N=3±SEM.

Figure 11:
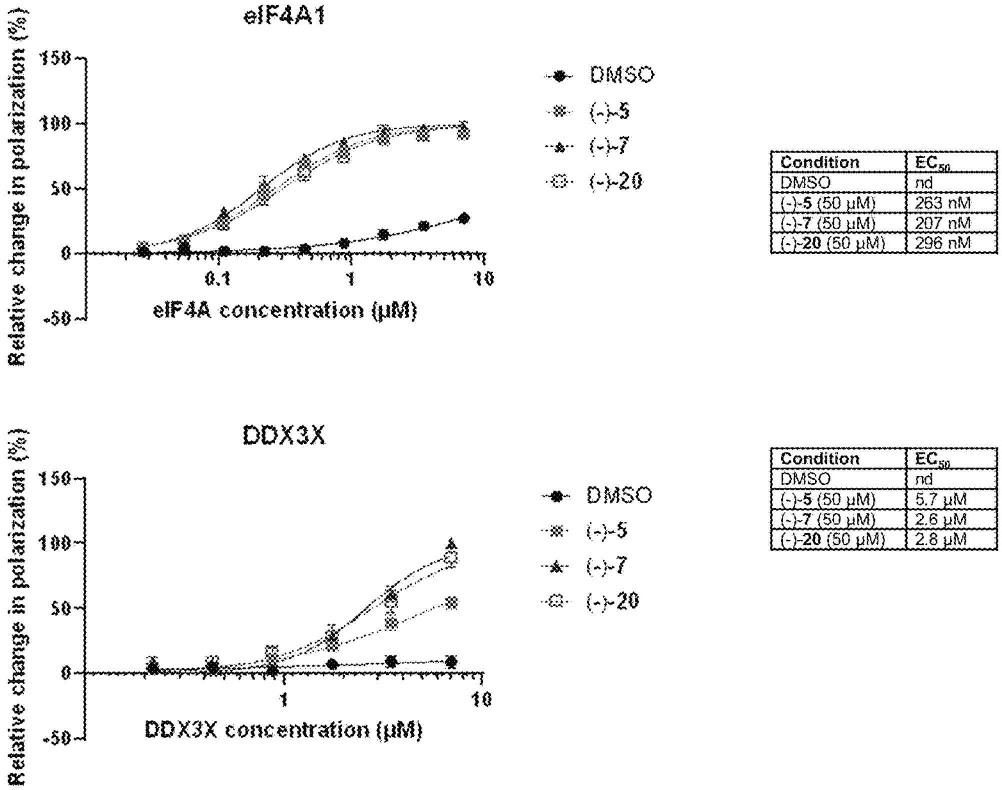

FIG. 11 shows protein titration experiments measuring rocaglate-induced stimulation of complex formation between DEAD-box proteins and a FAM-labeled $(AG)_8$ RNA probe. Top: Rocaglate (50 μM) stimulation of eIF4A1 binding to $(AG)_8$ RNA probe (10 nM) in the presence of ATP (1 mM) shows comparable stimulation by all three compounds relative to DMSO, with $EC_{50}$s for complex formation between 200-300 nM. Bottom: Rocaglate stimulation of DDX3X binding to $(AG)_8$ RNA probe in the presence of ATP shows significant enhancement of binding stimulation for C4'-brominated congeners (−)-7 and (−)-20 over C4'-methoxy substituted (−)-5. N=3±SEM.

Figure 12:
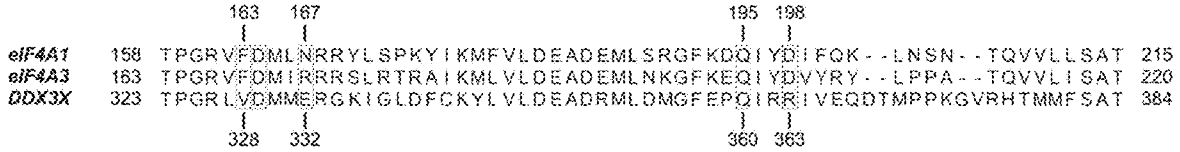

FIG. 12 shows the sequence alignment for eIF4A1 (SEQ ID NO: 1), eIF4A3 (SEQ ID NO: 2), and DDX3X (SEQ ID NO: 3) protein sequences at the rocaglate binding site. Key residues at the rocaglate binding site are boxed. Residue labels reflect eIF4A1 (top) and DDX3X (bottom) sequence numbering. Sequence shown are:

```
eIF4A1:
                                          (SEQ ID NO: 1)
TPGRVFDMLNRRYLSPKYIKMFVLDEADEMLSRGFKDQIYDIFQKLNSN
TQVVLLSAT,

eIFA4A3:
                                          (SEQ ID NO: 2)
TPGRVFDMIRRRSLRTRAIKMLVLDEADEMLNKGFKEQIYDVYRYLPPA
TQVVLISAT, and
```

-continued

```
DDX3X:
                                          (SEQ ID NO: 3)
TPGRLVDMMERGKIGLDFCKYLVLDEADRMLDMGFEPQIRRIVEQDTMP
PKGVRHTMMFSAT.
```

Figures 13A, 13B, 13C:
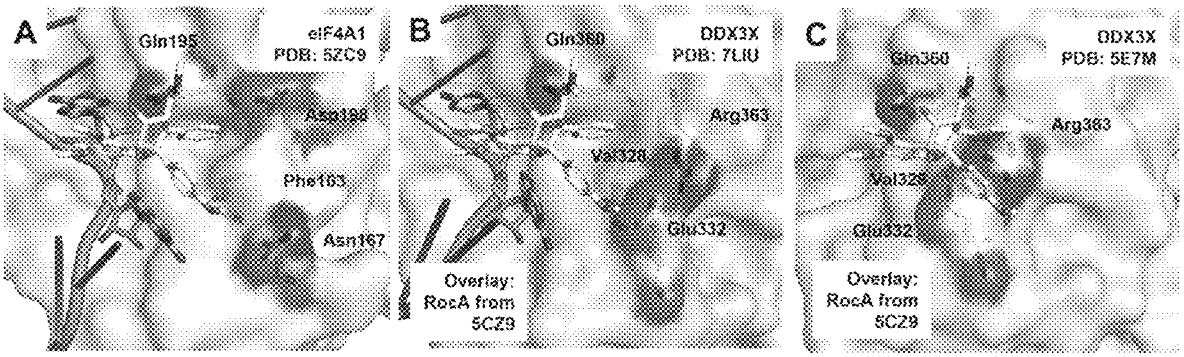

FIG. 13A shows ligand RocA (−)-1 in the rocaglate binding pocket of the crystallographically-determined eIF4A-RNA-RocA complex (PDB: 5ZC9). Overlay analysis reveals varying degrees of steric clashes between the RocA B-ring and Glu332 in both DDX3X structures (B-C), as well as significant C-ring clashes with DDX3X Arg363 in the 5E7M structure (C). The 7LIU structure was selected for rigid receptor and induced-fit modeling experiments based on this analysis.

FIG. 13B shows ligand RocA (−)-1 in the rocaglate binding pocket of a DDX3X-DNA/RNA hybrid complex (PDB: 7LIU). Overlay analysis reveals varying degrees of steric clashes between the RocA B-ring and Glu332 in both DDX3X structures (B-C), as well as significant C-ring clashes with DDX3X Arg363 in the 5E7M structure (C). The 7LIU structure was selected for rigid receptor and induced-fit modeling experiments based on this analysis.

FIG. 13C shows ligand RocA (−)-1 in the rocaglate binding pocket of a non-oligo-bound DDX3X structure (PDB: 5E7M). Overlay analysis reveals varying degrees of steric clashes between the RocA B-ring and Glu332 in both DDX3X structures (B-C), as well as significant C-ring clashes with DDX3X Arg363 in the 5E7M structure (C). The 7LIU structure was selected for rigid receptor and induced-fit modeling experiments based on this analysis.

Figure 14A:
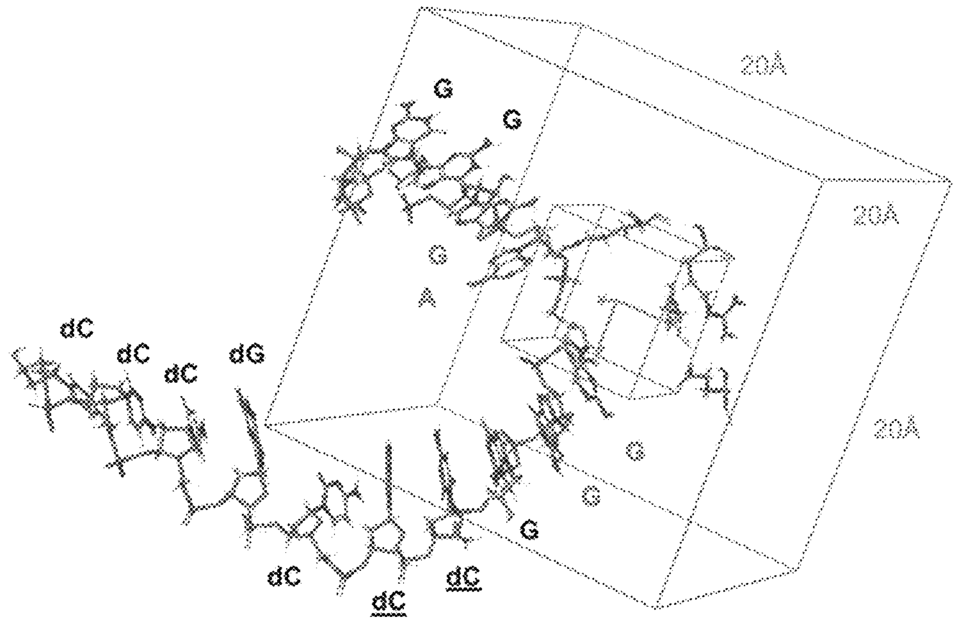

FIG. 14A shows analysis of the 7LIU-C704A receptor used for rocaglate-DDX3X modeling experiments: in the modified model, all residues within the docking grid are purines (GGGAGGG). The residues highlighted in red flank the rocaglate binding site and are consistent with the enriched tetramer motifs identified by a Bind-n-Seq experiment with RocA and DDX3X.[S1]

Figure 14B:
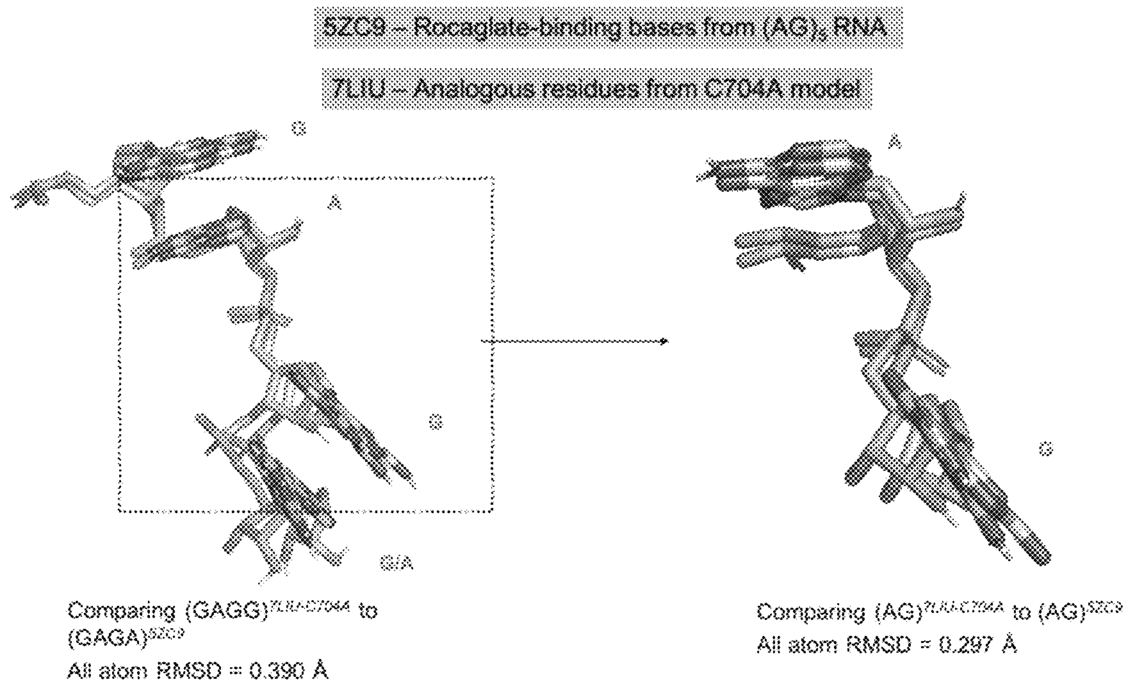

FIG. 14B shows analysis of the 7LIU-C704A receptor used for rocaglate-DDX3X modeling experiments: superposition of (GAGG) from the 7LIU-C704A model and (GAGA) from a RocA-eIF4A1-poly (AG) complex (PDB: 5ZC9) shows excellent overlap with low root mean square deviations (RMSD), suggesting an RNA conformation competent for rocaglate binding.

Figures 15A, 15B, 15C, 15D:
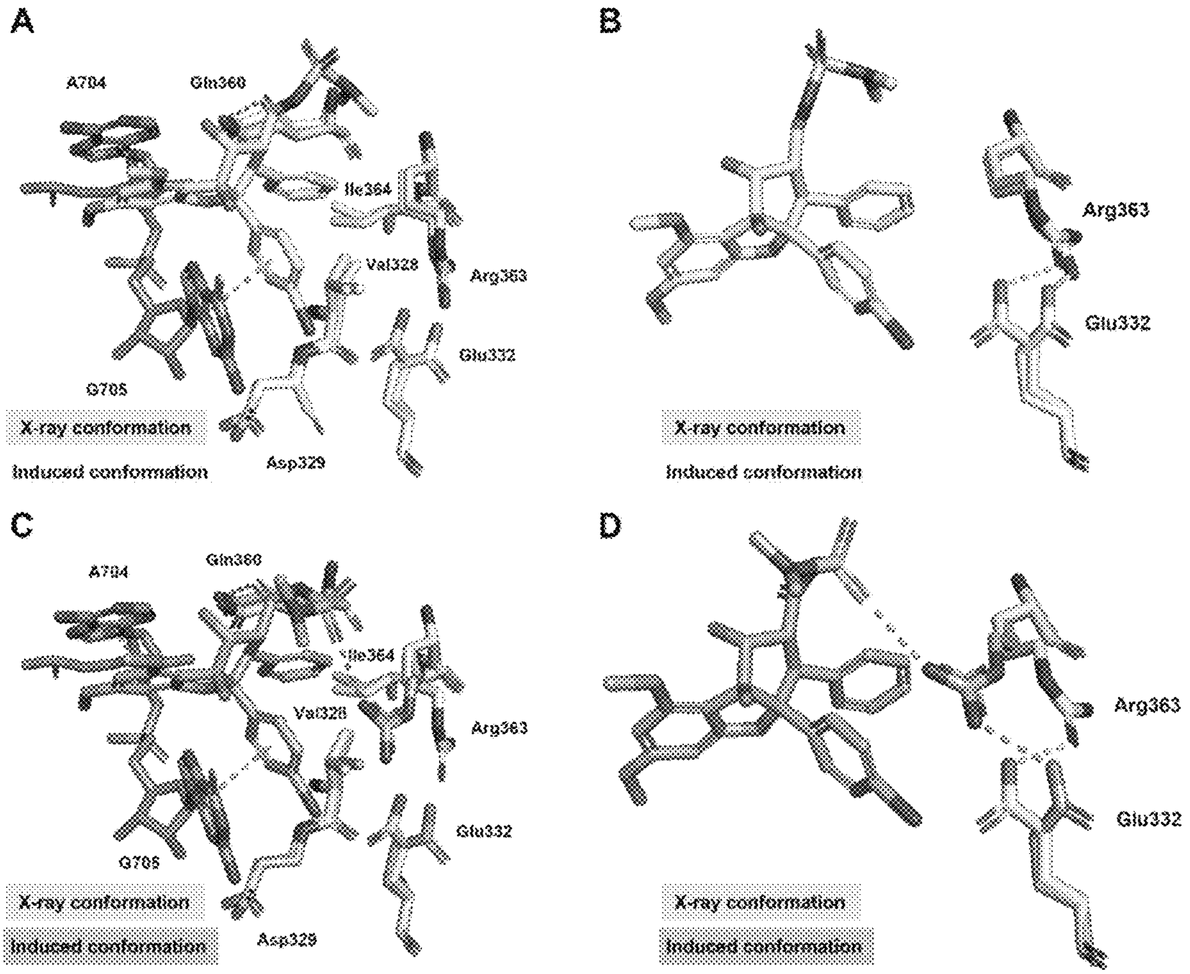

FIG. 15A shows a comparison of induced fit docking (IFD) poses for (−)-20 and DDX3X to the parent DDX3X X-ray structure (PDB: 7LIU): view of the top-scored IFD pose comparing the ligand-accommodating adjustments for binding site residues between the parent X-ray (lime) and the induced-fit receptor (yellow). C704A-mutated RNA (lavender) was held rigid in the induced fit docking.

FIG. 15B shows a comparison of induced-fit docking (IFD) poses for (−)-20 and DDX3X to the parent DDX3X X-ray structure (PDB: 7LIU): adjusted view of (A) highlighting the rotation of Glu332, to avoid steric clash with the C4' bromine substituent while maintaining a salt bridge to Arg363.

FIG. 15C shows a comparison of induced fit docking (IFD) poses for (−)-20 and DDX3X to the parent DDX3X X-ray structure (PDB: 7LIU): view of the second-ranked IFD pose comparing the ligand-accommodating adjustments for binding site residues between the parent X-ray (lime) and the induced-fit receptor (olive). C704A-mutated RNA (lavender) was held rigid in the induced fit docking.

FIG. 15D shows a comparison of induced fit docking (IFD) poses for (−)-20 and DDX3X to the parent DDX3X X-ray structure (PDB: 7LIU): close-up view of (C) highlighting the rotation of Glu332 to avoid steric clash with the C4' bromine substituent, rotation of the Arg363 sidechain to engage in a hydrogen bond with (−)-20, and the Glu332-Arg363 salt bridge interaction.

Figure 16:
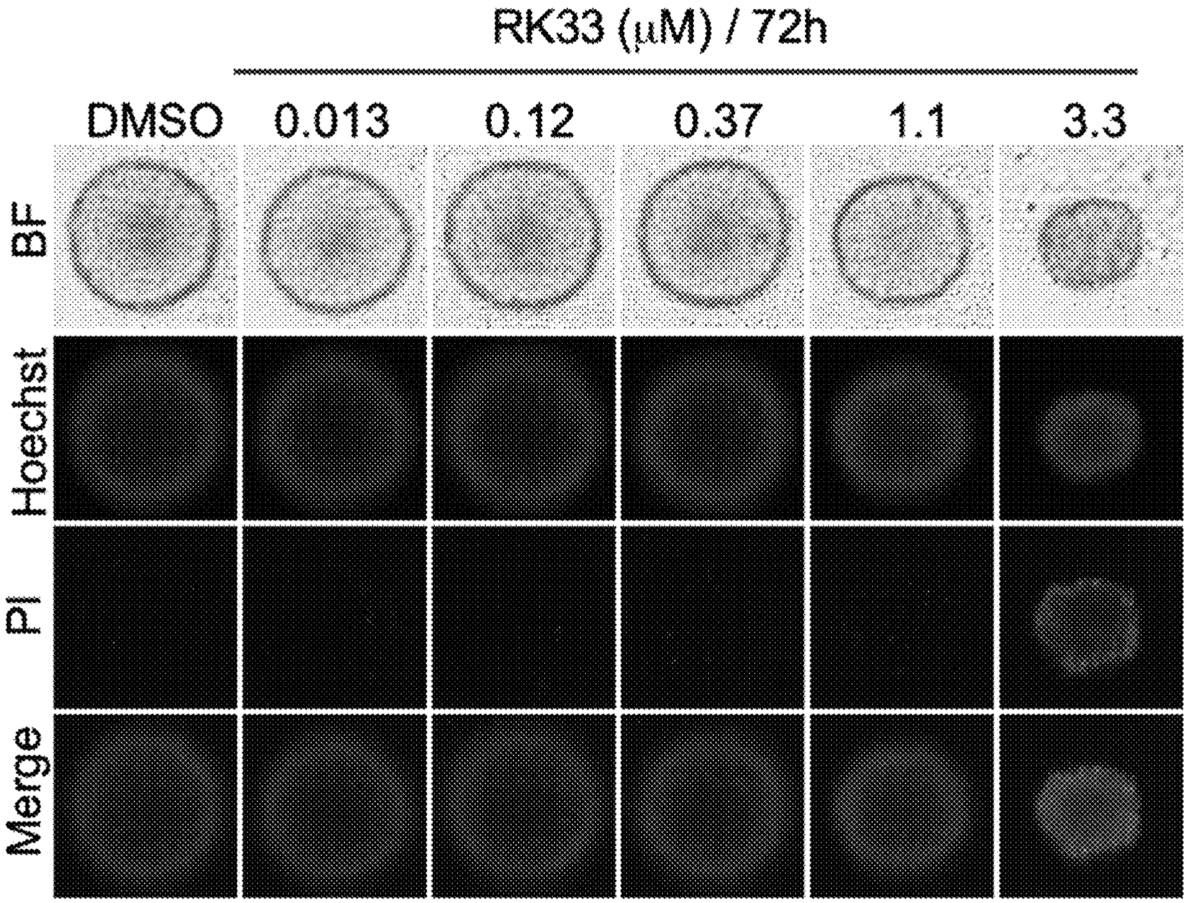

FIG. 16 shows the propidium iodide (PI) and Hoechst staining of GBM neurospheres treated with varying doses of RK-33 for 72 hours.

Figures 17A, 17B, 17C:
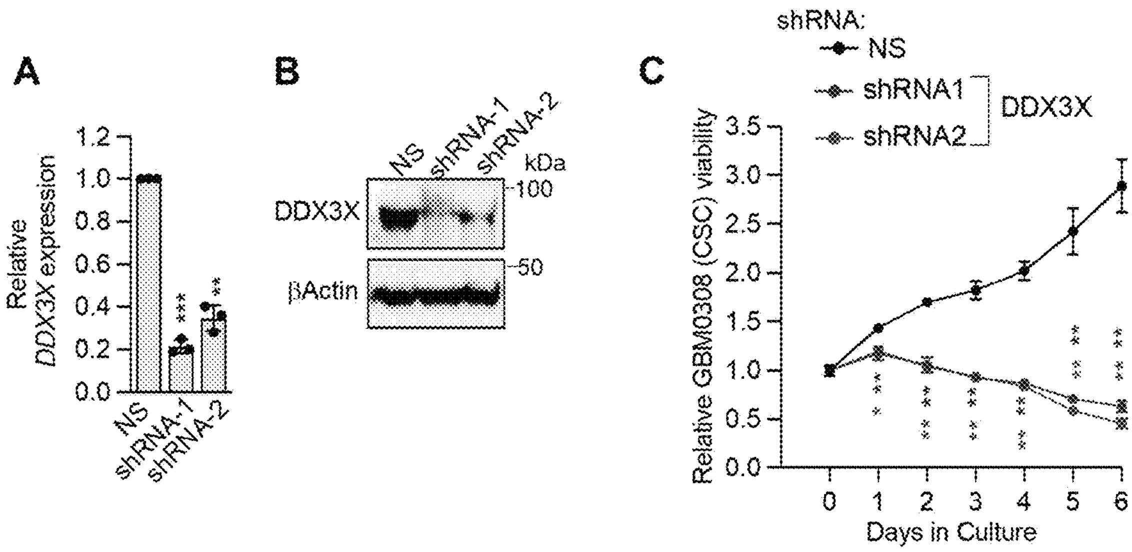

FIG. 17A shows QRT PCR of DDX3X knockdown in GBM0308 (CSCs).

FIG. 17B shows immunoblot monitoring DDX3X mRNA and protein levels in GBM0308 cells expressing either non-silencing (NS) or the two independent DDX3X shRNAs (shRNA-1 and shRNA-2).

FIG. 17C shows a cell viability assay in GBM0308 (CSCs) after shRNA-mediated knockdown of DDX3X. GBM0308 cells were transduced with two independent DDX3X shRNA lentiviruses. 12 hours post-transduction, cells were subjected to puromycin selection for 2 days. After selection, an equal number of cells expressing either non-specific (NS) shRNA or the two independent DDX3X shRNAs were seeded in a 96-well plate in triplicates. Cell viability was measured from day 1 to day 7 using a PrestoBlue reagent. Data are presented as mean±SD. P values were calculated using Welch's t-test for (A) and Two-way ANOVA for (C). *P<0.05, P<0.01, *P<0.001.

Figures 18A, 18B:
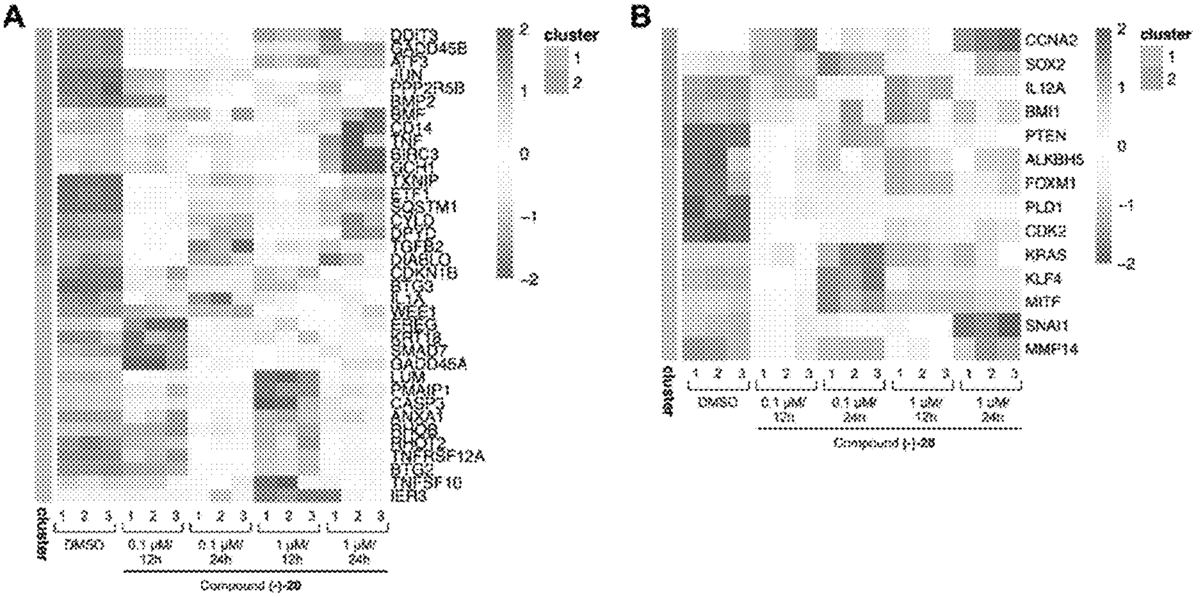
Figure 19A:
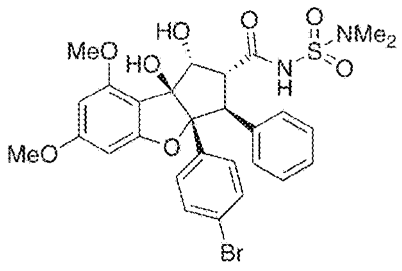
Figure 19A:
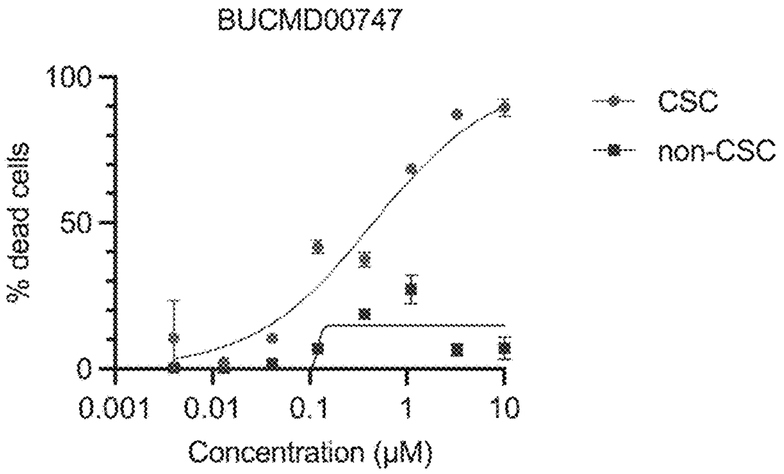
Figure 19B:
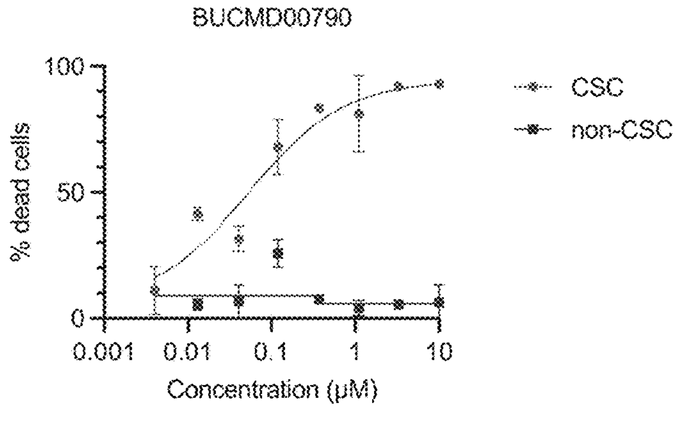
Figure 19C:
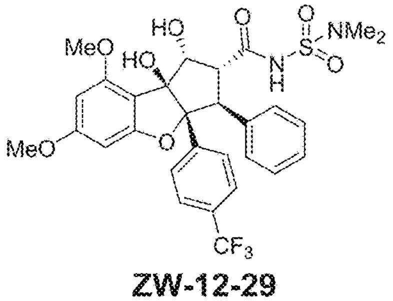
Figure 19C:
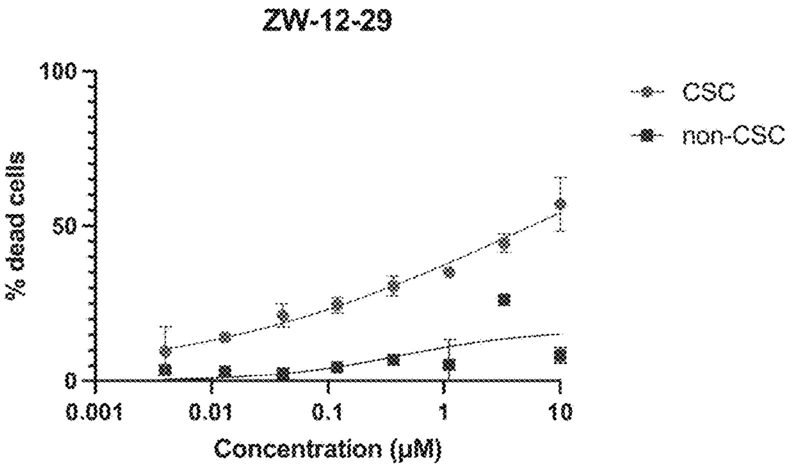
Figure 19D:
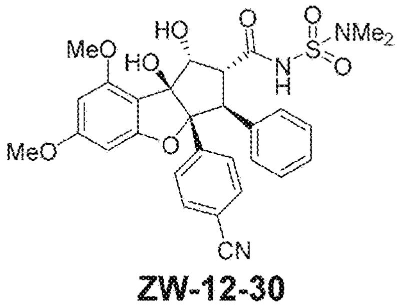
Figure 19D:
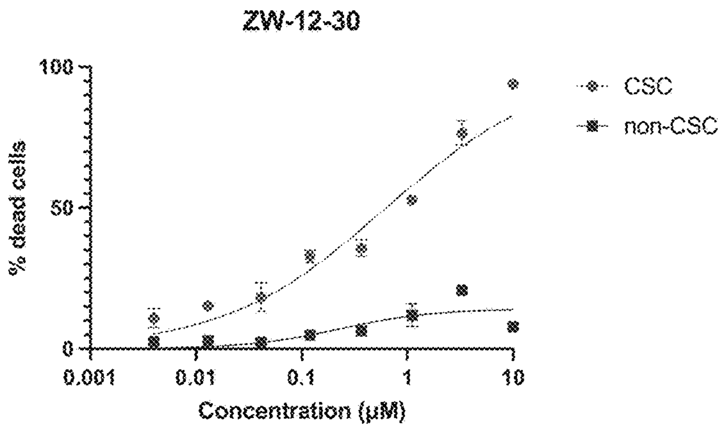
Figure 19E:
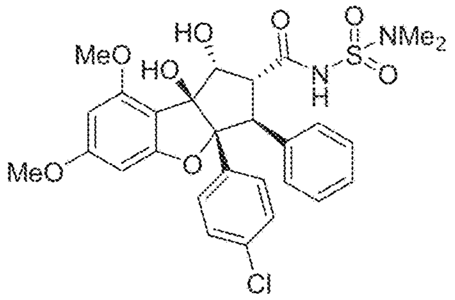
Figure 19E:
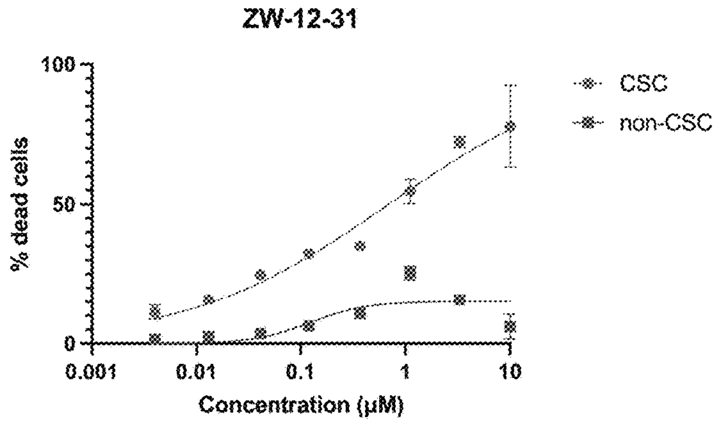
Figure 19F:
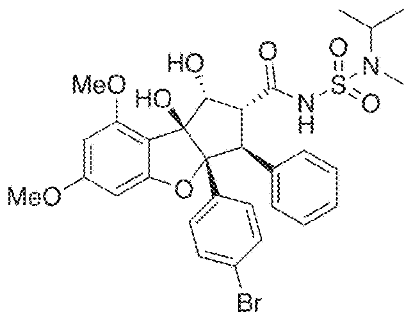
Figure 19F:
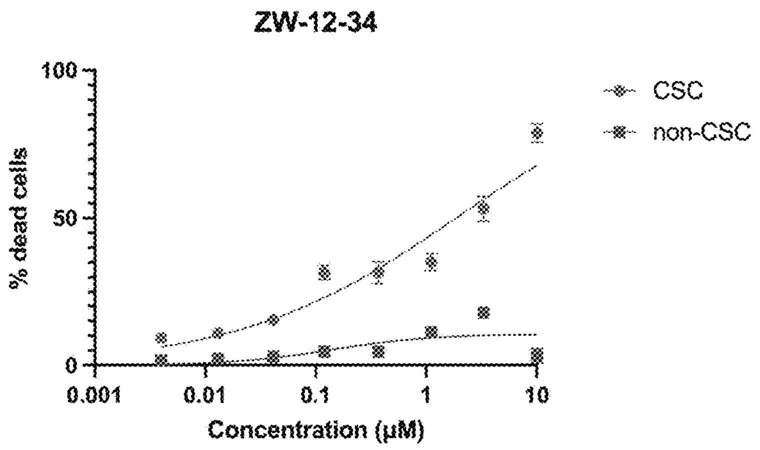
Figure 19G:
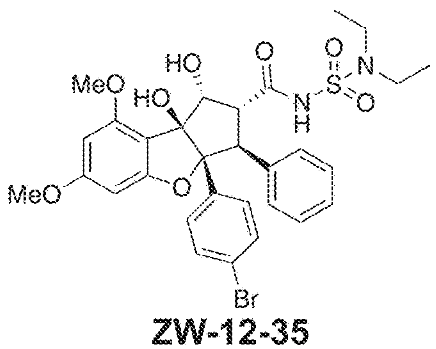
Figure 19G:
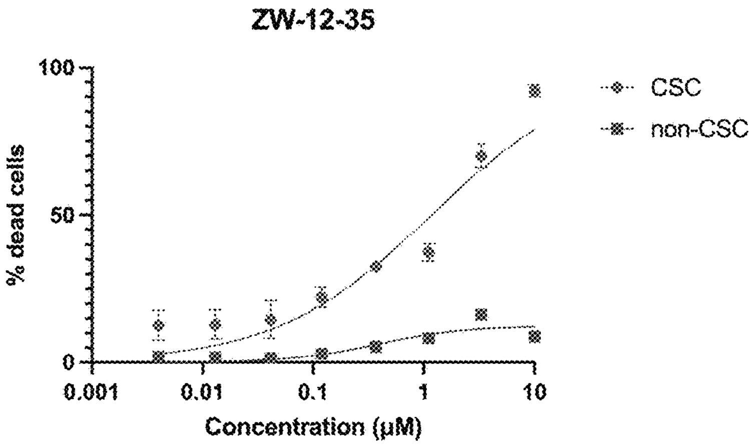
Figure 19H:
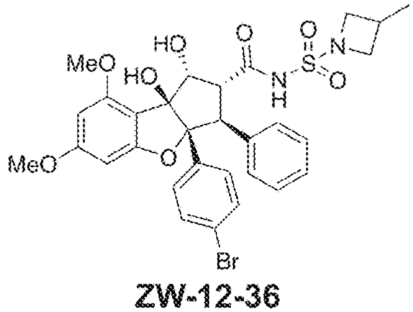
Figure 19H:
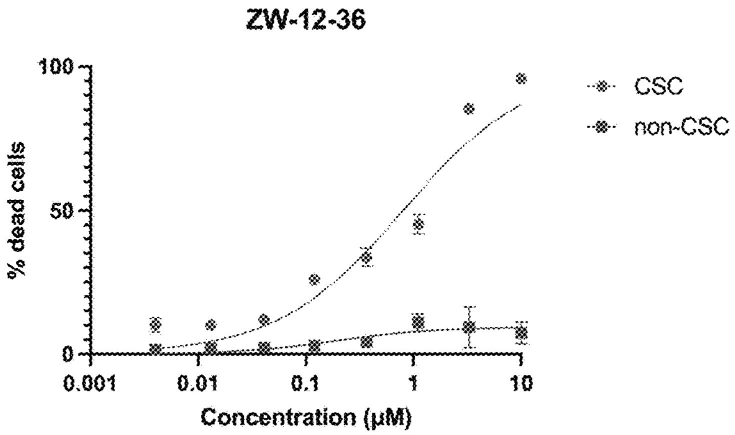
Figure 19I:
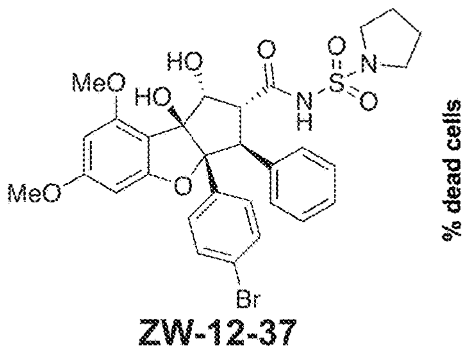
Figure 19I:
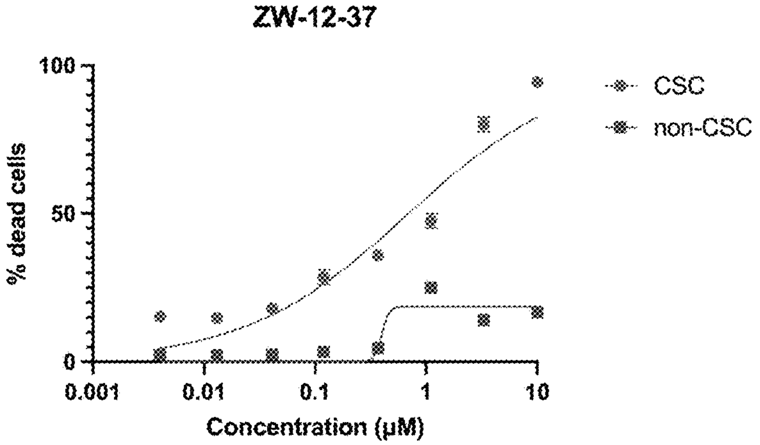
Figure 19J:
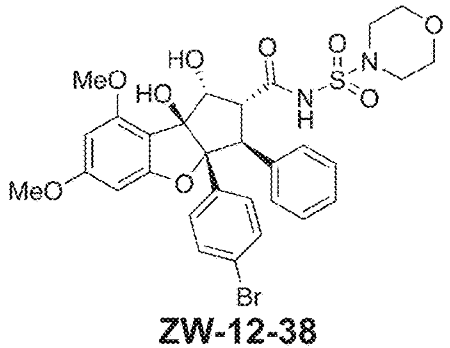
Figure 19J:
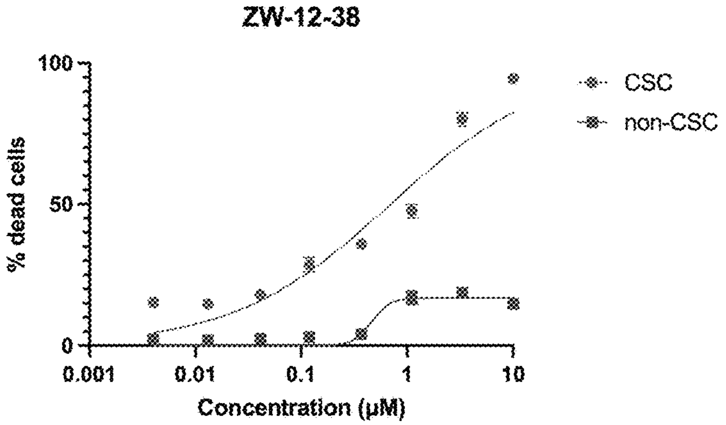

FIG. 18A shows a Z-score heatmap showing differentially expressed gene (DEG) signatures in GBM0308 stem cells treated with either DMSO or compound (−)-20 for the indicated time and concentration. Only significant genes (FDR<0.05 and |LFC|>0.585) are presented here. Hierarchical clustering was performed using the complete linkage method and 1-Pearson as the distance. The genes were then classified into two clusters based on the dendrogram. Heatmap visualizing significantly enriched DEGs in apoptotic pathways. See Wang, Z. et al., ACS Cent. Sci. 2024, 10, 8, 1640-1656 for a color version of this heatmap.

FIG. 18B shows a Z-score heatmap showing differentially expressed gene (DEG) signatures in GBM0308 stem cells treated with either DMSO or compound (−)-20 for the indicated time and concentration. Only significant genes (FDR<0.05 and |LFC|>0.585) are presented here. Hierarchical clustering was performed using the complete linkage method and 1-Pearson as the distance. The genes were then classified into two clusters based on the dendrogram. Downstream of DDX3X.

FIG. 19A-19J are show comparative dose-response for killing of CSC and non-CSC populations for some exemplary compounds described herein.

Figure 20A:
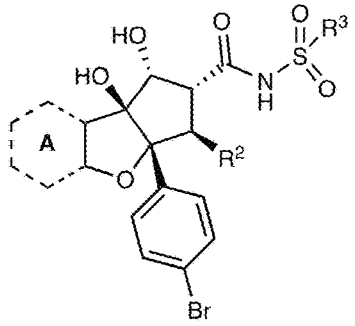
Figure 20A:
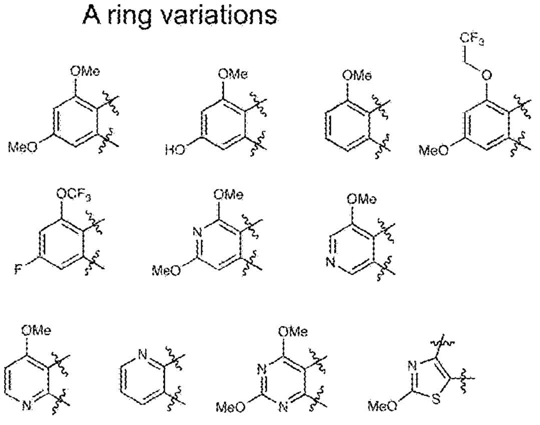
Figure 20A:
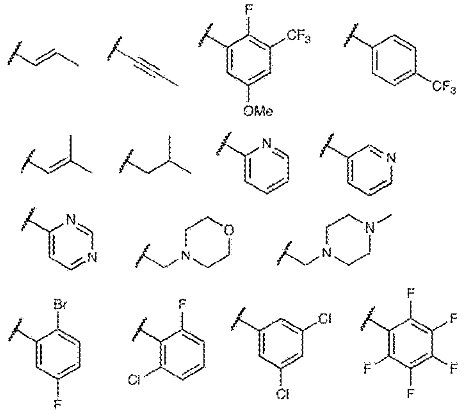
Figure 20A:
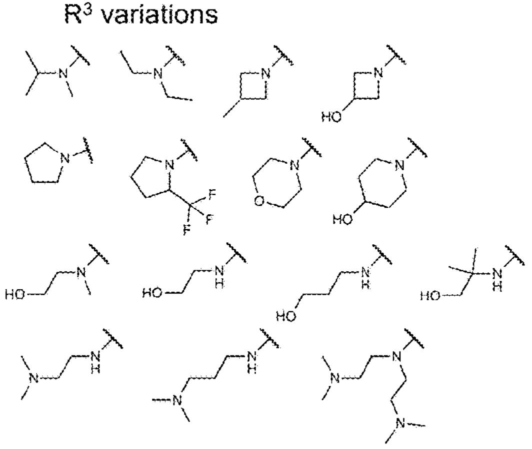
Figure 20B:
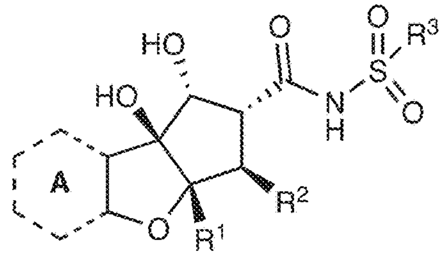
Figure 20B:
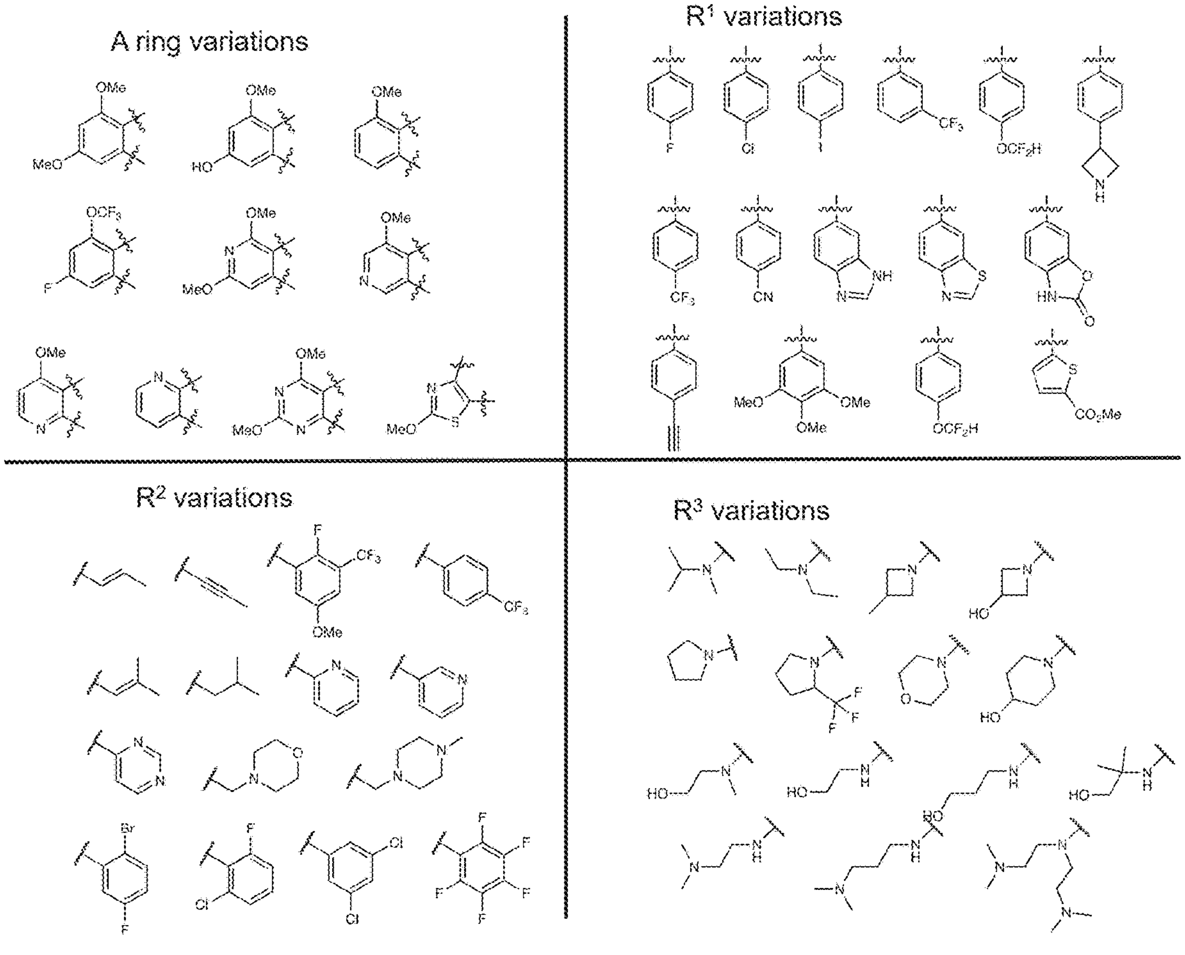
Figure 21:
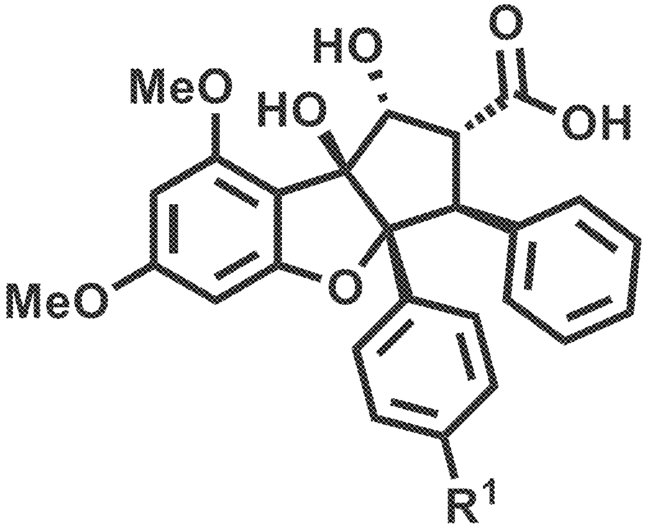
Figure 21:
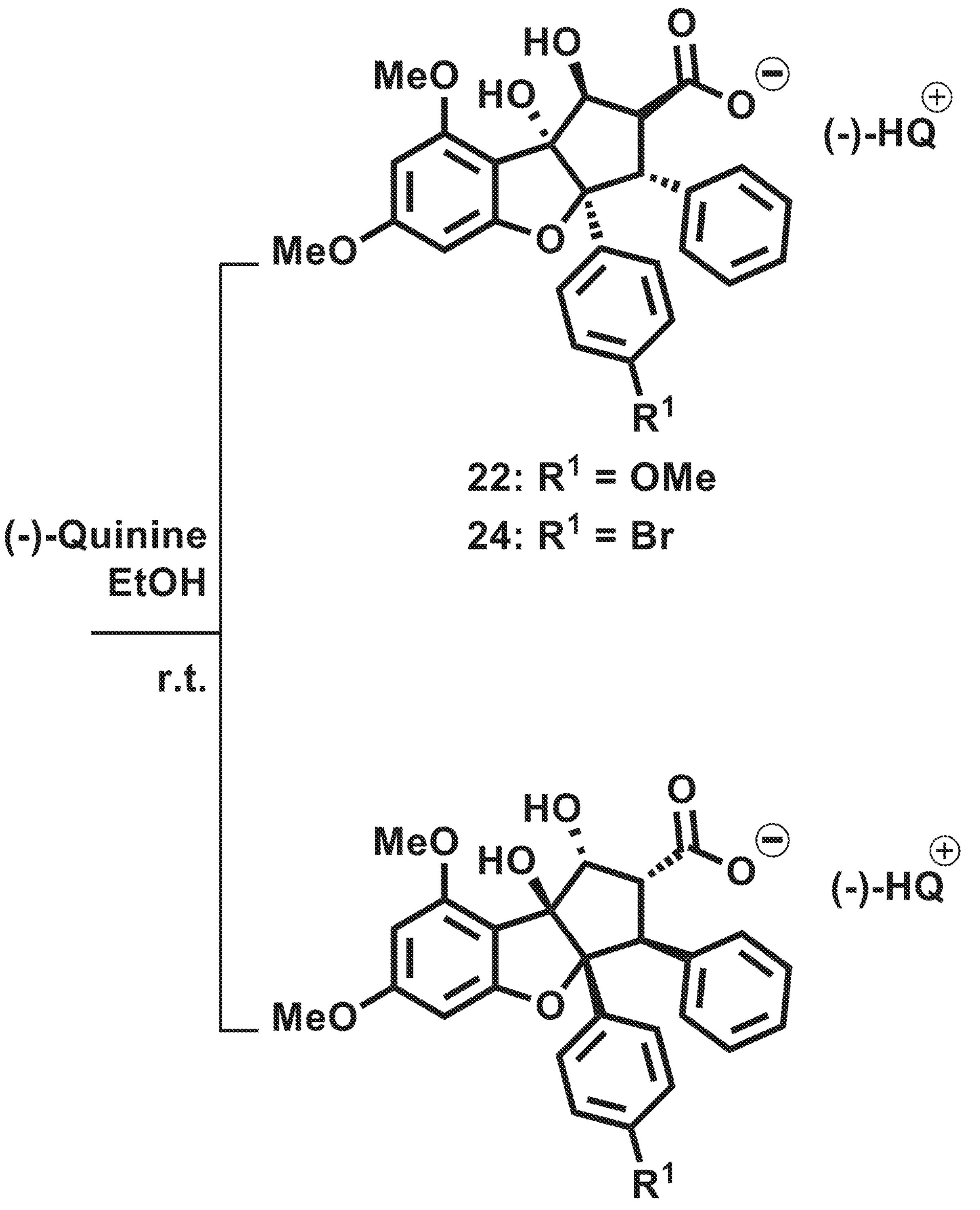
Figure 21:
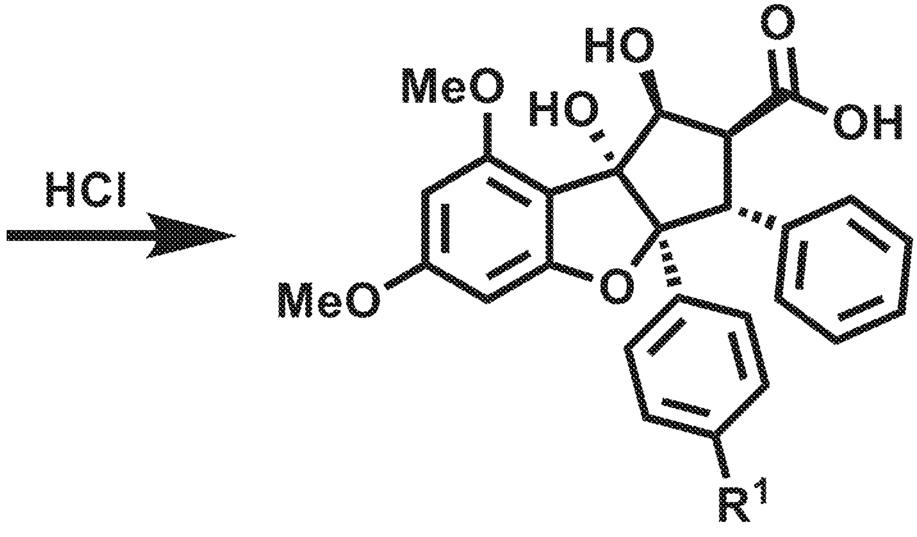
Figure 21:
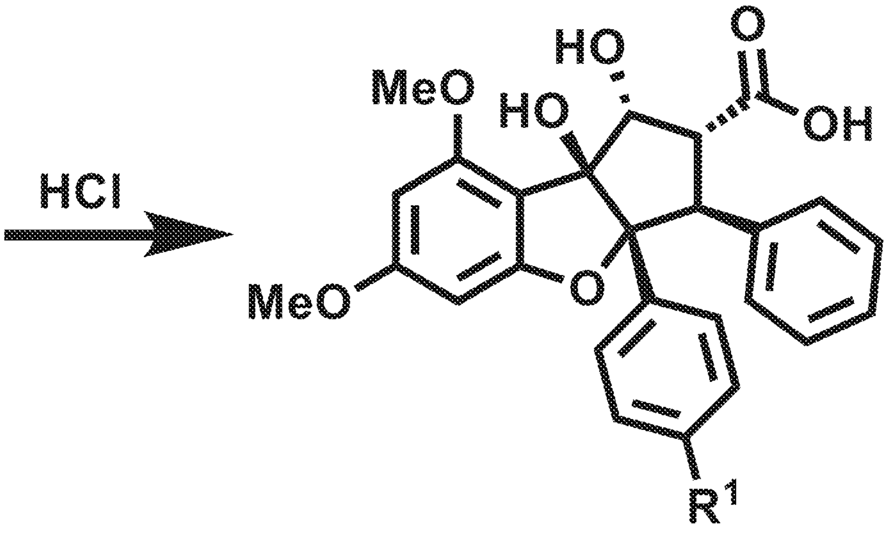
Figure 21:
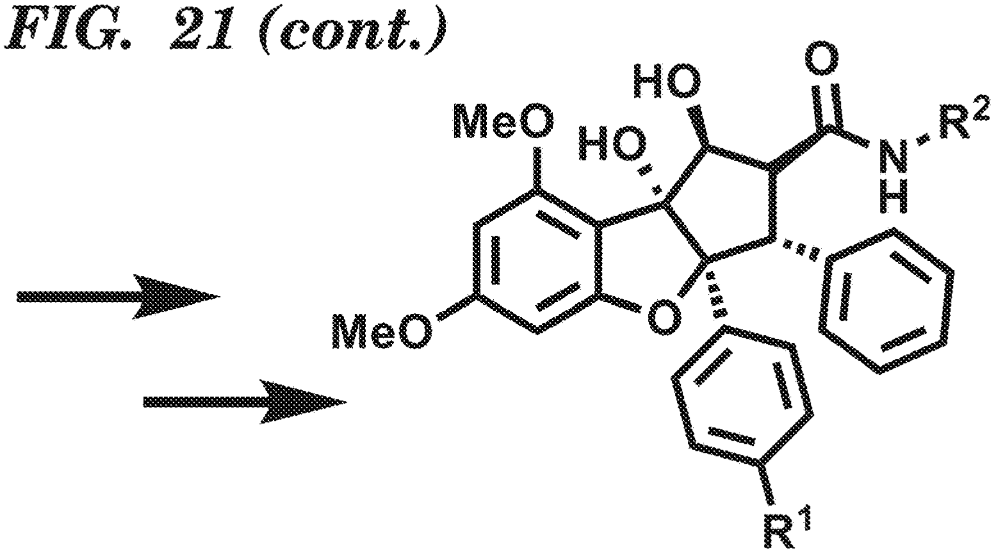
Figure 21:
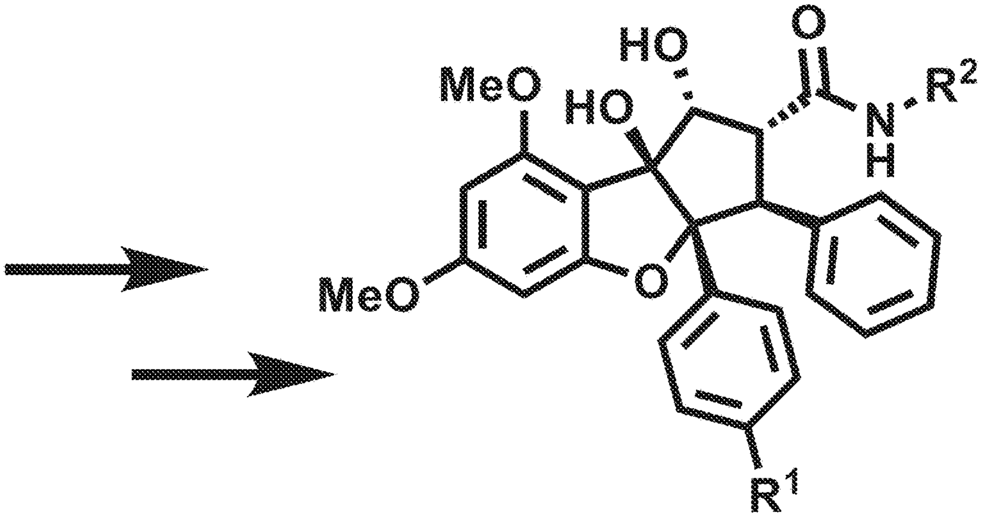
Figure 21:
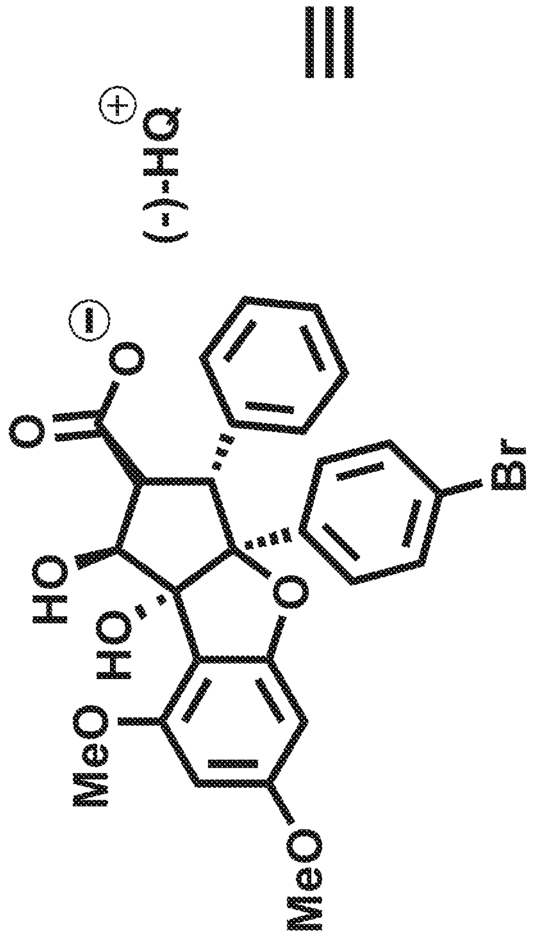
Figure 21:
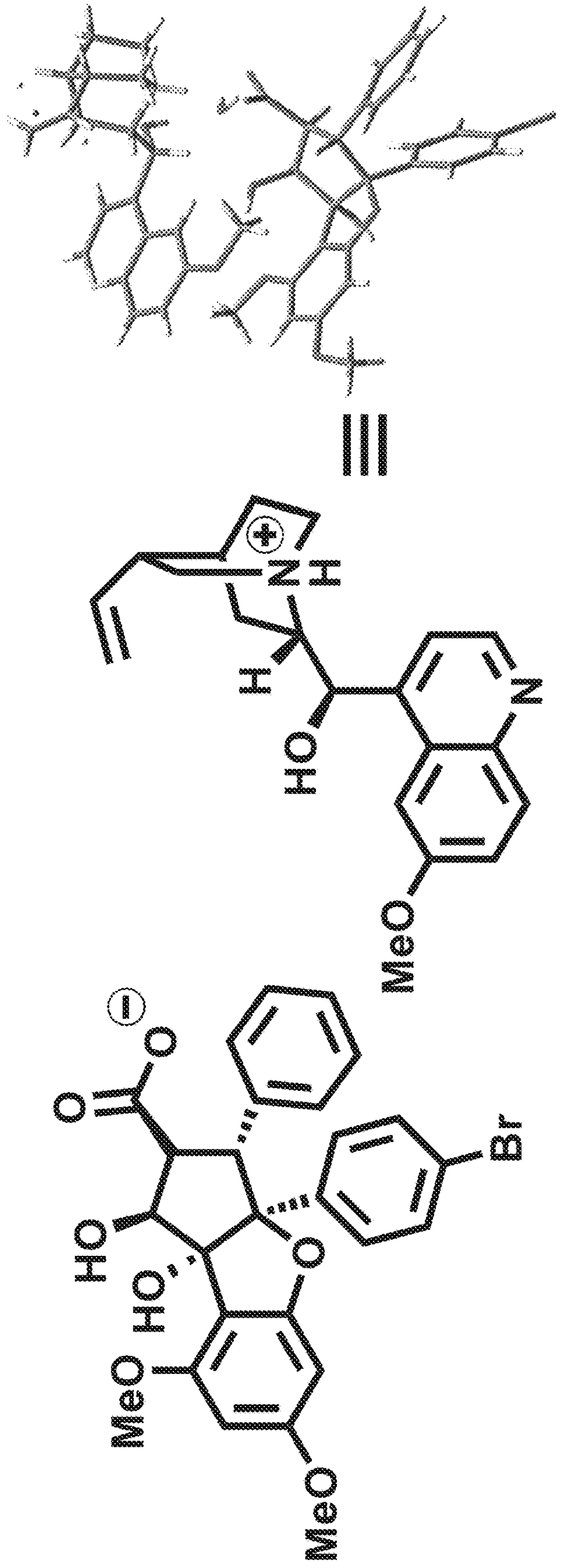

FIGS. 20A and 20B depict some exemplary compounds of the disclosure.

DETAILED DESCRIPTION

It is to be understood that both the foregoing general description and the following detailed description are exemplary and explanatory only and are not restrictive of the invention, as claimed.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

Compounds

In one aspect, the disclosure provides a compound having the structure of Formula (I), (Formula I)

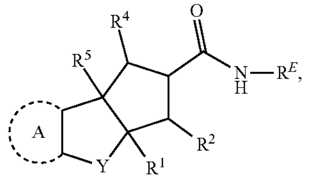

stereoisomers, tautomers, or a pharmaceutically acceptable salt or solvate thereof.

In some embodiments, $R^E$ is —$SO_2$—$R^3$, i.e., the compound is of Formula (Ia), (Formula Ia)

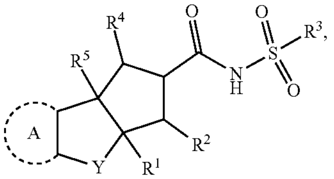

stereoisomers, tautomers, or a pharmaceutically acceptable salt or solvate thereof.

In some embodiments, Ring A is an optionally substituted aryl, optionally substituted heteroaryl, optionally substituted cycloalkyl, or optionally substituted heterocycle. For example, Ring A can be a 3-12 membered aryl, 3-12 membered heteroaryl, 3-12 membered cycloalkyl, or 3-12 membered heterocycle, each of which can be optionally substituted with 1, 2, 3, 4 or more substituents selected independently from OH, oxo (═O), CN, SH, $SO_2NH_2$, $SO_2(C_1\text{-}C_4)$alkyl, $SO_2NH(C_1\text{-}C_4)$alkyl, halogen, $NH_2$, $NH(C_1\text{-}C_4)$alkyl, $N[(C_1\text{-}C_4)alkyl]_2$, $C(O)NH_2$, COOH, COOMe, acetyl, $(C_1\text{-}C_8)$alkyl, $O(C_1\text{-}C_8)$alkyl, $O(C_1\text{-}C_8)$haloalkyl, $(C_2\text{-}C_8)$alkenyl, $(C_2\text{-}C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy, where "m" and "p" are independently 1, 2, 3, 4, 5 or 6.

In some embodiments, Ring A can be an optionally substituted six membered aryl or heteroaryl. For example, Ring A can have the structure

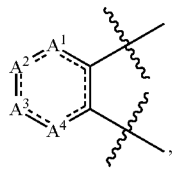

where $A^1$ is N, C(O), NH or $CR^{120}$; $A^2$ is N, C(O), NH or $CR^{121}$; $A^3$ is N, C(O), NH or $CR^{122}$; $A^4$ is N, C(O), NH or $CR^{123}$, $R^{120}$, $R^{121}$, $R^{122}$ and $R^{123}$ are independently are H, halogen, CN, $C_1\text{-}C_8$(alkyl), $(C_1\text{-}C_8)$haloalkyl, $(C_2\text{-}C_8)$alkenyl, $(C_2\text{-}C_8)$alkynyl, $OR^O$, $NR^OR^P$, $[(C_1\text{-}C_8)alkylene]OR^O$, $[(C_1\text{-}C_8)alkylene]NHR^A$, $[(C_1\text{-}C_8)alkylene]NR^OR^P$, $C(O)R^O$, $C(O)NHR^O$, $C(O)NR^OR^P$, $C(O)[(C_1\text{-}C_8)alkylene]NHR^O$, $C(O)[(C_1\text{-}C_8)alkylene]NR^OR^P$, $CO_2R^O$, $C(S)NHR^O$, $C(S)NR^OR^P$, $SR^O$, $S(O)R^O$, $SO_2R^O$, $SO_2NHR^O$, $SO_2NR^OR^P$, $NHC(O)R^O$, $NR^OC(O)R^P$, $NHC(O)NHR^O$, $NHC(O)NR^OR^P$, $NR^OC(O)NHR^P$, $NR^OC(O)NR^PR^Q$, P(O)(OH)($OR^O$), P(O)($OR^O$)($OR^P$), tosylate, aryl, heteroaryl, cycloalkyl or heterocyclyl. $R^O$, $R^P$ and $R^Q$ independently are H, —OH, aryl, ($C_1$-$C_8$)alkyl, [($C_1$-$C_8$)alkyl]aryl ($C_1$-$C_8$) alkoxy, ($C_1$-$C_8$)haloalkyl, cycloalkyl, heterocyclyl, [($C_1$-$C_8$) alkylene]heterocyclyl, [($C_1$-$C_8$)alkylene]aryl or heteroaryl; or $R^O$ and $R^P$ together with the nitrogen atom to which they are attached form a heterocyclyl ring. In some embodiments, $A^1$ is $CR^{120}$; $A^2$ is $CR^{121}$; $A^3$ is $CR^{122}$; $A^4$ is $CR^{123}$; and $R^{120}$, $R^{121}$, $R^{122}$ and $R^{123}$ independently are H or $OR^O$ and at least one of $R^{120}$, $R^{121}$, $R^{122}$ and $R^{123}$ are $OR^O$. In some embodiments, $A^1CR^{120}$ where $R^{120}$ is methoxy, $A^3$ is methoxy is $CR^{122}$ where $R^{122}$ is methoxy, $A^2$ is $CR^{121}$ where $R^{121}$ is H, and $A^4$ is $CR^{123}$ where $R^{123}$ is H. In some embodiments, $A^1$ is $CR^{120}$ where $R^{120}$ is a halide, $A^3$ is methoxy where is $CR^{122}$ where $R^{122}$ is methoxy, $A^2$ is N, and $A^4$ is $CR^{123}$ where $R^{123}$ is H. $A^1CR^{120}$ where $R^{120}$ is methoxy, $A^3$ is $CR^{122}$ where $R^{122}$ is methoxy, $A^2$ is N, and $A^4$ is $CR^{123}$ where $R^{123}$ is H. In some embodiments, $A^1$ is N, $A^3$ is methoxy is $CR^{122}$ where $R^{122}$ is methoxy, $A^2$ is $CR^{121}$ where $R^{121}$ is H, and $A^4$ is $CR^{123}$ where $R^{123}$ is H. In some embodiments, $A^1$ is C(C═O) or NH, $A^4$ is C(C═O) or NH, $A^2$ is $CR^{121}$, and $A^3$ is $CR^{123}$, In some embodiments, $A^1$ is C(C═O), $A^4$ is NH, $A^2$ is $CR^{121}$, and $A^3$ is $CR^{123}$. In some embodiments, $A^1$ is C(C═O), $A^4$ is NH, $A^2$ is $CR^{121}$, and $A^3$ is $CR^{123}$ wherein $R^{123}$ is methoxy. In some embodiments, $A^1$ is C(C═O), $A^4$ is N, and $A^3$ is $CR^{123}$ wherein $R^{123}$ is methoxy. In some instances, $A^1$ is $CR^{120}$ where $R^{120}$ is H, $A^3$ is $CR^{122}$ where $R^{120}$ is H, $A^2$ is $CR^{121}$ and $A^4$ is $CR^{123}$; where at least one of $R^{121}$ or $R^{123}$ are $NR^OR^P$ and $R^{121}$ and $R^{123}$ together with the carbon to which they are attached for a heterocycle. In some further embodiments and $R^{120}$, $R^{121}$, $R^{122}$ and $R^{123}$ independently are H or $OR^O$ and at least one of $R^{120}$, $R^{121}$, $R^{122}$ and $R^{123}$ are $OR^O$.

In some instances, Ring A can be an optionally substituted five-membered aryl or heteroaryl. For example, Ring A can have the structure

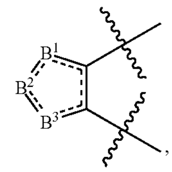

where any two of $B^1$, $B^2$ and $B^3$ are $CR^{130}$ and N and the remaining ring atom is N($R^{131}$) or S, wherein $R^{130}$ is H, CN, halogen, $OR^R$, $SR^R$, ($C_1$-$C_8$)alkyl, C(O)O($C_1$-$C_8$)alkyl, C(O)($C_1$-$C_8$)alkyl, $SO_2$($C_1$-$C_8$)alkyl, $SO_2NR^RR^S$, C(O) $NR^RR^S$, $NR^RR^S$ or $NR^RC(O)R^S$, and $R^{131}$ is H or ($C_1$-$C_8$) alkyl. $R^R$ and $R^S$, independently are H, —OH, aryl, ($C_1$-$C_8$) alkyl, [($C_1$-$C_8$)alkyl]aryl ($C_1$-$C_8$)alkoxy, ($C_1$-$C_8$)haloalkyl, cycloalkyl, heterocyclyl, [($C_1$-$C_8$)alkylene]heterocyclyl, [($C_1$-$C_8$)alkylene]aryl or heteroaryl; or the $R^R$ and $R^S$ together with the nitrogen atom to which they are attached of $NR^RR^S$ or $NR^RC(O)R^S$, optionally form a heterocyclyl ring. In some embodiments, $B^1$ is N or S, $B^3$ is N or S, and $B^2$ is $CR^{130}$ wherein $R^{130}$ is methoxy. In some embodiments, $B^1$ is N, $B^3$ is S, and $B^2$ is $CR^{130}$ wherein $R^{130}$ is methoxy. In some embodiments, $B^1$ is $CR^{130}$ where $R^{130}$ is H, $B^2$ is S or N, and $B^3$ is S or N. In some embodiments, $B^1$ is $CR^{130}$ where $R^{130}$ is H, $B^2$ is S, and $B^3$ is N. In some embodiments, Ring A is:

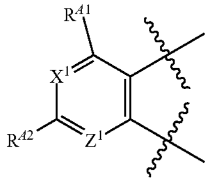

wherein $X^1$ is CH or N; $Z^1$ is CH or N; and $R^{A1}$ and $R^{A2}$ are selected independently from the group consisting of H, alkyl, alkoxy, alkylamino, acyloxy, fluorine, chlorine, bromine, $OCF_3$, $OCH_2CF_3$, and nitrile. In some embodiments, Ring A is:

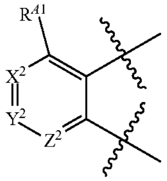

wherein $X^2$ is CH or N; $Y^2$ is CH or N; $Z^2$ is CH or N; and $R^{A1}$ is selected independently from the group consisting of H, alkyl, alkoxy, alkylamino, acyloxy, fluorine, chlorine, bromine, $OCF_3$, $OCH_2CF_3$, and nitrile.

In some embodiments, Ring A is:

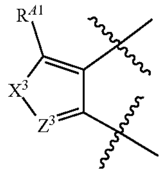

wherein $X^3$ is NH, O or S; $Z^3$ is CH or N; and $R^{A1}$ is selected independently from the group consisting of H, alkyl, alkoxy, alkylamino, acyloxy, fluorine, chlorine, bromine, $OCF_3$, $OCH_2CF_3$, and nitrile. In some embodiments, Ring A is:

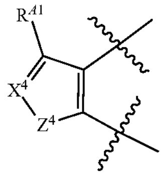

wherein $X^4$ is NH, O or S; $Z^4$ is CH or N; and $R^{A1}$ is selected independently from the group consisting of H, alkyl, alkoxy, alkylamino, acyloxy, fluorine, chlorine, bromine, $OCF_3$, $OCH_2CF_3$, and nitrile. In some embodiments, Ring A is:

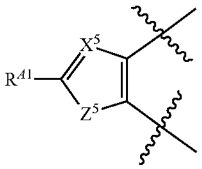

wherein $X^5$ is NH, O or S; $Z^5$ is CH or N; and $R^{A1}$ is selected independently from the group consisting of H, alkyl, alkoxy, alkylamino, acyloxy, fluorine, chlorine, bromine, $OCF_3$, $OCH_2CF_3$, and nitrile. In some embodiments, Ring A is:

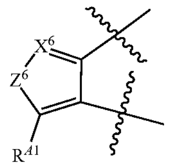

wherein $X^6$ is NH, O or S; $Z^6$ is CH or N; and $R^{A1}$ is selected independently from the group consisting of H, alkyl, alkoxy, alkylamino, acyloxy, fluorine, chlorine, bromine, $OCF_3$, $OCH_2CF_3$, and nitrile. In some embodiments, Ring A is:

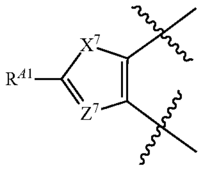

wherein $X^7$ is NH, O or S; $Z^7$ is CH or N; and $R^{A1}$ is selected independently from the group consisting of H, alkyl, alkoxy, alkylamino, acyloxy, fluorine, chlorine, bromine, $OCF_3$, $OCH_2CF_3$, and nitrile. In some embodiments, Ring A is:

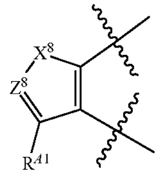

wherein $X^8$ is NH, O or S; $Z^8$ is CH or N; and $R^{A1}$ is selected independently from the group consisting of H, alkyl, alkoxy, alkylamino, acyloxy, fluorine, chlorine, bromine, $OCF_3$, $OCH_2CF_3$, and nitrile.

In some embodiments, Ring A is an aryl, heteroaryl, cycloalkyl, or heterocycle described herein, and where the aryl, heteroaryl, cycloalkyl, and heterocycle can be optionally substituted. For example, Ring A can be an aryl, heteroaryl, cycloalkyl, or heterocycle described herein, and where the aryl, heteroaryl, cycloalkyl, and heterocycle can be optionally substituted with 1, 2, 3, 4 or more substituents selected independently from OH, oxo (=O), CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)$alkyl$]_2$, $C(O)NH_2$, COOH, COOMe, acetyl, $(C_1$-$C_8)$alkyl, $O(C_1$-$C_8)$alkyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy, where "m" and "p" are independently 1, 2, 3, 4, 5 or 6. In some embodiments, Ring A is benzene, pyridine, pyrimidine, or thiazole, each of which can be optionally substituted with 1, 2, 3, 4 or more substituents selected independently from OH, oxo (=O), CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)$alkyl$]_2$, $C(O)NH_2$, COOH, COOMe, acetyl, $(C_1$-$C_8)$alkyl, $O(C_1$-$C_8)$alkyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy, where "m" and "p" are independently 1, 2, 3, 4, 5 or 6. For example, Ring A can be

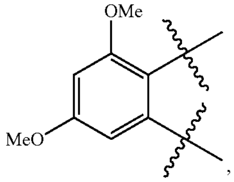,
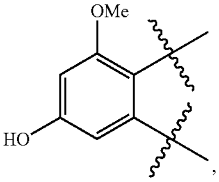,
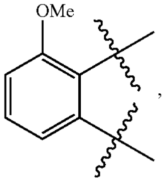,
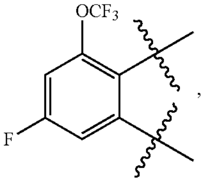,
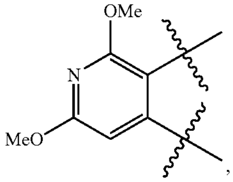,
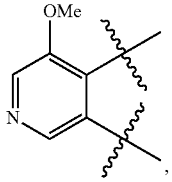,
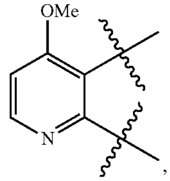,
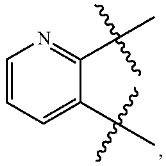,
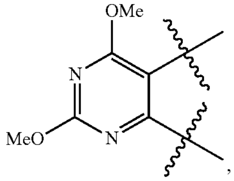, or
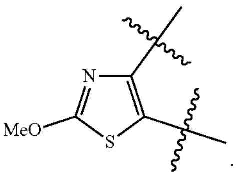.

In some embodiments, Y is O, S, $NR^{YA}$, $CR^{YA}R^{YB}$, C=$CR^{YA}R^{YB}$, SO or $SO_2$, where $R^{YA}$ and $R^{YB}$ are independently aryl, heteroaryl, cycloalkyl, heterocyclyl, H, halogen, CN, alkyl, haloalkyl, alkenyl, alkynyl, $OR^A$, $NR^AR^B$, —$C(O)R^A$, $C(O)NHR^A$, $C(O)NR^AR^B$, C(O)[alkylene]$NHR^A$, C(O)[alkylene]$NR^AR^B$, $CO_2R^A$, $C(S)NHR^A$, $C(S)NR^AR^B$, $SR^A$, $S(O)R^A$, $SO_2R^A$, $SO_2NHR^A$, $SO_2NR^AR^B$, $NHC(O)R^A$, $NR^AC(O)R^B$, $NHC(O)NHR^A$, $NHC(O)NR^AR^B$, $NR^AC(O)NHR^B$, $NR^AC(O)NR^BR^C$, $P(O)(OH)(OR^A)$, or $P(O)(OR^A)(OR^B)$. For example, Y can be O or S. In some embodiments, Y is O.

In some embodiments, $R^1$ is aryl, heteroaryl, cycloalkyl, heterocyclyl, H, halogen, CN, alkyl, haloalkyl, alkenyl, alkynyl, $OR^A$, $NR^AR^B$, —$C(O)R^A$, $C(O)NHR^A$, $C(O)NR^AR^B$, C(O)[alkylene]$NHR^A$, C(O)[alkylene]$NR^AR^B$, $CO_2R^A$, $C(S)NHR^A$, $C(S)NR^AR^B$, $SR^A$, $S(O)R^A$, $SO_2R^A$, $SO_2NHR^A$, $SO_2NR^AR^B$, $NHC(O)R^A$, $NR^AC(O)R^B$, $NHC(O)NHR^A$, $NHC(O)NR^AR^B$, $NR^AC(O)NHR^B$, $NR^AC(O)NR^BR^C$, $P(O)(OH)(OR^A)$, or $P(O)(OR^A)(OR^B)$; where any aryl, heteroaryl, cycloalkyl, heterocyclyl, alkyl, alkenyl, or alkynyl can be optionally substituted. In some embodiments, $R^1$ is an optionally substituted aryl, optionally substituted heteroaryl, optionally substituted cycloalkyl, or optionally substituted heterocyclyl. For example, $R^1$ can be a 3-12 membered aryl, 3-12 membered heteroaryl, 3-12 membered cycloalkyl, or 3-12 membered heterocyclyl, each of which can be optionally substituted with 1, 2, 3, 4 or more substituents selected independently from OH, oxo (=O), CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)$alkyl$]_2$, C(O)$NH_2$, COOH, COOMe, acetyl, $(C_1$-$C_8)$alkyl, $O(C_1$-$C_8)$alkyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy, where "m" and "p" are independently 1, 2, 3, 4, 5 or 6.

In some embodiments, $R^1$ is a 3-12 membered heteroaryl or heterocycle comprising 1, 2, or 3 independently selected heteroatoms, optionally substituted with 1, 2, 3, 4 or more substituents selected independently from OH, oxo (=O), CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)$alkyl$]_2$, C(O)$NH_2$, COOH, COOMe, acetyl, $(C_1$-$C_8)$alkyl, $O(C_1$-$C_8)$alkyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy, where "m" and "p" are independently 1, 2, 3, 4, 5 or 6.

In some embodiments, $R^1$ can be an aryl, heteroaryl, cycloalkyl, or heterocycle described herein, and where the aryl, heteroaryl, cycloalkyl, and heterocycle can be optionally substituted. For example, $R^1$ can be an aryl, heteroaryl, cycloalkyl, or heterocycle described herein, and where the aryl, heteroaryl, cycloalkyl, and heterocycle can be optionally substituted with 1, 2, 3, 4 or more substituents selected independently from OH, oxo (=O), CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)$alkyl$]_2$, C(O)$NH_2$, COOH, COOMe, acetyl, $(C_1$-$C_8)$alkyl, $O(C_1$-$C_8)$alkyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy, where "m" and "p" are independently 1, 2, 3, 4, 5 or 6. In some embodiments, $R^1$ is phenyl, thiophenyl, benzo[d]thiazolyl (benzthiazolyl), benzo[d]oxazolyl (benzoxazolyl), or benzoxazolinonyl, each of which is optionally substituted with 1, 2, 3, 4 or more substituents selected independently from OH, oxo (=O), CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)$alkyl$]_2$, C(O)$NH_2$, COOH, COOMe, acetyl, $(C_1$-$C_8)$alkyl, $O(C_1$-$C_8)$alkyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy, where "m" and "p" are independently 1, 2, 3, 4, 5 or 6.

In some embodiments, $R^1$ can be

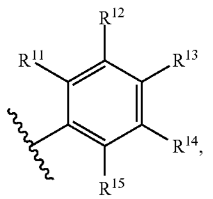

wherein $R^{11}$, $R^{12}$, $R^{13}$, $R^{14}$ and $R^{15}$ are independently H, OH, CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)$alkyl$]_2$, C(O)$NH_2$, COOH, COOMe, acetyl, $(C_1$-$C_8)$alkyl, $O(C_1$-$C_8)$alkyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy, where "m" and "p" are independently 1, 2, 3, 4, 5 or 6. In some embodiments, any two vicinal $R^{11}$, $R^{12}$, $R^{13}$, $R^{14}$, and $R^{15}$ together with the carbons they are attached to can form a 3-12 membered aryl, 3-12 membered heteroaryl, 3-12 membered cycloalkyl or 3-12 membered heterocyclyl, each of which can be optionally substituted with 1, 2, 3, 4 or more substituents selected independently from OH, oxo (=O), CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)$alkyl$]_2$, C(O)$NH_2$, COOH, COOMe, acetyl, $(C_1$-$C_8)$alkyl, $O(C_1$-$C_8)$alkyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy, where "m" and "p" are independently 1, 2, 3, 4, 5 or 6. For example, $R^1$ can be

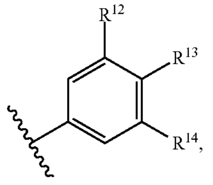

where $R^{12}$, $R^{13}$, and $R^{14}$ are independently H, halogen, CN, OH, SH, COOH, COOMe, acetyl, $(C_1$-$C_8)$alkyl, $O(C_1$-$C_8)$alkyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH. In some embodiments, $R^1$ is

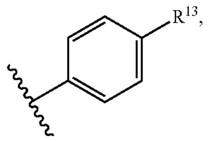

wherein $R^{13}$ is methoxy, fluorine, bromine, chlorine, iodine, trifluoromethyl, nitrile, acetylene, and $OCF_2H$. In some embodiments, $R^1$ is phenyl, thiophenyl, or benzothiazolyl, each of which can be optionally substituted. For example, $R^1$ is 4-bromophenyl, 4-methoxyphenyl, 4-fluorophenyl, 4-chlorophenyl, 4-iodophenyl, 3-trifluoromethylphenyl, 4-trifluoromethylphenyl, 4-cyanophenyl, benzothiazol-6-yl, benzothiazole-5-yl, 2-benzoxazolinon-6-yl, 2-benzoxazolinon-5-yl, 4-ethynylphenyl, 3,4,5-trimethylphenyl, 5-carboxythiophen-2-yl, 5-carboxythiophen-3-yl, 5-carboxythiophen-4-yl, trifluorotoluenyl, 3-phenylazetidinyl, (3-phenyl-2-azetidinyl) methanol, (3-phenyl-2-azetidinyl) ethanol, 3-benzylazetidinyl, 3-phenoxyazetidinyl, benzimidazolyl, 3-phenylpyrrolidinyl, 4-phenylpiperidinyl, or 4-difluoromethoxyphenyl. In some embodiments, $R^1$ is

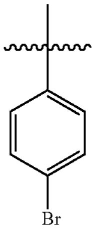,
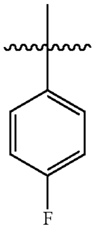,
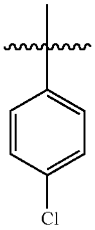,
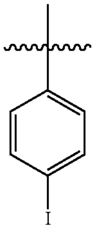,
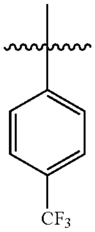,
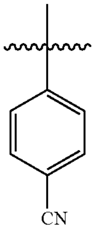,
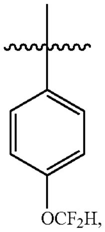, or
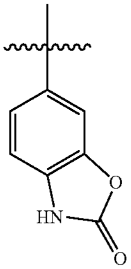,
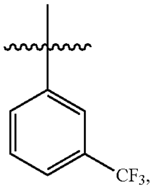,
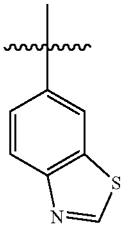,
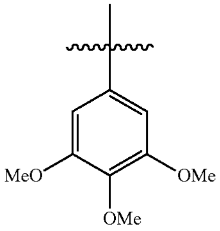,
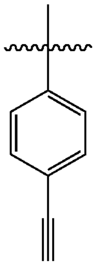,
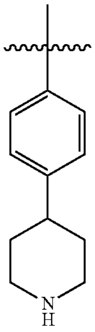,
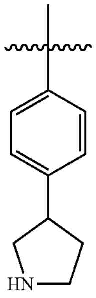,
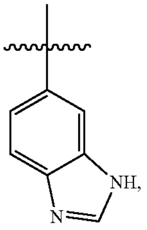,
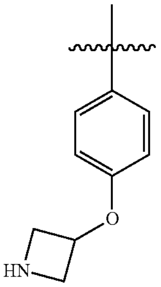,
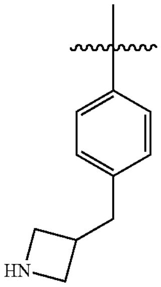, -continued

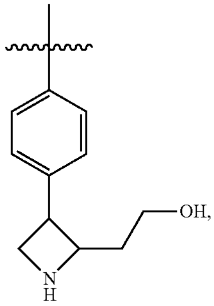,
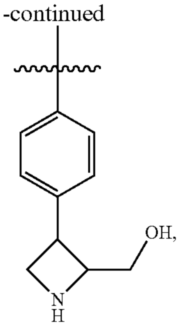,
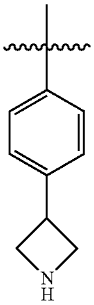 or
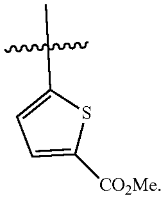.

In some preferred embodiments, $R^1$ is 4-bromophenyl.

In compounds of Formula (I), $R^2$ can be aryl, heteroaryl, alkyl, alkenyl, alkynyl, cycloalkyl, heterocyclyl, H, halogen, CN, haloalkyl, $OR^A$, $NR^AR^B$, —C(O)$R^A$, C(O)$NHR^A$, C(O)$NR^AR^B$, C(O)[alkylene]$NHR^A$, C(O)[alkylene]$NR^AR^B$, $CO_2R^A$, C(S)$NHR^A$, C(S)$NR^AR^B$, $SR^A$, S(O)$R^A$, $SO_2R^A$, $SO_2NHR^A$, $SO_2NR^AR^B$, NHC(O)$R^A$, $NR^A$C(O)$R^B$, NHC(O)$NHR^A$, NHC(O)$NR^AR^B$, $NR^A$C(O)$NHR^B$, $NR^A$C(O)$NR^BR^C$, P(O)(OH)($OR^A$), or P(O)($OR^A$)($OR^B$), where any aryl, heteroaryl, cycloalkyl, heterocyclyl, alkyl, alkenyl, or alkynyl can be optionally substituted. For example, $R^2$ can be an aryl, heteroaryl, cycloalkyl, heterocyclyl, alkyl, alkenyl, alkynyl, halogen, CN, or haloalkyl, where each alkyl, alkenyl, alkynyl, cycloalkyl, heterocyclyl, heteroaryl or aryl is optionally substituted with 1, 2, 3, 4 or more substituents selected independently from OH, oxo (=O), CN, SH, $SO_2NH_2$, $SO_2$($C_1$-$C_4$)alkyl, $SO_2NH$($C_1$-$C_4$)alkyl, halogen, $NH_2$, NH($C_1$-$C_4$)alkyl, N[($C_1$-$C_4$)alkyl]$_2$, C(O)$NH_2$, COOH, COOMe, acetyl, ($C_1$-$C_8$)alkyl, O($C_1$-$C_8$)alkyl, O($C_1$-$C_8$)haloalkyl, ($C_2$-$C_8$)alkenyl, ($C_2$-$C_8$)alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—[CH(OH)]$_m$—($CH_2$)$_p$—OH, $CH_2$—[CH(OH)]$_m$—($CH_2$)$_p$—$NH_2$ or $CH_2$-aryl-alkoxy, where "m" and "p" are independently 1, 2, 3, 4, 5 or 6.

In some embodiments, $R^2$ is an optionally substituted 3-12 membered aryl, optionally substituted 3-12 membered heteroaryl, optionally substituted 3-12 membered cycloalkyl, or optionally substituted 3-12 membered heterocycle. In some embodiments, $R^2$ is an optionally substituted 3-12 membered heteroaryl, optionally substituted 3-12 membered heterocycle, comprising 1, 2, or 3 independently selected heteroatoms.

In some embodiments, $R^2$ is ($C_1$-$C_8$)alkyl, ($C_1$-$C_8$)haloalkyl, ($C_2$-$C_8$)alkenyl), or ($C_2$-$C_8$)alkynyl, and wherein the ($C_1$-$C_8$)alkyl, ($C_1$-$C_8$)haloalkyl, ($C_2$-$C_8$)alkenyl), or ($C_2$-$C_8$)alkynyl, each of which can be optionally substituted. For example, $R^2$ can be methyl, ethyl, propyl, isopropyl, butyl, butan-2-yl, 2-methylpropyl, tert-butyl, pentyl, 2-methylbutan-2-yl, pentan-2-yl, pentan-3-yl, 3-methylbutan-2-yl, each of which can be optionally substituted. In some embodiments, $R^2$ is 2-butene, 2-butyne, 4-fluoro-3-(trifluoromethyl) anisole, trifluorotoluene, 2-methyl-2-butene, isopentane, 2-pyridine, 3-pyridine, pyrimidine, 4-ethylmorpholine, 2-bromo-5-fluorobenzene, 1-chloro-5-fluorobenzene, 2,4-dichlorobenzene, or 1,2,3,4,5,-pentafluorobenzene.

In some embodiments, $R^2$ is —$CH_2L$, wherein L is alkoxy, alkylamino, or heterocycle.

In some embodiments, $R^2$ can be an aryl, heteroaryl, cycloalkyl, or heterocycle described herein, and where the aryl, heteroaryl, cycloalkyl, and heterocycle can be optionally substituted. For example, $R^1$ can be an aryl, heteroaryl, cycloalkyl, or heterocycle described herein, and where the aryl, heteroaryl, cycloalkyl, and heterocycle is optionally substituted with 1, 2, 3, 4 or more substituents selected independently from OH, oxo (═O), CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)$alkyl$]_2$, $C(O)NH_2$, COOH, COOMe, acetyl, $(C_1$-$C_8)$alkyl, $O(C_1$-$C_8)$alkyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy, where "m" and "p" are independently 1, 2, 3, 4, 5 or 6 . . . . For example, $R^2$ can be phenyl, pyridinyl, or pyrimidinyl, each of which is optionally substituted with 1, 2, 3, 4 or more substituents selected independently from OH, oxo (═O), CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)$alkyl$]_2$, $C(O)NH_2$, COOH, COOMe, acetyl, $(C_1$-$C_8)$alkyl, $O(C_1$-$C_8)$alkyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy, where "m" and "p" are independently 1, 2, 3, 4, 5 or 6.

In some embodiments, $R^2$ is

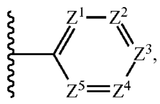, where $Z^1$, $Z^2$, $Z^3$, $Z^4$ and $Z^5$ are independently $CR^{21}$ or N, where each $R^{21}$ is independently H, OH, CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)$alkyl$]_2$, $C(O)NH_2$, COOH, COOMe, acetyl, $(C_1$-$C_8)$alkyl, $O(C_1$-$C_8)$alkyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy, where "m" and "p" are independently 1, 2, 3, 4, 5 or 6; and optionally any two vicinal $R^{11}$, $R^{12}$, $R^{13}$, $R^{14}$, and $R^{15}$ together with the carbons they are attached to can form a 5-8 membered aryl, heteroaryl, cycloalkyl or heterocyclyl, each of which can be optionally substituted with 1, 2, 3, 4 or more substituents selected independently from OH, oxo (═O), CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)$alkyl$]_2$, $C(O)NH_2$, COOH, COOMe, acetyl, $(C_1$-$C_8)$alkyl, $O(C_1$-$C_8)$alkyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy, where "m" and "p" are independently 1, 2, 3, 4, 5 or 6, and provided that only 0, 1, 2, 3 or 4 of $Z^1$, $Z^2$, $Z^3$, $Z^4$ and $Z^5$ are N. In some embodiments, $R^2$ is

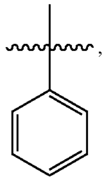, 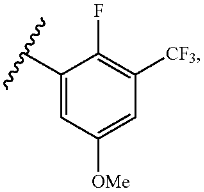, 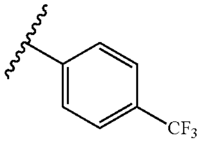, 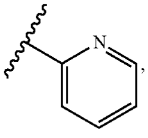, 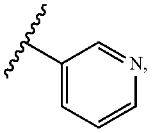, 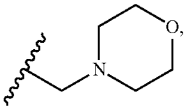, 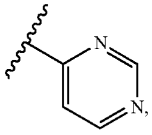, 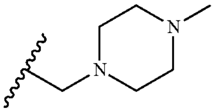, 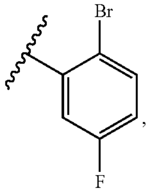, 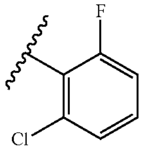, 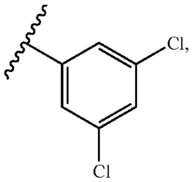, 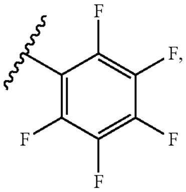, 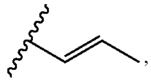, 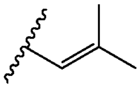, 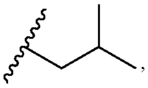, or 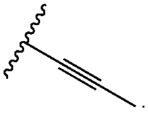.

In some preferred embodiments, $R^2$ is phenyl.

In some compounds of Formula (Ia), $R^3$ is $NR^{N1}R^{N2}$, alkyl, alkenyl, alkynyl, aryl, heteroaryl, cycloalkyl, heterocyclyl, H, halogen, CN, haloalkyl, $OR^A$, —$C(O)R^A$, $C(O)NHR^A$, $C(O)NR^AR^B$, C(O)[alkylene]$NHR^A$, C(O)[alkylene]$NR^AR^B$, $CO_2R^A$, $C(S)NHR^A$, $C(S)NR^AR^B$, $SR^A$, $S(O)R^A$, $SO_2R^A$, $SO_2NHR^A$, $SO_2NR^AR^B$, $NHC(O)R^A$, $NR^AC(O)R^B$, $NHC(O)NHR^A$, $NHC(O)NR^AR^B$, $NR^AC(O)NHR^B$, $NR^AC(O)NR^BR^C$, $P(O)(OH)(OR^A)$, or $P(O)(OR^A)(OR^B)$, $R^{N1}$ and $R^{N2}$ are independently H, alkyl, alkenyl, cycloalkyl, heterocyclyl, H, halogen, CN, haloalkyl, $OR^A$, —$C(O)R^A$, $C(O)NHR^A$, $C(O)NR^AR^B$, C(O)[alkylene]$NHR^A$, C(O)[alkylene]$NR^AR^B$, $CO_2R^A$, $C(S)NHR^A$, $C(S)NR^AR^B$, $SR^A$, $S(O)R^A$, $SO_2R^A$, $SO_2NHR^A$, $SO_2NR^AR^B$, $NHC(O)R^A$, $NR^AC(O)R^B$, $NHC(O)NHR^A$, $NHC(O)NR^AR^B$, $NR^AC(O)NHR^B$, $NR^AC(O)NR^BR^C$, $P(O)(OH)(OR^A)$, or $P(O)(OR^A)(OR^B)$, and where any aryl, heteroaryl, cycloalkyl, heterocyclyl, alkyl, alkenyl, or alkynyl can be optionally substituted. It is noted that $R^{N1}$ and $R^{N2}$ can be same or different. In some embodiments, $R^{N1}$ and $R^{N2}$ are same. In some other embodiments, $R^{N1}$ and $R^{N2}$ are different.

In some embodiments, $R^{N1}$ and $R^{N2}$ are independently H, methyl, ethyl, propyl, isopropyl, butyl, butan-2-yl, 2-methylpropyl, tert-butyl, pentyl, 2-methylbutan-2-yl, 2,2-dimethylpropyl, 3-methylbutyl, pentan-2-yl, pentan-3-yl, 3-methylbutan-2-yl, 2-methylbutyl, 2-methylpentyl, 3-methylpentyl, 2,3-dimethylbutyl, 2,2-dimethylbutyl, linear or branched hexyl, heptyl, or octyl, vinyl, allyl, acetylenyl, propylenyl, 1-butynl, 2-butynl, 1-pentynyl, 2-pentynyl, 3-methyl-1-butynl, 1-hexynyl, 2-hexynl, 3-hexynl, 4-methyl-1-pentynl, 4-methyl-2-pentynl, or 3-methyl-1-pentynl, 3,3-dimethyl-1-butynl, each of which can be optionally substituted with 1, 2, 3, 4 or more substituents selected independently from OH, oxo (=O), CN, SH, $SO_2NH_2$, $SO_2(C_1\text{-}C_4)$alkyl, $SO_2NH(C_1\text{-}C_4)$alkyl, halogen, $NH_2$, $NH(C_1\text{-}C_4)$alkyl, $N[(C_1\text{-}C_4)alkyl]_2$, $C(O)NH_2$, COOH, COOMe, acetyl, $(C_1\text{-}C_8)$alkyl, $O(C_1\text{-}C_8)$alkyl, $O(C_1\text{-}C_8)$haloalkyl, $(C_2\text{-}C_8)$alkenyl, $(C_2\text{-}C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy, where "m" and "p" are independently 1, 2, 3, 4, 5 or 6. For example, $R^{N1}$ and $R^{N2}$ are independently H, methyl, ethyl, propyl, isopropyl, butyl, butan-2-yl, 2-methylpropyl, tert-butyl, pentyl, 2-methylbutan-2-yl, 2,2-dimethylpropyl, 3-methylbutyl, pentan-2-yl, pentan-3-yl, 3-methylbutan-2-yl, 2-methylbutyl, 2-methylpentyl, 3-methylpentyl, 2,3-dimethylbutyl, 2,2-dimethylbutyl, vinyl, allyl, acetylenyl, or propylenyl.

In some embodiments, at least one of $R^{N1}$ and $R^{N2}$ is H. For example, $R^{N1}$ is H. In another example, $R^{N2}$ is H. In some embodiments, both of $R^{N1}$ and $R^{N2}$ are H.

In some embodiments, at least one of $R^{N1}$ and $R^{N2}$ is not H. For example, $R^{N1}$ is not H. In another example, $R^{N2}$ is not H. In some embodiments, both of $R^{N1}$ and $R^{N2}$ are not H.

In some embodiments, $R^{N1}$ and $R^{N2}$ together with the nitrogen they are attached to form a 3-12 membered heterocyclyl, and wherein 3-12 membered heterocyclyl is optionally substituted with 1, 2, 3, 4 or more substituents selected independently from OH, oxo (=O), CN, SH, $SO_2NH_2$, $SO_2(C_1\text{-}C_4)$alkyl, $SO_2NH(C_1\text{-}C_4)$alkyl, halogen, $NH_2$, $NH(C_1\text{-}C_4)$alkyl, $N[(C_1\text{-}C_4)alkyl]_2$, $C(O)NH_2$, COOH, COOMe, acetyl, $(C_1\text{-}C_8)$alkyl, $O(C_1\text{-}C_8)$alkyl, $O(C_1\text{-}C_8)$haloalkyl, $(C_2\text{-}C_8)$alkenyl, $(C_2\text{-}C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy, where "m" and "p" are independently 1, 2, 3, 4, 5 or 6. For example, $R^{N1}$ and $R^{N2}$ together with the nitrogen they are attached to attached to can form a heterocyclyl described herein and which can be optionally substituted. For example, $R^{N1}$ and $R^{N2}$ together with the nitrogen they are attached to attached to can form a heterocyclyl described herein and which can be optionally substituted with 1, 2, 3, 4 or more substituents selected independently from OH, oxo (=O), CN, SH, $SO_2NH_2$, $SO_2(C_1\text{-}C_4)$alkyl, $SO_2NH(C_1\text{-}C_4)$alkyl, halogen, $NH_2$, $NH(C_1\text{-}C_4)$alkyl, $N[(C_1\text{-}C_4)alkyl]_2$, $C(O)NH_2$, COOH, COOMe, acetyl, $(C_1\text{-}C_8)$alkyl, $O(C_1\text{-}C_8)$alkyl, $O(C_1\text{-}C_8)$haloalkyl, $(C_2\text{-}C_8)$alkenyl, $(C_2\text{-}C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy, where "m" and "p" are independently 1, 2, 3, 4, 5 or 6.

In some embodiments, $R^3$ is azirdinyl, azetidinyl, piperdinyl, or morpholinyl, each of which can be optionally substituted with 1, 2, 3, 4 or more substituents selected independently from OH, oxo (=O), CN, SH, $SO_2NH_2$, $SO_2(C_1\text{-}C_4)$alkyl, $SO_2NH(C_1\text{-}C_4)$alkyl, halogen, $NH_2$, $NH(C_1\text{-}C_4)$alkyl, $N[(C_1\text{-}C_4)alkyl]_2$, $C(O)NH_2$, COOH, COOMe, acetyl, $(C_1\text{-}C_8)$alkyl, $O(C_1\text{-}C_8)$alkyl, $O(C_1\text{-}C_8)$haloalkyl, $(C_2\text{-}C_8)$alkenyl, $(C_2\text{-}C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy, where "m" and "p" are independently 1, 2, 3, 4, 5 or 6. For example, $R^3$ can be 2-propanamino, 2-propynylaminyl, 2-propynyl, methyl, dimethylamino, diethylamino, azetidinyl, 3-methylazetidinyl, 3-hydroxyazetidinyl, pyrrolidinyl, 2-(trifluoromethyl)pyrrolidinyl, morpholinyl, or piperidinolyl. In some embodiments, $R^3$ is

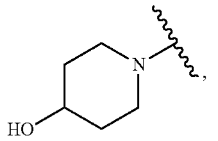,
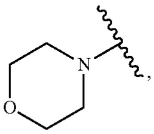,
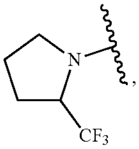,
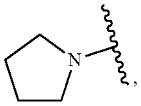,
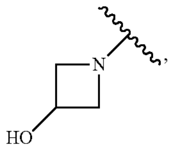,
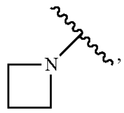,
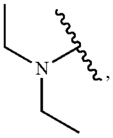,
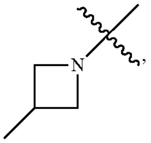, or
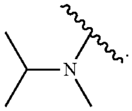.

In some compounds of Formula (I), e.g., Formula (Ia), $R^4$ is $OR^{4A}$, H, halogen, CN, alkyl, haloalkyl, alkenyl, alkynyl, aryl, heteroaryl, cycloalkyl, heterocylcyl, $NR^AR^B$, —C(O)$R^A$, C(O)$NHR^A$, C(O)$NR^AR^B$, C(O)[alkylene]$NHR^A$, C(O)[alkylene]$NR^AR^B$, $CO_2R^A$, C(S)$NHR^A$, C(S)$NR^AR^B$, $SR^A$, S(O)$R^A$, $SO_2R^A$, $SO_2NHR^A$, $SO_2NR^AR^B$, NHC(O)$R^A$, $NR^A$-C(O)$R^B$, NHC(O)$NHR^A$, NHC(O)$NR^AR^B$, $NR^A$C(O)$NHR^B$, $NR^A$C(O)$NR^BR^C$, P(O)(OH)($OR^A$), or P(O)($OR^A$)($OR^B$), where any aryl, heteroaryl, cycloalkyl, heterocyclyl, alkyl, alkenyl, or alkynyl can be optionally substituted. In some embodiments, $R^{4A}$ is H, alkyl, alkenyl, or alkynyl, where the alkyl, alkenyl, or alkynyl can be optionally substituted. Preferably, $R^4$ is OH.

In some compounds of Formula (I), e.g., Formula (Ia), $R^5$ is $OR^{5A}$, H, halogen, CN, alkyl, haloalkyl, alkenyl, alkynyl, aryl, heteroaryl, cycloalkyl, heterocylcyl, $NR^AR^B$, —C(O)$R^A$, C(O)$NHR^A$, C(O)$NR^AR^B$, C(O)[alkylene]$NHR^A$, C(O)[alkylene]$NR^AR^B$, $CO_2R^A$, C(S)$NHR^A$, C(S)$NR^AR^B$, $SR^A$, S(O)$R^A$, $SO_2R^A$, $SO_2NHR^A$, $SO_2NR^AR^B$, NHC(O)$R^A$, $NR^A$-C(O)$R^B$, NHC(O)$NHR^A$, NHC(O)$NR^AR^B$, $NR^A$C(O)$NHR^B$, $NR^A$C(O)$NR^BR^C$, P(O)(OH)($OR^A$), or P(O)($OR^A$)($OR^B$), where any aryl, heteroaryl, cycloalkyl, heterocyclyl, alkyl, alkenyl, or alkynyl can be optionally substituted. In some embodiments, $R^{5A}$ is H, alkyl, alkenyl, or alkynyl, where the alkyl, alkenyl, or alkynyl can be optionally substituted. Preferably, $R^5$ is OH.

In some compounds of Formula (I), e.g., Formula (Ia), $R^5$ together with the carbon $R^4$ is attached to forms a heterocyclyl. For example, $R^5$ together with the carbon $R^4$ is attached to forms an optionally substituted 3-12 membered heterocyclyl comprising 1, 2 or 3 independently selected heteroatoms (e.g., independently selected from N, O, and S). For example, $R^4$ and $R^5$ together with the carbons they are attached to can form a 3-12 membered aryl, 3-12 membered heteroaryl, 3-12 membered cycloalkyl or 3-12 membered heterocyclyl, each of which can be optionally substituted with 1, 2, 3, 4 or more substituents selected independently from OH, oxo (=O), CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)alkyl]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2—[CH(OH)]_m—(CH_2)_p—OH$, $CH_2—[CH(OH)]_m—(CH_2)_p—NH_2$ or $CH_2$-aryl-alkoxy, where "m" and "p" are independently 1, 2, 3, 4, 5 or 6.

In some embodiments, the compound of Formula Ia is of structure

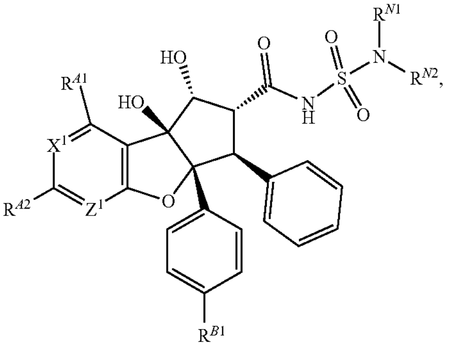

or stereoisomers, tautomers, or a pharmaceutically acceptable salt or solvate thereof, wherein $X^1$ is CH or N; $Z^1$ is CH or N; $R^{A1}$ and $R^{A2}$ are independently H, alkyl, alkoxy, alkylamino, acyloxy, fluorine, chlorine, bromine, $OCF_3$, or nitrile; $R^{N1}$ and $R^{N2}$ are independently methyl, linear, branched or cyclic alkyl; $R^{B1}$ is methoxy, fluorine, bromine, chlorine, iodine, trifluoromethyl, nitrile, acetylene, $OCF_2H$, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached to, form imidazole.

In some embodiments, the compound of Formula Ia is of structure

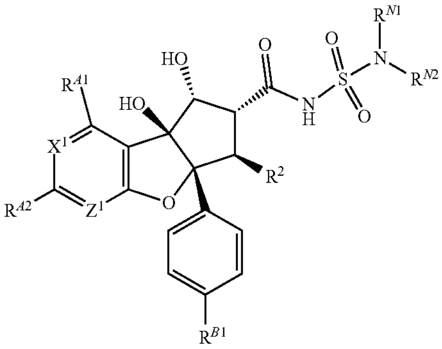

or stereoisomers, tautomers, or a pharmaceutically acceptable salt or solvate thereof, wherein: $X^1$ is CH or N; $Z^1$ is CH or N; $R^{A1}$ and $R^{A2}$ are independently H, alkyl, alkoxy, alkylamino, acyloxy, fluorine, chlorine, bromine, $OCF_3$, or nitrile; $R^{N1}$ and $R^{N2}$ are independently linear or branched alkyl (e.g., methyl) or cyclic alkyl; $R^{B1}$ is methoxy, fluorine, bromine, chlorine, iodine, trifluoromethyl, nitrile, acetylene, $OCF_2H$, alkyl, alkoxy, alkylamine, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached to, form imidazole; and $R^2$ is alkyl, alkenyl, alkynyl, substituted aryl, substituted heteroaryl, or $CH_2L$, where L is selected independently from the group consisting of alkoxy, alkylamino, or heterocycle.

In some embodiments, the compound of Formula Ia is of structure

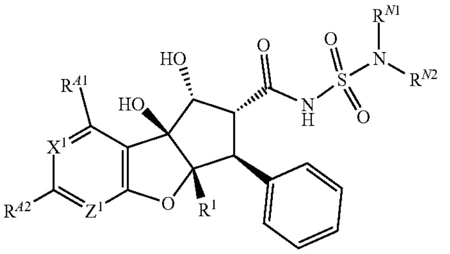

or stereoisomers, tautomers, or a pharmaceutically acceptable salt or solvate thereof, wherein: $X^1$ is CH or N; $Z^1$ is CH or N; $R^{A1}$ and $R^{A2}$ are independently H, alkyl, alkoxy, alkylamino, acyloxy, fluorine, chlorine, bromine, $OCF_3$, or nitrile; $R^{N1}$ and $R^{N2}$ are independently linear or branched alkyl (e.g., methyl) or cyclic alkyl; and $R^1$ is f substituted aryl, heteroaryl, and substituted heteroaryl, optionally $R^1$ is 4-bromophenyl, 4-methoxyphenyl, 4-cyanophenyl, 4-trifluoromethylphenyl, 4-(azetidin-3-yl)phenyl, 4-(2-hydroxymethylazetidin-3-yl)phenyl, 4-(2-(2-hydroxyethyl) azetidine-3-yl)phenyl, 4-(azetidine-3-ylmethyl)phenyl, 4-(azetidine-3-yl-hydroxy)phenyl, 4-(pyrrolidine-3-yl)phenyl, 4-piperidin-4-yl)phenyl, or benzimidazol-6-yl.

In some embodiments, the compound of Formula Ia is of structure

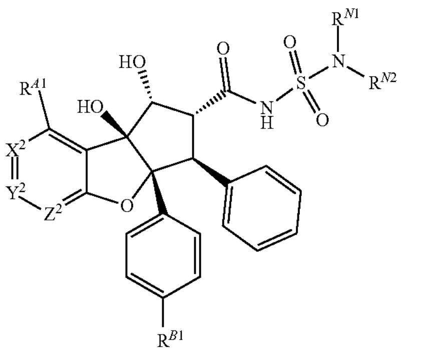

or stereoisomers, tautomers, or a pharmaceutically acceptable salt or solvate thereof, wherein $X^2$ is CH or N; $Z^2$ is CH or N; $Y^2$ is CH or N; $R^{A1}$ is selected from the group consisting of H, alkyl, alkoxy, alkylamino, acyloxy, fluorine, chlorine, bromine, $OCF_3$, $OCH_2CF_3$, and nitrile; $R^{N1}$ and $R^{N2}$ are independently methyl, linear, branched or cyclic alkyl; $R^{B1}$ is methoxy, fluorine, bromine, chlorine, iodine, trifluoromethyl, nitrile, acetylene, $OCF_2H$, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached to, form imidazole.

In some embodiments, the compound of Formula Ia is of structure

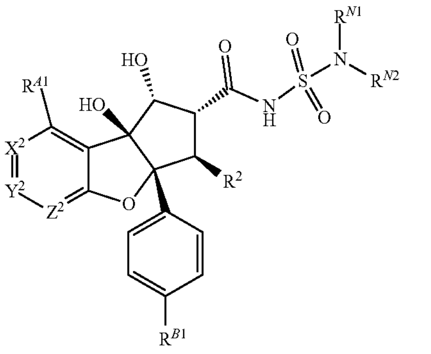

or stereoisomers, tautomers, or a pharmaceutically acceptable salt or solvate thereof, wherein: $X^2$ is CH or N; $Z^2$ is CH or N; $Y^2$ is CH or N; $R^{A1}$ is selected independently from the group consisting of H, alkyl, alkoxy, alkylamino, acyloxy, fluorine, chlorine, bromine, $OCF_3$, $OCH_2CF_3$, and nitrile; $R^{N1}$ and $R^{N2}$ are independently linear or branched alkyl (e.g., methyl) or cyclic alkyl; $R^{B1}$ is methoxy, fluorine, bromine, chlorine, iodine, trifluoromethyl, nitrile, acetylene, $OCF_2H$, alkyl, alkoxy, alkylamine, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached to, form imidazole; and $R^2$ is selected independently from the group consisting of alkyl, alkenyl, alkynyl, substituted aryl, substituted heteroaryl, and $CH_2L$ where L is selected independently from the group consisting of alkoxy, alkylamino, or heterocycle.

In some embodiments, the compound of Formula I is of structure

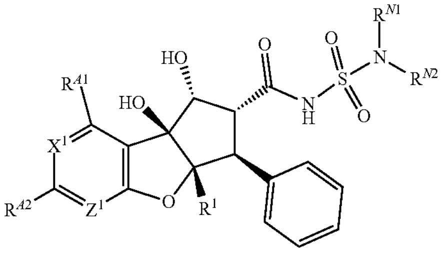

or stereoisomers, tautomers, or a pharmaceutically acceptable salt or solvate thereof, wherein: $X^2$ is CH or N; $Z^2$ is CH or N; $Y^2$ is CH or N; $R^{A1}$ and $R^{A2}$ are selected independently from the group consisting of H, alkyl, alkoxy, alkylamino, acyloxy, fluorine, chlorine, bromine, $OCF_3$, and nitrile; $R^{N1}$ and $R^{N2}$ are independently linear or branched alkyl (e.g., methyl) or cyclic alkyl; and $R^1$ is substituted aryl, heteroaryl, and substituted heteroaryl, optionally $R^1$ is 4-bromophenyl, 4-methoxyphenyl, 4-cyanophenyl, 4-trifluoromethylphenyl, 4-(azetidin-3-yl)phenyl, 4-(2-hydroxymethylazetidin-3-yl) phenyl, 4-(2-(2-hydroxyethyl) azetidine-3-yl)phenyl, 4-(azetidine-3-ylmethyl)phenyl, 4-(azetidine-3-yl-hydroxy) phenyl, 4-(pyrrolidine-3-yl)phenyl, 4-piperidin-4-yl)phenyl, or benzimidazol-6-yl.

In some embodiments, the compound of Formula I is of structure

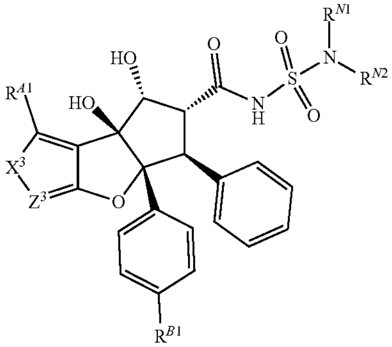

or stereoisomers, tautomers, or a pharmaceutically acceptable salt or solvate thereof, wherein $X^3$ is CH or N; $Z^3$ is CH or N; $R^{A1}$ is selected from the group consisting of H, alkyl, alkoxy, alkylamino, acyloxy, fluorine, chlorine, bromine, $OCF_3$, $OCH_2CF_3$, and nitrile; $R^{N1}$ and $R^{N2}$ are independently methyl, linear, branched or cyclic alkyl; and $R^{B1}$ is selected independently from the group consisting of methoxy, fluorine, bromine, chlorine, iodine, trifluoromethyl, nitrile, acetylene, $OCF_2H$, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached, to form an imidazole.

In some embodiments, the compound of Formula Ia is of structure

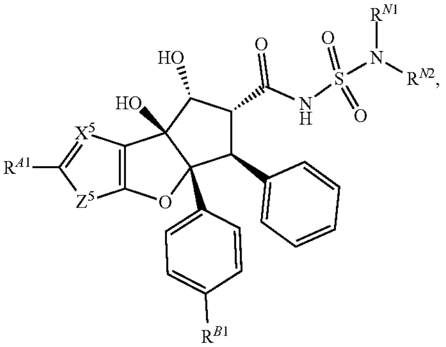

or stereoisomers, tautomers, or a pharmaceutically acceptable salt or solvate thereof, wherein $X^5$ is CH or N; $Z^3$ is CH or N; $R^{A1}$ is selected from the group consisting of H, alkyl, alkoxy, alkylamino, acyloxy, fluorine, chlorine, bromine, $OCF_3$, $OCH_2CF_3$, and nitrile; $R^{N1}$ and $R^{N2}$ are independently methyl, linear, branched or cyclic alkyl; and $R^{B1}$ is selected independently from the group consisting of: methoxy, fluorine, bromine, chlorine, iodine, trifluoromethyl, nitrile, acetylene, $OCF_2H$, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached, to form an imidazole.

In some embodiments, the compound of Formula Ia is of structure

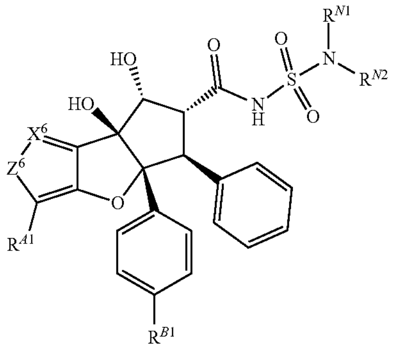

or stereoisomers, tautomers, or a pharmaceutically acceptable salt or solvate thereof, wherein $X^6$ is CH or N; $Z^6$ is CH or N; $R^{1A1}$ is selected from the group consisting of H, alkyl, alkoxy, alkylamino, acyloxy, fluorine, chlorine, bromine, $OCF_3$, $OCH_2CF_3$, and nitrile; $R^{N1}$ and $R^{N2}$ are independently methyl, linear, branched or cyclic alkyl; and $R^{B1}$ is methoxy, fluorine, bromine, chlorine, iodine, trifluoromethyl, nitrile, acetylene, $OCF_2H$, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached to, form imidazole.

In some embodiments, the compound of Formula Ia is of structure

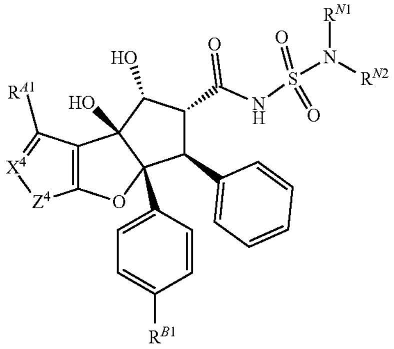

or stereoisomers, tautomers, or a pharmaceutically acceptable salt or solvate thereof, wherein $X^4$ is CH or N; $Z^4$ is CH or N; $R^{A1}$ is selected from the group consisting of H, alkyl, alkoxy, alkylamino, acyloxy, fluorine, chlorine, bromine, $OCF_3$, $OCH_2CF_3$, and nitrile; $R^{N1}$ and $R^{N2}$ are independently methyl, linear, branched or cyclic alkyl; and $R^{B1}$ is methoxy, fluorine, bromine, chlorine, iodine, trifluoromethyl, nitrile, acetylene, $OCF_2H$, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached to, to form an imidazole.

In some embodiments, the compound of Formula Ia is of structure

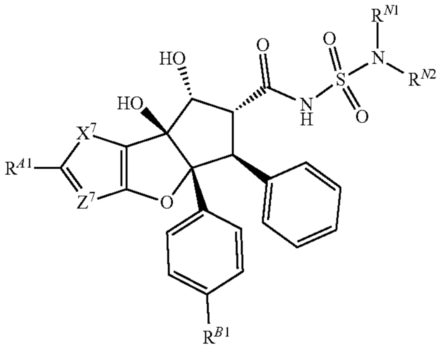

or stereoisomers, tautomers, or a pharmaceutically acceptable salt or solvate thereof, wherein $X^7$ is CH or N; $Z^7$ is CH or N; $R^{A1}$ is selected from the group consisting of H, alkyl, alkoxy, alkylamino, acyloxy, fluorine, chlorine, bromine, $OCF_3$, $OCH_2CF_3$, and nitrile; $R^{N1}$ and $R^{N2}$ are independently methyl, linear, branched or cyclic alkyl; and $R^{B1}$ is selected independently from the group consisting of: methoxy, fluorine, bromine, chlorine, iodine, trifluoromethyl, nitrile, acetylene, $OCF_2H$, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached, to form an imidazole.

In some embodiments, the compound of Formula Ia is of structure

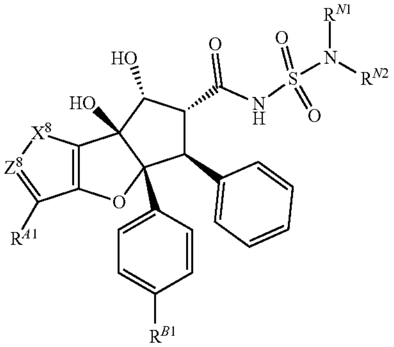

or stereoisomers, tautomers, or a pharmaceutically acceptable salt or solvate thereof, wherein $X^8$ is CH or N; $Z^8$ is CH or N; $R^{A1}$ is selected from the group consisting of H, alkyl, alkoxy, alkylamino, acyloxy, fluorine, chlorine, bromine, $OCF_3$, $OCH_2CF_3$, and nitrile; $R^{N1}$ and $R^{N2}$ are independently methyl, linear, branched or cyclic alkyl; and $R^{B1}$ is selected independently from the group consisting of: methoxy, fluorine, bromine, chlorine, iodine, trifluoromethyl, nitrile, acetylene, $OCF_2H$, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached to, form imidazole.

Compositions

In another aspect provided herein is a composition comprising a compound of Formula (I). and a pharmaceutically acceptable carrier, diluent, or excipient.

In some embodiments, the composition further comprises a therapeutic agent. For example, the composition comprises, in addition to a compound of Formula (I), e.g., Formula (Ia), an anticancer agent, an anti-inflammatory agent or an antimicrobial agent. In some embodiments, the composition comprises a compound of Formula (I), e.g., Formula (Ia), and an anticancer agent or chemotherapeutic. In some embodiments, the composition comprises a compound of Formula (I), e.g., Formula (Ia), and an antimicrobial agent. For example, the composition comprises a compound of Formula (I), e.g., Formula (Ia), and an antibacterial agent, and antifungal agent, an antiviral agent, an antihelminthic agent and/or an antiprotozoal agent. In some embodiments, the composition comprises a compound of Formula (I), e.g., Formula (Ia), and an anti-inflammatory agent.

Embodiments of the various aspects described herein include an anticancer agent or chemotherapeutic. Exemplary anticancer agents and chemotherapeutic agents include, but are not limited to, ABT-737; acetogenins (such as bullatacin and bullatacinone); aclacinomysins; actinomycin; actinomycin D; Aldesleukin; Alemtuzumab; alitretinoin; alkyl sulfonates such as busulfan, improsulfan and piposulfan; alkylating agents such as thiotepa and CYTOXAN® cyclosphosphamide; allopurinol; altretamine; AMG479; amifostine; anastrozole; antibiotics such as the enediyne antibiotics (e.g., calicheamicin, especially calicheamicin gammaII and calicheamicin omegaI1 (see, e.g., Agnew, Chem. Intl. Ed. Engl., 33:183-186 (1994)); arsenic trioxide; Asparaginase; authramycin; azaserine; aziridines such as benzodopa, carboquone, meturedopa, and uredopa; BCG Live; bexarotene; bisphosphonates, such as clodronate; bleomycin; bortezomib; bryostatin; busulfan; busulfanoral; cactinomycin; callystatin; calusterone; caminomycin; camptothecin (including the synthetic analogue topotecan); capecitabine; carabicin; carboplatin; carmustine; CC-1065 (including its adozelesin, carzelesin and bizelesin synthetic analogues); celecoxib; chlorambucil; cisplastin; cladribine; cryptophycins (such as cryptophycin 1 and cryptophycin 8); cyclophosphamide; cytarabine; dacarbazine; dactinomycin; Darbepoetin alfa; daunomycin; daunorubicin; Denileukin diftitox; dexrazoxane; docetaxel; dolastatin; doxorubicin; Dromostanolone propionate; duocarmycin (including the synthetic analogues, KW-2189 and CB1-TM1); dynemicin, including dynemicin A; eleutherobin; Elliott's B Solution; epipodophyllotoxins; epirubicin; Epoetin alfa estramustine; esperamicin; ethylenimines and methylamelamines including altretamine, triethylenemelamine, triethylenephosphoramide, triethiylenethiophosphoramide and trimethylolomelamine; etoposide (VP-16); etoposide phosphate; exemestane; Filgrastim; floxuridine (intraarterial); fludarabine; fluorouracil (5-FU); fulvestrant; gemcitabine; gemtuzumab ozogamicin; goserelin acetate; hydroxyurea; Ibritumomab Tiuxetan; idarubicin; ifosfamide; imatinib; imatinib mesylate; immune checkpoint inhibitors (such as inhibitors of CTLA-4, PD-1, LAG-3, B7-H3, 67-H4, TIM3, A2AR, and IDO, e.g., an inhibitor of Programmed Death-Ligand 1 (PD-L1, also known as B7-HI, CD274), Programmed Death 1 (PD-1), CTLA-4, PD-L2 (B7-DC, CD273), LAG3, TIM3, 2B4, A2aR, B7HI, B7H3, B7H4, BTLA, CD2, CD27, CD28, CD30, CD40, CD70, CD80, CD86, CDI37, CDI60, CD226, CD276, DR3, GAL9, GITR, HAVCR2, HVEM, IDO1, ID02, ICOS (inducible T cell costimulator), KIR, LAIRI, LIGHT, MARCO (macrophage receptor with collagenous structure), PS (phosphatidylserine), OX-40, SLAM, TIGIT, VISTA, and VTCNI, such as an anti-PD-1 antibody, an anti PD-L1 antibody, or an anti-CTLA-4 antibody); Interferon alfa-2a; Interferon alfa-2b; irinotecan; letrozole; leucovorin; levamisole; LOddC; lomustine (CCNU); masitinib; mechlorethamine (nitrogen-mustard); megestrol acetate; melphalan (L-PAM); mercaptopurine (6-MP); mesna; methotrexate; methoxsalen; mithramycin; mitomycin C; mitotane; mitoxantrone; nandrolone phenpropionate; neocarzinostatin chromophore and related chromoprotein enediyne antiobiotic chromophores); nilotinib; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; Nofetumomab; olaparib; Oprelvekin; oxaliplatin; paclitaxel; pamidronate; pancratistatin; pegademase; Pegaspargase; Pegfilgrastim; pentostatin; PI-103; pipobroman; plicamycin; porfimer sodium; procarbazine; quinacrine; rapamycin; Rasburicase; Rituximab; rituximab; rucaparib; sarcodictyin; Sargramostim; spongistatin; streptozocin; talbuvidine (LDT); talc; tamoxifen; taxol; temozolomide; teniposide (VM-26); testolactone; thioguanine (6-TG); thiotepa; toceranib; topotecan; toremifene; Tositumomab; Trastuzumab; tretinoin (ATRA); tyrosine kinase inhibitors; Uracil Mustard; valrubicin; valtorcitabine (monoval LDC); vinca alkaloids; vinblastine; vinorelbine; vorinostat; or zoledronate.

Embodiments of the various aspects described include an antimicrobial agent.

In some embodiments, the antimicrobial agent is an antifungal agent. Exemplary antifungal agents include, but are not limited to, Flycytosine, Bifonazole, Butoconazole, Chlordantoin, Chlorphenesin, Ciclopirox Olamine, Clotrimazole, Eberconazole, Econazole, Fluconazole, Flutrimazole, Isoconazole, Itraconazole, Ketoconazole, Miconazole, Nifuroxime, Tioconazole, Terconazole, Undecenoic Acid, azoles (e.g., barleyconazole, butoconazole, clortrimazole, econazole, fluconazole, isavuconazole, itraconazole, ketoconazole, miconazole, oxyconazole, posaconazole, ravuconazole, saperconazole, sulconazole, tercocnazole, tioconazole, voriconazole, and ciclopirox), polyenes (e.g., natamycin, lucensomycin, nystatin, amphotericin B, etc.), echinocandins (e.g., Cancidas), pradimicins (e.g., beanomicins, nikkomycins, sordarins, allylamines, etc.), Triclosan, Piroctone, fenpropimorph, terbinafine, cyclopyroxolamine, flucitocin, griseofulvin haloprozin, tolnaftate, naphthypine, hydrochloride, morpholine, butenapin, undecylenic acid, propionic acid, or azoffluxin.

In some embodiments, the antimicrobial agent is an antibacterial agent. Exemplary antibacterial agents include but are not limited to macrolides or ketolides such as erythromycin, azithromycin, clarithromycin, and telithromycin; beta-lactams including penicillin, cephalosporin, and carbapenems such as carbapenem, imipenem, and meropenem; monolactams such as penicillin G, penicillin V, methicillin, oxacillin, cloxacillin, dicloxacillin, nafcillin, ampicillin, amoxicillin, carbenicillin, ticarcillin, meziocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefmetazole, cefotaxime, ceftizoxime, cefiriaxone, cefoperazone, ceftazidime, cefixime, cefpodoxime, ceftibuten, cefdinir, cefpirome, cefepime, cefadroxil, ceftriaxone, ceftobiprole and astreonam; quinolones such as nalidixic acid, oxolinic acid, norfloxacin, pefloxacin, enoxacin, ofloxacin, levofloxacin, ciprofloxacin, temafloxacin, lomefloxacin, fleroxacin, grepafloxacin, sparfloxacin, trovafloxacin, clinafloxacin, gatifloxacin, moxifloxacin, sitafloxacin, ganefloxacin, gemifloxacin and pazufloxacin; antibacterial sulfonamides and antibacterial sulphanilamides, including para-aminobenzoic acid, sulfadiazine, sulfisoxazole, sulfamethoxazole and sulfathalidine; aminoglycosides such as streptomycin, neomvcin, kanamycin, paromycin, gentamicin, tobramycin, amikacin, netilmicin, spectinomycin, sisomicin, dibekalin and isepamicin; tetracyclines such as tetracycline, chlortetracycline, demeclocycline, minocycline, oxytetracycline, methacycline, doxycycline; rifamycins such as rifampicin (also called rifampin), rifapentine, rifabutin, bezoxazinorifamycin and rifaximin; lincosamides such as lincomycin and clindamycin; glycopeptides such as vancomycin and teicoplanin; streptogramins such as quinupristin and daflopristin; oxazolidinones such as linezolid; polymyxin, colistin and colymycin; trimethoprim, bacitracin, and phosphonomycin.

In some embodiments, the antimicrobial agent is an antiprotozoal agent. Exemplary antiprotozoal agents include, but are not limited to, Acetarsol, Azanidazole, Chloroquine, Metronidazole, Nifuratel, Nimorazole, Omidazole, Propenidazole, Secnidazole, Sineflngin, Tenonitrozole, Temidazole, Tinidazole, Nitazoxinide, Miltefosine, Pentavalent antimonials (e.g. Sodium stibogluconate, meglumine antimonate), Paromomycin, Pentamidine, Benzoxaboroles (e.g. acoziborole, tavaborole, crisaborole), Atovaquone, Proguanil, Benznidazole, Diminazene, Elflornithine, Melarsoprol, or Nifurtimox.

In some embodiments, the antimicrobial agent is an antiviral agent. Exemplary antiviral agents include, but are not limited to, 1-docosanol, acyclovir, brivudine, cidofovir, curcumin, daclatasvir, desciclovir, edoxudine, elbasvir, famciclovir, fiacitabine, glecaprevir, ibacitabine, imiquimod, interferon alpha-2a, interferon alpha-2b, interferon aphacon-1, lamivudine, ledipasvir/sofosbuvir, grazoprevir, pegylated interferon, pegylated interferon alpha-2b, penciclovir, pibrentasvir, ribavirin, simeprevir, sofosbuvir, telaprevir, valacyclovir, valganciclovir, velpatasvir, Entecavir, adefovir, telbivudine, ganciclovir, oseltamivir, zanamivir, nirmatrelvir, remdesivir, molnupiravir, atanzavir, cobicistat, dolutegravir, rilpivirine, enfuvirtide, etravirine, raltegravir, tenofovir, or mRNA.

Embodiments of the various aspects described herein include an anti-inflammatory agent. Exemplary anti-inflammatory agents include, but are not limited to, steroidal anti-inflammatory agents (e.g., 21-acetoxypregnenolone, alclometasone, algestone, amcinonide, beclomethasone, betamethasone, budesonide, chloroprednisone, clobetasol, clobetansone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furcate, paramethosone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, and analogues and derivatives thereof); or a nonsteroidal anti-inflammatory agent (e.g., COX inhibitors (COX-1 or COX nonspecific inhibitors (e.g., salicylic acid derivatives such as aspirin, sodium salicylate, choline magnesium trisalicylate, salicylate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam); alkanones such as nabumetone; and analogues and derivatives thereof), and COX-2 inhibitors, e.g., diarylsubstituted furanones such as refecoxib; diaryl-substituted pyrazoles such as celecoxib; indole acetic acids such as etodolac and sulfonanilides such as nimesulide; and analogues and derivatives thereof))

Methods of Use

Without wishing to be bound by a theory, compounds of Formula (I) are selective inhibitors of cancer stem cell, e.g., glioblastoma stem cells. Accordingly, a compound of Formula (I), or a pharmaceutically acceptable salt or solvate thereof, can be administered to a cancer stem cell for inhibiting the cancer stem cell, e.g., inhibiting propagation of the cancer stem cell.

It is noted that administering to the stem cell can be in vitro or in-vivo. Methods for administering a compound to a cell are well known and available to one of skill in the art. As used herein, administering the compound to the cell means contacting the cell with the compound so that the compound is taken up by the cell. Generally, the cell can be contacted with the compound in a cell culture e.g., in vitro or ex vivo, or the compound can be administrated to a subject, e.g., in vivo. The term "contacting" or "contact" as used herein in connection with contacting a cell includes subjecting the cells to an appropriate culture media, which comprises a compound of Formula (I), e.g., Formula (Ia). Where the cell is in vivo, "contacting" or "contact" includes administering the compound, e.g., in a pharmaceutical composition to a subject via an appropriate administration route such that the compound contacts the cell in vivo.

For example, when the cell is in vitro, said administering to the cell can include subjecting the cell to an appropriate culture media which comprises the indicated compound. Where the cell is in vivo, said administering to the cell includes administering the compound to a subject via an appropriate administration route such that the compound is administered to the cell in vivo. In some embodiments, the said administering is to a subject having or diagnosed with cancer. In some embodiments, the method further comprises co-administering an anticancer therapy to the subject. In some embodiments, the subject is a mammal. In some embodiments, the subject is a primate. In some embodiments, the subject is human. In some embodiments, the subject is a non-human primate.

The stem cell to be administered a compound of Formula (I), e.g., Formula (Ia), can be any desired cancer stem cell. Exemplary cancer stem cells amenable to the methods described herein include, but are not limited to, glioblastoma (GBM), acoustic neuroma, acute lymphoblastic leukemia (ALL), acute myeloid leukemia, adenocarcinoma, angiosarcoma, astrocytoma, basal cell carcinoma, B-cell lymphoma, bile duct carcinoma, bladder cancer, bone cancer, brain cancer, breast cancer, bronchogenic carcinoma, Burkitt's lymphoma, cancer of the peritoneum, castration-resistant prostate cancer, cervical cancer, chondrosarcoma, chordoma, choriocarcinoma, chronic leukemia (chronic myelocytic (granulocytic) leukemia and chronic lymphocytic leukemia)), colon carcinoma, colorectal cancer, craniopharyngioma, cystadenocarcinoma, diffuse large B-cell lymphoma (DLBCL), embryonal carcinoma, endometrial or uterine carcinoma, endotheliosarcoma, ependymoma, epithelial carcinoma, esophageal cancer, Ewing's tumor, fibrosarcoma, fibrotic diseases, gastric cancer, hairy cell lymphoma, head and neck cancer, heavy chain disease, hemangioblastoma, hepatocellular cancers, Hodgkins lymphoma, kidney or renal cancer, leiomyosarcoma, leukemia (e.g. acute lymphocytic leukemia, chronic lymphocytic leukemia (CLL) and acute myeloid leukemia (e.g. myeloblastic-promyelocytic-myelomonocytic-monocytic and erythroleukemia)), liposarcoma, lung cancer, lymphangioendothelial sarcoma, lymphangiosarcoma, lymphoma (Hodgkin's disease and non-Hodgkin's disease), malignant glioma, medullary carcinoma, medulloblastoma, melanoma, meningioma, mesothelioma, multiple melanoma, myelodysplastic syndrome, myeloma, myxosarcoma, neuroblastoma, non-Hodgkins lymphoma, non-small cell lung cancer, oligodendroglioma, osteogenic sarcoma, ovarian cancer, pancreatic cancer, pancreatic carcinoma, papillary adenocarcinomas, papillary carcinoma, pinealoma, polycythemia vera, prostate cancer, renal cancer, renal cell carcinoma, retinoblastoma, rhabdomyosarcoma, salivary gland carcinoma, sebaceous gland carcinoma, seminoma, small cell lung carcinoma, solid tumor, squamous cell carcinoma, sweat gland carcinoma, synovial sarcoma, synovioma, T-cell lymphoma, testicular cancer, thyroid cancer, triple-negative breast cancer, urothelial cancer, vulvar cancer, Waldenstrom macroglobulinemia, or Wilms' tumor cancer stem cell.

In some embodiments, the cancer stem cell is a GBM, DLBCL, hepatocellular cancers, acute myeloid leukemia, breast cancer, colorectal cancer, small cell lung cancer, or non-small cell lung cancer stem cell.

In some embodiments, the cancer stem cell is a GBM stem cell.

In some embodiments, the said administering is in vitro. In some embodiments, the said administering is ex vivo. In some embodiments, the said administering is in vivo.

In another aspect provided herein is a method for treating a eukaryotic initiation factor 4A (eIF4A) dependent condition. The method comprises administering a therapeutically effective amount of any of the compounds describe herein to a subject in need of treatment for a eIF4A dependent disease or condition. The eIF4A-dependent condition can be a disease of uncontrolled cell growth, proliferation and/or survival, a disease of inappropriate cellular inflammatory responses, a disease caused by a parasite/pathogen or a neurodegenerative disease requiring neuroprotection.

In yet another aspect provided herein is a method for treating a DEAD box helicase-dependent condition. Exemplary DEAD box helicase-dependent conditions include, but are not limited to, cancer, infection, and fibrosis. See, for example, Bol, G. M., Xie, M. & Raman, V. DDX3, a potential target for cancer treatment. *Mol Cancer* 14, 188 (2015); Marina K. Kukhanova, Inna L. Karpenko, and Alexander V. Ivanov, DEAD-box RNA Helicase DDX3: Functional Properties and Development of DDX3 Inhibitors as Antiviral and Anticancer Drugs, *Molecules* 25(4), 1015 (2020); and Wensheng Chen, Darrell Pilling, and Richard H Gomer, The mRNA-binding protein DDX3 mediates TGF-β1 upregulation of translation and promotes pulmonary fibrosis, *JCI Insight*. 8(7):e167566 (2023), contents of all of which are incorporated herein by reference in their entireties.

In some embodiments, the eIF4A-dependent condition or DEAD box helicase dependent condition is cancer. Thus, in one aspect provided herein a method for treating cancer. The method comprises administering a therapeutically effective amount of any of the compounds herein to a subject in need thereof.

Exemplary cancers amenable to methods of treatment described herein include, but are not limited to, glioblastoma (GBM), acoustic neuroma, acute lymphoblastic leukemia (ALL), acute myeloid leukemia, adenocarcinoma, angiosarcoma, astrocytoma, basal cell carcinoma, B-cell lymphoma, bile duct carcinoma, bladder cancer, bone cancer, brain cancer, breast cancer, bronchogenic carcinoma, Burkitt's lymphoma, cancer of the peritoneum, castration-resistant prostate cancer, cervical cancer, chondrosarcoma, chordoma, choriocarcinoma, chronic leukemia (chronic myelocytic (granulocytic) leukemia and chronic lymphocytic leukemia)), colon carcinoma, colorectal cancer, craniopharyngioma, cystadenocarcinoma, diffuse large B-cell lymphoma (DLBCL), embryonal carcinoma, endometrial or uterine carcinoma, endotheliosarcoma, ependymoma, epithelial carcinoma, esophageal cancer, Ewing's tumor, fibrosarcoma, fibrotic diseases, gastric cancer, hairy cell lymphoma, head and neck cancer, heavy chain disease, hemangioblastoma, hepatocellular cancers, Hodgkins lymphoma, kidney or renal cancer, leiomyosarcoma, leukemia (e.g. acute lymphocytic leukemia, chronic lymphocytic leukemia (CLL) and acute myeloid leukemia (e.g. myeloblastic-promyelocytic-myelomonocytic-monocytic and erythroleukemia)), liposarcoma, lung cancer, lymphangioendothelial sarcoma, lymphangiosarcoma, lymphoma (Hodgkin's disease and non-Hodgkin's disease), malignant glioma, medullary carcinoma, medulloblastoma, melanoma, meningioma, mesothelioma, multiple melanoma, myelodysplastic syndrome, myeloma, myxosarcoma, neuroblastoma, non-Hodgkins lymphoma, non-small cell lung cancer, oligodendroglioma, osteogenic sarcoma, ovarian cancer, pancreatic cancer, pancreatic carcinoma, papillary adenocarcinomas, papillary carcinoma, pinealoma, polycythemia vera, prostate cancer, renal cancer, renal cell carcinoma, retinoblastoma, rhabdomyosarcoma, salivary gland carcinoma, sebaceous gland carcinoma, seminoma, small cell lung carcinoma, solid tumor, squamous cell carcinoma, sweat gland carcinoma, synovial sarcoma, synovioma, T-cell lymphoma, testicular cancer, thyroid cancer, triple-negative breast cancer, urothelial cancer, vulvar cancer, Waldenstrom macroglobulinemia, or Wilms' tumor. In some embodiments, the cancer is GBM, DLBCL, hepatocellular cancers, acute myeloid leukemia, breast cancer, colorectal cancer, small cell lung cancer, or non-small cell lung cancer. In some preferred embodiments, the cancer is GBM.

In some embodiments, the cancer is a drug-resistant cancer.

In some embodiments, the method of treating cancer further comprises co-administering at least one additional anti-cancer therapy to the subject. For example, administering a standard of care anticancer agent or chemotherapeutic to the subject. Non-limiting examples of a standard of care chemotherapeutics or other anti-cancer therapy can include radiation therapy and/or surgery.

In some embodiments, the additional anti-cancer therapy is an anti-cancer agent or chemotherapeutic agent. For example, the method comprises administering a therapeutically effective amount of a compound of Formula (I), e.g., Formula (Ia), and an anticancer agent or chemotherapeutic described herein.

In some embodiments, the eIF4A or DEAD box helicase-dependent condition is an infection. Thus, another aspect provided herein is, a method for treating an infection. The method comprises administering a therapeutically effective amount of a compound described herein to a subject in need thereof is described. Without wishing to be bound by a theory, the infection to be treated can be a fungal infection, a bacterial infection, a viral infection or a protozoal infection.

In some embodiments, the infection is a fungal infection. For example, the infection can be aspergillosis, basidiobolomycosis, blastomycosis, candidosis, chromoblastomycosis, coccidioidomycosis, conidiobolomycosis, cryptococcosis, dermatophytosis, eumycetoma, histoplasmosis, lobomycosis, mucormycosis, paracoccidioidomycosis, phaeohyphomycosis, pneumocystosis, scedosporiosis, sporotrichosis, talaromycosis, emmonsiosis, or microsporidiosis. In some embodiments, the infection is a fungal infection, and the method further comprises co-administering an antifungal agent to the subject. For example, the method comprises co-administering a compound of Formula (I), e.g., Formula (Ia), and an antifungal agent to the subject in need of treatment. Exemplary antifungal agents are described herein.

In some embodiments, the infection is a bacterial infection. For example, the infection can be actinomycosis, anthrax, appendicitis, bacteremia, endocarditis, intraabdominal abscesses, whooping cough, bacterial pneumonia, atypical pneumonia, lyme disease, lyme arthritis, neuroborreliosis, from *B. recurrentis*, brucellosis, enteritis, from *C. jejuni*, trachoma, neonatal conjunctivitis, neonatal pneumonia, nongonococcal urethritis, urethritis, pelvic inflammatory disease, epidymitis, prostatitis, lymphogranuloma venereum, psittacosis, botulism, pseudomembranous colitis, anaerobic cellulitis, gas gangrene, food poisoning, tetanus, diphtheria, ehrilchoisis, bacterial endocarditis, biliary tract infection, urinary tract infection, meningitis, sepsis, from *E. coli*, tularemia, lymphadenopathy, upper respiratory tract infection, bronchitis, septic arthritis, pepic ulcer, gastritis, *Klebsiella pneumonia*, Legionnaire' Disease, Pontiac fever, leptospirosis, listeriosis, leprosy, tuberculosis, *mycoplasma* pneumonia, gonorrhea, urethritis, Ophthalmia neonatorum, meningococcal disease, Waterhouse-Friderichsen syndrome, corneal infection, endocarditis, osteomyelitis, Malignant external otitis, nocardiosis, keratitis, Rocky mountain spotted fever, *salmonellosis*, hepatosplenomegaly, paratyphoid fever, osteomyelitis, shigellosis, staphylococcal: impetigo, acute infective endocarditis, toxinoses, cystitis, endometritis, otitis media, sinusitis, streptococcal pharyngitis, scarlet fever, rheumatic feber, erysipelas, puerperal fever, necrotizing fasciitis, poststreptococcal glomerulonephritis, syphilis, cholera, bubonic plague, pneomic plague, or glanders, meliodiosis, campylobacteriosis, Q fever, or typhus fever.

In some embodiments, the infection is a bacterial infection, and the method further comprises co-administering an antibacterial agent to the subject. For example, the method comprises co-administering a compound of Formula (I), e.g., Formula (Ia), and an antibacterial agent to the subject in need of treatment. Exemplary antibacterial agents are described herein.

In some embodiments, the infection is caused by protozoa such as *Balantidium coli, Naegleria fowleri, Acanthamoeba* spp., *Balamuthia* spp. *Entamoeba histolytica, Cryptosporidium* spp., *Giardia* spp., *Cyclospora cayetanensis, Trichomonas vaginalis, Plasmodium* spp., *Trypanosoma brucei* rhodesiense, *Trypanosoma brucei* gambiense, *Trypanosoma cruzi, Leishmania* spp., or *Toxoplasma gondii*. In some embodiments, the infection is caused by a protozoa, and the method further comprises co-administering an antiprotozoal agent to the subject. For example, the method comprises co-administering a compound of Formula (I), e.g., Formula (Ia), and an antiprotozoal agent to the subject in need of treatment. Exemplary antiprotozoal agents are described herein.

In some embodiments, the infection is caused by a protozoa, and the method further comprises co-administering an antiprotozoal agent to the subject. For example, the method comprises co-administering a compound of Formula (I), e.g., Formula (Ia), and an antiprotozoal agent described herein to the subject in need of treatment.

Rocaglates have been described in the art as being useful for treating malaria, such as cerebral malaria. See, for example, Langlais et al., *Rocaglates as dual-targeting agents for experimental cerebral malaria*, PNAS (2018), vol. 115 (10), pp E2366-E2375, content of which is incorporated by reference herein. Thus, in some embodiments, the infection is malaria, e.g., cerebral malaria.

In some embodiments, the infection a viral infection. For example, the infection may be caused by Adenovirus, Herpes, Human papillomavirus, BK virus, JC virus, Smallpox, Parvovirus, Rotavirus, Orbivirus, Coltivirus, Banna virus, Human astrovirus, Norwalk virus, Coronavirus, Hepatitis, yellow fever virus, dengue virus, West Nile virus, TBE virus, Zika virus, Rubella virus, coxsackievirus, cytomegalovirus, Epstein-Barr virus, Middle East Respiratory syndrome-related coronavirus, Severe acute respiratory syndrome coronavirus, Severe acute respiratory syndrome coronavirus 2, Varicella-zoster virus, poliovirus, rhinovirus, Lassa virus, Crimean-Congo hemorrhagic fever virus, Hanta virus, Ebola virus, Marburg virus, Influenza virus, Measles virus, Mumps virus, Parainfluenza virus, Respiratory syncytial virus, Rabies virus, HIV, Alkhurma virus, Cache Valley virus, Calcivirus, California encephalitus virus, Chapare virus, Chikunguynya virus, Eastern Equine Encephalitis virus, Enterovirus, Guanarito virus, Heartland virus, Hendra virus, Japanese encephalitis virus, Junin virus, Kyasanur Forest virus, LaCrosse encephalitis virus, Langya virus, Lujo virus, Lymphocytic choriomeningitus virus, Machupo virus, Mayoro virus, Nipah virus, O'nyong-nyong virus, Omsk hemhorragic fever virus, Oroupouche virus, Powassan/Deer tick virus, Rift Valley fever virus, St. Louis encephalitis virus, or Monkeypox virus.

In some embodiments, the infection is a viral infection, and the method further comprises co-administering an antiviral agent to the subject. For example, the method comprises co-administering a compound of Formula (I), e.g., Formula (Ia), and an antiviral agent to the subject in need of treatment. Exemplary antiviral agents are described herein.

In some embodiments, the infection is a helminth infection. For example, the infection is an infection caused by *Dracunculus medinensis, Wuchereria bancrofti, Brugia malayi, Brugia timori, Onchocerca volvulus, Schistosoma* spp., *Ancylostoma duodenale, Necator americanus, Ascaris lumbricoides* or *Trichuris trichiura*. For example, the infection is Dracunculiasis, Lymphatic filariasis, Onchocerciasis, Schistosomiasis, Soil-transmitted helminthiases (e.g. hookworm, roundworm, whipworm), Granulomatous acanthameoba encephalitis (GAE), *Balamuthia* amoebic encephalitis (BAE), and/or Primary amobebic meningoencephalitis (PAM).

In some embodiments, the infection is a helminth infection, and the method further comprises co-administering an antihelminthic agent to the subject. For example, the method comprises co-administering a compound of Formula (I), e.g., Formula (Ia), and an antihelminthic agent to the subject in need of treatment. Exemplary antihelminthic, include, but are not limited to albendazole, ivermectin, mebendazole, nitazoxanide, pentamidine, praziquantel, pyrantel, thiabendazole, or triclabendazole.

In some embodiments, the DEAD box helicase-dependent condition is fibrosis. Thus, in another aspect provided herein is a method for treating fibrosis. The method comprises administering a compound of Formula (I), e.g., Formula (Ia), to a subject in need thereof. The fibrosis can be fibrosis of an organ of the respiratory system, cardiovascular system, gastrointestinal system, urinary system, nervous system, or musculoskeletal system, optionally the fibrosis is fibrosis of the lung, heart, blood vessels, liver, small intestine, large intestine, pancreas, kidney, eye, brain, skin, bone marrow, or muscle tissue. In some embodiments, the fibrosis is fibrosis in a disease or condition selected from the group consisting of: pulmonary fibrosis, cystic fibrosis, idiopathic pulmonary fibrosis, progressive massive fibrosis, scleroderma, obliterative bronchiolitis, Hermansky-Pudlak syndrome, asbestosis, silicosis, chronic pulmonary hypertension, AIDS-associated pulmonary hypertension, sarcoidosis, tumor stroma in lung disease, asthma, cardiac fibrosis, myocardial fibrosis, atrial fibrosis, ventricular fibrosis, atrial fibrillation, ventricular fibrillation, myocardial infarction, hypertrophic cardiomyopathy, dilated cardiomyopathy, Brugada syndrome, myocarditis, endomyocardial fibrosis, fibrotic vascular disease, hypertensive heart disease, arrhythmogenic right ventricular cardiomyopathy, hepatic fibrosis, chronic liver disease, liver cirrhosis, non-alcoholic steatohepatitis, primary biliary cirrhosis, primary sclerosing cholangitis, schistosomal liver disease, intestinal fibrosis, Crohn's disease, microscopic colitis, pancreatic fibrosis, renal fibrosis, chronic kidney disease, tubulointerstitial fibrosis, glomerular fibrosis, nephritic syndrome, Alport's syndrome, HIV associated nephropathy, polycystic kidney disease, Fabry's disease, diabetic nephropathy, chronic glomerulonephritis, nephritis associated with systemic lupus, eye fibrosis, Grave's opthalmopathy, epiretinal fibrosis, retinal fibrosis, subretinal fibrosis, macular degeneration, wet age-related macular degeneration, diabetic retinopathy, glaucoma, corneal fibrosis, post-surgical fibrosis of the posterior capsule following cataract surgery, post-surgical fibrosis of the bleb following trabeculectomy, conjunctival fibrosis, subconjunctival fibrosis, gliosis, Alzheimer's disease, skin fibrosis, scleroderma, nephrogenic systemic fibrosis, cutis keloid, Dupuytren's contracture, myelofibrosis, muscular dystrophy, Duchenne muscular dystrophy, Becker's muscular dystrophy (BMD), arthritis, adhesive capsulitis, mediastinal fibrosis, retroperitoneal fibrosis, Peyronie's disease, systemic sclerosis, progressive systemic sclerosis, chronic graft versus host disease, fibrotic pre-neoplastic disease, fibrotic neoplastic disease, and fibrosis induced by chemical or environmental insult In some embodiments, the method for treating fibrosis the method further comprises co-administering an antifibrotic agent to the subject. For example, the method comprises co-administering a compound of Formula (I), e.g., Formula (Ia), and an antifibrotic agent to the subject in need of treatment. Exemplary anti-fibrotic agents include, but are not limited to, pirfenidone and nintedanib In some embodiments, the subject is a mammal. In some embodiments, the subject is a primate. In some embodiments, the subject is human. In some embodiments, the subject is a non-human primate.

Synthesis of the Compounds

The synthesis of compounds described herein can be accomplished using means described in the chemical literature. For example, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey and Sundberg, Advanced Organic Chemistry $4^{th}$ Ed., Vols. A and B (Plenum 2000, 2001), and Green and Wuts, Protective Groups in Organic Synthesis $3^{rd}$ Ed., (Wiley 1999) (all of which are incorporated by reference for such disclosure). General methods for the preparation of compound as disclosed herein may be derived from reactions and the reactions may be modified by the use of appropriate reagents and conditions, for the introduction of the various moieties found in the formulae as provided herein. For example, compounds described herein can be synthesized using the methods described in the Examples section herein.

Routes of Administration

It is noted that the terms "administered" and "subjected" are used interchangeably in the context of treatment of a disease or disorder. In jurisdictions that forbid the patenting of methods that are practiced on the human body, the meaning of "administering" of a composition to a human subject shall be restricted to prescribing a controlled substance that a human subject will be administer to the subject by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, administration will generally be local rather than systemic.

In some embodiments, a compound of Formula (I), e.g., Formula (Ia), is orally administered. Without limitations, oral administration can be in the form of solutions, suspensions, tablets, pills, capsules, sustained-release formulations, oral rinses, powders and the like.

In some embodiments, a compound of Formula (I), e.g., Formula (Ia), is compound is administered in a local rather than systemic manner, for example, via topical application of the compound directly on to skin, or intravenously, or subcutaneously, often in a depot preparation or sustained release formulation. In specific embodiments, long-acting formulations are administered by implantation (for example subcutaneously or intramuscularly) or by intramuscular injection. In yet other embodiments, the compound as described herein is provided in the form of a rapid release formulation, in the form of an extended-release formulation, or in the form of an intermediate release formulation. In yet other embodiments, the compound described herein is administered topically (e.g., as a patch, an ointment, or in combination with a wound dressing, or as a wash or a spray). In alternative embodiments, a formulation is administered systemically (e.g., by injection, or as a pill).

"Effective amount" or "therapeutically effective amount" refers to that amount of a compound of the invention which, when administered to a subject, for example a human, is sufficient to effect treatment, as defined below, of an eIF4A-related condition or disease in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

Depending on the route of administration, effective doses can be calculated according to the body weight, body surface area, or organ size of the subject to be treated. Optimization of the appropriate dosages can readily be made by one skilled in the art in light of pharmacokinetic data observed in human clinical trials. Alternatively, or additionally, the dosage to be administered can be determined from studies using animal models for the particular type of condition to be treated, and/or from animal or human data obtained from agents which are known to exhibit similar pharmacological activities. The final dosage regimen will be determined by the attending surgeon or physician, considering various factors which modify the action of active agent, e.g., the agent's specific activity, the agent's specific half-life in vivo, the severity of the condition and the responsiveness of the patient, the age, condition, body weight, sex and diet of the patient, the severity of any present infection, time of administration, the use (or not) of other concomitant therapies, and other clinical factors.

Determination of an effective amount is well within the capability of those skilled in the art. Generally, the actual effective amount can vary with the specific compound, the use or application technique, the desired effect, the duration of the effect and side effects, the subject's history, age, condition, sex, as well as the severity and type of the medical condition in the subject, and administration of other pharmaceutically active agents. Accordingly, an effective dose of compound described herein is an amount sufficient to produce at least some desired therapeutic effect in a subject.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of use or administration utilized.

The effective dose can be estimated initially from cell culture assays. A dose can be formulated in animal models to achieve a circulating plasma concentration range that includes the $IC_{50}$ (i.e., the concentration of the therapeutic which achieves a half-maximal inhibition of symptoms) as determined in cell culture. Levels in plasma can be measured, for example, by high performance liquid chromatography. The effects of any particular dosage can be monitored by a suitable bioassay. The effective plasma concentration for a compound as disclosed herein can be about 0.01 μM to about 10 μM, about 0.2 μM to about 5 μM, or about 0.8 to about 3 μM in a subject, such as a rat, dog, or human.

Generally, the compositions are administered so that a compound of the disclosure herein is used or given at a dose from 1 μg/kg to 1000 mg/kg; 1 μg/kg to 500 mg/kg; 1 μg/kg to 150 mg/kg, 1 g/kg to 100 mg/kg, 1 μg/kg to 50 mg/kg, 1 μg/kg to 20 mg/kg, 1 μg/kg to 10 mg/kg, lug/kg to 1 mg/kg, 100 μg/kg to 100 mg/kg, 100 μg/kg to 50 mg/kg, 100 μg/kg to 20 mg/kg, 100 μg/kg to 10 mg/kg, 100 μg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. Further contemplated is a dose (either as a bolus or continuous infusion) of about 0.1 mg/kg to about 10 mg/kg, about 0.3 mg/kg to about 5 mg/kg, or 0.5 mg/kg to about 3 mg/kg. It is to be further understood that the ranges intermediate to those given above are also within the scope of this disclosure, for example, in the range 1 mg/kg to 10 mg/kg, for example use or dose ranges such as 2 mg/kg to 8 mg/kg, 3 mg/kg to 7 mg/kg, 4 mg/kg to 6 mg/kg, and the like.

The compounds described herein can be administered at once or can be divided into a number of smaller doses to be administered at intervals of time. It is understood that the precise dosage and duration of treatment will be a function of the location of where the composition is parenterally administered, the carrier and other variables that can be determined empirically using known testing protocols or by extrapolation from in vivo or in vitro test data. It is to be noted that concentrations and dosage values can also vary with the age of the individual treated. It is to be further understood that for any subject, specific dosage regimens can need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The compound can be administered as a single bolus or multiple boluses, as a continuous infusion, or a combination thereof. For example, the compound can be administered as a single bolus initially, and then administered as a continuous infusion following the bolus. The rate of the infusion can be any rate sufficient to maintain effective concentration, for example, to maintain effective plasma concentration. Some contemplated infusion rates include from 1 μg/kg/min to 100 mg/kg/min, or from 1 μg/kg/hr to 1000 mg/kg/hr. Rates of infusion can include 0.2 to 1.5 mg/kg/min, or more specifically 0.25 to 1 mg/kg/min, or even more specifically 0.25 to 0.5 mg/kg/min. It will be appreciated that the rate of infusion can be determined based upon the dose necessary to maintain effective plasma concentration and the rate of elimination of the compound, such that the compound is administered via infusion at a rate sufficient to safely maintain a sufficient effective plasma concentration of compound in the bloodstream.

Pharmaceutical Compositions/Formulations

For administration to a subject, the compounds of Formula (I) e.g., Formula (Ia), can be provided in pharmaceutically acceptable compositions. These pharmaceutically acceptable compositions comprise a compound of Formula (I), e.g., Formula (Ia), formulated together with one or more pharmaceutically acceptable carriers (additives) and/or diluents. As described in detail below, the pharmaceutical compositions described herein can be specially formulated for administration in solid or liquid form, including those adapted for the following: (1) oral administration, for example, drenches (aqueous or non-aqueous solutions or suspensions), gavages, lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24:199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960, content of all of which is herein incorporated by reference.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means pharmaceutically-acceptable material, composition or vehicle, such as a liquid or solid filler, diluent, excipient, manufacturing aid (e.g., lubricant, talc magnesium, calcium, or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Examples of solid carriers include starch, sugar, bentonite, silica, and other commonly used carriers. Further non-limiting examples of carriers and diluents which can be used in the formulations comprising a compound of Formula (I) as disclosed herein of the present invention include saline, syrup, dextrose, and water.

Pharmaceutically-acceptable antioxidants include, but are not limited to, (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acids, and the like.

The phrase "therapeutically effective amount" as used herein means that amount of a compound, material, or composition which is effective for producing some desired therapeutic effect in at least a sub-population of cells in an animal at a reasonable benefit/risk ratio applicable to any medical treatment. According, a "therapeutically effective amount" refers to an amount effective, at dosage and periods of time necessary, to achieve a desired therapeutic result. A therapeutic result can be, e.g., lessening of symptoms, prolonged survival, improved mobility, and the like. A therapeutic result need not be a "cure."

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

The compounds can be formulated in a gelatin capsule, in tablet form, dragee, syrup, suspension, topical cream, suppository, injectable solution, or kits for the preparation of syrups, suspension, topical cream, suppository or injectable solution just prior to use. Also, compounds can be included in composites, which facilitate its slow release into the blood stream, e.g., silicon disc, polymer beads.

The formulations can conveniently be presented in unit dosage form and may be prepared by any of the methods well known in the art of pharmacy. Techniques, excipients and formulations generally are found in, e.g., *Remington's Pharmaceutical Sciences, Mack Publishing Co., Easton, Pa.* 1985, 17th edition, Nema et al., *PDA J. Pharm. Sci. Tech.* 1997 51:166-171. Methods to make invention formulations include the step of bringing into association or contacting the compound with one or more excipients or carriers. In general, the formulations are prepared by uniformly and intimately bringing into association one or more compounds with liquid excipients or finely divided solid excipients or both, and then, if appropriate, shaping the product.

The preparative procedure may include the sterilization of the pharmaceutical preparations. The compounds may be mixed with auxiliary agents such as lubricants, preservatives, stabilizers, salts for influencing osmotic pressure, etc., which do not react deleteriously with the compounds.

Examples of injectable form include solutions, suspensions and emulsions. Injectable forms also include sterile powders for extemporaneous preparation of injectible solutions, suspensions or emulsions. The compounds of the present invention can be injected in association with a pharmaceutical carrier such as normal saline, physiological saline, bacteriostatic water, Cremophor™ EL (BASF, Parsippany, N.J.), phosphate buffered saline (PBS), Ringer's solution, dextrose solution, ethanol, polyol (e.g., glycerol, propylene glycol, and liquid polyethylene glycol), vegetable oils, and suitable mixtures thereof, and other aqueous carriers known in the art. Appropriate non-aqueous carriers may also be used and examples include fixed oils and ethyl oleate. In all cases, the composition must be sterile and should be fluid to the extent that easy syringability exists. It must be stable under the conditions of manufacture and storage and must be preserved against the contaminating action of microorganisms such as bacteria and fungi. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin. A suitable carrier is 5% dextrose in saline. Frequently, it is desirable to include additives in the carrier such as buffers and preservatives or other substances to enhance isotonicity and chemical stability.

In some embodiments, compounds can be administrated encapsulated within liposomes. The manufacture of such liposomes and insertion of molecules into such liposomes being well known in the art, for example, as described in U.S. Pat. No. 4,522,811. Liposomal suspensions (including liposomes targeted to particular cells, e.g., a pituitary cell) can also be used as pharmaceutically acceptable carriers.

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the composition can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185; content of each of which is incorporated herein by reference. These dosage forms can be used to provide slow or controlled release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some embodiments, the compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

In the case of oral ingestion, excipients useful for solid preparations for oral administration are those generally used in the art, and the useful examples are excipients such as lactose, sucrose, sodium chloride, starches, calcium carbonate, kaolin, crystalline cellulose, methyl cellulose, glycerin, sodium alginate, gum arabic and the like, binders such as polyvinyl alcohol, polyvinyl ether, polyvinyl pyrrolidone, ethyl cellulose, gum arabic, shellac, sucrose, water, ethanol, propanol, carboxymethyl cellulose, potassium phosphate and the like, lubricants such as magnesium stearate, talc and the like, and further include additives such as usual known coloring agents, disintegrators such as alginic acid and Primogel™, and the like. The compounds can be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these compounds may be incorporated with excipients and used in the form of tablets, capsules, elixirs, suspensions, syrups, and the like. Such compositions and preparations should contain at least 0.1% of compound. The percentage of the agent in these compositions may, of course, be varied and may conveniently be between about 2% to about 60% of the weight of the unit. The amount of compound in such therapeutically useful compositions is such that a suitable dosage will be obtained. Preferred compositions according to the present invention are prepared so that an oral dosage unit contains between about 100 and 2000 mg of compound. Examples of bases useful for formulation of suppositories are oleaginous bases such as cacao butter, polyethylene glycol, lanolin, fatty acid triglycerides, witepsol (trademark, Dynamite Nobel Co. Ltd.) and the like. Liquid preparations may be in the form of aqueous or oleaginous suspension, solution, syrup, elixir and the like, which can be prepared by a conventional way using additives. The compositions can be given as a bolus dose, to maximize the circulating levels for the greatest length of time after the dose. Continuous infusion may also be used after the bolus dose.

For oral administration, the compositions in some embodiments, are provided in the form of tablets containing, about 0.01 mg, about 0.05 mg, about 0.1 mg, about 0.5 mg, about 1.0 mg, about 2.5 mg, about 5.0 mg, about 10.0 mg, about 15.0 mg, about 25.0 mg, about 50.0 mg, about 100 mg, about 150 mg, about 200 mg, about 250 mg, and/or about 500 mg of the active ingredient for the symptomatic adjustment of the dosage to the patient to be treated.

The compounds can also be administrated directly to the airways in the form of an aerosol. For administration by inhalation, the compounds in solution or suspension can be delivered in the form of an aerosol spray from pressured container or dispenser which contains a suitable propellant, e.g., a gas such as carbon dioxide, or hydrocarbon propellant like propane, butane or isobutene. The compounds can also be administrated in a no-pressurized form such as in an atomizer or nebulizer.

In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

Representative intranasal formulations are described in, for example, U.S. Pat. Nos. 4,476,116, 5,116,817 and 6,391,452. Formulations that include a compound of Formula (I) are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are known to those skilled in the preparation of nasal dosage forms and some of these can be found in REMINGTON: THE SCIENCE AND PRACTICE OF PHARMACY, 21st edition, 2005. The choice of suitable carriers is dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents are optionally present. Preferably, the nasal dosage form should be isotonic with nasal secretions.

The compounds can also be administered parenterally. Solutions or suspensions of these compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

It may be advantageous to formulate oral or parenteral compositions in dosage unit form for ease of administration and uniformity of dosage. As used herein, "dosage unit" refers to physically discrete units suited as unitary dosages for the subject to be treated; each unit containing a predetermined quantity of compound calculated to produce the desired therapeutic effect in association with the required pharmaceutical carrier.

Administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the compounds are formulated into ointments, salves, gels, or creams as generally known in the art.

For oral or enteral formulations as disclosed herein for use with the present invention, tablets can be formulated in accordance with conventional procedures employing solid carriers well-known in the art. Capsules employed for oral formulations to be used with the methods of the present invention can be made from any pharmaceutically acceptable material, such as gelatin or cellulose derivatives. Sustained release oral delivery systems and/or enteric coatings for orally administered dosage forms are also contemplated, such as those described in U.S. Pat. No. 4,704,295, "Enteric Film-Coating Compositions," issued Nov. 3, 1987; U.S. Pat. No. 4,556,552, "Enteric Film-Coating Compositions," issued Dec. 3, 1985; U.S. Pat. No. 4,309,404, "Sustained Release Pharmaceutical Compositions," issued Jan. 5, 1982; and U.S. Pat. No. 4,309,406, "Sustained Release Pharmaceutical Compositions," issued Jan. 5, 1982.

Also provided herein is a tablet formulation comprising a compound of Formula I with an enteric polymer casing. An example of such a preparation can be found in WO2005/021002. The active material in the core can be present in a micronized or solubilized form. In addition to active materials the core can contain additives conventional to the art of compressed tablets. Appropriate additives in such a tablet can comprise diluents such as anhydrous lactose, lactose monohydrate, calcium carbonate, magnesium carbonate, dicalcium phosphate or mixtures thereof; binders such as microcrystalline cellulose, hydroxypropylmethylcellulose, hydroxypropyl-cellulose, polyvinylpyrrolidone, pre-gelatinized starch or gum acacia or mixtures thereof; disintegrants such as microcrystalline cellulose (fulfilling both binder and disintegrant functions) cross-linked polyvinylpyrrolidone, sodium starch glycollate, croscarmellose sodium or mixtures thereof; lubricants, such as magnesium stearate or stearic acid, glidants or flow aids, such as colloidal silica, talc or starch, and stabilisers such as desiccating amorphous silica, colouring agents, and flavors. Preferably the tablet comprises lactose as diluent. When a binder is present, it is preferably hydroxypropylmethyl cellulose. Preferably, the tablet comprises magnesium stearate as lubricant. Preferably the tablet comprises croscarmellose sodium as disintegrant. Preferably, the tablet comprises microcrystalline cellulose.

The diluent can be present in a range of 10-80% by weight of the core. The lubricant can be present in a range of 0.25-2% by weight of the core. The disintegrant can be present in a range of 1-10% by weight of the core. Microcrystalline cellulose, if present, can be present in a range of 10-80% by weight of the core.

The active ingredient, e.g., compound of Formula I preferably comprises between 10 and 50% of the weight of the core, more preferably between 15 and 35% of the weight of the core (calculated as free base equivalent). The core can contain any therapeutically suitable dosage level of the active ingredient, but preferably contains up to 150 mg of the active ingredient. Particularly preferably, the core contains 20, 30, 40, 50, 60, 80 or 100 mg of the active ingredient. The active ingredient can be present as is or as any pharmaceutically acceptable salt. If the active ingredient is present as a salt, the weight is adjusted such that the tablet contains the desired amount of active ingredient, calculated as free base or free acid of the salt.

The core can be made from a compacted mixture of its components. The components can be directly compressed, or can be granulated before compression. Such granules can be formed by a conventional granulating process as known in the art. In an alternative embodiment, the granules can be individually coated with an enteric casing, and then enclosed in a standard capsule casing.

The core is surrounded by a casing which comprises an enteric polymer. Examples of enteric polymers are cellulose acetate phthalate, cellulose acetate succinate, methylcellulose phthalate, ethylhydroxycellulose phthalate, polyvinylacetate pthalate, polyvinylbutyrate acetate, vinyl acetate-maleic anhydride copolymer, styrene-maleic mono-ester copolymer, methyl acrylate-methacrylic acid copolymer or methacrylate-methacrylic acid-octyl acrylate copolymer. These can be used either alone or in combination, or together with other polymers than those mentioned above. The casing can also include insoluble substances which are neither decomposed nor solubilised in living bodies, such as alkyl cellulose derivatives such as ethyl cellulose, crosslinked polymers such as styrene-divinylbenzene copolymer, polysaccharides having hydroxyl groups such as dextran, cellulose derivatives which are treated with bifunctional cross-linking agents such as epichlorohydrin, dichlorohydrin or 1, 2-, 3, 4-diepoxybutane. The casing can also include starch and/or dextrin.

In some embodiments, an entericcoating materials are the commercially available Eudragit® enteric polymers such as Eudragit® L, Eudragit® S and Eudragit® NE used alone or with a plasticiser. Such coatings are normally applied using a liquid medium, and the nature of the plasticiser depends upon whether the medium is aqueous or non-aqueous. Plasticisers for use with aqueous medium include propylene glycol, triethyl citrate, acetyl triethyl citrate or Citroflex® or Citroflex® A2. Non-aqueous plasticisers include these, and also diethyl and dibutyl phthalate and dibutyl sebacate. A preferred plasticiser is Triethyl citrate. The quantity of plasticiser included will be apparent to those skilled in the art.

The casing can also include an anti-tack agent such as talc, silica or glyceryl monostearate. Preferably the anti-tack agent is glyceryl monostearate. Typically, the casing can include around 5-25 wt % Plasticizers and up to around 50 wt % of anti-tack agent, preferably 1-10 wt % of anti-tack agent.

If desired, a surfactant can be included to aid with forming an aqueous suspension of the polymer. Many examples of possible surfactants are known to the person skilled in the art. Preferred examples of surfactants are polysorbate 80, polysorbate 20, or sodium lauryl sulphate. If present, a surfactant can form 0.1-10% of the casing, preferably 0.2-5% and particularly preferably 0.5-2%.

A seal coat can also be included between the core and the enteric coating. A seal coat is a coating material which can be used to protect the enteric casing from possible chemical attack by any alkaline ingredients in the core. The seal coat can also provide a smoother surface, thereby allowing easier attachment of the enteric casing. A person skilled in the art would be aware of suitable coatings. Preferably the seal coat is made of an Opadry coating, and particularly preferably it is Opadry White OY-S-28876. Other enteric-coated preparations of this sort can be prepared by one skilled in the art, using these materials or their equivalents.

For intravenous injections or drips or infusions, compounds described herein are formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations include aqueous or nonaqueous solutions, preferably with physiologically compatible buffers or excipients. Such excipients are known.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspension, solutions or emulsions in oily or aqueous vehicles, and may contain formulatory agents such as suspending, stabilizing and/or dispersing agents. In one aspect, the active ingredient is in powder form for constitution with a suitable vehicle, e.g., sterile pyrogen-free water, before use.

To prepare a pharmaceutical composition according to some embodiments, a compound prepared according to any of the processes described herein as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in The Handbook of Pharmaceutical Excipients, published by the American Pharmaceutical Association and the Pharmaceutical Society of Great Britain, the entirety of which is incorporated herein by reference.

Methods of formulating pharmaceutical compositions have been described in numerous publications such as Pharmaceutical Dosage Forms: Tablets, Second Edition, Revised and Expanded, Volumes 1-3, edited by Lieberman et al; Pharmaceutical Dosage Forms: Parenteral Medications, Volumes 1-2, edited by Avis et al; and Pharmaceutical Dosage Forms: Disperse Systems, Volumes 1-2, edited by Lieberman et al; published by Marcel Dekker, Inc., the entirety of which are incorporated herein by reference.

Kits

In another aspect provided herein is a kit. The kit can comprise any of the compounds of Formula (I) or compositions comprising same provided herein and packaging and materials, therefore. Accordingly, in some embodiments the kit comprises a compound of Formula (I). In some embodiments, the kit further comprises a second therapeutic agent. For example, the kit further comprises an anticancer agent or chemotherapeutic, an antimicrobial agent (e.g., antifungal agent, antiviral agent, antiprotozoal agent, or antihelminthic agent) and/or an anti-inflammatory agent.

Generally, the kit comprises an effective amount of the compounds, e.g., compound of Formula (I) and, if present, the additional therapeutic agent. As will be appreciated by one of skill in the art, the components of the kit can be supplied in a lyophilized form or a concentrated form that can be diluted or suspended in liquid prior to use. The kit components described herein can be supplied in aliquots or in unit doses.

In some embodiments, the components described herein can be provided singularly or in any combination as a kit. Such a kit includes the components described herein and packaging materials thereof.

In addition, a kit optionally comprises informational material. The informational material can be descriptive, instructional, marketing or other material that relates to the methods described herein. The informational material of the kits is not limited in its form. In some embodiments, the informational material can include information about production of the components, concentration, date of expiration, batch or production site information, and so forth. In some embodiments, the informational material relates to methods for using or administering the components of the kit.

The packaging material can comprise a label or package insert with relevant information, including but not limited to the formulation can be administered to the subject for the treatment of a subject with a disease or condition described herein, e.g., an eIF4A dependent condition, a DEAD box helicase dependent condition, cancer, infection and/or inflammatory disease or condition.

In some embodiments, the compounds in a kit can be provided in a watertight or gas tight container which in some embodiments is substantially free of other components of the kit. For example, the compounds described herein can be supplied in more than one container, e.g., it can be supplied in a container having sufficient amount of the compounds for a predetermined number of applications, i.e., doses or administrations, e.g., 1, 2, 3 or greater. One or more components as described herein can be provided in any form, e.g., liquid, dried or lyophilized form. Liquids or components for suspension or solution of the reagents can be provided in sterile form and should not contain microorganisms or other contaminants. When the components described herein are provided in a liquid solution, the liquid solution preferably is an aqueous solution.

The kit will typically be provided with its various elements included in one package, e.g., a fiber-based, e.g., a cardboard, or polymeric, e.g., a Styrofoam box. The enclosure can be configured so as to maintain a temperature differential between the interior and the exterior, e.g., it can provide insulating properties to keep the reagents at a preselected temperature for a preselected time.

Definitions

As used herein a "stereoisomer" refers to each of two or more compounds differing only in the spatial arrangement of their atom.

As used herein "tautomers" refers to two molecules with the same molecular formula but different connectivity, for example, a keto-enol pair.

The compound in some embodiments, can exist in various isomeric forms, as well as in one or more tautomeric forms, including both single tautomers and mixtures of tautomers. The term "isomer" is intended to encompass all isomeric forms of a compound described herein, including tautomeric forms of the compound.

Some compounds described here can have asymmetric centers and therefore exist in different enantiomeric and diastereomeric forms. A compound of the invention can be in the form of an optical isomer or a diastereomer. Accordingly, some embodiments, encompass compounds and their uses as described herein in the form of their optical isomers, diastereoisomers and mixtures thereof, including a racemic mixture. Optical isomers of the compounds according to some embodiments, can be obtained by known techniques such as asymmetric synthesis, chiral chromatography, or via chemical separation of stereoisomers through the employment of optically active resolving agents.

Unless otherwise indicated "stereoisomer" means one stereoisomer of a compound that is substantially free of other possible stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given to that structure, then the depicted structure dominates. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

As use herein a "pharmaceutically acceptable salt" refers to an excipient that is useful in preparing a pharmaceutical composition that is generally safe, non-toxic, and desirable. Without limitation, pharmaceutically acceptable salts include, e.g. alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

As used herein the term “aryl”, whether alone or as part of a substituent group, refers to an unsubstituted carboxylic aromatic ring comprising between 6 and 14 carbon atoms. Suitable examples include, but are not limited to, phenyl, and naphthyl.

As used herein “cycloalkyl” refers to a stable non-aromatic monocyclic or polycyclic hydrocarbon group consisting solely of carbon and hydrogen atoms. The cycloalkyl can be a monocyclic, bicyclic, tricyclic or tetracyclic ring system, which may include fused, spiro or bridged ring systems, having from three to fifteen carbon atoms, in some embodiments, having from three to ten carbon atoms, three to nine carbon atoms, three to eight carbon atoms, three to seven carbon atoms, three to six carbon atoms, three to five carbon atoms, a ring with four carbon atoms, or a ring with three carbon atoms. The cycloalkyl ring may be saturated or unsaturated and attached to the rest of the molecule by a single bond. Monocyclic variants include, for example, cyclopropyl, cyclobutyl, cyclopentyl, cyclohexyl, cycloheptyl, and cyclooctyl. Polycyclic variants include, for example, adamantyl, norbornyl, decalinyl, 7,7-dimethyl-bicyclo[2.2.1]heptanyl, and the like.

As used herein “heterocyclyl”, “heterocycle”, or “heterocyclic ring” refers to a stable 3-to 18-membered saturated or unsaturated group which consists of two to twelve carbon atoms and from one to six heteroatoms, for example, one to five heteroatoms, one to four heteroatoms, one to three heteroatoms, or one to two heteroatoms selected from the group consisting of nitrogen, oxygen and sulfur. Exemplary heterocycles include without limitation stable 3-15 membered saturated or unsaturated variants, stable 3-12 membered saturated or unsaturated variants, stable 3-9 membered saturated or unsaturated variants, stable 8-membered saturated or unsaturated variants, stable 7-membered saturated or unsaturated variants, stable 6-membered saturated or unsaturated variants, or stable 5-membered saturated or unsaturated variants.

Unless stated otherwise specifically in the specification, the heterocyclyl group may be a monocyclic, bicyclic, tricyclic or tetracyclic ring system, which may include fused, spiro or bridged ring systems; and the nitrogen, carbon or sulfur atoms in the heterocyclyl variant may be optionally oxidized; the nitrogen atom may be optionally quaternized; and the heterocyclyl variant may be partially or fully saturated. Examples of non-aromatic heterocyclyl variants include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, thietanyl, trithianyl, tetrahydropyranyl, thiomorpholinyl, thiamorpholinyl, 1-oxo-thiomorpholinyl, and 1,1-dioxo-thiomorpholinyl. Heterocyclyls include heteroaryls as defined herein, and examples of aromatic heterocyclyls are listed in the definition of heteroaryls below.

As used herein the term “heteroaryl” or “heteroarylene” refers to a 5- to 14-membered ring system group comprising hydrogen atoms, one to thirteen carbon atoms, one to six heteroatoms selected from the group consisting of nitrogen, oxygen and sulfur, and at least one aromatic ring. In some embodiments, the heteroaryl variant may be a stable 5-12 membered ring, a stable 5-10 membered ring, a stable 5-9 membered ring, a stable 5-8 membered ring, a stable 5-7 membered ring, or a stable 6 membered ring that comprises at least 1 heteroatom, at least 2 heteroatoms, at least 3 heteroatoms, at least 4 heteroatoms, at least 5 heteroatoms or at least 6 heteroatoms. Heteroaryls may be a monocyclic, bicyclic, tricyclic or tetracyclic ring system, which may include fused or bridged ring systems; and the nitrogen, carbon or sulfur atoms in the heteroaryl variant may be optionally oxidized; the nitrogen atom may be optionally quaternized. The heteroatom may be a member of an aromatic or non-aromatic ring, provided at least one ring in the heteroaryl is aromatic. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (e.g. thienyl).

As used herein the term “acyl” refers to a group of the Formula —CO—$C_n$ wherein $C_n$ represent a straight or branched alkyl chain wherein n can be 1, 2, 3, 4, 5, 6, 7, 8, 9 or 10.

As used herein a “ester” refers to a group of the formula —C(O)—O$C_n$$C_n$ represent a straight or branched alkyl chain wherein n can be 1, 2, 3, 4, 5, 6, 7, 8, 9 or 10. For example a chemical compound derived from an acid in which at least one-OH (hydroxyl) group is replaced by an —O-alkyl (alkoxy) group.

As used herein the term “alkyl”, whether alone or as part of a substituent group, refers to a saturated $C_1$-$C_n$ carbon chain, wherein the carbon chain may be straight or branched; wherein n can be 2, 3, 4, 5, 6, 7, 8, 9 or 10. Suitable examples include, but are not limited to methyl, ethyl, propyl, isopropyl, butyl, isobutyl, sec-butyl, t-butyl, n-pentyl and n-hexyl.

As used herein the term "alkenyl", whether alone or as part of a substituent group, refers to a $C_2$-$C_n$ carbon chain, wherein the carbon chain may be straight or branched, wherein the carbon chain contains at least one carbon-carbon double bond, and wherein n can be 3, 4, 5, 6, 7, 8, 9, or 10.

As used herein the term "alkynyl", whether alone or as part of a substituent group, refers to a $C_2$-$C_n$ wherein the carbon chain may be straight or branched, wherein the carbon chain contains at least one carbon-carbon triple bond, and wherein n can be 3, 4, 5, 6, 7, 8, 9, or 10.

The groups of the present disclosure can be unsubstituted or substituted, as herein defined. In addition, the substituted groups can be substituted with one or more groups such as a $C_1$-$C_6$ alkyl, $C_{1-4}$ alkyl, —O—$C_{1-4}$ alkyl, hydroxyl, amino, ($C_{1-4}$ alkyl) amino, di($C_{1-4}$ alkyl) amino, —S—($C_{1-4}$ alkyl), —SO—($C_{1-4}$ alkyl), —$SO_2$—($C_{1-4}$ alkyl), halogen, aryl, heteroaryl, and the like.

With reference to substituents, the term "independently" means that when more than one of such substituents is possible, such substituents may be the same or different from each other.

"Amino" refers to a —$NH_2$ substituent.

"Aminocarbonyl" or "Amido" or "amido" refers to a group containing a carbonyl group linked to a nitrogen atom. The amide group is represented by RC(O)NR'R". In some embodiments, the amide has a formula —NHC(O)—$C_n$, or —C(O)NH—$C_n$, wherein $C_n$ represent a straight, branched and optionally substituted alkyl chain wherein n can be 1, 2, 3, 4, 5, 6, 7, 8, 9, or 10. In some options the hydrogen (H) atom is replaced by a second alkyl chain Cm which is a straight, branched and optionally substituted alkyl chain wherein n can be 1, 2, 3, 4, 5, 6, 7, 8, 9, or 10. In some embodiments, the amide has a formula —C(O)NH—$C_n$. In some embodiments, the alkyl chains represented by $C_n$ and Cm are linked, for example making a cyclic structure.

"Carboxyl" refers to the —$CO_2H$ substituent.

"Carbonyl" refers to a —C(O)—, —(CO)— or —C(═O)— group. All notations are used interchangeably herein.

"Cyano" refers to the —C≡N substituent, e.g., CN.

"Hydroxy" or "hydroxyl" refers to the —OH substituent.

"Oxo" refers to a ═O substituent

"Thio" or "thiol" refer to a —SH substituent.

"Halo" or "halogen" refers to bromo (bromine), chloro (chlorine), fluoro (fluorine), or iodo (iodine).

Compound words have the meaning of the individual functional groups or fragments as would be understood in the art. For example, "hydroxyalkyl" refers to the -(alkyl)-OH substituent, "thioalkyl" refers to the -(alkyl)-SH substituent, "cyanoalkylene" refers to the -(alkylene)C≡N substituent; "hydroxyalkylene" refers to the -(alkylene)OH substituent; "arylmethoxy" refers to a methoxy substituted aryl group.

The term "optionally substituted" means that the specified group or moiety is unsubstituted or is substituted with one or more (typically 1, 2, 3, 4, 5 or 6 substituents) independently selected from the group of substituents listed below in the definition for "substituents" or otherwise specified. The term "substituents" refers to a group "substituted" on a substituted group at any atom of the substituted group. Suitable substituents include, without limitation, halogen, hydroxyl, caboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carboxy, hydroxylalkyl, alkanesulfonyl, arenesulfonyl, alkanesulfonamido, arenesulfonamido, aralkylsulfonamido, alkylcarbonyl, acyloxy, cyano or ureido. In some cases, two substituents, together with the carbons to which they are attached to can form a ring.

For example, any alkyl, alkenyl, cycloalkyl, heterocyclyl, heteroaryl or aryl is optionally substituted with 1, 2, 3, 4 or 5 groups selected from OH, CN, —SC(O)Ph, oxo (═O), SH, $SO_2NH_2$, $SO_2$($C_1$-$C_4$)alkyl, $SO_2NH$($C_1$-$C_4$)alkyl, halogen, carbonyl, thiol, cyano, $NH_2$, $NH$($C_1$-$C_4$)alkyl, N[($C_1$-$C_4$)alkyl]$_2$, C(O)$NH_2$, COOH, COOMe, acetyl, ($C_1$-$C_8$) alkyl, O($C_1$-$C_8$)alkyl, O($C_1$-$C_8$)haloalkyl, ($C_2$-$C_8$)alkenyl, ($C_2$-$C_8$)alkynyl, haloalkyl, thioalkyl, cyanomethylene, alkylaminyl, aryl, heteroaryl, substituted aryl, $NH_2$—C(O)-alkylene, NH(Me)-C(O)-alkylene, $CH_2$—C(O)-alkyl, C(O)-alkyl, alkylcarbonylaminyl, $CH_2$—[CH(OH)]$_m$—$(CH_2)_p$—OH, $CH_2$—[CH(OH)]$_m$—$(CH_2)_p$—$NH_2$ or $CH_2$-aryl-alkoxy; "m" and "p" are independently 1, 2, 3, 4, 5 or 6.

In some embodiments, an optionally substituted group is substituted with 1 substituent. In some other embodiments, an optionally substituted group is substituted with 2 independently selected substituents, which can be same or different. In some other embodiments, an optionally substituted group is substituted with 3 independently selected substituents, which can be same, different or any combination of same and different. In still some other embodiments, an optionally substituted group is substituted with 4 independently selected substituents, which can be same, different or any combination of same and different. In yet some other embodiments, an optionally substituted group is substituted with 5 independently selected substituents, which can be same, different or any combination of same and different.

As used herein, a "therapeutic agent" is a substance used to influence the outcome of a disease, whether it be to cure, reduce, eliminate (some of) its symptoms, or improve the quality of life.

As used herein, an "anticancer agent" or "chemotherapeutic" are used interchangeably to describe an agent that is effective in the treatment of a malignant disease.

As used herein, an "antimicrobial agent" suppresses the multiplication and/or growth of microorganisms, and/or results in the death of microorganisms.

As used herein, an "antifungal agent" is a pharmaceutical fungicide or fungistatic used to treat and prevent mycosis.

As used herein, an "antibacterial agent" is an agent used to eliminate bacteria and/or prevent their development.

As used herein, an "antiprotozoal agent" or "antiprotozoals" are used to treat a variety of protozoal diseases by inhibiting growth and/or eliminating protozoan organisms.

As used herein, an "antiviral agent" is any agent used in the treatment of an infectious disease caused by a virus.

As used herein, an "eukaryotic initiation factor—4A (eIF4A) dependent condition" is a disease, infection, or other undesirable biological impact mediated by eIF4A.

A compound administered to treat an eIF4A dependent condition is useful in preventing, treating, ameliorating, or reducing the symptoms or progression of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by eIF4A, such as, for example, haematological tumors, solid tumors, and/or metastases thereof, including leukaemias and myelodysplastic syndrome, Waldenstrom macroglobulinemia, and malignant lymphomas, for example, GBM, B-cell lymphoma, T-cell lymphoma, hairy cell lymphoma, Hodgkin's lymphoma, non-Hodgin's lymphoma, and Burkitt's lymphoma, head and neck tumors including brain tumors and brain metastases, tumors of the thorax including non-small cell and small cell lung tumors, gastrointestinal tumors, endocrine tumors, mammary and other gynecological tumors, urological tumors including renal, bladder and prostate tumors, skin tumors, and sarcomas, and/or metastases thereof. In some embodiments, the eIF4A-dependent condition is GBM, diffuse large B-cell lymphoma, hepatocellular cancers, acute myeloid leukemia, breast cancer, colorectal cancer, small cell lung cancer, metastasis of tumors and non-small cell lung cancer. In some embodiments, the eIF4A-dependent condition is a drug resistant cancer, e.g., drug resistant GBM.

The term "co-administered" refers to administering a second agent and/or treatment to the subject, e.g. as part of a combinatorial therapy.

The terms "treat", "treatment" and "treating" used interchangeably, with respect to treatment of a disease or disorder, mean preventing the development of the disease, or altering the course of the disease (for example, but not limited to, slowing the progression of the disease), or reversing a symptom of the disease or reducing one or more symptoms and/or one or more biochemical markers in a subject, preventing one or more symptoms from worsening or progressing, promoting recovery or improving prognosis in a subject who is at risk of the disease, as well as slowing or reducing progression of existing disease. The term treating encompasses reducing or alleviating at least one adverse effect or symptom of a condition, disease or disorder associated with inappropriate proliferation, for example cancer.

As used herein, the term "subject" or "patient" refers to any organism to which a compound or composition disclosed herein can be administered, e.g., for experimental, diagnostic, and/or therapeutic purposes. Typical subjects include animals (e.g., mammals such as mice, rats, rabbits, non-human primates, and humans) and/or plants. Usually, the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. A subject can be male or female.

Preferably, the subject is a mammal. The mammal can be a human, non-human primate, mouse, rat, dog, cat, horse, or cow, but are not limited to these examples. Mammals other than humans can be advantageously used as subjects that represent animal models of human diseases and disorders. In addition, compounds, compositions and methods described herein can be used to with domesticated animals and/or pets In some embodiments, the subject is human. In another embodiment, the subject is an experimental animal or animal substitute as a disease model. The term does not denote a particular age or sex. Thus, adult and newborn subjects, as well as fetuses, whether male or female, are intended to be covered. Examples of subjects include humans, dogs, cats, cows, goats, and mice. The term subject is further intended to include transgenic species. In some embodiments, the subject can be of European ancestry. In some embodiments, the subject can be of African American ancestry. In some embodiments, the subject can be of Asian ancestry.

In one embodiment, a patient is a human, such as a human infant (e.g. less than 1 years old), child (e.g. between 1 and 12 years old), adolescent (e.g. between 12 and 18 years old), adult (e.g. 18 to 65 years), or elderly (e.g. older than 65).

A subject can be one who has been previously diagnosed with or identified as suffering from or an eIF4A dependent condition. A subject can be one who has been previously diagnosed with or identified as having cancer. A subject can be one who has been previously diagnosed with or identified as having an infection. A "subject in need" of treatment for a particular condition can be a subject having that condition, diagnosed as having that condition, or at risk of developing that condition, e.g., an eIF4A dependent condition, cancer or an infection.

The term "cancer" and "malignancy" are used interchangeably herein, and refer to a disease that is characterized by uncontrolled, abnormal growth of cells. Cancer cells can spread locally or through the bloodstream and lymphatic system to other parts of the body. The term is also intended to include any disease of an organ or tissue in mammals characterized by poorly controlled or uncontrolled multiplication of normal or abnormal cells in that tissue and its effect on the body as a whole. Cancer diseases within the scope of the definition comprise benign neoplasms, dysplasias, hyperplasias as well as neoplasms showing metastatic growth or any other transformations like e.g. leukoplakias which often precede a breakout of cancer. The term cancer also includes metastases which are cancer cells (e.g. a primary tumor, or a metastasis tumor) which has migrated to other locations in the subject and to establish new tumors at such locations. A small molecule LSF inhibitor as disclosed herein which "inhibits" cancer metastasis may result in the delayed appearance of secondary tumors, slowed development of primary or secondary tumors, decreased occurrence of secondary tumors, slowed or decreased severity of secondary effects of disease, arrested tumor growth and regression of tumors, among others. In the extreme, complete inhibition is referred to herein as prevention (e.g., virtually complete inhibition, no metastasis if it had not occurred, no further metastasis if there had already been metastasis of a cancer, or virtually complete inhibition of the growth of a primary tumor caused by re-seeding of the tumor by a metastasized cell).

A "cancer cell" refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage dependence, proliferation, malignancy, lack of contact inhibition and density limitation of growth, lack of growth factor or serum dependence, tumor specific markers levels, invasiveness, tumor growth in suitable animal hosts such as nude mice, and the like, in vitro, in vivo, and ex vivo (see also Freshney, Culture of Animal Cells: A Manual of Basic Technique (3rd ed. 1994)).

A "cancer stem cell" refers to a cell that is capable of self-renewal and differentiating into the lineages of cancer cells that comprise a tumor or hematological malignancy. Cancer stem cells are uniquely able to initiate and sustain the disease. Without being bound by theory, a cancer stem cell can have a variety of cellular properties. For instance, a cancer stem cell can re-grow a tumor. Cancer stem cells can divide asymmetrically and symmetrically and can show variable rates of proliferation. Additionally, a cancer stem cell can grow in vitro under established cancer stem cell conditions such as in a serum-free medium and/or in suspension or on low-attachment plates. "Activated cancer stem cells" refers generally to cancer stem cells that are actively self-renewing and/or actively expanding.

A "tumorigenic cell," as used herein, is a cell that, when introduced into a suitable site in a subject, can form a tumor. The cell may be non-metastatic or metastatic. A variety of types of tumorigenic and/or metastatic cells can be used in a method of the invention, including cells from metastatic epithelial cancers, carcinomas, melanoma, leukemia, etc. The tumor cells may be, e.g., from cancers of breast, lung, colon, bladder, prostate, liver, gastrointestinal tract, endometrium, tracheal-bronchial tract, pancreas, uterus, ovary, nasopharynges, prostate, bone or bone marrow, brain, skin or other suitable tissues or organs. In a preferred embodiment, the cancer cells are of human origin.

The term "tumor" or "tumor cell" are used interchangeably herein, refers to the tissue mass or tissue type of cell that is undergoing abnormal proliferation.

A "metastatic" cell, as used herein, refers to a cell that has a potential for metastasis and, when used in a method of the invention, is able to seed a tumor or a cell colony of interest. A "highly metastatic" cell, as used herein, refers to a cell that has a high potential for metastasis; e.g., cells from a cell line such as, but not limited to LM2, MDA-MB-231, PC-3, DU-145, Lewis Lung carcinoma, can be considered to be highly metastatic cells. Metastatic cells can be generated in a variety of ways, which are discussed further below.

A "sarcoma" refers to a type of cancer cell that is derived from connective tissue, e.g., bone (osteosarcoma) cartilage (chondrosarcoma), muscle (rhabdomyosarcoma or rhabdosarcoma), fat cells (liposarcoma), lymphoid tissue (lymphosarcoma), collagen-producing fibroblasts (fibrosarcoma). Sarcomas may be induced by infection with certain viruses, e.g., Kaposi's sarcoma, Rous sarcoma virus, etc.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

In certain embodiments, the disclosed compounds are useful for inhibiting the activity of eIF4A and/or can be useful in analyzing eIF4A signaling activity in model systems and/or for preventing, treating, or ameliorating a symptom associated with a disease, disorder, or pathological condition involving eIF4A, including a disease caused by a parasite, a virus, a fungus or a neurodegenerative disease requiring neuroprotection, for example one afflicting humans. A compound which inhibits the activity of eIF4A will be useful in preventing, treating, ameliorating, or reducing the symptoms or progression of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by eIF4A, such as, for example, haematological tumors, solid tumors, and/or metastases thereof, including leukaemias and myelodysplastic syndrome, Waldenstrom macroglobulinemia, and malignant lymphomas, for example, B-cell lymphoma, T-cell lymphoma, hairy cell lymphoma, Hodgkin's lymphoma, non-Hodgin's lymphoma, and Burkitt's lymphoma, head and neck tumors including brain tumors and brain metastases, tumors of the thorax including non-small cell and small cell lung tumors, gastrointestinal tumors, endocrine tumors, mammary and other gynecological tumors, urological tumors including renal, bladder and prostate tumors, skin tumors, and sarcomas, and/or metastases thereof. In some embodiments, the eIF4A-dependent condition is diffuse large B-cell lymphoma, hepatocellular cancers, acute myeloid leukemia, breast cancer, colorectal cancer, small cell lung cancer, metastasis of tumors and non-small cell lung cancer. In some embodiments, the eIF4A-dependent condition is a drug resistant cancer.

In some embodiments, the compounds or pharmaceutically acceptable salt thereof may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e. sequentially; combination therapy is understood to include all these regimens.

In some embodiments, of the various aspects disclosed herein, the composition or method can further comprise administering an additional anti-cancer therapy to the subject. For example, administering a standard of care chemotherapeutic to the subject. Non-limiting examples of a standard of care chemotherapeutics or other anti-cancer therapy can include radiation therapy, surgery, gemcitabine, cisplastin, paclitaxel, carboplatin, bortezomib, AMG479, vorinostat, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g. calicheamicin, especially calicheamicin gamma1I and calicheamicin omegaI (see, e.g. Agnew, Chem. Intl. Ed. Engl., 33:183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g. erlotinib (Tarceva®)) and VEGF-A that reduce cell proliferation and pharmaceutically acceptable salts, acids or derivatives of any of the above. Additional anti-cancer treatment can further include the use of radiation or radiation therapy. Further, the additional anti-cancer treatment can also include the use of surgical treatments.

In some embodiments, of the various aspects disclosed herein, the treatment is administered to a subject currently receiving standard of care chemotherapeutics or other alternative anti-cancer treatments. Generally, cancer treatment may involve one or more of the treatment options, but not limited to surgery, radiation, chemotherapy, immunotherapy, targeted therapy and hormonal therapy. The single agent therapy or current combination therapies for the treatment of cancer cause side effects such as nausea, rashes, swelling, flu-like symptoms, fatigue, digestive tract problems, allergic reactions and immunosuppression. In some embodiments, the invention described herein provides a more effective treatment of cancer by administering one or more compounds represented by Formula (I) in combination with other cancer treatments. In some embodiments, the combination therapy induces additive or synergistic therapeutic effect. In some embodiments, the method described herein can reduce or prevent one or more adverse effects or toxicities associated with the administration of a chemotherapeutic agent or radiation therapy. In some embodiments, the method described herein can increase the anti-tumor activity of a chemotherapeutic agent or radiation therapy or increase the selective cytotoxicity of a chemotherapeutic agent.

In some embodiments, the combination therapy includes administering therapeutic, diagnostic or preventive monoclonal antibodies. Without limitation these can be selected from comprising burosumab, brolucizumab, suvizumab, secukinumab, enfortumab vedotin, minretumomab, sacituzumab govitecan, pateclizumab, teprotumumab, caplacizumab, biciromab, duligotuzumab, metelimumab, olendalizumab, zolimomab aritox, belimumab, anifrolumab, rontalizumab, tefibazumab, ibi, nimotuzumab, zalutumumab, bivatuzumab mertansine, elezanumab, varlilumab, intetumumab, cixutumumab, ramucirumab, rilotumumab, volociximab, vesencumab, lirilumab, mitumomab, rovalpituzumab tesirine, sifalimumab, crizanlizumab, aselizumab, ligelizumab, bertilimumab, edobacomab, pagibaximab, afelimomab, nebacumab, golimumab, zanolimumab, fezakinumab, toralizumab, ocrelizumab, monalizumab, adalimumab, infliximab, sarilumab, clazakizumab, clenoliximab, fletikumab, gimsilumab, mavrilimumab, olokizumab, sirukumab, tocilizumab, ruplizumab, roledumab, idarucizumab, felvizumab, motavizumab, palivizumab, nirsevimab, tisotumab vedotin, pexelizumab, lerdelimumab, derlotuximab biotin, refanezumab, foravirumab, rafivirumab, briakinumab, siplizumab, efalizumab, guselkumab, itolizumab, mirikizumab, panobacumab, capromab pendetide, adecatumumab, gosuranemab, cedelizumab, daclizumab, odulimomab, basiliximab, muromonab-cd, blinatumomab, rmab, abciximab, brodalumab, netakimab, tadocizumab, eculizumab, ravulizumab, prasinezumab, clivatuzumab tetraxetan, oleclumab, placulumab, fulranumab, tanezumab, catumaxomab, citatuzumab bogatox, igovomab, abagovomab, farletuzumab, mirvetuximab soravtansine, oregovomab, pankomab, sofituzumab vedotin, denosumab, blosozumab, romosozumab, sulesomab, otilimab, ranevetmab, bleselumab, carlumab, suvratoxumab, tremelimumab, naptumomab estafenatox, anatumomab mafenatox, necitumumab, racotumomab, tislelizumab, bectumomab, ibritumomab tiuxetan, veltuzumab, satralizumab, dinutuximab, rinucumab, bimagrumab, stamulumab, landogrozumab, trevogrumab, ustekinumab, natalizumab, ublituximab, afasevikumab, alemtuzumab, opicinumab, lucatumumab, milatuzumab, daratumumab, elotuzumab, isatuximab, fremanezumab, eptinezumab, erenumab, galcanezumab, cabiralizumab, cetuximab, bevacizumab, etaracizumab, glembatumumab vedotin, pembrolizumab, flanvotumab, ipilimumab, pdr, relatlimab, spartalizumab, trbs, suptavumab, ecromeximab, ranibizumab, rituximab, detumomab, efungumab, diridavumab, besilesomab, letolizumab, abrilumab, etrolizumab, vobarilizumab, reslizumab, ozoralizumab, vepalimomab, tildrakizumab, fresolimumab, pamrevlumab, alirocumab, evolocumab, frovocimab, lodelcizumab, iratumumab, tnx-, brentuximab vedotin, ibalizumab, naxitamab, camrelizumab, exbivirumab, lenvervimab, libivirumab, emapalumab, atorolimumab, flotetuzumab, apolizumab, ulocuplumab, dacetuzumab, erlizumab, moxetumomab pasudotox, rovelizumab, emicizumab, gavilimomab, inolimomab, Depatuxizumab mafodotin, Lampalizumab, Solitomab, Arcitumomab, IMAB, DS-zolbetuximab, claudiximab, andecaliximab, bemarituzumab, tositumomab, simtuzumab, nemolizumab, porgaviximab, cosfroviximab, larcaviximab, bococizumab, evinacumab, ralpancizumab, domagrozumab, polatuzumab vedotin, utomilumab, urtoxazumab, lemalesomab, plozalizumab, otelixizumab, teplizumab, gevokizumab, crotedumab, regavirumab, sevirumab, cemiplimab, canakinumab, eldelumab, vedolizumab, visilizumab, certolizumab pegol, risankizumab, priliximab, fontolizumab, brazikumab, ravagalimab, SHP, matuzumab, votumumab, edrecolomab, cantuzumab mertansine, altumomab pentetate, bermekimab, labetuzumab, nacolomab tafenatox, panitumumab, sutimlimab, actoxumab, bezlotoxumab, lokivetmab, girentuximab, lenzilumab, TGN, ofatumumab, cirmtuzumab, lumiliximab, FBTA, obinutuzumab, tuvirumab, keliximab, sonepcizumab, inclacumab, imeiromab, cantuzumab ravtansine, taplitumomab paptox, bavituximab, inebilizumab, epratuzumab, dalotuzumab, drozitumab, enavatuzumab, ficlatuzumab, icrucumab, urelumab, pidilizumab, nofetumomab merpentan, satumomab pendetide, abituzumab, alacizumab pegol, amatuximab, anetumab ravtansine, ascrinvacumab, atezolizumab, avelumab, azintuxizumab vedotin, belantamab mafodotin, brontictuzumab, cbr-doxorubicin immunoconjugate, cergutuzumab amunaleukin, cetrelimab, cibisatamab, codrituzumab, cofetuzumab pelidotin, coltuximab ravtansine, conatumumab, cusatuzumab, demcizumab, denintuzumab mafodotin, dostarlimab, durvalumab, duvortuxizumab, elgemtumab, emactuzumab, emibetuzumab, enapotamab vedotin, enoblituzumab, ensituximab, futuximab, gancotamab, ganitumab, gatipotuzumab, iladatuzumab vedotin, imalumab, imgatuzumab, indatuximab ravtansine, indusatumab vedotin, lacnotuzumab, ladiratuzumab vedotin, lexatumumab, lifastuzumab vedotin, lilotomab satetraxetan, lintuzumab, loncastuximab tesirine, lorvotuzumab mertansine, losatuxizumab vedotin, lumretuzumab, mapatumumab, modotuximab, mosunetuzumab, narnatumab, navicixizumab, nesvacumab, nivolumab, ocaratuzumab, olaratumab, omburtamab, onartuzumab, ontuxizumab, otlertuzumab, parsatuzumab, pasotuxizumab, patritumab, pemtumomab, pertuzumab, pinatuzumab vedotin, radretumab, robatumumab, rosmantuzumab, samalizumab, samrotamab vedotin, seribantumab, sibrotuzumab, siltuximab, sirtratumab vedotin, tacatuzumab tetraxetan, tarextumab, tavolimab, telisotuzumab vedotin, tenatumomab, tepoditamab, tetulomab, tigatuzumab, timigutuzumab, tiragotumab, tomuzotuximab, tovetumab, tucotuzumab celmoleukin, vandortuzumab vedotin, vantictumab, vanucizumab, vonlerolizumab, vorsetuzumab mafodotin, zatuximab, zenocutuzumab, ertumaxomab, margetuximab, trastuzumab, trastuzumab emtansine, pritumumab, marstacimab, concizumab, oportuzumab monatox, obiltoxaximab, dusigitumab, galiximab, camidanlumab tesirine, tabalumab, ianalumab, tibulizumab, teneliximab, ixekizumab, lulizumab pegol, OMS, dupilumab, tezepelumab, tralokinumab, mepolizumab, anrukinzumab, benralizumab, enokizumab, lebrikizumab, oxelumab, pascolizumab, quilizumab, perakizumab, fanolesomab, raxibacumab, bimekizumab, carotuximab, faricimab, varisacumab, lanadelumab, birtamimab, aducanumab, bapineuzumab, crenezumab, gantenerumab, ponezumab, solanezumab, ozanezumab, talizumab, gomiliximab, omalizumab, inotuzumab ozogamicin, istiratumab, mogamulizumab, figitumumab, pintumomab, fasinumab, vadastuximab talirine, gemtuzumab ozogamicin, SGN-CD A, Iomab-B, abrezekimab, aprutumab ixadotin, atidortoxumab, atinumab, begelomab, berlimatoxumab, bersanlimab, dapirolizumab pegol, dectrekumab, dezamizumab, dorlimomab aritox, elsilimomab, enlimomab pegol, enoticumab, epitumomab cituxetan, etigilimab, faralimomab, fibatuzumab, firivumab, foralumab, frunevetmab, gedivumab, gilvetmab, ifabotuzumab, imaprelimab, iscalimab, laprituximab emtansine, lendalizumab, leronlimab, lesofavumab, lupartumab amadotin, lutikizumab, nerelimomab, onvatilimab, pogalizumab, prezalizumab, pritoxaximab, remtolumab, rivabazumab pegol, romilkimab, rozanolixizumab, selicrelumab, setoxaximab, setrusumab talacotuzumab, vanalimab, vopratelimab, vunakizumab, xentuzumab, ziralimumab, blontuvetmab, maslimomab, morolimumab, namilumab, naratuximab emtansine, navivumab, orticumab, sontuzumab, tamtuvetmab, telimomab aritox, tesidolumab, timolumab, tosatoxumab, tregalizumab, vapaliximab, and vatelizumab.

In some embodiments, a compound of Formula (I) is administered to a patient with one or more additional antiviral agent. In some embodiments, the antiviral compound is one or more of ribavirin, daclatasvir, sofosbuvir, velpatasvir, ledipasvir/sofosbuvir, telaprevir, interferon aphacon-1, interferon alpha-2b, glecaprevir and pibrentasvir, simeprevir, pegylated interferon, pegylated interferon alpha-2b, interferon alpha-2a, elbasvir, and grazoprevir.

Furthermore, in some embodiments, the compounds and their pharmaceutical compositions are candidate therapeutics for the prophylaxis and/or therapy of cytokine related diseases, such as inflammatory diseases, allergies, or other conditions associated with proinflammatory cytokines. Exemplary inflammatory diseases include without limitation, chronic or acute inflammation, inflammation of the joints such as chronic inflammatory arthritis, rheumatoid arthritis, psoriatic arthritis, osteoarthritis, juvenile rheumatoid arthritis, Reiter's syndrome, rheumatoid traumatic arthritis, rubella arthritis, acute synovitis and gouty arthritis; inflammatory skin diseases such as sunburn, psoriasis, erythrodermic psoriasis, pustular psoriasis, eczema, dermatitis, acute or chronic graft formation, atopic dermatitis, contact dermatitis, urticaria and scleroderma; inflammation of the gastrointestinal tract such as inflammatory bowel disease, Crohn's disease and related conditions, ulcerative colitis, colitis, and diverticulitis; nephritis, urethritis, salpingitis, oophoritis, endomyometritis, spondylitis, systemic lupus erythematosus and related disorders, multiple sclerosis, asthma, meningitis, myelitis, encephalomyelitis, encephalitis, phlebitis, thrombophlebitis, respiratory diseases such as asthma, bronchitis, chronic obstructive pulmonary disease (COPD), inflammatory lung disease and adult respiratory distress syndrome, and allergic rhinitis; endocarditis, osteomyelitis, rheumatic fever, rheumatic pericarditis, rheumatic endocarditis, rheumatic myocarditis, rheumatic mitral valve disease, rheumatic aortic valve disease, prostatitis, prostatocystitis, spondoarthropathies ankylosing spondylitis, synovitis, tenosynovotis, myositis, pharyngitis, polymyalgia rheumatica, shoulder tendonitis or bursitis, gout, pseudo gout, vasculitides, inflammatory diseases of the thyroid selected from granulomatous thyroiditis, lymphocytic thyroiditis, invasive fibrous thyroiditis, acute thyroiditis; Hashimoto's thyroiditis, Kawasaki's disease, Raynaud's phenomenon, Sjogren's syndrome, neuroinflammatory disease, sepsis, conjunctivitis, keratitis, iridocyclitis, optic neuritis, otitis, lymphoadenitis, nasopaharingitis, sinusitis, pharyngitis, tonsillitis, laryngitis, epiglottitis, bronchitis, pneumonitis, stomatitis, gingivitis, oesophagitis, gastritis, peritonitis, hepatitis, cholelithiasis, cholecystitis, glomerulonephritis, goodpasture's disease, crescentic, glomerulonephritis, pancreatitis, endomyometritis, myometritis, metritis, cervicitis, endocervicitis, exocervicitis, parametritis, tuberculosis, vaginitis, vulvitis, silicosis, sarcoidosis, pneumoconiosis, pyresis, inflammatory polyarthropathies, psoriatric arthropathies, intestinal fibrosis, bronchiectasis and enteropathic arthropathies.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

One skilled in the art will recognize that, both in vivo and in vitro trials using suitable, known, and generally accepted cell and/or animal models are predictive of the ability of a test compound to treat or prevent a given disorder.

One skilled in the art will further recognize that human clinical trials, including first-in-human, dose ranging, and efficacy trials, in healthy patients and/or those suffering from a given disorder, may be completed according to methods well known in the clinical and medical arts.

Embodiments of various aspects described herein can be defined as in any of the following numbered paragraphs:

Embodiment 1: A compound of Formula (I), wherein Ring A is aryl or heteroaryl; Y is O, S, $NR^{YA}$, $CR^{YA}R^{YB}$, $C{=}CR^{YA}R^{YB}$, SO or $SO_2$, where $R^{YA}$ and $R^{YB}$ are independently aryl, heteroaryl, cycloalkyl, heterocyclyl, H, halogen, cyano (CN), alkyl, haloalkyl, alkenyl, alkynyl, $OR^A$, $NR^AR^B$, $—C(O)R^A$, $C(O)NHR^A$, $C(O)NR^AR^B$, $C(O)[alkylene]NHR^A$, $C(O)[alkylene]NR^AR^B$, $CO_2R^A$, $C(S)NHR^A$, $C(S)NR^AR^B$, $SR^A$, $S(O)R^A$, $SO_2R^A$, $SO_2NHR^A$, $SO_2NR^AR^B$, $NHC(O)R^A$, $NR^AC(O)R^B$, $NHC(O)NHR^A$, $NHC(O)NR^AR^B$, $NR^AC(O)NHR^B$, $NR^AC(O)NR^BR^C$, $P(O)(OH)(OR^A)$, or $P(O)(OR^A)(OR^B)$; $R^1$ is aryl, heteroaryl, cycloalkyl, heterocyclyl, H, halogen, CN, alkyl, haloalkyl, alkenyl, alkynyl, $OR^A$, $NR^AR^B$, $—C(O)R^A$, $C(O)NHR^A$, $C(O)NR^AR^B$, $C(O)[alkylene]NHR^A$, $C(O)[alkylene]NR^AR^B$, $CO_2R^A$, $C(S)NHR^A$, $C(S)NR^AR^B$, $SR^A$, $S(O)R^A$, $SO_2R^A$, $SO_2NHR^A$, $SO_2NR^AR^B$, $NHC(O)R^A$, $NR^AC(O)R^B$, $NHC(O)NHR^A$, $NHC(O)NR^AR^B$, $NR^AC(O)NHR^B$, $NR^AC(O)NR^BR^C$, $P(O)(OH)(OR^A)$, or $P(O)(OR^A)(OR^B)$; $R^2$ is aryl, heteroaryl, alkyl, alkenyl, alkynyl, cycloalkyl, heterocyclyl, H, halogen, CN, haloalkyl, $OR^A$, $NR^AR^B$, $—C(O)R^A$, $C(O)NHR^A$, $C(O)NR^AR^B$, $C(O)[alkylene]NHR^A$, $C(O)[alkylene]NR^AR^B$, $CO_2R^A$, $C(S)NHR^A$, $C(S)NR^AR^B$, $SR^A$, $S(O)R^A$, $SO_2R^A$, $SO_2NHR^A$, $SO_2NR^AR^B$, $NHC(O)R^A$, $NR^AC(O)R^B$, $NHC(O)NHR^A$, $NHC(O)NR^AR^B$, $NR^AC(O)NHR^B$, $NR^AC(O)NR^BR^C$, $P(O)(OH)(OR^A)$, or $P(O)(OR^A)(OR^B)$; RE is $—SO_2R^3$ or CN; $R^3$ is $NR^{N1}R^{N2}$, alkyl, alkenyl, alkynyl, aryl, heteroaryl, cycloalkyl, heterocyclyl, H, halogen, CN, haloalkyl, $OR^A$, $—C(O)R^A$, $C(O)NHR^A$, $C(O)NR^AR^B$, $C(O)[alkylene]NHR^A$, $C(O)[alkylene]NR^AR^B$, $CO_2R^A$, $C(S)NHR^A$, $C(S)NR^AR^B$, $SR^A$, $S(O)R^A$, $SO_2R^A$, $SO_2NHR^A$, $SO_2NR^AR^B$, $NHC(O)R^A$, $NR^AC(O)R^B$, $NHC(O)NHR^A$, $NHC(O)NR^AR^B$, $NR^AC(O)NHR^B$, $NR^AC(O)NR^BR^C$, $P(O)(OH)(OR^A)$, or $P(O)(OR^A)(OR^B)$; wherein $R^{N1}$ and $R^{N2}$ are independently H, alkyl, alkenyl, cycloalkyl, heterocyclyl, H, halogen, CN, haloalkyl, $OR^A$, $—C(O)R^A$, $C(O)NHR^A$, $C(O)NR^AR^B$, $C(O)[alkylene]NHR^A$, $C(O)[alkylene]NR^AR^B$, $CO_2R^A$, $C(S)NHR^A$, $C(S)NR^AR^B$, $SR^A$, $S(O)R^A$, $SO_2R^A$, $SO_2NHR^A$, $SO_2NR^AR^B$, $NHC(O)R^A$, $NR^AC(O)R^B$, $NHC(O)NHR^A$, $NHC(O)NR^AR^B$, $NR^AC(O)NHR^B$, $NR^AC(O)NR^BR^C$, $P(O)(OH)(OR^A)$, or $P(O)(OR^A)(OR^B)$; or $R^{N1}$ and $R^{N2}$ together with the nitrogen they are attached to form a heterocyclyl or heteroaryl; $R^4$ is $OR^{4A}$, H, halogen, CN, alkyl, haloalkyl, alkenyl, alkynyl, aryl, heteroaryl, cycloalkyl, heterocyclyl, $NR^AR^B$, $—C(O)R^A$, $C(O)NHR^A$, $C(O)NR^AR^B$, $C(O)[alkylene]NHR^A$, $C(O)[alkylene]NR^AR^B$, $CO_2R^A$, $C(S)NHR^A$, $C(S)NR^AR^B$, $SR^A$, $S(O)R^A$, $SO_2R^A$, $SO_2NHR^A$, $SO_2NR^AR^B$, $NHC(O)R^A$, $NR^AC(O)R^B$, $NHC(O)NHR^A$, $NHC(O)NR^AR^B$, $NR^AC(O)NHR^B$, $NR^AC(O)NR^BR^C$, $P(O)(OH)(OR^A)$, or $P(O)(OR^A)(OR^B)$; $R^5$ is $OR^{5A}$, H, halogen, CN, alkyl, haloalkyl, alkenyl, alkynyl, aryl, heteroaryl, cycloalkyl, heterocyclyl, $NR^AR^B$, $—C(O)R^A$, $C(O)NHR^A$, $C(O)NR^AR^B$, $C(O)[alkylene]NHR^A$, $C(O)[alkylene]NR^AR^B$, $CO_2R^A$, $C(S)NHR^A$, $C(S)NR^AR^B$, $SR^A$, $S(O)R^A$, $SO_2R^A$, $SO_2NHR^A$, $SO_2NR^AR^B$, $NHC(O)R^A$, $NR^AC(O)R^B$, $NHC(O)NHR^A$, $NHC(O)NR^AR^B$, $NR^AC(O)NHR^B$, $NR^AC(O)NR^BR^C$, $P(O)(OH)(OR^A)$, or $P(O)(OR^A)(OR^B)$; or $R^5$ together with the carbon $R^4$ is attached to forms a heterocyclyl; and RA, RB, R4A and R5A are independently H, substituted or unsubstituted (C1-C8)alkyl, (C1-C8) haloalkyl, (C1-C8) branched alkyl, (C1-C8) linear alkyl, (C1-C8) cycloalkyl, (C1-C8) aryl or phenyl, (C1-C8) alkenyl, or (C1-C8) alkynyl; or a solvate, stereoisomer, or pharmaceutical acceptable salt thereof, and wherein any alkyl, alkenyl, cycloalkyl, heterocyclyl, heteroaryl or aryl is optionally substituted with 1, 2, 3, 4 or more substituents selected independently from the group consisting of heterocycle, OH, oxo (=O), CN, SH, $SO_2NH_2$, $SO_2(C_1\text{-}C_4)$alkyl, $SO_2NH(C_1\text{-}C_4)$alkyl, halogen, $NH_2$, $NH(C_1\text{-}C_4)$alkyl, $N[(C_1\text{-}C_4)alkyl]_2$, $C(O)NH_2$, COOH, COOMe, acetyl, $(C_1\text{-}C_8)$alkyl, $O(C_1\text{-}C_8)$alkyl, —O-heterocyclyl, $O(C_1\text{-}C_8)$ haloalkyl, $(C_2\text{-}C_8)$alkenyl, $(C_2\text{-}C_8)$alkynyl, haloalkyl, thioalkyl, cyanomethylene, alkylaminyl, $NH_2—C(O)$-alkylene, NH(Me)-C(O)-alkylene, $CH_2—C(O)$-lower alkyl, C(O)-lower alkyl, alkylcarbonylaminyl, $CH_2—[CH(OH)]_m—(CH_2)_p—OH$, $CH_2—[CH(OH)]_m—(CH_2)_p—NH_2$ and $CH_2$-aryl-alkoxy, where "m" and "p" are independently 1, 2, 3, 4, 5 or 6.

Embodiment 2: The compound of Embodiment 1, wherein $R^1$ is aryl, heteroaryl, cycloalkyl, or heterocyclyl, each of which can be optionally substituted with 1, 2, 3, 4 or more substituents selected independently from the group consisting of OH, oxo (=O), CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)alkyl]_2$, C(O)$NH_2$, COOH, COOMe, acetyl, $(C_1-C_8)$alkyl, $O(C_1-C_8)$alkyl, —O-heterocyclyl, heterocyclyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ and $CH_2$-aryl-alkoxy, where "m" and "p" are independently 1, 2, 3, 4, 5 or 6.

Embodiment 3: The compound of Embodiments 1 or 2, wherein $R^1$ is an aryl or heteroaryl, each of which can be optionally substituted with 1, 2, 3, 4 or more substituents selected independently from the group consisting of OH, oxo (═O), CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)alkyl]_2$, C(O)$NH_2$, COOH, COOMe, acetyl, $(C_1-C_8)$alkyl, $O(C_1-C_8)$alkyl, —O-heterocyclyl, heterocyclyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ and $CH_2$-aryl-alkoxy, where "m" and "p" are independently 1, 2, 3, 4, 5 or 6.

Embodiment 4: The compound of any one of Embodiments 1-3, wherein $R^1$ is a 3-12 membered heteroaryl comprising 1, 2 or 3 independently selected heteroatoms, or $R^1$ is a 3-12 membered aryl, wherein the 3-12 membered heteroaryl or 3-12 membered aryl is optionally substituted with 1, 2, 3, 4 or more substituents selected independently from the group consisting of OH, oxo (═O), CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)alkyl]_2$, C(O)$NH_2$, COOH, COOMe, acetyl, $(C_1-C_8)$alkyl, $O(C_1-C_8)$alkyl, —O-heterocyclyl, heterocyclyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ and $CH_2$-aryl-alkoxy, where "m" and "p" are independently 1, 2, 3, 4, 5 or 6.

Embodiment 5: The compound of any one of Embodiments 1-4, wherein $R^1$ is phenyl, thiophenyl, benzo[d]thiazolyl (benzthiazolyl), benzo[d]oxazolyl (benzoxazolyl), benzoxazolinonyl, aziridinyl, 2H-azirinyl, oxiranyl, thiiranyl, azetidinyl, 2,3-hydroazetyl, azetyl, 1,3-diazetidinyl, oxetanyl, 2H-oxetyl, thietanyl, 2H-thietyl, azetidin-2-onyl, pyrrolidinyl, 3-pyrrolinyl, 2-pyrrolinyl, 2H-pyrrolyl, 1H-pyrrolyl, pyrazolidinyl, imidazolidinyl, 2-pyrazolinyl, 2-imidazolinyl, pyrazolyl, imidazolyl, 1,2,4-triazolyl, 1,2,3-triazolyl, tetrazolyl, tetrahydrofuran, furan, 1,3-dioxolanyl, tetrahydrothiophenyl, oxazolyl, isoxazolyl, isothiazolyl, thiazolyl, 1,2-oxathiolanyl, 1,3-oxathiolanyl, 1,2,5-oxadiazolyl, 1,2,3-oxadiazolyl, 1,3,4-thiadiazolyl, 1,2,5-thiadiazolyl, sulfolanyl, 2,4-thiazolidinedionyl, succinimidyl, 2-oxazolidonyl, hydantoin, piperidinyl, pyridinyl, piperazinyl, pyridazinyl, pyrimidinyl, pyrazinyl, 1,2,4-triazinyl, 1,3,5-triazinyl, tetrahydropyran, 2H-pyran, 4H-pyran, pyrylium, 1,4-dioxanyl, 1,4-dioxinyl, thianyl, 2H-thiopyran, 4H-thiopyran, 1,3-dithianyl, 1,4-dithianyl, 1,3,5-trithianyl, morpholinyl, 4H-1,2-oxazinyl, 2H-1,2-oxazinyl, 6H-1,2-oxazinyl, 4H-1,3-oxazinyl, 2H-1,3-oxazinyl, 6H-1,3-oxazinyl, 4H-1,4-oxazinyl, 2H-1,4-oxazinyl, thiomorpholinyl, 4H-1,4-thiazinyl, 2H-1,2-thiazinyl, 6H-1,2-thiazinyl, 2H-1,4-thiazinyl, cytosinyl, thyminyl, uracil, thiomorpholine dioxidyl, hexahydro-1H-pyrrolizinyl, 1,4,5,6-tetrahydrocyclopenta[b]pyrrolyl, 1,3a,4,6a-tetrahydropyrrolo[3,2-b]pyrrolyl, 1,4-dihydropyrrolo[3,2-b]pyrrolyl, 1,6-dihydropyrrolo[2,3-b]pyrrolyl, 6H-furo[2,3-b]pyrrolyl, 4H-furo[3,2-b]pyrrolyl, 4H-thieno[3,2-b]pyrrolyl, 6H-thieno[2,3-b]pyrrolyl, 2,3-dihydro-1H-indenyl, indenyl, indolinyl, 3H-indolyl, 1H-indolyl, 2H-isoindolyl, indolizinyl, 1H-indazolyl, benzimidazolyl, 7-azaindolyl, 4-azaindolyl, 5-azaindolyl, 6-azaindolyl, 7-azaindolyl, pyrazolo[1,5-a]pyrimidinyl, purinyl, benzofuran, isobenzofuran, benzo[c]thiophenyl, benzo[b]thiophenyl, benzo[d]isoxazolyl, benzo[c]isoxazolyl, benzo[d]isothiazolyl, benzo[c]isothiazolyl, benzo[d]oxazolyl, benzo[c][1,2,5]thiadiazolyl, 1,2-benzisothiazole-3(2H)-onyl, adeninyl, guaninyl, decahydroisoquinolinyl, decahydroquinolinyl, 1,2,3,4-tetrahydroquinolinyl, 1,2-dihydroquinolinyl, 1,2-dihydroisoquinolinyl, quinolinyl, isoquinolinyl, 4H-quinolizinyl, quinoxalinyl, phthalazinyl, quinazolinyl, cinnolinyl, 1,8-naphthridinyl, pyrido[3,2-d]pyrimidinyl, pyrido[4,3-d]pyrimidinyl, pyrido[3,4-b]pyrazinyl, pyrido[2,3-b]pyrazinyl, pteridinyl, 2H-chromenyl, 1H-isochromenyl, 3H-isochromenyl, 2H-chromen-2-onyl, 2H-benzo[e][1,2]oxazinyl, 2H-benzo[e][1,3]oxazinyl, 2H-benzo[b][1,4]oxazinyl, quinoline-2(1H)-onyl, isoquinolin-1(2H)-onyl, fluorenyl, carbazolyl, dibenzofuran, acridinyl, phenazinyl, phenoxazinyl, phenothiazinyl, phenoxathiinyl, quinuclidinyl, 1-azaadamantanyl, 2-azaadamantanyl, 2,3-dihydroazepinyl, 2,5-dihydroazepinyl, 4,5-dihydroazepinyl, azepinyl, 2H-azepinyl, 3H-azepinyl, 4H-azepinyl, 1,2-diazepinyl, 1,3-diazepinyl, oxepanyl, thiepinyl, 1,4-thiazepinyl, azocanyl, azocinyl, thiocanyl, azonanyl, azecinyl, spiro[cyclobutene-1,3]-indole], 1-oxaspiro[4.5]decanyl, 1,6-dioxaspiro[3.4]octanyl, 3',4',5',6'-tetrahydro-3H-spiro[isobenzofuran-1,2'-pyran], 1-oxaspiro[4.4]nonan-2-onyl, 2-oxa-7-azaspiro[3.5]nonanyl, 1,4-dioxa-7-azaspiro[4.4.]nonanyl, 1,3-diazaspiro[4.4]non-2-en-4-onyl, 2,9-diazaspiro[5.5]undecan-1-onyl, 8-azaspiro[4.5]decane-7,9-dionyl, 1,3,8-triazaspiro[4.5]decan-4-onyl, or 1,4-dithia-7-azaspiro[4.4]nonanyl, each of which can be optionally substituted with 1, 2, 3, 4 or more substituents selected independently from the group consisting of OH, oxo (═O), CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)alkyl]_2$, C(O)$NH_2$, COOH, COOMe, acetyl, $(C_1-C_8)$alkyl, $O(C_1-C_8)$alkyl, —O-heterocyclyl, heterocyclyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ and $CH_2$-aryl-alkoxy, where "m" and "p" are independently 1, 2, 3, 4, 5 or 6.

Embodiment 6: The compound of any one of Embodiments 1-5, wherein $R^1$ is phenyl, thiophenyl, benzo[d]thiazolyl (benzthiazolyl), benzo[d]oxazolyl (benzoxazolyl), or benzoxazolinonyl, each of which is optionally substituted with 1, 2, 3, 4 or more substituents selected independently from OH, oxo (═O), CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)alkyl]_2$, $C(O)NH_2$, COOH, COOMe, acetyl, $(C_1$-$C_8)$alkyl, $O(C_1$-$C_8)$alkyl, —O-heterocyclyl, heterocyclyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ and $CH_2$-aryl-alkoxy, where "m" and "p" are independently 1, 2, 3, 4, 5 or 6.

Embodiment 7: The compound of any one of Embodiments 1-6, wherein $R^1$ is

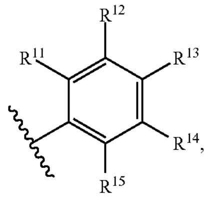

wherein $R^{11}$, $R^{12}$, $R^{13}$, $R^{14}$ and $R^{15}$ are independently H, OH, CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)alkyl]_2$, $C(O)NH_2$, COOH, COOMe, acetyl, $(C_1$-$C_8)$alkyl, $O(C_1$-$C_8)$alkyl, —O-heterocyclyl, heterocyclyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy, where "m" and "p" are independently 1, 2, 3, 4, 5 or 6; and optionally any two vicinal $R^{11}$, $R^{12}$, $R^{13}$, $R^{14}$, and $R^{15}$ together with the carbons they are attached to can form a 3-12 membered aryl, 3-12 membered heteroaryl, 3-12 membered cycloalkyl or 3-12 membered heterocyclyl, each of which can be optionally substituted with 1, 2, 3, 4 or more substituents selected independently from the group consisting of OH, oxo (═O), CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)alkyl]_2$, $C(O)NH_2$, COOH, COOMe, acetyl, $(C_1$-$C_8)$alkyl, $O(C_1$-$C_8)$alkyl, —O-heterocyclyl, heterocyclyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ and $CH_2$-aryl-alkoxy, where "m" and "p" are independently 1, 2, 3, 4, 5 or 6.

Embodiment 8: The compound of any one of Embodiments 1-7, wherein $R^1$ is

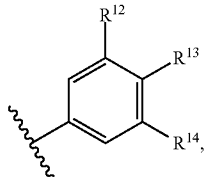

where $R^{12}$, $R^{13}$, and $R^{14}$ are independently H, halogen, CN, OH, SH, COOH, COOMe, acetyl, $(C_1$-$C_8)$alkyl, $O(C_1$-$C_8)$alkyl, —O-heterocyclyl, heterocyclyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, or $CH_2$—$[CH(OH)]_m$—$(CH_2)_p$—OH, optionally any two vicinal $R^{12}$, $R^{13}$, and $R^{14}$ together with the carbons they are attached to can form a 3-12 membered aryl, 3-12 membered heteroaryl, 3-12 membered cycloalkyl or 3-12 membered heterocyclyl, each of which can be optionally substituted with 1, 2, 3, 4 or more substituents selected independently from the group consisting of OH, oxo (═O), CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)alkyl]_2$, $C(O)NH_2$, COOH, COOMe, acetyl, $(C_1$-$C_8)$alkyl, $O(C_1$-$C_8)$alkyl, —O-heterocyclyl, heterocyclyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ and $CH_2$-aryl-alkoxy, where "m" and "p" are independently 1, 2, 3, 4, 5 or 6.

Embodiment 9: The compound of any one of Embodiments 1-8, wherein $R^1$ is phenyl, 4-bromophenyl, 4-cyanophenyl, 4-methoxyphenyl, 4-fluorophenyl, 4-chlorophenyl, 4-iodophenyl, 4-trifluoromethylphenyl, 3-trifluoromethylphenyl, 4-trifluoromethylphenyl, 4-cyanophenyl, benzothiazol-6-yl, benzothiazole-5-yl, 2-benzoxazolinon-6-yl, 2-benzoxazolinon-5-yl, 4-ethynylphenyl, 3,4,5-trimethylphenyl, 5-carboxythiophen-2-yl, 5-carboxythiophen-3-yl, 5-carboxythiophen-4-yl, 4-difluoromethoxyphenyl, 4-(azetidin-3-yl)phenyl, 4-(2-hydroxymethylazetidin-3-yl)phenyl, 4-(2-(2-hydroxyethyl) azetidine-3-yl)phenyl, 4-(azetidine-3-ylmethyl)phenyl, 4-(azetidine-3-yl-hydroxy)phenyl, 4-(pyrrolidine-3-yl)phenyl, 4-piperidin-4-yl)phenyl, or benzimidazol-6-yl.

Embodiment 10: The compound of any one of Embodiments 1-8, wherein $R^1$ is

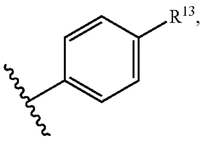

wherein $R^{13}$ is methoxy, fluorine, bromine, chlorine, iodine, trifluoromethyl, nitrile, acetylene, $OCF_2H$, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{13}$ and a vicinal hydrogen, together with the carbons they are attached to, form imidazole.

Embodiment 11: The compound of any one of Embodiments 1-9, wherein $R^1$ is 4-bromophenyl, 4-methoxyphenyl, 4-cyanophenyl, 4-trifluoromethylphenyl, 4-(azetidin-3-yl)phenyl, 4-(2-hydroxymethylazetidin-3-yl)phenyl, 4-(2-(2-hydroxyethyl) azetidine-3-yl)phenyl, 4-(azetidine-3-ylmethyl)phenyl, 4-(azetidine-3-yl-hydroxy)phenyl, 4-(pyrrolidine-3-yl)phenyl, 4-piperidin-4-yl)phenyl, or benzimidazol-6-yl.

Embodiment 12: The compound of any one of Embodiments 1-11, wherein $R^2$ is an aryl, heteroaryl, cycloalkyl, heterocyclyl, alkyl, alkenyl, alknyl, halogen, CN, or haloalkyl, wherein alkyl, alkenyl, alkynyl, cycloalkyl, heterocyclyl, heteroaryl or aryl is optionally substituted with 1, 2, 3, 4 or more substituents selected independently from the group consisting of heterocycle, OH, oxo (=O), CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)alkyl]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ and $CH_2$-aryl-alkoxy, where “m” and “p” are independently 1, 2, 3, 4, 5 or 6.

Embodiment 13: The compound of any one of claims 1-12, wherein $R^2$ is an aryl, heteroaryl, cycloalkyl, heterocyclyl, alkyl, alkenyl, or alkynyl, and wherein the aryl, heteroaryl, cycloalkyl, heterocyclyl, alkyl, alkenyl, or alkynyl is optionally substituted with 1, 2, 3, 4 or more substituents selected independently from the group consisting of heterocycle, OH, oxo (=O), CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)alkyl]2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ and $CH_2$-aryl-alkoxy, where “m” and “p” are independently 1, 2, 3, 4, 5 or 6.

Embodiment 14: The compound of any one of Embodiments 1-13, wherein $R^2$ is a 3-12 membered heteroaryl comprising 1, 2 or 3 independently selected heteroatoms, or $R^2$ is a 3-12 membered aryl, or $R^2$ is a 3-12 membered heterocyclyl comprising 1, 2 or 3 independently selected heteroatoms, 3-12 membered cycloalkyl, $(C_1-C_8)$alkyl, $(C_1-C_8)$haloalkyl, $(C_2-C_8)$alkenyl, or $(C_2-C_8)$alkynyl, and wherein the 3-12 membered heteroaryl, 3-12 membered aryl, 3-12 membered heterocyclyl, 3-12 membered cycloalkyl, $(C_1-C_8)$alkyl, $(C_1-C_8)$haloalkyl, $(C_2-C_8)$alkenyl, or $(C_2-C_8)$alkynyl is optionally substituted with 1, 2, 3, 4 or more substituents selected independently from the group consisting of OH, oxo (=O), CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)alkyl]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ and $CH_2$-aryl-alkoxy, where “m” and “p” are independently 1, 2, 3, 4, 5 or 6.

Embodiment 15: The compound of any one of Embodiments 1-14, wherein $R^2$ is a 3-12 membered heteroaryl comprising 1, 2 or 3 independently selected heteroatoms, or $R^2$ is a 3-12 membered aryl, and wherein the 3-12 membered heteroaryl or 3-12 membered aryl is optionally substituted with 1, 2, 3, 4 or more substituents selected independently from the group consisting of OH, oxo (=O), CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)alkyl]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy, where “m” and “p” are independently 1, 2, 3, 4, 5 or 6.

Embodiment 16: The compound of any one of Embodiments 1-15, wherein $R^2$ is phenyl, thiophenyl, benzo[d]thiazolyl (benzthiazolyl), benzo[d]oxazolyl (benzoxazolyl), benzoxazolinonyl, aziridinyl, 2H-azirinyl, oxiranyl, thiiranyl, azetidinyl, 2,3-hydroazetyl, azetyl, 1,3-diazetidinyl, oxetanyl, 2H-oxetyl, thietanyl, 2H-thietyl, azetidin-2-onyl, pyrrolidinyl, 3-pyrrolinyl, 2-pyrrolinyl, 2H-pyrrolyl, 1H-pyrrolyl, pyrazolidinyl, imidazolidinyl, 2-pyrazolinyl, 2-imidazolinyl, pyrazolyl, imidazolyl, 1,2,4-triazolyl, 1,2,3-triazolyl, tetrazolyl, tetrahydrofuran, furan, 1,3-dioxolanyl, tetrahydrothiophenyl, oxazolyl, isoxazolyl, isothiazolyl, thiazolyl, 1,2-oxathiolanyl, 1,3-oxathiolanyl, 1,2,5-oxadiazolyl, 1,2,3-oxadiazolyl, 1,3,4-thiadiazolyl, 1,2,5-thiadiazolyl, sulfolanyl, 2,4-thiazolidinedionyl, succinimidyl, 2-oxazolidonyl, hydantoin, piperidinyl, pyridinyl, piperazinyl, pyridazinyl, pyrimidinyl, pyrazinyl, 1,2,4-triazinyl, 1,3,5-triazinyl, tetrahydropyran, 2H-pyran, 4H-pyran, pyrylium, 1,4-dioxanyl, 1,4-dioxinyl, thianyl, 2H-thiopyran, 4H-thiopyran, 1,3-dithianyl, 1,4-dithianyl, 1,3,5-trithianyl, morpholinyl, 4H-1,2-oxazinyl, 2H-1,2-oxazinyl, 6H-1,2-oxazinyl, 4H-1,3-oxazinyl, 2H-1,3-oxazinyl, 6H-1,3-oxazinyl, 4H-1,4-oxazinyl, 2H-1,4-oxazinyl, thiomorpholinyl, 4H-1,4-thiazinyl, 2H-1,2-thiazinyl, 6H-1,2-thiazinyl, 2H-1,4-thiazinyl, cytosinyl, thyminyl, uracil, thiomorpholine dioxidyl, hexahydro-1H-pyrrolizinyl, 1,4,5,6-tetrahydrocyclopenta[b]pyrrolyl, 1,3a,4,6a-tetrahydropyrrolo[3,2-b]pyrrolyl, 1,4-dihydropyrrolo[3,2-b]pyrrolyl, 1,6-dihydropyrrolo[2,3-b]pyrrolyl, 6H-furo[2,3-b]pyrrolyl, 4H-furo[3,2-b]pyrrolyl, 4H-thieno[3,2-b]pyrrolyl, 6H-thieno[2,3-b]pyrrolyl, 2,3-dihydro-1H-indenyl, indenyl, indolinyl, 3H-indolyl, 1H-indolyl, 2H-isoindolyl, indolizinyl, 1H-indazolyl, benzimidazolyl, 7-azaindolyl, 4-azaindolyl, 5-azaindolyl, 6-azaindolyl, 7-azaindolyl, pyrazolo[1,5-a]pyrimidinyl, purinyl, benzofuran, isobenzofuran, benzo[c]thiophenyl, benzo[b]thiophenyl, benzo[d]isoxazolyl, benzo[c]isoxazolyl, benzo[d]isothiazolyl, benzo[c]isothiazolyl, benzo[d]oxazolyl, benzo[c][1,2,5]thiadiazolyl, 1,2-benzisothiazole-3(2H)-onyl, adeninyl, guaninyl, decahydroisoquinolinyl, decahydroquinolinyl, 1,2,3,4-tetrahydroquinolinyl, 1,2-dihydroquinolinyl, 1,2-dihydroisoquinolinyl, quinolinyl, isoquinolinyl, 4H-quinolizinyl, quinoxalinyl, phthalazinyl, quinazolinyl, cinnolinyl, 1,8-naphthridinyl, pyrido[3,2-d]pyrimidinyl, pyrido[4,3-d]pyrimidinyl, pyrido[3,4-b]pyrazinyl, pyrido[2,3-b]pyrazinyl, pteridinyl, 2H-chromenyl, 1H-isochromenyl, 3H-isochromenyl, 2H-chromen-2-onyl, 2H-benzo[e][1,2]oxazinyl, 2H-benzo[e][1,3]oxazinyl, 2H-benzo[b][1,4]oxazinyl, quinoline-2(1H)-onyl, isoquinolin-1(2H)-onyl, fluorenyl, carbazolyl, dibenzofuran, acridinyl, phenazinyl, phenoxazinyl, phenothiazinyl, phenoxathiinyl, quinuclidinyl, 1-azaadamantanyl, 2-azaadamantanyl, 2,3-dihydroazepinyl, 2,5-dihydroazepinyl, 4,5-dihydroazepinyl, azepinyl, 2H-azepinyl, 3H-azepinyl, 4H-azepinyl, 1,2-diazepinyl, 1,3-diazepinyl, oxepanyl, thiepinyl, 1,4-thiazepinyl, azocanyl, azocinyl, thiocanyl, azonanyl, azecinyl, spiro[cyclobutene-1,3]-indole], 1-oxaspiro[4.5]decanyl, 1,6-dioxaspiro[3.4]octanyl, 3',4',5',6'-tetrahydro-3H-spiro[isobenzofuran-1,2'-pyran], 1-oxaspiro[4.4]nonan-2-onyl, 2-oxa-7-azaspiro[3.5]nonanyl, 1,4-dioxa-7-azaspiro[4.4.]nonanyl, 1,3-diazaspiro[4.4]non-2-en-4-onyl, 2,9-diazaspiro[5.5]undecan-1-onyl, 8-azaspiro[4.5]decane-7,9-dionyl, 1,3,8-triazaspiro[4.5]decan-4-onyl, or 1,4-dithia-7-azaspiro[4.4]nonanyl, and each of which is optionally substituted with 1, 2, 3, 4 or more substituents selected independently from the group consisting of OH, oxo (=O), CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)alkyl]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ and $CH_2$-aryl-alkoxy, where "m" and "p" are independently 1, 2, 3, 4, 5 or 6.

Embodiment 17: The compound of any one of Embodiments 1-16, wherein $R^2$ is phenyl, pyridinyl, or pyrimidinyl, each of which is optionally substituted with 1, 2, 3, 4 or more substituents selected independently from the group consisting of OH, oxo (=O), CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)alkyl]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ and $CH_2$-aryl-alkoxy, where "m" and "p" are independently 1, 2, 3, 4, 5 or 6.

Embodiment 18: The compound of any one of Embodiments 1-15, wherein $R^2$ is

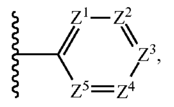

where $Z^1$, $Z^2$, $Z^3$, $Z^4$ and $Z^5$ are independently $CR^{21}$ or N, where each $R^{21}$ is independently H, OH, CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)alkyl]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy, where "m" and "p" are independently 1, 2, 3, 4, 5 or 6; and optionally any two vicinal $R^{11}$, $R^{12}$, $R^{13}$, $R^{14}$, and $R^{15}$ together with the carbons they are attached to can form a 5-8 membered aryl, heteroaryl, cycloalkyl or heterocyclyl, each of which can be optionally substituted with 1, 2, 3, 4 or more substituents selected independently from OH, oxo (=O), CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)alkyl]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy, where "m" and "p" are independently 1, 2, 3, 4, 5 or 6, and provided that only 0, 1, 2, 3 or 4 of $Z^1$, $Z^2$, $Z^3$, $Z^4$ and $Z^5$ are N.

Embodiment 19: The compound of any one of Embodiments 1-18, wherein $R^2$ is phenyl, 4-trifluoromethylphenyl, 2-bromo-5-fluoropheyl, 2-chloro-6-fluorohenyl, 3,5-dichlorophenyl, pentafluorophenyl, 2-fluoro-3-trifluoromethyl-5-methoxyphenyl,
4-trifluoromethylphenyl, 2-pyridinyl, 3-pyridinyl, or 4-pyrimidinyl, optionally, $R^2$ is phenyl.

Embodiment 20: The compound of any one of Embodiments 1-14, wherein $R^2$ is $(C_1-C_8)$alkyl, $(C_1-C_8)$haloalkyl, $(C_2-C_8)$alkenyl), or $(C_2-C_8)$alkynyl, and wherein the $(C_1-C_8)$alkyl, $(C_1-C_8)$haloalkyl, $(C_2-C_8)$alkenyl), or $(C_2-C_8)$alkynyl is optionally substituted with 1, 2, 3, 4 or more substituents selected independently from the group consisting of heterocycle, OH, oxo (=O), CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)alkyl]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ and $CH_2$-aryl-alkoxy, where "m" and "p" are independently 1, 2, 3, 4, 5 or 6.

Embodiment 21: The compound of Embodiment 20, wherein $R^2$ is methyl, ethyl, propyl, propenyl, propynyl, isopropyl, butyl, isobutenyl, butan-2-yl, 2-methylpropyl, tert-butyl, pentyl, 2-methylbutan-2-yl, pentan-2-yl, pentan-3-yl, 3-methylbutan-2-yl, each of which can be optionally substituted with 1, 2, 3, 4 or more substituents selected independently from the group consisting of heterocycle, H, oxo (=O), CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)alkyl]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ and $CH_2$-aryl-alkoxy, where "m" and "p" are independently 1, 2, 3, 4, 5 or 6.

Embodiment 22: The compound of Embodiments 20 or 21, wherein $R^2$ is methyl, ethyl, propyl, propenyl, propynyl, isopropyl, butyl, isobutenyl, butan-2-yl, 2-methylpropyl, tert-butyl, pentyl, 2-methylbutan-2-yl, pentan-2-yl, pentan-3-yl, or 3-methylbutan-2-yl.

Embodiment 23: The compound of any one of Embodiments 20-23, wherein $R^2$ is methyl, ethyl, propyl, propenyl, propynyl, isopropyl, 2-methylpropyl, isobutenyl, or tert-butyl.

Embodiment 24: The compound of Embodiment 21 or 22, wherein $R^2$ is —$CH_2L$, wherein L is alkoxy, alkylamino, or heterocycle.

Embodiment 25: The compound of Embodiment 24, wherein L is a heterocycle, optionally L is diazinanyl (e.g., 1,4-diazinyl such as N-methyl-1,4-diazinzyl), morpholinyl or N-methyl-morpholinyl.

Embodiment 26: The compound of any one of Embodiments 1-25, wherein $R^E$ is —$SO_2$—$R^3$ and the compound is of Formula (Ia), or a solvate, stereoisomer, or pharmaceutical acceptable salt thereof.

Embodiment 27: The compound of Embodiment 26, wherein $R^3$ is $NR^{N1}R^{N2}$, and $R^{N1}$ and $R^{N2}$ are independently H, $(C_1$-$C_8)$alkyl, $(C_2$-$C_8)$alkenyl, $(C_2$-$C_8)$alkynyl, $(C_1$-$C_8)$ cycloalkyl, heterocyclyl, H, halogen, CN, $(C_1$-$C_8)$haloalkyl, $OR^A$, —$C(O)R^A$, $C(O)NHR^A$, $C(O)NR^AR^B$, $C(O)$[alkylene]$NHR^A$, $C(O)$[alkylene]$NR^AR^B$, $CO_2R^A$, $C(S)NHR^A$, $C(S)NR^AR^B$, $SR^A$, $S(O)R^A$, $SO_2R^A$, $SO_2NHR^A$, $SO_2NR^AR^B$, $NHC(O)R^A$, $NR^AC(O)R^B$, $NHC(O)NHR^A$, $NHC(O)NR^AR^B$, $NR^AC(O)NHR^B$, $NR^AC(O)NR^BR^C$, $P(O)(OH)(OR^A)$, or $P(O)(OR^A)(OR^B)$; or $R^{N1}$ and $R^{N2}$ together with the nitrogen they are attached to form a heterocyclyl or heteroaryl, each of which can be optionally substituted with substituted with 1, 2, 3, 4 or more substituents selected independently from the group consisting of OH, oxo (=O), CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)$alkyl$]_2$, $C(O)NH_2$, COOH, COOMe, acetyl, $(C_1$-$C_8)$alkyl, $O(C_1$-$C_8)$alkyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ and $CH_2$-aryl-alkoxy, where "m" and "p" are independently 1, 2, 3, 4, 5 or 6.

Embodiment 28: The compound of any one Embodiments 26-27, wherein $R^{N1}$ and $R^{N2}$ are independently H, $(C_1$-$C_8)$alkyl, $(C_1$-$C_8)$haloalkyl, $(C_2$-$C_8)$alkenyl), or $(C_2$-$C_8)$alkynyl; or $R^{N1}$ and $R^{N2}$ together with the nitrogen they are attached to form a 3-12 membered heterocyclyl, and wherein the $(C_1$-$C_8)$alkyl, $(C_1$-$C_8)$haloalkyl, $(C_2$-$C_8)$alkenyl), $(C_2$-$C_8)$alkynyl, or 3-12 membered heterocyclyl is optionally substituted with 1, 2, 3, 4 or more substituents selected independently from the group consisting of OH, oxo (=O), CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)$alkyl$]_2$, $C(O)NH_2$, COOH, COOMe, acetyl, $(C_1$-$C_8)$alkyl, $O(C_1$-$C_8)$alkyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ and $CH_2$-aryl-alkoxy, where "m" and "p" are independently 1, 2, 3, 4, 5 or 6.

Embodiment 29: The compound of any one of Embodiments 26-28, wherein $R^{N1}$ and $R^{N2}$ are independently H, methyl, ethyl, propyl, isopropyl, butyl, butan-2-yl, 2-methylpropyl, tert-butyl, pentyl, 2-methylbutan-2-yl, 2,2-dimethylpropyl, 3-methylbutyl, pentan-2-yl, pentan-3-yl, 3-methylbutan-2-yl, 2-methylbutyl, 2-methylpentyl, 3-methylpentyl, 2,3-dimethylbutyl, 2,2-dimethylbutyl, linear or branched hexyl, heptyl, or octyl, vinyl, allyl, acetylenyl, propylenyl, 1-butynl, 2-butynl, 1-pentynyl, 2-pentynyl, 3-methyl-1-butynl, 1-hexynyl, 2-hexynl, 3-hexynl, 4-methyl-1-pentynl, 4-methyl-2-pentynl, or 3-methyl-1-pentynl, 3,3-dimethyl-1-butynl, each of which can be optionally substituted with 1, 2, 3, 4 or more substituents selected independently from the group consisting of OH, oxo (=O), CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)$alkyl$]_2$, $C(O)NH_2$, COOH, COOMe, acetyl, $(C_1$-$C_8)$alkyl, $O(C_1$-$C_8)$alkyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ and $CH_2$-aryl-alkoxy, where "m" and "p" are independently 1, 2, 3, 4, 5 or 6.

Embodiment 30: The compound of any one of Embodiments 26-29, wherein $R^{N1}$ and $R^{N2}$ are independently H, methyl, ethyl, 2-hydroxyethyl, 2-dimetylaminoethyl, 2-hydroxy-1,1-dimethylethyl, propyl, isopropyl, 3-hyroxypropyl, 3-dimetylaminopropyl, butyl, butan-2-yl, 2-methylpropyl, tert-butyl, pentyl, 2-methylbutan-2-yl, 2,2-dimethylpropyl, 3-methylbutyl, pentan-2-yl, pentan-3-yl, 3-methylbutan-2-yl, 2-methylbutyl, 2-methylpentyl, 3-methylpentyl, 2,3-dimethylbutyl, 2,2-dimethylbutyl, vinyl, allyl, acetylenyl, or propylenyl, optionally, $R^{N1}$ and $R^{N2}$ are independently H, methyl, ethyl, 2-hydroxyethyl, 2-dimetylaminoethyl, 2-hydroxy-1,1-dimethylethyl, propyl, isopropyl, 3-hyroxypropyl, or 3-dimetylaminopropyl.

Embodiment 31: The compound of any one of Embodiments 26-30, wherein at least one of $R^{N1}$ and $R^{N2}$ (e.g., only one or both of $R^{N1}$ and $R^{N2}$) is not H.

Embodiment 32: The compound of any one of Embodiments 26-30, wherein at least one of $R^{N1}$ and $R^{N2}$ (e.g., only one of $R^{N1}$ and $R^{N2}$) is H.

Embodiment 33: The compound of any one of Embodiments 26-30, wherein $R^3$ is N-isopropyl-N-methylamino, dimethylamino, diethylamino, N-2-hydoxyethyl-N-methylamino, 2-hydroxyethylamino, 3-hydroxypropylamino, 2-hydroxy-2,2-dimethylamino, 2-dimethylaminoethylamino, 3-dimethylaminopropylamino or di (2-dimethylaminoethyl) amino.

Embodiment 34: The compound of any one of Embodiments 26-28, wherein $R^3$ is $NR^{N1}R^{N2}$, and $R^{N1}$ and $R^{N2}$ together with the nitrogen they are attached to form a heterocyclyl or heteroaryl, each of which can be optionally substituted with 1, 2, 3, 4 or more substituents selected independently from OH, oxo (=O), CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)$alkyl$]_2$, $C(O)NH_2$, COOH, COOMe, acetyl, $(C_1$-$C_8)$alkyl, $O(C_1$-$C_8)$alkyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy, where "m" and "p" are independently 1, 2, 3, 4, 5 or 6.

Embodiment 35: The compound of Embodiment 34, wherein $R^{N1}$ and $R^{N2}$ together with the nitrogen they are attached to attached to form 3-12 membered heterocycle comprising 1, 2, or 3 heteroatoms selected independently from the group consisting of O, S, and N, or $R^{N1}$ and $R^{N2}$ together with the nitrogen they are attached to attached to form a 3-12 membered heteroaryl comprising 1, 2, or 3 heteroatoms selected independently from the group consisting of O, S, and N, and wherein the 3-12 membered heteroaryl or 3-12 membered aryl is optionally substituted with 1, 2, 3, 4 or more substituents selected independently from OH, oxo (=O), CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)$alkyl$]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2—[CH(OH)]_m—(CH_2)_p—OH$, $CH_2—[CH(OH)]_m—(CH_2)_p—NH_2$ or $CH_2$-aryl-alkoxy, where "m" and "p" are independently 1, 2, 3, 4, 5 or 6.

Embodiment 36: The compound of Embodiment 34 or 35, wherein $R^{N1}$ and $R^{N2}$ together with the nitrogen they are attached to attached to form aziridine, 2H-azirine, azetidine, 2,3-hydroazete, azete, 1,3-diazetidine, azetidin-2-one, pyrrolidine, 3-pyrroline, 2-pyrroline, 2H-pyrrole, 1H-pyrrole, pyrazolidine, imidazolidine, 2-pyrazoline, 2-imidazoline, pyrazole, imidazole, 1,2,4-triazole, 1,2,3-triazole, tetrazole, oxazole, isoxazole, isothiazole, thiazole, 1,2,5-oxadiazole, 1,2,3-oxadiazole, 1,3,4-thiadiazole, 1,2,5-thiadiazole, 2,4-thiazolidinedione, succinimide, 2-oxazolidone, hydantoin, piperidine, pyridine, piperazine, pyridazine, pyrimidine, pyrazine, 1,2,4-triazine, 1,3,5-triazine, morpholine, 4H-1,2-oxazine, 2H-1,2-oxazine, 6H-1,2-oxazine, 4H-1,3-oxazine, 2H-1,3-oxazine, 6H-1,3-oxazine, 4H-1,4-oxazine, 2H-1,4-oxazine, thiomorpholine, 4H-1,4-thiazine, 2H-1,2-thiazine, 6H-1,2-thiazine, 2H-1,4-thiazine, cytosine, thymine, uracil, thiomorpholine dioxide, hexahydro-1H-pyrrolizine, 1,4,5,6-tetrahydrocyclopenta[b]pyrrole, 1,3a,4,6a-tetrahydropyrrolo[3,2-b]pyrrole, 1,4-dihydropyrrolo[3,2-b]pyrrole, 1,6-dihydropyrrolo[2,3-b]pyrrole, 6H-furo[2,3-b]pyrrole, 4H-furo[3,2-b]pyrrole, 4H-thieno[3,2-b]pyrrole, 6H-thieno[2,3-b]pyrrole, indoline, 3H-indole, 1H-indole, 2H-isoindole, indolizine, 1H-indazole, benzimidazole, 7-azaindole, 4-azaindole, 5-azaindole, 6-azaindole, 7-azaindole, pyrazolo[1,5-a]pyrimidine, purine, benzo[d]isoxazole, benzo[c]isoxazole, benzo[d]isothiazole, benzo[c]isothiazole, benzo[d]oxazole, benzo[d]thiazole, benzo[c][1,2,5]thiadiazole, 1,2-benzisothiazole-3(2H)-one, adenine, guanine, decahydroisoquinoline, decahydroquinoline, 1,2,3,4-tetrahydroquinoline, 1,2-dihydroquinoline, 1,2-dihydroisoquinoline, quinoline, isoquinoline, 4H-quinolizine, quinoxaline, phthalazine, quinazoline, cinnoline, 1,8-naphthridine, pyrido[3,2-d]pyrimidine, pyrido[4,3-d]pyrimidine, pyrido[3,4-b]pyrazine, pyrido[2,3-b]pyrazine, pteridine, 2H-benzo[e][1,2]oxazine, 2H-benzo[e][1,3]oxazine, 2H-benzo[b][1,4]oxazine, quinoline-2(1H)-one, isoquinolin-1(2H)-one, carbazole, acridine, phenazine, phenoxazine, phenothiazine, quinuclidine, 1-azaadamantane, 2-azaadamantane, 2,3-dihydroazepine, 2,5-dihydroazepine, 4,5-dihydroazepine, azepine, 2H-azepine, 3H-azepine, 4H-azepine, 1,2-diazepine, 1,3-diazepine, 1,4-diazepine, 1,4-thiazepine, azocane, azocine, azonane, azecine, spiro[cyclobutene-1,3]-indole], 2-oxa-7-azaspiro[3.5]nonane, 1,4-dioxa-7-azaspiro[4.4.]nonane, 1,3-diazaspiro[4.4]non-2-en-4-one, 2,9-diazaspiro[5.5]undecan-1-one, 8-azaspiro[4.5]decane-7,9-dione, 1,3,8-triazaspiro[4.5]decan-4-one, or 1,4-dithia-7-azaspiro[4.4]nonane, and each of which is optionally substituted with 1, 2, 3, 4 or more substituents selected independently from OH, oxo (=O), CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)alkyl]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2—[CH(OH)]_m—(CH_2)_p—OH$, $CH_2—[CH(OH)]_m—(CH_2)_p—NH_2$ or $CH_2$-aryl-alkoxy, where "m" and "p" are independently 1, 2, 3, 4, 5 or 6.

Embodiment 37: The compound of any one of Embodiments 34-36, wherein $R^3$ is azirdinyl, azetidinyl, piperdinyl, pyrrolidinyl, or morpholinyl, each of which can be optionally substituted with 1, 2, 3, 4 or more substituents selected independently from OH, oxo (=O), CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)alkyl]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2—[CH(OH)]_m—(CH_2)_p—OH$, $CH_2—[CH(OH)]_m—(CH_2)_p—NH_2$ or $CH_2$-aryl-alkoxy, where "m" and "p" are independently 1, 2, 3, 4, 5 or 6.

Embodiment 38: The compound of any one of Embodiments 34-37, wherein $R^3$ is azetidinyl, 3-methylazetidinyl, 3-hydroxyazetidinyl, pyrrolidinyl, 2-(trifluoromethyl)pyrrolidinyl, morpholinyl, piperidinyl or 4-hydroxypiperdinyl.

Embodiment 39: The compound of Embodiment 26, wherein $R^3$ is $(C_1-C_8)$alkyl, $(C_1-C_8)$haloalkyl, $(C_2-C_8)$alkenyl, or $(C_2-C_8)$alkynyl, each of which can be optionally substituted with 1, 2, 3, 4 or more substituents selected independently from OH, oxo (=O), CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)alkyl]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2—[CH(OH)]_m—(CH_2)_p—OH$, $CH_2—[CH(OH)]_m—(CH_2)_p—NH_2$ or $CH_2$-aryl-alkoxy, where "m" and "p" are independently 1, 2, 3, 4, 5 or 6, optionally, $R^3$ is $(C_1-C_8)$ alkyl, e.g., methyl.

Embodiment 40: The method of any one of Embodiments 1-25, wherein RE is cyano (—CN).

Embodiment 41: The compound of any one of Embodiments 1-40, wherein $R^4$ is $OR^{4A}$, halogen, CN, alkyl, alkenyl, alkynyl, or haloalkyl, and wherein alkyl, alkenyl, or alkynyl, is optionally substituted with 1, 2, 3, 4 or more substituents selected independently from OH, oxo (=O), CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)alkyl]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2—[CH(OH)]_m—(CH_2)_p—OH$, $CH_2—[CH(OH)]_m—(CH_2)_p—NH_2$ or $CH_2$-aryl-alkoxy, where "m" and "p" are independently 1, 2, 3, 4, 5 or 6.

Embodiment 42: The compound of any one of Embodiment 1-41, wherein $R^4$ is $OR^{4A}$, halogen or CN, and where $R^{4A}$ is H, $(C_1-C_8)$alkyl, $(C_1-C_8)$haloalkyl, $(C_2-C_8)$alkenyl, or $(C_2-C_8)$ alkynyl.

Embodiment 43: The compound of any one of Embodiments 1-42, wherein $R^4$ is $OR^{4A}$, where $R^{4A}$ is H, methyl, ethyl, propyl, isopropyl, or butyl.

Embodiment 44: The compound of any one of Embodiments 1-43, wherein $R^4$ is OH.

Embodiment 45: The compound of any one of Embodiments 1-44, wherein $R^5$ is $OR^{5A}$, halogen, CN, alkyl, alkenyl, alknyl, or haloalkyl, and wherein alkyl, alkenyl, or alkynyl, is optionally substituted with 1, 2, 3, 4 or more substituents selected independently from OH, oxo (=O), CN, SH, $SO_2NH_2$, $SO_2(C_1\text{-}C_4)$alkyl, $SO_2NH(C_1\text{-}C_4)$alkyl, halogen, $NH_2$, $NH(C_1\text{-}C_4)$alkyl, $N[(C_1\text{-}C_4)alkyl]_2$, $C(O)NH_2$, COOH, COOMe, acetyl, $(C_1\text{-}C_8)$alkyl, $O(C_1\text{-}C_8)$alkyl, $O(C_1\text{-}C_8)$haloalkyl, $(C_2\text{-}C_8)$alkenyl, $(C_2\text{-}C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2—[CH(OH)]_m—(CH_2)_p$—OH, $CH_2—[CH(OH)]_m—(CH_2)_p—NH_2$ or $CH_2$-aryl-alkoxy, where "m" and "p" are independently 1, 2, 3, 4, 5 or 6.

Embodiment 46: The compound of any one of Embodiments 1-45, wherein $R^5$ is $OR^{5A}$, halogen or CN, and where $R^{5A}$ is H, $(C_1\text{-}C_8)$alkyl, $(C_1\text{-}C_8)$haloalkyl, $(C_2\text{-}C_8)$alkenyl, or $(C_2\text{-}C_8)$ alkynyl.

Embodiment 47: The compound of any one of Embodiments 1-46, wherein $R^5$ is $OR^{5A}$, where $R^{5A}$ is H, methyl, ethyl, propyl, isopropyl, or butyl.

Embodiment 48: The compound of any one of Embodiments 1-47, wherein $R^5$ is OH.

Embodiment 49: The compound of any one of Embodiments 1-40, wherein $R^4$ and $R^5$ together with the carbons they are attached to can form a 3-12 membered aryl, heteroaryl, cycloalkyl or heterocyclyl, each of which can be optionally substituted with 1, 2, 3, 4 or more substituents selected independently from OH, oxo (=O), CN, SH, $SO_2NH_2$, $SO_2(C_1\text{-}C_4)$alkyl, $SO_2NH(C_1\text{-}C_4)$alkyl, halogen, $NH_2$, $NH(C_1\text{-}C_4)$alkyl, $N[(C_1\text{-}C_4)alkyl]_2$, $C(O)NH_2$, COOH, COOMe, acetyl, $(C_1\text{-}C_8)$alkyl, $O(C_1\text{-}C_8)$alkyl, $O(C_1\text{-}C_8)$haloalkyl, $(C_2\text{-}C_8)$alkenyl, $(C_2\text{-}C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2—[CH(OH)]_m—(CH_2)_p$—OH, $CH_2—[CH(OH)]_m—(CH_2)_p—NH_2$ or $CH_2$-aryl-alkoxy, where "m" and "p" are independently 1, 2, 3, 4, 5 or 6.

Embodiment 50: The compound of any one of Embodiments 1-49, wherein Ring A is a 3-12 membered aryl, 3-12 membered heteroaryl, 3-12 membered cycloalkyl, or 3-12 membered heterocycle, each of which can be optionally substituted with 1, 2, 3, 4 or more substituents selected independently from OH, oxo (=O), CN, SH, $SO_2NH_2$, $SO_2(C_1\text{-}C_4)$alkyl, $SO_2NH(C_1\text{-}C_4)$alkyl, halogen, $NH_2$, $NH(C_1\text{-}C_4)$alkyl, $N[(C_1\text{-}C_4)alkyl]_2$, $C(O)NH_2$, COOH, COOMe, acetyl, $(C_1\text{-}C_8)$alkyl, $O(C_1\text{-}C_8)$alkyl, $O(C_1\text{-}C_8)$haloalkyl, $(C_2\text{-}C_8)$alkenyl, $(C_2\text{-}C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2—[CH(OH)]_m—(CH_2)_p$—OH, $CH_2—[CH(OH)]_m—(CH_2)_p—NH_2$ or $CH_2$-aryl-alkoxy, where "m" and "p" are independently 1, 2, 3, 4, 5 or 6.

Embodiment 51: The compound of any one of Embodiment 1-50, wherein Ring A has the structure

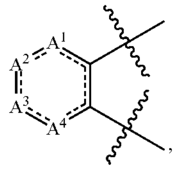

where $A^1$ is N, C(O), NH or $CR^{120}$; $A^2$ is N, C(O), NH or $CR^{121}$; $A^3$ is N, C(O), NH or $CR^{122}$; $A^4$ is N, C(O), NH or $CR^{123}$, $R^{120}$, $R^{121}$, $R^{122}$ and $R^{123}$ are independently are H, halogen, CN, $C_1\text{-}C_8$(alkyl), $(C_1\text{-}C_8)$haloalkyl, $(C_2\text{-}C_8)$alkenyl, $(C_2\text{-}C_8)$alkynyl, $OR^O$, $NR^OR^P$, $[(C_1\text{-}C_8)alkylene]OR^O$, $[(C_1\text{-}C_8)alkylene]NHR^A$, $[(C_1\text{-}C_8)alkylene]NR^OR^P$, $C(O)R^O$, $C(O)NHR^O$, $C(O)NR^OR^P$, $C(O)[(C_1\text{-}C_8)alkylene]NHR^O$, $C(O)[(C_1\text{-}C_8)alkylene]NR^OR^P$, $CO_2R^O$, $C(S)NHR^O$, $C(S)NR^OR^P$, $SR^O$, $S(O)R^O$, $SO_2R^O$, $SO_2NHR^O$, $SO_2NR^OR^P$, $NHC(O)R^O$, $NR^OC(O)R^P$, $NHC(O)NHR^O$, $NHC(O)NR^OR^P$, $NR^OC(O)NHR^P$, $NR^OC(O)NR^PR^Q$, $P(O)(OH)(OR^O)$, $P(O)(OR^O)(OR^P)$, tosylate, aryl, heteroaryl, cycloalkyl or heterocyclyl. $R^O$, $R^P$ and $R^Q$ independently are H, —OH, aryl, $(C_1\text{-}C_8)$alkyl, $[(C_1\text{-}C_8)alkyl]$aryl $(C_1\text{-}C_8)$alkoxy, $(C_1\text{-}C_8)$haloalkyl, cycloalkyl, heterocyclyl, $[(C_1\text{-}C_8)alkylene]$heterocyclyl, $[(C_1\text{-}C_8)alkylene]$aryl or heteroaryl; or $R^O$ and $R^P$ together with the nitrogen atom to which they are attached form a heterocyclyl ring.

Embodiment 52: The compound of Embodiment 51, wherein $A^1$ is $CR^{120}$; $A^2$ is $CR^{121}$; $A^3$ is $CR^{122}$; $A^4$ is $CR^{123}$; and $R^{120}$, $R^{121}$, $R^{122}$ and $R^{123}$ independently are H or $OR^O$ and at least one of $R^{120}$, $R^{121}$, $R^{122}$ and $R^{123}$ are $OR^O$.

Embodiment 53: The compound of Embodiment 51, wherein $A^1CR^{120}$ where $R^{120}$ is methoxy, $A^3$ is methoxy is $CR^{122}$ where $R^{122}$ is methoxy, $A^2$ is $CR^{121}$ where $R^{121}$ is H, and $A^4$ is $CR^{123}$ where $R^{123}$ is H.

Embodiment 54: The compound of Embodiment 51, wherein $A^1$ is $CR^{120}$ where $R^{120}$ is a halide, $A^3$ is methoxy where is $CR^{122}$ where $R^{122}$ is methoxy, $A^2$ is N, and $A^4$ is $CR^{123}$ where $R^{123}$ is H. $A^1CR^{120}$ where $R^{120}$ is methoxy, $A^3$ is $CR^{122}$ where $R^{122}$ is methoxy, $A^2$ is N, and $A^4$ is $CR^{123}$ where $R^{123}$ is H.

Embodiment 55: The compound of Embodiment 51, wherein $A^1$ is N, $A^3$ is methoxy is $CR^{122}$ where $R^{122}$ is methoxy, $A^2$ is $CR^{121}$ where $R^{121}$ is H, and $A^4$ is $CR^{123}$ where $R^{123}$ is H.

Embodiment 56: The compound of Embodiment 51, wherein: (i) $A^1$ is C(C=O) or NH, $A_4$ is C(C=O) or NH, $A_2$ is $CR^{121}$, and $A^3$ is $CR^{123}$; or (ii) $A^1$ is C(C=O), $A^4$ is NH, $A^2$ is $CR^{121}$, and $A^3$ is $CR^{123}$; or (iii) $A^1$ is C(C=O), $A^4$ is NH, $A^2$ is $CR^{121}$, and $A^3$ is $CR^{123}$ wherein $R^{123}$ is methoxy; or (iv) $A^1$ is C(C=O), $A^4$ is N, and $A^3$ is $CR^{123}$ wherein $R^{123}$ is methoxy.

Embodiment 57: The compound of Embodiment 51, wherein: (i) $A^1$ is $CR^{120}$ where $R^{120}$ is H, $A^3$ is $CR^{122}$ where $R^{120}$ is H, $A^2$ is $CR^{121}$ and $A^4$ is $CR^{123}$; where at least one of $R^{121}$ or $R^{123}$ are $NR^OR^P$ and $R^{121}$ and $R^{123}$ together with the carbon to which they are attached for a heterocycle; or (ii) $R^{120}$, $R^{121}$, $R^{122}$ and $R^{123}$ independently are H or $OR^O$ and at least one of $R^{120}$, $R^{121}$, $R^{122}$ and $R^{123}$ are $OR^O$.

Embodiment 58: The compound of any of one Embodiments 1-50, wherein Ring A has the structure

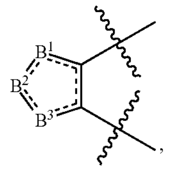

where any two of $B^1$, $B^2$ and $B^3$ are $CR^{130}$ and N and the remaining ring atom is $N(R^{131})$ or S, wherein $R^{130}$ is H, CN, halogen, $OR^R$, $SR^R$, $(C_1-C_8)$alkyl, C (O) $O(C_1-C_8)$alkyl, $C(O)(C_1-C_8)$alkyl, $SO_2(C_1-C_8)$alkyl, $SO_2NR^RR^S$, C(O) $NR^RR^S$, $NR^RR^S$ or $NR^RC(O)R^S$, and $R^{131}$ is H or $(C_1-C_8)$ alkyl. $R^R$ and $R^S$, independently are H, —OH, aryl, $(C_1-C_8)$ alkyl, $[(C_1-C_8)$alkyl]aryl $(C_1-C_8)$alkoxy, $(C_1-C_8)$haloalkyl, cycloalkyl, heterocyclyl, $[(C_1-C_8)$alkylene]heterocyclyl, $[(C_1-C_8)$alkylene]aryl or heteroaryl; or the $R^R$ and $R^S$ together with the nitrogen atom to which they are attached of $NR^RR^S$ or $NR^RC(O)R^S$, optionally form a heterocyclyl ring.

Embodiments 59: The compound of Embodiments 58, wherein: i) $B^1$ is N or S, $B^3$ is N or S, and $B^2$ is $CR^{130}$ wherein $R^{130}$ is a methoxy; ii) $B^1$ is N, $B^3$ is S, and $B^2$ is $CR^{130}$ wherein $R^{130}$ is a methoxy; iii) $B^1$ is $CR^{130}$ where $R^{130}$ is H, $B^2$ is S or N, and $B^3$ is S or N; iv) $B^1$ is $CR^{130}$ where $R^{130}$ is H, $B^2$ is S, and $B^3$ is N.

Embodiments 60: The compound of any one of Embodiments 1-50, wherein Ring A ring is aziridine, 2H-azirine, oxirane, thiirane, azetidine, 2,3-hydroazete, azete, 1,3-diazetidine, oxetane, 2H-oxete, thietane, 2H-thiete, azetidin-2-one, pyrrolidine, 3-pyrroline, 2-pyrroline, 2H-pyrrole, 1H-pyrrole, pyrazolidine, imidazolidine, 2-pyrazoline, 2-imidazoline, pyrazole, imidazole, 1,2,4-triazole, 1,2,3-triazole, tetrazole, tetrahydrofuran, furan, 1,3-dioxolane, tetrahydrothiophene, thiophene, oxazole, isoxazole, isothiazole, thiazole, 1,2-oxathiolane, 1,3-oxathiolane, 1,2,5-oxadiazole, 1,2,3-oxadiazole, 1,3,4-thiadiazole, 1,2,5-thiadiazole, sulfolane, 2,4-thiazolidinedione, succinimide, 2-oxazolidone, hydantoin, piperidine, pyridine, piperazine, pyridazine, pyrimidine, pyrazine, 1,2,4-triazine, 1,3,5-triazine, tetrahydropyran, 2H-pyran, 4H-pyran, pyrylium, 1,4-dioxane, 1,4-dioxine, thiane, 2H-thiopyran, 4H-thiopyran, 1,3-dithiane, 1,4-dithiane, 1,3,5-trithiane, morpholine, 4H-1,2-oxazine, 2H-1,2-oxazine, 6H-1,2-oxazine, 4H-1,3-oxazine, 2H-1,3-oxazine, 6H-1,3-oxazine, 4H-1,4-oxazine, 2H-1,4-oxazine, thiomorpholine, 4H-1,4-thiazine, 2H-1,2-thiazine, 6H-1,2-thiazine, 2H-1,4-thiazine, cytosine, thymine, uracil, thiomorpholine dioxide, hexahydro-1H-pyrrolizine, 1,4,5,6-tetrahydrocyclopenta[b]pyrrole, 1,3a,4,6a-tetrahydropyrrolo[3,2-b]pyrrole, 1,4-dihydropyrrolo[3,2-b]pyrrole, 1,6-dihydropyrrolo[2,3-b]pyrrole, 6H-furo[2,3-b]pyrrole, 4H-furo[3,2-b]pyrrole, 4H-thieno[3,2-b]pyrrole, 6H-thieno[2,3-b]pyrrole, 2,3-dihydro-1H-indene, indene, indoline, 3H-indole, 1H-indole, 2H-isoindole, indolizine, 1H-indazole, benzimidazole, 7-azaindole, 4-azaindole, 5-azaindole, 6-azaindole, 7-azaindole, pyrazolo[1,5-a]pyrimidine, purine, benzofuran, isobenzofuran, benzo[c]thiophene, benzo[b]thiophene, benzo[d]isoxazole, benzo[c]isoxazole, benzo[d]isothiazole, benzo[c]isothiazole, benzo[d]oxazole, benzo[d]thiazole, benzo[c][1,2,5]thiadiazole, 1,2-benzisothiazole-3(2H)-one, adenine, guanine, decahydroisoquinoline, decahydroquinoline, 1,2,3,4-tetrahydroquinoline, 1,2-dihydroquinoline, 1,2-dihydroisoquinoline, quinoline, isoquinoline, 4H-quinolizine, quinoxaline, phthalazine, quinazoline, cinnoline, 1,8-naphthridine, pyrido[3,2-d]pyrimidine, pyrido[4,3-d]pyrimidine, pyrido[3,4-b]pyrazine, pyrido[2,3-b]pyrazine, pteridine, 2H-chromene, 1H-isochromene, 3H-isochromene, 2H-chromen-2-one, 2H-benzo[e][1,2]oxazine, 2H-benzo[e][1,3]oxazine, 2H-benzo[b][1,4]oxazine, quinoline-2(1H)-one, isoquinolin-1(2H)-one, fluorene, carbazole, dibenzofuran, acridine, phenazine, phenoxazine, phenothiazine, phenoxathiine, quinuclidine, 1-azaadamantane, 2-azaadamantane, 2,3-dihydroazepine, 2,5-dihydroazepine, 4,5-dihydroazepine, azepine, 2H-azepine, 3H-azepine, 4H-azepine, 1,2-diazepine, 1,3-diazepine, oxepane, thiepine, 1,4-thiazepine, azocane, azocine, thiocane, azonane, azecine, spiro[cyclobutene-1,3]-indole], 1-oxaspiro[4.5]decane, 1,6-dioxaspiro[3.4]octane, 3',4',5',6'-tetrahydro-3H-spiro[isobenzofuran-1,2'-pyran], 1-oxaspiro[4.4]nonan-2-one, 2-oxa-7-azaspiro[3.5]nonane, 1,4-dioxa-7-azaspiro[4.4.]nonane, 1,3-diazaspiro[4.4]non-2-en-4-one, 2,9-diazaspiro[5.5]undecan-1-one, 8-azaspiro[4.5]decane-7,9-dione, 1,3,8-triazaspiro[4.5]decan-4-one, or 1,4-dithia-7-azaspiro[4.4]nonane.

Embodiment 61: The compound of any one of Embodiments 1-50, wherein Ring A is:

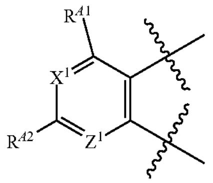

wherein $X^1$ is CH or N; $Z^1$ is CH or N; and $R^{A1}$ and $R^{A2}$ are selected independently from the group consisting of H, alkyl, alkoxy, alkylamino, acyloxy, fluorine, chlorine, bromine, $OCF_3$, and nitrile.

Embodiment 62: The compound of any of Embodiments 1-50, wherein Ring A is:

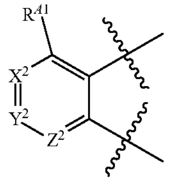

wherein $X^2$ is CH or N; $Y^2$ is CH or N; $Z^2$ is CH or N; and $R^{A1}$ is selected independently from the group consisting of H, alkyl, alkoxy, alkylamino, acyloxy, fluorine, chlorine, bromine, $OCF_3$, and nitrile.

Embodiment 63: The compound of any of Embodiments 1-50, wherein Ring A is:

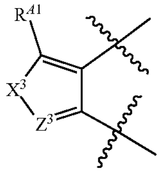

wherein $X^3$ is NH, O or S; $Z^3$ is CH or N; and $R^{A1}$ is selected independently from the group consisting of H, alkyl, alkoxy, alkylamino, acyloxy, fluorine, chlorine, bromine, $OCF_3$, $—OCH_2CF_3$, and nitrile.

Embodiment 64: The compound of any of Embodiments 1-50, wherein Ring A is:

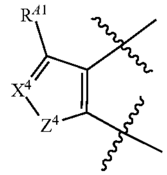

wherein $X^4$ is NH, O or S; $Z^4$ is CH or N; and $R^{A1}$ is selected independently from the group consisting of H, alkyl, alkoxy, alkylamino, acyloxy, fluorine, chlorine, bromine, $OCF_3$, $—OCH_2CF_3$, and nitrile.

Embodiment 65: The compound of any of Embodiments 1-50, wherein Ring A is:

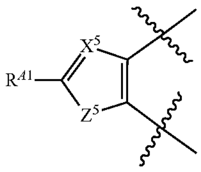

wherein $X^5$ is NH, O or S; $Z^5$ is CH or N; and $R^{A1}$ is selected independently from the group consisting of H, alkyl, alkoxy, alkylamino, acyloxy, fluorine, chlorine, bromine, $OCF_3$, $—OCH_2CF_3$, and nitrile.

Embodiment 66: The compound of any of Embodiments 1-50, wherein Ring A is:

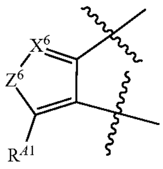

wherein $X^6$ is NH, O or S; $Z^6$ is CH or N; and $R^{A1}$ is selected independently from the group consisting of H, alkyl, alkoxy, alkylamino, acyloxy, fluorine, chlorine, bromine, $OCF_3$, and nitrile.

Embodiment 67: The compound of any of Embodiments 1-50, wherein Ring A is:

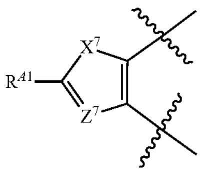

wherein $X^7$ is NH, O or S; $Z^7$ is CH or N; and $R^{A1}$ is selected independently from the group consisting of H, alkyl, alkoxy, alkylamino, acyloxy, fluorine, chlorine, bromine, $OCF_3$, and nitrile.

Embodiment 68: The compound of any of Embodiments 1-50, wherein Ring A is:

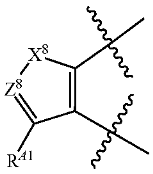

wherein $X^8$ is NH, O or S; $Z^8$ is CH or N; and $R^{A1}$ is selected independently from the group consisting of H, alkyl, alkoxy, alkylamino, acyloxy, fluorine, chlorine, bromine, $OCF_3$, $—OCH_2CF_3$, and nitrile.

Embodiment 69: The compound of any of Embodiments 1-50, wherein Ring A is benzene, pyridine, pyrimidine, or thiazole, each of which can be optionally substituted with 1, 2, 3, 4 or more substituents selected independently from OH, oxo (=O), CN, SH, $SO_2NH_2$, $SO_2(C_1\text{-}C_4)$alkyl, $SO_2NH(C_1\text{-}C_4)$alkyl, halogen, $NH_2$, $NH(C_1\text{-}C_4)$alkyl, $N[(C_1\text{-}C_4)\text{alkyl}]_2$, $C(O)NH_2$, COOH, COOMe, acetyl, $(C_1\text{-}C_8)$alkyl, $O(C_1\text{-}C_8)$alkyl, $O(C_1\text{-}C_8)$haloalkyl, $(C_2\text{-}C_8)$ alkenyl, $(C_2\text{-}C_8)$alkynyl, haloalkyl, thioalkyl, cyanomethylene, alkylaminyl, $NH_2—C(O)$-alkylene, NH(Me)-C(O)-alkylene, $CH_2—C(O)$-lower alkyl, C(O)-lower alkyl, alkylcarbonylaminyl, $CH_2—[CH(OH)]_m—(CH_2)_p—OH$, $CH_2—[CH(OH)]_m—(CH_2)_p—NH_2$ or $CH_2$-aryl-alkoxy, where "m" and "p" are independently 1, 2, 3, 4, 5 or 6.

Embodiment 70: The compound of any of Embodiments 1-50, wherein Ring A is

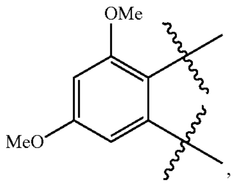
,
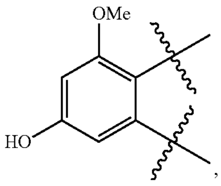
,
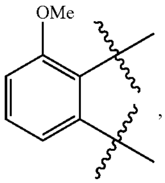
,
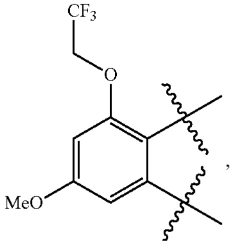
,
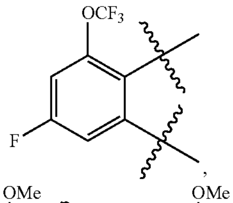
,
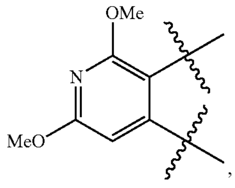
,
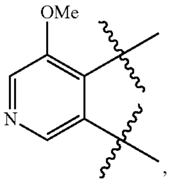
,
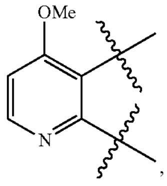
,
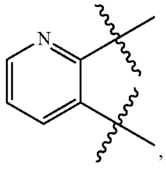
, -continued

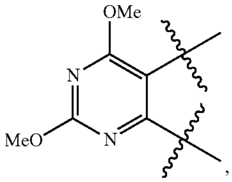
, or
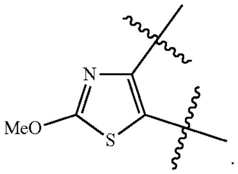
.

Embodiment 71: The compound of any of Embodiments 1-50, wherein Ring A is

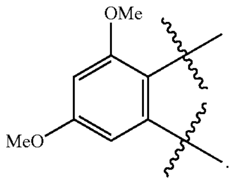 [SMILES: *c1cc(OC)cc(OC)c1*]

Embodiment 72: The compound of any of Embodiments 1-50, wherein Ring A is

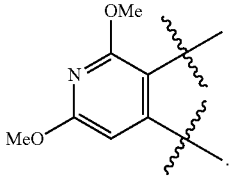 [SMILES: *c1cc(OC)nc(OC)c1*]

Embodiment 73: The compound of any one of Embodiments 1-72, wherein the compound is of structure:

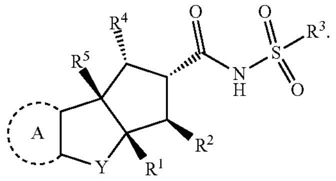

Embodiment 74: The compound of any one of Embodiments 1-72, wherein the compound is of structure:

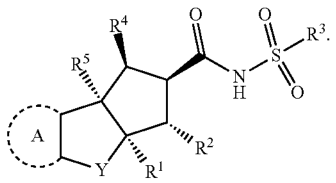

Embodiment 75: The compound of Embodiment 1, wherein the compound is of structure:

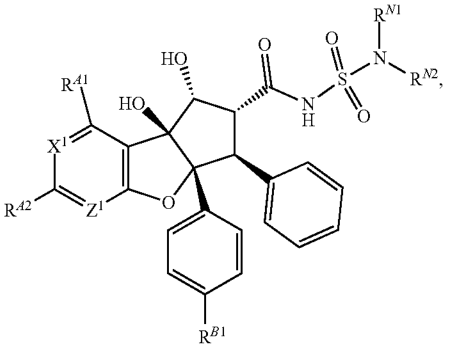

wherein: $X^1$ is CH or N; $Z^1$ is CH or N; $R^{A1}$ and $R^{A2}$ are independently H, alkyl, alkoxy, alkylamino, acyloxy, fluorine, chlorine, bromine, $OCF_3$, or nitrile; $R^{N1}$ and $R^{N2}$ are independently linear or branched alkyl (e.g. methyl) or cyclic alkyl; $R^{B1}$ is methoxy, fluorine, bromine, chlorine, iodine, trifluoromethyl, nitrile, acetylene, $OCF_2H$, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached to, form imidazole.

Embodiment 76: The compound of Embodiment 1, wherein the compound is of structure:

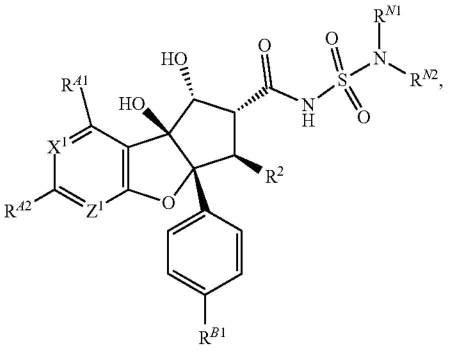

wherein: $X^1$ is CH or N; $Z^1$ is CH or N; $R^{A1}$ and $R^{A2}$ are independently H, alkyl, alkoxy, alkylamino, acyloxy, fluorine, chlorine, bromine, $OCF_3$, or nitrile; $R^{N1}$ and $R^{N2}$ are independently linear or branched alkyl (e.g. methyl) or cyclic alkyl; $R^{B1}$ is methoxy, fluorine, bromine, chlorine, iodine, trifluoromethyl, nitrile, acetylene, $OCF_2H$, alkyl, alkoxy, alkylamine, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached to, form imidazole; and $R^2$ is alkyl, alkenyl, alkynyl, substituted aryl, substituted heteroaryl, or $CH_2L$, where L is selected independently from the group consisting of alkoxy, alkylamino, and heterocyclyl.

Embodiment 77: The compound of Embodiment 1, wherein the compound is of structure:

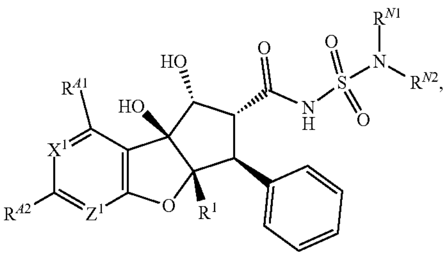

wherein: $X^1$ is CH or N; $Z^1$ is CH or N; $R^{A1}$ and $R^{A2}$ are independently H, alkyl, alkoxy, alkylamino, acyloxy, fluorine, chlorine, bromine, $OCF_3$, or nitrile; $R^{N1}$ and $R^{N2}$ are independently linear or branched alkyl (e.g. methyl) or cyclic alkyl; and $R^1$ is substituted aryl, heteroaryl, and substituted heteroaryl, optionally $R^1$ is 4-bromophenyl, 4-methoxyphenyl, 4-cyanophenyl, 4-trifluoromethylphenyl, 4-(azetidin-3-yl)phenyl, 4-(2-hydroxymethylazetidin-3-yl) phenyl, 4-(2-(2-hydroxyethyl) azetidine-3-yl)phenyl, 4-(azetidine-3-ylmethyl)phenyl, 4-(azetidine-3-yl-hydroxy) phenyl, 4-(pyrrolidine-3-yl)phenyl, 4-piperidin-4-yl)phenyl, or benzimidazol-6-yl.

Embodiment 78: The compound of Embodiment 1, wherein the compound is of structure:

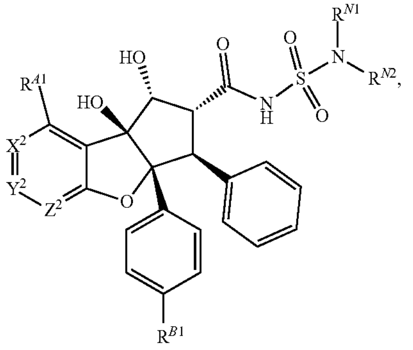

wherein: $X^2$ is CH or N; $Z^2$ is CH or N; $Y^2$ is CH or N; $R^{A1}$ is selected independently from the group consisting of H, alkyl, alkoxy, alkylamino, acyloxy, fluorine, chlorine, bromine, $OCF_3$, and nitrile; $R^{N1}$ and $R^{N2}$ are independently linear or branched alkyl (e.g. methyl) or cyclic alkyl; $R^{B1}$ is methoxy, fluorine, bromine, chlorine, iodine, trifluoromethyl, nitrile, acetylene, $OCF_2H$, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached to, form imidazole.

Embodiment 79: The compound of Embodiment 1, wherein the compound is of structure:

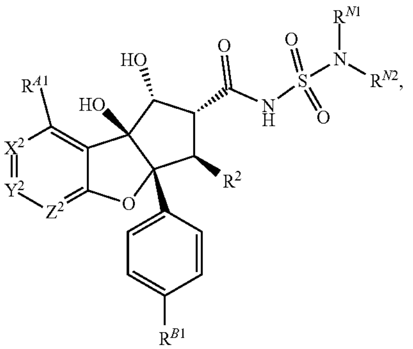

wherein: $X^2$ is CH or N; $Z^2$ is CH or N; $Y^2$ is CH or N; $R^{A1}$ is selected independently from the group consisting of H, alkyl, alkoxy, alkylamino, acyloxy, fluorine, chlorine, bromine, $OCF_3$, and nitrile; $R^{N1}$ and $R^{N2}$ are independently linear or branched alkyl (e.g. methyl) or cyclic alkyl; $R^{B1}$ is methoxy, fluorine, bromine, chlorine, iodine, trifluoromethyl, nitrile, acetylene, $OCF_2H$, alkyl, alkoxy, alkylamine, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached to, form imidazole; and $R^2$ is alkyl, alkenyl, alkynyl, substituted aryl, substituted heteroaryl, and $CH_2L$ where L is selected independently from the group consisting of alkoxy, alkylamino, or heterocyclyl.

Embodiment 80: The compound of Embodiment 1, wherein the compound is of structure:

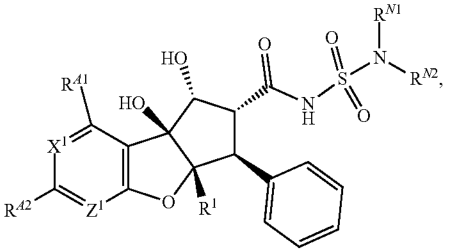

wherein: $X^2$ is CH or N; $Z^2$ is CH or N; $Y^2$ is CH or N; $R^{A1}$ and $R^{A2}$ are selected independently from the group consisting of H, alkyl, alkoxy, alkylamino, acyloxy, fluorine, chlorine, bromine, $OCF_3$, and nitrile; $R^{N1}$ and $R^{N2}$ are independently linear or branched alkyl (e.g. methyl) or cyclic alkyl; and $R^1$ is substituted aryl, heteroaryl, and substituted heteroaryl, optionally RI is 4-bromophenyl, 4-methoxyphenyl, 4-cyanophenyl, 4-trifluoromethylphenyl, 4-(azetidin-3-yl) phenyl, 4-(2-hydroxymethylazetidin-3-yl)phenyl, 4-(2-(2-hydroxyethyl) azetidine-3-yl)phenyl, 4-(azetidine-3-ylmethyl)phenyl, 4-(azetidine-3-yl-hydroxy)phenyl, 4-(pyrrolidine-3-yl)phenyl, 4-piperidin-4-yl)phenyl, or benzimidazol-6-yl.

Embodiment 81: The compound of Embodiment 1, wherein the compound is of structure:

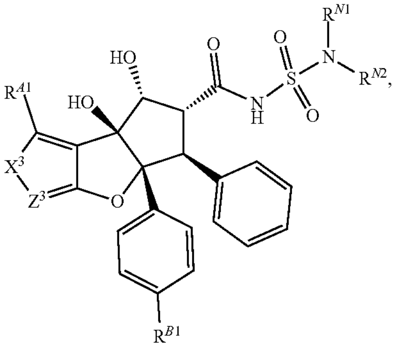

wherein: $X^3$ is CH or N; $Z^3$ is CH or N; $R^{A1}$ is H, alkyl, alkoxy, alkylamino, acyloxy, fluorine, chlorine, bromine, $OCF_3$, or nitrile; $R^{N1}$ and $R^{N2}$ are independently linear or branched alkyl (e.g., methyl) or cyclic alkyl; and $R^{B1}$ is selected independently from the group consisting of methoxy, fluorine, bromine, chlorine, iodine, trifluoromethyl, nitrile, acetylene, $OCF_2H$, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached to, form imidazole.

Embodiment 82: The compound of Embodiment 1, wherein the compound is of structure:

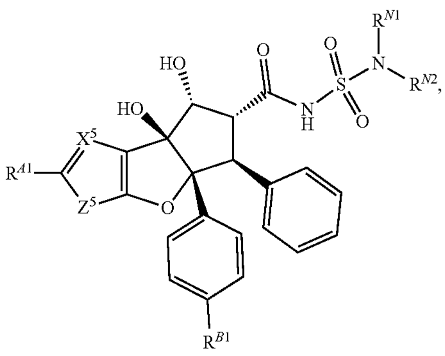

wherein: $X^5$ is CH or N; $Z^5$ is CH or N; $R^{A1}$ is H, alkyl, alkoxy, alkylamino, acyloxy, fluorine, chlorine, bromine, $OCF_3$, and nitrile; $R^{N1}$ and $R^{N2}$ are independently linear or branched alkyl (e.g., methyl) or cyclic alkyl; and $R^{B1}$ is selected independently from the group consisting of: methoxy, fluorine, bromine, chlorine, iodine, trifluoromethyl, nitrile, acetylene, $OCF_2H$, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached to, form imidazole.

Embodiment 83: The compound of Embodiment 1, wherein the compound is of structure:

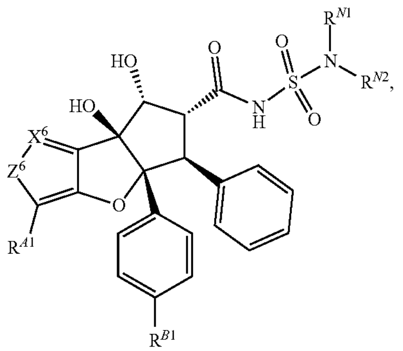

wherein: $X^6$ is CH or N; $Z^6$ is CH or N; $R^{A1}$ is selected independently from the group consisting of H, alkyl, alkoxy, alkylamino, acyloxy, fluorine, chlorine, bromine, $OCF_3$, and nitrile; $R^{N1}$ and $R^{N2}$ are independently linear or branched alkyl (e.g., methyl) or cyclic alkyl; and $R^{B1}$ is methoxy, fluorine, bromine, chlorine, iodine, trifluoromethyl, nitrile, acetylene, $OCF_2H$, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached to, form imidazole.

Embodiment 84: The compound of Embodiment 1, wherein the compound is of structure:

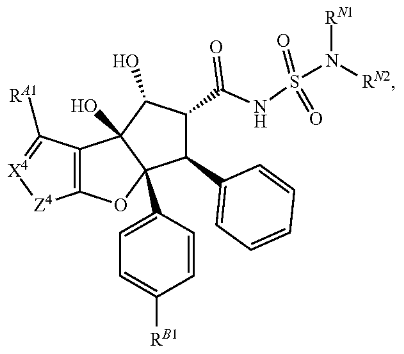

wherein: $X^4$ is CH or N; $Z^4$ is CH or N; $R^{A1}$ is selected from the group consisting of H, alkyl, alkoxy, alkylamino, acyloxy, fluorine, chlorine, bromine, $OCF_3$, and nitrile; $R^{N1}$ and $R^{N2}$ are independently linear or branched alkyl (e.g., methyl) or cyclic alkyl; and $R^{B1}$ is methoxy, fluorine, bromine, chlorine, iodine, trifluoromethyl, nitrile, acetylene, $OCF_2H$, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached to, form imidazole.

Embodiment 85: The compound of Embodiment 1, wherein the compound is of structure:

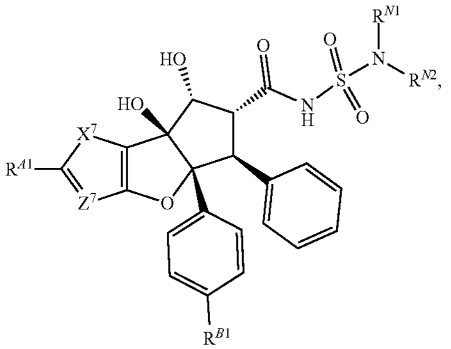

wherein: $X^7$ is CH or N; $Z^7$ is CH or N; $R^{A1}$ H, alkyl, alkoxy, alkylamino, acyloxy, fluorine, chlorine, bromine, $OCF_3$, and nitrile; $R^{N1}$ and $R^{N2}$ are independently linear or branched alkyl (e.g., methyl) or cyclic alkyl; and $R^{B1}$ is selected independently from the group consisting of: methoxy, fluorine, bromine, chlorine, iodine, trifluoromethyl, nitrile, acetylene, $OCF_2H$, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached to, form imidazole.

Embodiment 86: The compound of Embodiment 1, wherein the compound is of structure:

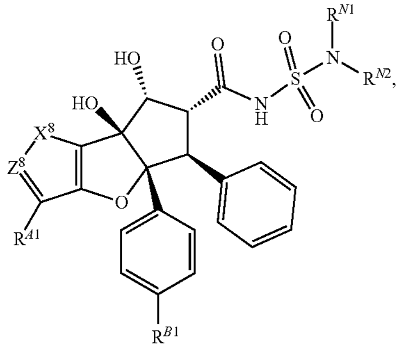

wherein $X^8$ is CH or N; $Z^8$ is CH or N; $R^{A1}$ is H, alkyl, alkoxy, alkylamino, acyloxy, fluorine, chlorine, bromine, $OCF_3$, and nitrile; $R^{N1}$ and $R^{N2}$ are independently linear or branched alkyl (e.g., methyl) or cyclic alkyl; and $R^{B1}$ is methoxy, fluorine, bromine, nitrile, chlorine, iodine, trifluoromethyl, acetylene, —$OCF_2H$, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached to, form imidazole.

Embodiment 87: The compound of Embodiment 1, wherein the compound is selected independently from the group consisting of:

BUCMD00773

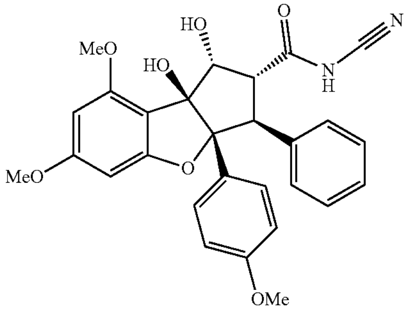

BUCMD00705

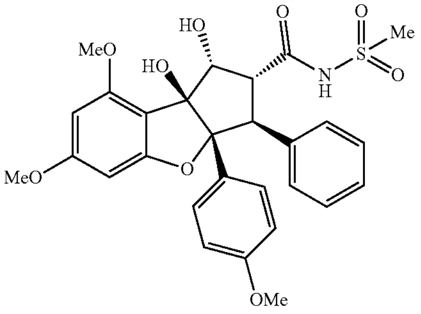

-continued

BUCMD00707

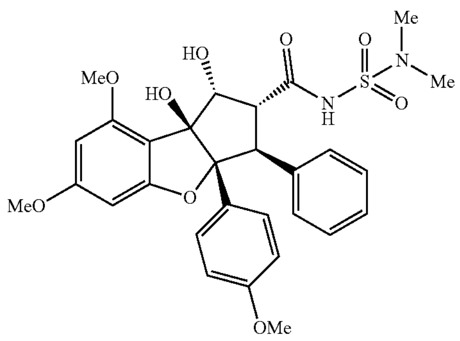

BUCMD00736

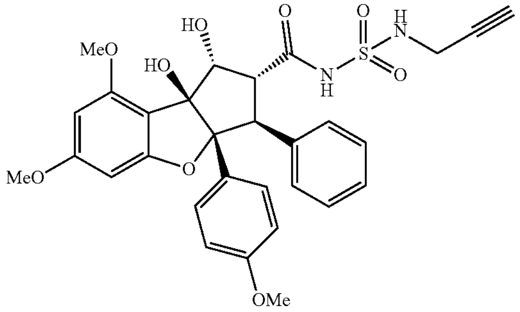

BUCMD00735

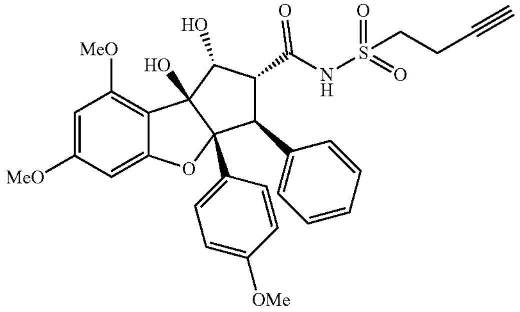

BUCMD00789

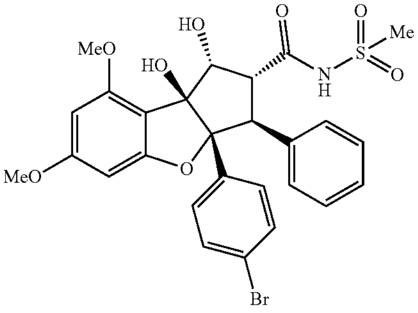

BUCMD00790
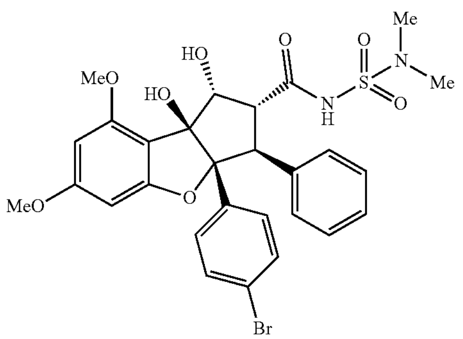
BUCMD00836
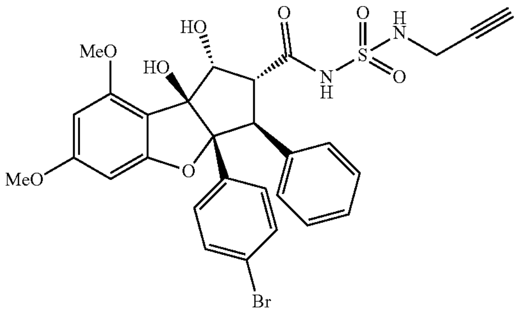
ZW-12-29
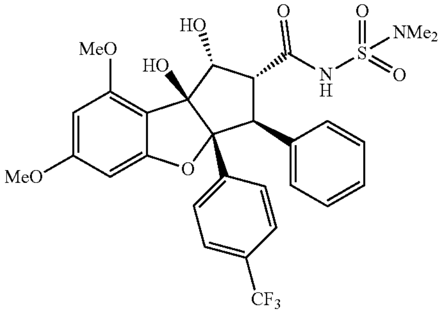
ZW-12-30
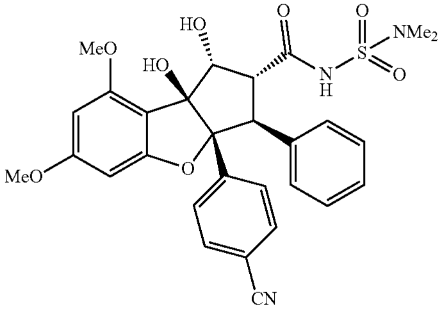
ZW-12-31
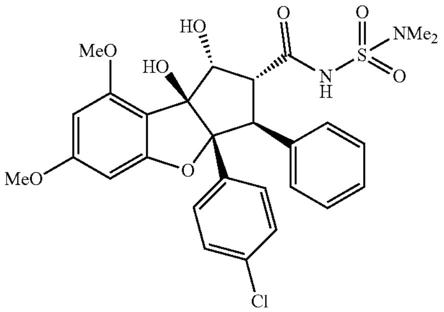
ZW-12-34
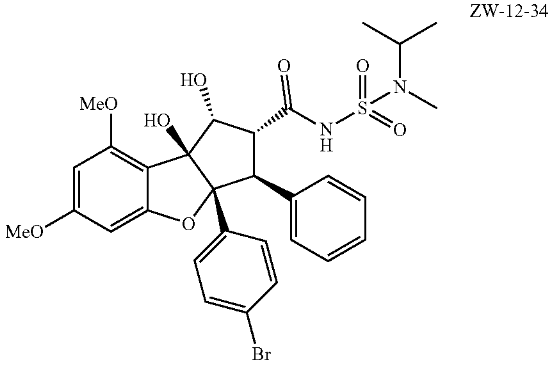
ZW-12-35
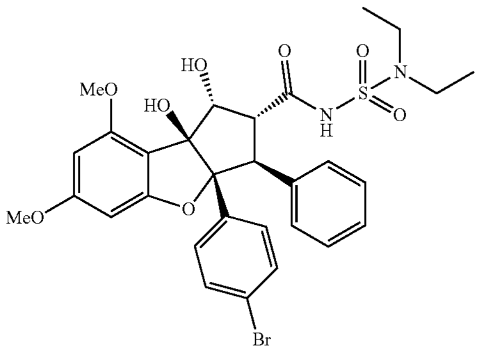
ZW-12-36
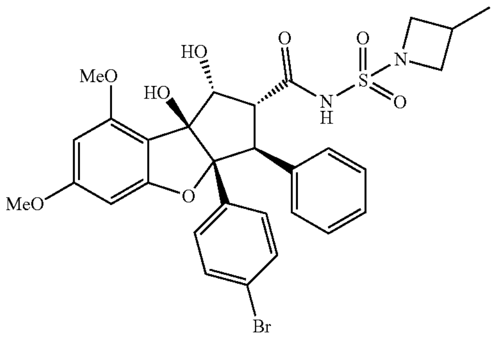
ZW-12-37
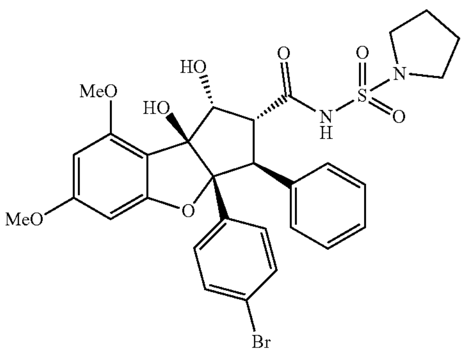

-continued
ZW-12-38
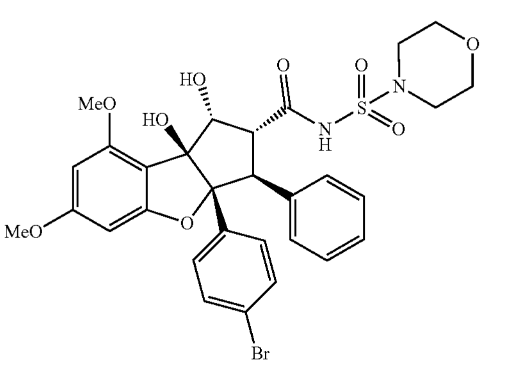
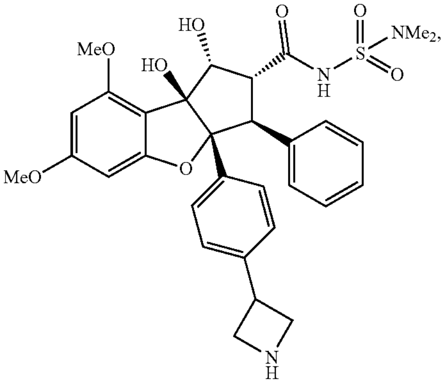
,
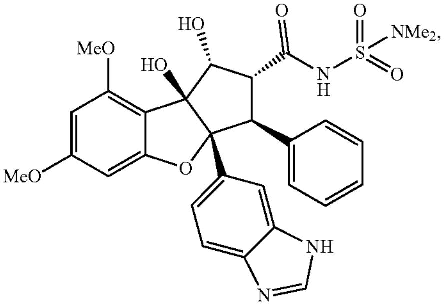
,
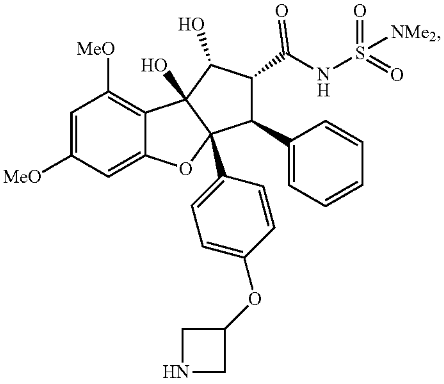
,
-continued
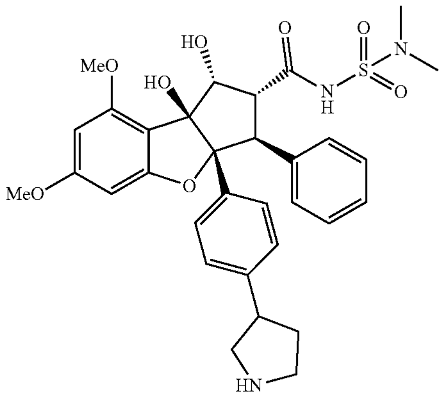
,
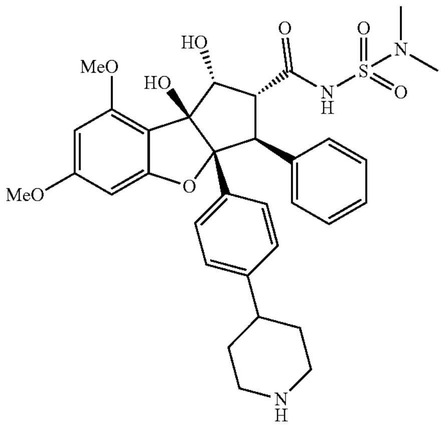
,
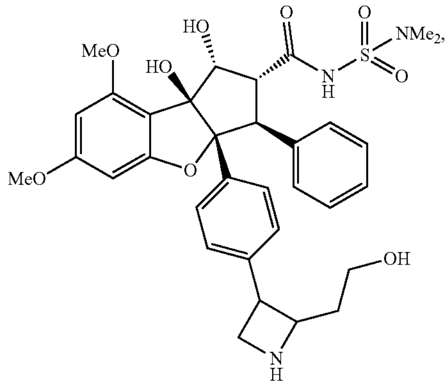
,
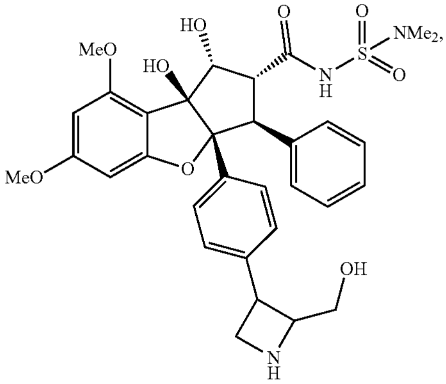
, and -continued

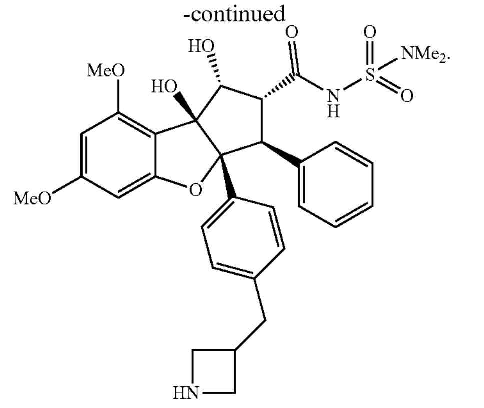

Embodiment 88: A pharmaceutical composition comprising a compound of any one of Embodiment 1-87 and a pharmaceutically acceptable carrier, diluent, or excipient.

Embodiment 89: The composition of Embodiment 88, wherein the composition further comprises a therapeutic agent.

Embodiment 90: The composition of Embodiment 89, wherein the therapeutic agent is an anticancer agent or chemotherapeutic, optionally, the anticancer agent is ABT-737; acetogenins (such as bullatacin and bullatacinone); aclacinomysins; actinomycin; actinomycin D; Aldesleukin; Alemtuzumab; alitretinoin; alkyl sulfonates such as busulfan, improsulfan and piposulfan; alkylating agents such as thiotepa and CYTOXAN® cyclosphosphamide; allopurinol; altretamine; AMG479; amifostine; anastrozole; antibiotics such as the enediyne antibiotics (e.g., calicheamicin, especially calicheamicin gamma1I and calicheamicin omegaI1 (see, e.g., Agnew, Chem. Intl. Ed. Engl., 33:183-186 (1994)); arsenic trioxide; Asparaginase; authramycin; azaserine; aziridines such as benzodopa, carboquone, meturedopa, and uredopa; BCG Live; bexarotene; bisphosphonates, such as clodronate; bleomycin; bortezomib; bryostatin; busulfan; busulfanoral; cactinomycin; callystatin; calusterone; caminomycin; camptothecin (including the synthetic analogue topotecan); capecitabine; carabicin; carboplatin; carmustine; CC-1065 (including its adozelesin, carzelesin and bizelesin synthetic analogues); celecoxib; chlorambucil; cisplastin; cladribine; cryptophycins (such as cryptophycin 1 and cryptophycin 8); cyclophosphamide; cytarabine; dacarbazine; dactinomycin; Darbepoetin alfa; daunomycin; daunorubicin; Denileukin diftitox; dexrazoxane; docetaxel; dolastatin; doxorubicin; Dromostanolone propionate; duocarmycin (including the synthetic analogues, KW-2189 and CB1-TM1); dynemicin, including dynemicin A; eleutherobin; Elliott's B Solution; epipodophyllotoxins; epirubicin; Epoetin alfa estramustine; esperamicin; ethylenimines and methylamelamines including altretamine, triethylenemelamine, triethylenephosphoramide, triethiylenethiophosphoramide and trimethylolomelamine; etoposide (VP-16); etoposide phosphate; exemestane; Filgrastim; floxuridine (intraarterial); fludarabine; fluorouracil (5-FU); fulvestrant; gemcitabine; gemtuzumab ozogamicin; goserelin acetate; hydroxyurea; Ibritumomab Tiuxetan; idarubicin; ifosfamide; imatinib; imatinib mesylate; immune checkpoint inhibitors (such as inhibitors of CTLA-4, PD-1, LAG-3, B7-H3, 67-H4, TIM3, A2AR, and IDO, e.g. an inhibitor of Programmed Death-Ligand 1 (PD-L1, also known as B7-HI, CD274), Programmed Death 1 (PD-1), CTLA-4, PD-L2 (B7-DC, CD273), LAG3, TIM3, 2B4, A2aR, B7HI, B7H3, B7H4, BTLA, CD2, CD27, CD28, CD30, CD40, CD70, CD80, CD86, CDI37, CDI60, CD226, CD276, DR3, GAL9, GITR, HAVCR2, HVEM, IDO1, ID02, ICOS (inducible T cell costimulator), KIR, LAIRI, LIGHT, MARCO (macrophage receptor with collagenous structure), PS (phosphatidylserine), OX-40, SLAM, TIGIT, VISTA, and VTCNI, such as an anti-PD-1 antibody, an anti PD-L1 antibody, or an anti-CTLA-4 antibody); Interferon alfa-2a; Interferon alfa-2b; irinotecan; letrozole; leucovorin; levamisole; LOddC; lomustine (CCNU); masitinib; mechlorethamine (nitrogenmustard); megestrol acetate; melphalan (L-PAM); mercaptopurine (6-MP); mesna; methotrexate; methoxsalen; mithramycin; mitomycin C; mitotane; mitoxantrone; nandrolone phenpropionate; neocarzinostatin chromophore and related chromoprotein enediyne antiobiotic chromophores); nilotinib; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; Nofetumomab; olaparib; Oprelvekin; oxaliplatin; paclitaxel; pamidronate; pancratistatin; pegademase; Pegaspargase; Pegfilgrastim; pentostatin; PI-103; pipobroman; plicamycin; porfimer sodium; procarbazine; quinacrine; rapamycin; Rasburicase; Rituximab; rituximab; rucaparib; sarcodictyin; Sargramostim; spongistatin; streptozocin; talbuvidine (LDT); talc; tamoxifen; taxol; temozolomide; teniposide (VM-26); testolactone; thioguanine (6-TG); thiotepa; toceranib; topotecan; toremifene; Tositumomab; Trastuzumab; tretinoin (ATRA); tyrosine kinase inhibitors; Uracil Mustard; valrubicin; valtorcitabine (monoval LDC); vinca alkaloids; vinblastine; vinorelbine; vorinostat; or zoledronate.

Embodiment 91: The composition of Embodiment 89, wherein the therapeutic agent is anti-inflammatory agent, optionally, the anti-inflammatory agent is a steroidal anti-inflammatory agent (e.g., 21-acetoxypregnenolone, alclometasone, algestone, amcinonide, beclomethasone, betamethasone, budesonide, chloroprednisone, clobetasol, clobetansone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furcate, paramethosone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, and analogues and derivatives thereof); or a nonsteroidal anti-inflammatory agent (e.g., COX inhibitors (COX-1 or COX nonspecific inhibitors (e.g., salicylic acid derivatives such as aspirin, sodium salicylate, choline magnesium trisalicylate, salicylate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam); alkanones such as nabumetone; and analogues and derivatives thereof), and COX-2 inhibitors, e.g., diarylsubstituted furanones such as refecoxib; diaryl-substituted pyrazoles such as celecoxib; indole acetic acids such as etodolac and sulfonanilides such as nimesulide; and analogues and derivatives thereof)).

Embodiment 92: The composition of Embodiment 89, wherein the therapeutic agent is an antihelminthic agent, optionally the antihelminthic agent is albendazole, ivermectin, mebendazole, nitazoxanide, pentamidine, praziquantel, pyrantel, thiabendazole, or triclabendazole.

Embodiment 93: The composition of Embodiment 89, wherein the therapeutic agent is an antimicrobial agent.

Embodiment 94: The composition of Embodiment 93, wherein the antimicrobial agent is an antibacterial agent, optionally, the anti-bacterial agent is selected independently from the group consisting of macrolides or ketolides such as erythromycin, azithromycin, clarithromycin, and telithromycin; beta-lactams including penicillin, cephalosporin, and carbapenems such as carbapenem, imipenem, and meropenem; monolactams such as penicillin G, penicillin V, methicillin, oxacillin, cloxacillin, dicloxacillin, nafcillin, ampicillin, amoxicillin, carbenicillin, ticarcillin, meziocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefmetazole, cefotaxime, ceftizoxime, cefiriaxone, cefoperazone, ceftazidime, cefixime, cefpodoxime, ceftibuten, cefdinir, cefpirome, cefepime, cefadroxil, ceftriaxone, ceftobiprole and astreonam; quinolones such as nalidixic acid, oxolinic acid, norfloxacin, pefloxacin, enoxacin, ofloxacin, levofloxacin, ciprofloxacin, temafloxacin, lomefloxacin, fleroxacin, grepafloxacin, sparfloxacin, trovafloxacin, clinafloxacin, gatifloxacin, moxifloxacin, sitafloxacin, ganefloxacin, gemifloxacin and pazufloxacin; antibacterial sulfonamides and antibacterial sulphanilamides, including para-aminobenzoic acid, sulfadiazine, sulfisoxazole, sulfamethoxazole and sulfathalidine; aminoglycosides such as streptomycin, neomvcin, kanamycin, paromycin, gentamicin, tobramycin, amikacin, netilmicin, spectinomycin, sisomicin, dibekalin and isepamicin; tetracyclines such as tetracycline, chlortetracycline, demeclocycline, minocycline, oxytetracycline, methacycline, doxycycline; rifamycins such as rifampicin (also called rifampin), rifapentine, rifabutin, bezoxazinorifamycin and rifaximin; lincosamides such as lincomycin and clindamycin; glycopeptides such as vancomycin and teicoplanin; streptogramins such as quinupristin and daflopristin; oxazolidinones such as linezolid; polymyxin, colistin and colymycin; trimethoprim, bacitracin, and phosphonomycin, optionally, the antibacterial agent is gentamicin, ampicillin, vancomycin, ceftriaxone and cefepime.

Embodiment 95: The composition of Embodiment 93, wherein the antimicrobial agent is an antiviral agent, optionally, the antiviral agent is 1-docosanol, acyclovir, brivudine, cidofovir, curcumin, daclatasvir, desciclovir, edoxudine, elbasvir, fameyclovir, fiacitabine, glecaprevir, ibacitabine, imiquimod, interferon alpha-2a, interferon alpha-2b, interferon aphacon-1, lamivudine, ledipasvir/sofosbuvir, grazoprevir, pegylated interferon, pegylated interferon alpha-2b, penciclovir, pibrentasvir, ribavirin, simeprevir, sofosbuvir, telaprevir, valacyclovir, valganciclovir, Paxlovid, or velpatasvir.

Embodiment 96: The composition of Embodiment 93, wherein the antimicrobial agent is an antifungal agent, optionally, the antifungal agent is Bifonazole, Butoconazole, Chlordantoin, Chlorphenesin, Ciclopirox Olamine, Clotrimazole, Eberconazole, Econazole, Fluconazole, Flutrimazole, Isoconazole, Itraconazole, Ketoconazole, Miconazole, Nifuroxime, Tioconazole, Terconazole, Undecenoic Acid, azoles (e.g., barleyconazole, butoconazole, clortrimazole, econazole, fluconazole, isavuconazole, itraconazole, ketoconazole, miconazole, oxyconazole, posaconazole, ravuconazole, saperconazole, sulconazole, tercocnazole, tioconazole, voriconazole, and ciclopirox), polyenes (e.g., natamycin, lucensomycin, nystatin, amphotericin B, etc.), echinocandins (e.g., Cancidas), pradimicins (e.g., beanomicins, nikkomycins, sordarins, allylamines, etc.), Triclosan, Piroctone, fenpropimorph, terbinafine, cyclopyroxolamine, flucitocin, griseofulvin haloprozin, tolnaftate, naphthypine, hydrochloride, morpholine, butenapin, undecylenic acid, propionic acid, or azoffluxin.

Embodiment 97: The composition of Embodiment 93, wherein the antimicrobial agent is an antiprotozoal agent, optionally, the antiprotozoal agent is Acetarsol, Azanidazole, Chloroquine, Metronidazole, Nifuratel, Nimorazole, Omidazole, Propenidazole, Secnidazole, Sineflngin, Tenonitrozole, Temidazole, Tinidazole, Nitazoxinide, Miltefosine, Pentavalent antimonials (e.g. Sodium stibogluconate, meglumine antimonate), Paromomycin, Pentamidine, Benzoxaboroles (e.g. acoziborole, tavaborole, crisaborole), Atovaquone, Proguanil, Benznidazole, Diminazene, Elflornithine, Melarsoprol, or Nifurtimox.

Embodiment 98: A method for treating a eukaryotic initiation factor 4A (eIF4A)-dependent condition, the method comprising administering a therapeutically effective amount of a compound of any one of Embodiments 1-87 to a subject in need thereof.

Embodiment 99: The method of Embodiment 98, wherein the eIF4A-dependent condition is a disease of uncontrolled cell growth, proliferation and/or survival, a disease of inappropriate cellular inflammatory responses, a disease caused by a parasite/pathogen or a neurodegenerative disease requiring neuroprotection.

Embodiment 100: A method for treating DEAD box helicase-dependent condition, the method comprising administering a therapeutically effective amount of a compound of any one of Embodiments 1-87 to a subject in need thereof.

Embodiment 101: The method of Embodiment 100, wherein the DEAD box helicase dependent condition is a DDX3, DDX21, DDX50, or DDX41 dependent condition.

Embodiment 102: The method of Embodiment 100 or 101, wherein the DEAD box helicase-dependent condition is a DDX3 condition.

Embodiment 103: The method of any one of Embodiments 100-102, wherein the DEAD box helicase-dependent condition is fibrosis.

Embodiment 104: A method of treating fibrosis, the method comprising administering a therapeutically effective amount of a compound of any one of Embodiments 1-87 to a subject in need thereof.

Embodiment 105: The method of Embodiments 103 or 104, wherein the fibrosis is fibrosis of an organ of the respiratory system, cardiovascular system, gastrointestinal system, urinary system, nervous system, or musculoskeletal system, optionally the fibrosis is fibrosis of the lung, heart, blood vessels, liver, small intestine, large intestine, pancreas, kidney, eye, brain, skin, bone marrow, or muscle tissue.

Embodiment 106: The method of any one of Embodiments 103-105, wherein the fibrosis disease or condition is selected from the group consisting of: pulmonary fibrosis, cystic fibrosis, idiopathic pulmonary fibrosis, progressive massive fibrosis, scleroderma, obliterative bronchiolitis, Hermansky-Pudlak syndrome, asbestosis, silicosis, chronic pulmonary hypertension, AIDS-associated pulmonary hypertension, sarcoidosis, tumor stroma in lung disease, asthma, cardiac fibrosis, myocardial fibrosis, atrial fibrosis, ventricular fibrosis, atrial fibrillation, ventricular fibrillation, myocardial infarction, hypertrophic cardiomyopathy, dilated cardiomyopathy, Brugada syndrome, myocarditis, endomyocardial fibrosis, fibrotic vascular disease, hypertensive heart disease, arrhythmogenic right ventricular cardiomyopathy, hepatic fibrosis, chronic liver disease, liver cirrhosis, non-alcoholic steatohepatitis, primary biliary cirrhosis, primary sclerosing cholangitis, schistosomal liver disease, intestinal fibrosis, Crohn's disease, microscopic colitis, pancreatic fibrosis, renal fibrosis, chronic kidney disease, tubulointerstitial fibrosis, glomerular fibrosis, nephritic syndrome, Alport's syndrome, HIV associated nephropathy, polycystic kidney disease, Fabry's disease, diabetic nephropathy, chronic glomerulonephritis, nephritis associated with systemic lupus, eye fibrosis, Grave's opthalmopathy, epiretinal fibrosis, retinal fibrosis, subretinal fibrosis, macular degeneration, wet age-related macular degeneration, diabetic retinopathy, glaucoma, corneal fibrosis, post-surgical fibrosis of the posterior capsule following cataract surgery, post-surgical fibrosis of the bleb following trabeculectomy, conjunctival fibrosis, subconjunctival fibrosis, gliosis, Alzheimer's disease, skin fibrosis, scleroderma, nephrogenic systemic fibrosis, cutis keloid, Dupuytren's contracture, myelofibrosis, muscular dystrophy, Duchenne muscular dystrophy, Becker's muscular dystrophy (BMD), arthritis, adhesive capsulitis, mediastinal fibrosis, retroperitoneal fibrosis, Peyronie's disease, systemic sclerosis, progressive systemic sclerosis, chronic graft versus host disease, fibrotic pre-neoplastic disease, fibrotic neoplastic disease, and fibrosis induced by chemical or environmental insult.

Embodiment 107: The method of any one of Embodiments 102-106, wherein the method further comprises co-administering an anti-fibrotic agent to the subject, optionally the anti-fibrotic agent is pirfenidone, nintedanib, or BI 1015550 (nerandomilast).

Embodiments 108: The method of any one of Embodiments 100-102, wherein the DEAD box helicase dependent condition is cancer.

Embodiment 109: The method of Embodiments 98 or 99, wherein the eIF4A-dependent condition is cancer.

Embodiment 110: A method for treating cancer, the method comprising administering a therapeutically effective amount of a compound of any one of Embodiments 1-87 to a subject in need thereof.

Embodiment 111: The method of any one of Embodiments 108-110, wherein the cancer is glioblastoma (GBM), acoustic neuroma, acute lymphoblastic leukemia (ALL), acute myeloid leukemia, adenocarcinoma, angiosarcoma, astrocytoma, basal cell carcinoma, B-cell lymphoma, bile duct carcinoma, bladder cancer, bone cancer, brain cancer, breast cancer, bronchogenic carcinoma, Burkitt's lymphoma, cancer of the peritoneum, castration-resistant prostate cancer, cervical cancer, chondrosarcoma, chordoma, choriocarcinoma, chronic leukemia (chronic myelocytic (granulocytic) leukemia and chronic lymphocytic leukemia)), colon carcinoma, colorectal cancer, craniopharyngioma, cystadenocarcinoma, diffuse large B-cell lymphoma (DLBCL), embryonal carcinoma, endometrial or uterine carcinoma, endotheliosarcoma, ependymoma, epithelial carcinoma, esophageal cancer, Ewing's tumor, fibrosarcoma, fibrotic diseases, gastric cancer, hairy cell lymphoma, head and neck cancer, heavy chain disease, hemangioblastoma, hepatocellular cancers, Hodgkins lymphoma, kidney or renal cancer, leiomyosarcoma, leukemia (e.g. acute lymphocytic leukemia, chronic lymphocytic leukemia (CLL) and acute myeloid leukemia (e.g. myeloblastic-promyelocytic-myelomonocytic-monocytic and erythroleukemia)), liposarcoma, lung cancer, lymphangioendothelial sarcoma, lymphangiosarcoma, lymphoma (Hodgkin's disease and non-Hodgkin's disease), malignant glioma, medullary carcinoma, medulloblastoma, melanoma, meningioma, mesothelioma, multiple melanoma, myelodysplastic syndrome, myeloma, myxosarcoma, neuroblastoma, non-Hodgkins lymphoma, non-small cell lung cancer, oligodendroglioma, osteogenic sarcoma, ovarian cancer, pancreatic cancer, pancreatic carcinoma, papillary adenocarcinomas, papillary carcinoma, pinealoma, polycythemia vera, prostate cancer, renal cancer, renal cell carcinoma, retinoblastoma, rhabdomyosarcoma, salivary gland carcinoma, sebaceous gland carcinoma, seminoma, small cell lung carcinoma, solid tumor, squamous cell carcinoma, sweat gland carcinoma, synovial sarcoma, synovioma, T-cell lymphoma, testicular cancer, thyroid cancer, triple-negative breast cancer, urothelial cancer, vulvar cancer, Waldenstrom macroglobulinemia, or Wilms' tumor.

Embodiment 112: The method of Embodiment 111, wherein the cancer is GBM, DLBCL, hepatocellular cancers, acute myeloid leukemia, breast cancer, colorectal cancer, small cell lung cancer, or non-small cell lung cancer, optionally the cancer is GBM.

Embodiment 113: The method of any one of Embodiments 108-112, further comprising co-administering at least one additional anti-cancer therapy to the subject.

Embodiment 114: The method of Embodiment 113, wherein the additional anti-cancer therapy is an anti-cancer agent or chemotherapeutic, radiation therapy or surgery.

Embodiment 115: The method of Embodiment 114, wherein the additional anti-cancer therapy is an anti-cancer agent or chemotherapeutic agent.

Embodiment 116: The method of Embodiment 115, wherein the anti-cancer agent or chemotherapeutic is ABT-737; acetogenins (such as bullatacin and bullatacinone); aclacinomysins; actinomycin; actinomycin D; Aldesleukin; Alemtuzumab; alitretinoin; alkyl sulfonates such as busulfan, improsulfan and piposulfan; alkylating agents such as thiotepa and CYTOXAN® cyclosphosphamide; allopurinol; altretamine; AMG479; amifostine; anastrozole; antibiotics such as the enediyne antibiotics (e.g., calicheamicin, especially calicheamicin gamma1I and calicheamicin omegaI1 (see, e.g., Agnew, Chem. Intl. Ed. Engl., 33:183-186 (1994)); arsenic trioxide; Asparaginase; authramycin; azaserine; aziridines such as benzodopa, carboquone, meturedopa, and uredopa; BCG Live; bexarotene; bisphosphonates, such as clodronate; bleomycin; bortezomib; bryostatin; busulfan; busulfanoral; cactinomycin; callystatin; calusterone; caminomycin; camptothecin (including the synthetic analogue topotecan); capecitabine; carabicin; carboplatin; carmustine; CC-1065 (including its adozelesin, carzelesin and bizelesin synthetic analogues); celecoxib; chlorambucil; cisplastin; cladribine; cryptophycins (such as cryptophycin 1 and cryptophycin 8); cyclophosphamide; cytarabine; dacarbazine; dactinomycin; Darbepoetin alfa; daunomycin; daunorubicin; Denileukin diftitox; dexrazoxane; docetaxel; dolastatin; doxorubicin; Dromostanolone propionate; duocarmycin (including the synthetic analogues, KW-2189 and CB1-TM1); dynemicin, including dynemicin A; eleutherobin; Elliott's B Solution; epipodophyllotoxins; epirubicin; Epoetin alfa estramustine; esperamicin; ethylenimines and methylamelamines including altretamine, triethylenemelamine, triethylenephosphoramide, triethiylenethiophosphoramide and trimethylolomelamine; etoposide (VP-16); etoposide phosphate; exemestane; Filgrastim; floxuridine (intraarterial); fludarabine; fluorouracil (5-FU); fulvestrant; gemcitabine; gemtuzumab ozogamicin; goserelin acetate; hydroxyurea; Ibritumomab Tiuxetan; idarubicin; ifosfamide; imatinib; imatinib mesylate; immune checkpoint inhibitors (such as inhibitors of CTLA-4, PD-1, LAG-3, B7-H3, 67-H4, TIM3, A2AR, and IDO, e.g., an inhibitor of Programmed Death-Ligand 1 (PD-L1, also known as B7-HI, CD274), Programmed Death 1 (PD-1), CTLA-4, PD-L2 (B7-DC, CD273), LAG3, TIM3, 2B4, A2aR, B7HI, B7H3, B7H4, BTLA, CD2, CD27, CD28, CD30, CD40, CD70, CD80, CD86, CDI37, CDI60, CD226, CD276, DR3, GAL9, GITR, HAVCR2, HVEM, IDO1, ID02, ICOS (inducible T cell costimulator), KIR, LAIRI, LIGHT, MARCO (macrophage receptor with collagenous structure), PS (phosphatidylserine), OX-40, SLAM, TIGIT, VISTA, and VTCNI, such as an anti-PD-1 antibody, an anti PD-L1 antibody, or an anti-CTLA-4 antibody); Interferon alfa-2a; Interferon alfa-2b; irinotecan; letrozole; leucovorin; levamisole; LOddC; lomustine (CCNU); masitinib; mechlorethamine (nitrogenmustard); megestrol acetate; melphalan (L-PAM); mercaptopurine (6-MP); mesna; methotrexate; methoxsalen; mithramycin; mitomycin C; mitotane; mitoxantrone; nandrolone phenpropionate; neocarzinostatin chromophore and related chromoprotein enediyne antiobiotic chromophores); nilotinib; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; Nofetumomab; olaparib; Oprelvekin; oxaliplatin; paclitaxel; pamidronate; pancratistatin; pegademase; Pegaspargase; Pegfilgrastim; pentostatin; PI-103; pipobroman; plicamycin; porfimer sodium; procarbazine; quinacrine; rapamycin; Rasburicase; Rituximab; rituximab; rucaparib; sarcodictyin; Sargramostim; spongistatin; streptozocin; talbuvidine (LDT); talc; tamoxifen; taxol; temozolomide; teniposide (VM-26); testolactone; thioguanine (6-TG); thiotepa; toceranib; topotecan; toremifene; Tositumomab; Trastuzumab; tretinoin (ATRA); tyrosine kinase inhibitors; Uracil Mustard; valrubicin; valtorcitabine (monoval LDC); vinca alkaloids; vinblastine; vinorelbine; vorinostat; or zoledronate.

Embodiment 117: The method of any one of Embodiments 100-102, wherein the DEAD box helicase dependent condition is an infection.

Embodiment 118: The method of Embodiments 98 or 99, wherein the eIF4A-dependent condition is an infection.

Embodiment 119: A method for treating an infection, the method comprising administering a therapeutically effective amount of a compound of any one of Embodiments 1-87 to a subject in need thereof.

Embodiment 120: The method of Embodiments 117-119, wherein the infection is a fungal, bacterial, viral, helminth, or protozoal infection.

Embodiment 121: The method any one of the Embodiments 117-120, wherein the infection is a fungal infection, optionally, the fungal infection is aspergillosis, basidiobolomycosis, blastomycosis, candidiasis, chromoblastomycosis, coccidioidomycosis, conidiobolomycosis, cryptococcosis, dermatophytosis, eumycetoma, histoplasmosis, lobomycosis, mucormycosis, paracoccidioidomycosis, phaeohyphomycosis, pneumocystosis, scedosporiosis, sporotrichosis, talaromycosis, emmonsiosis, or microsporidiosis.

Embodiments 122: The method of Embodiment 121, further comprising co-administering an antifungal agent to the subject, optionally, the antifungal agent is Flycytosine, Bifonazole, Butoconazole, Chlordantoin, Chlorphenesin, Ciclopirox Olamine, Clotrimazole, Eberconazole, Econazole, Fluconazole, Flutrimazole, Isoconazole, Itraconazole, Ketoconazole, Miconazole, Nifuroxime, Tioconazole, Terconazole, Undecenoic Acid, azoles (e.g., barleyconazole, butoconazole, clortrimazole, econazole, fluconazole, isavuconazole, itraconazole, ketoconazole, miconazole, oxyconazole, posaconazole, ravuconazole, saperconazole, sulconazole, tercocnazole, tioconazole, voriconazole, and ciclopirox), polyenes (e.g., natamycin, lucensomycin, nystatin, amphotericin B, etc.), echinocandins (e.g., Cancidas), pradimicins (e.g., beanomicins, nikkomycins, sordarins, allylamines, etc.), Triclosan, Piroctone, fenpropimorph, terbinafine, cyclopyroxolamine, flucitocin, griseofulvin haloprozin, tolnaftate, naphthypine, hydrochloride, morpholine, butenapin, undecylenic acid, or propionic acid.

Embodiment 123: The method of any one of the Embodiments 117-120, wherein the infection is a bacterial infection, optionally, the bacterial infection is actinomycosis, anthrax, appendicitis, bacteremia, endocarditis, intraabdominal abscesses, whooping cough, bacterial pneumonia, atypical pneumonia, lyme disease, lyme arthritis, neuroborreliosis, from *B. recurrentis*, brucellosis, enteritis, from *C. jejuni*, trachoma, neonatal conjunctivitis, neonatal pneumonia, nongonococcal urethritis, urethritis, pelvic inflammatory disease, epidymitis, prostatitis, lymphogranuloma venereum, psittacosis, botulism, pseudomembranous colitis, anaerobic cellulitis, gas gangrene, food poisoning, tetanus, diphtheria, ehrilchoisis, bacterial endocarditis, biliary tract infection, urinary tract infection, meningitis, sepsis, from *E. coli*, tularemia, lymphadenopathy, upper respiratory tract infection, bronchitis, septic arthritis, pepic ulcer, gastritis, *Klebsiella pneumonia*, Legionnaire' Disease, Pontiac fever, leptospirosis, listeriosis, leprosy, tuberculosis, *Mycoplasma* pneumonia, gonorrhea, urethritis, Ophthalmia neonatorum, meningococcal disease, Waterhouse-Friderichsen syndrome, corneal infection, endocarditis, osteomyelitis, Malignant external otitis, nocardiosis, keratitis, Rocky mountain spotted fever, *salmonellosis*, hepatosplenomegaly, paratyphoid fever, osteomyelitis, shigellosis, staphylococcal: impetigo, acute infective endocarditis, toxinoses, cystitis, endometritis, otitis media, sinusitis, streptococcal pharyngitis, scarlet fever, rheumatic feber, erysipelas, puerperal fever, necrotizing fasciitis, poststreptococcal glomerulonephritis, syphilis, cholera, bubonic plague, pneumonic plague, or glanders, meliodiosis, campylobacteriosis, Q fever, or typhus fever.

Embodiment 124: The method of Embodiment 123, further comprising co-administering an antibacterial agent to the subject, optionally the anti-bacterial agent is selected independently from the group consisting of macrolides or ketolides such as erythromycin, azithromycin, clarithromycin, and telithromycin; beta-lactams including penicillin, cephalosporin, and carbapenems such as carbapenem, imipenem, and meropenem; monolactams such as penicillin G, penicillin V, methicillin, oxacillin, cloxacillin, dicloxacillin, nafcillin, ampicillin, amoxicillin, carbenicillin, ticarcillin, meziocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefmetazole, cefotaxime, ceftizoxime, cefiriaxone, cefoperazone, ceftazidime, cefixime, cefpodoxime, ceftibuten, cefdinir, cefpirome, cefepime, cefadroxil, ceftriaxone, ceftobiprole and astreonam; quinolones such as nalidixic acid, oxolinic acid, norfloxacin, pefloxacin, enoxacin, ofloxacin, levofloxacin, ciprofloxacin, temafloxacin, lomefloxacin, fleroxacin, grepafloxacin, sparfloxacin, trovafloxacin, clinafloxacin, gatifloxacin, moxifloxacin, sitafloxacin, ganefloxacin, gemifloxacin and pazufloxacin; antibacterial sulfonamides and antibacterial sulphanilamides, including para-aminobenzoic acid, sulfadiazine, sulfisoxazole, sulfamethoxazole and sulfathalidine; aminoglycosides such as streptomycin, neomvcin, kanamycin, paromycin, gentamicin, tobramycin, amikacin, netilmicin, spectinomycin, sisomicin, dibekalin and isepamicin; tetracyclines such as tetracycline, chlortetracycline, demeclocycline, minocycline, oxytetracycline, methacycline, doxycycline; rifamycins such as rifampicin (also called rifampin), rifapentine, rifabutin, bezoxazinorifamycin and rifaximin; lincosamides such as lincomycin and clindamycin; glycopeptides such as vancomycin and teicoplanin; streptogramins such as quinupristin and daflopristin; oxazolidinones such as linezolid; polymyxin, colistin and colymycin; trimethoprim, bacitracin, and phosphonomycin, optionally, the antibacterial agent is gentamicin, ampicillin, vancomycin, ceftriaxone or cefepime.

Embodiment 125: The method of any one of Embodiments 117-120, wherein the infection is a helminth infection, optionally caused by a nematode such as *Dracunculus medinensis, Wuchereria bancrofti, Brugia malayi, Brugia timori, Onchocerca volvulus, Schistosoma* spp., *Ancylostoma duodenale, Necator americanus, Ascaris lumbricoides*, or *Trichuris trichiura.*

Embodiments 126: The method of Embodiment 125, further comprising co-administering an antihelminthic agent to the subject, optionally the antihelminthic agent is albendazole, ivermectin, mebendazole, nitazoxanide, pentamidine, praziquantel, pyrantel, thiabendazole, or triclabendazole.

Embodiment 127: The method of any one of Embodiments 117-120, wherein the infection is a protozoal infection, optionally caused by a protozoa such as *Balantidium coli, Naegleria fowleri, Acanthamoeba* spp., *Balamuthia* spp. *Entamoeba histolytica, Cryptosporidium* spp., *Giardia* spp., *Cyclospora cayetanensis, Trichomonas vaginalis, Plasmodium* spp., *Trypanosoma brucei* rhodesiense, *Trypanosoma brucei gambiense, Trypanosoma cruzi, Leishmania* spp., or *Toxoplasma gondii*

Embodiment 128: The method of Embodiment 127, further comprising co-administering an antiprotozoal agent to the subject in which case the antiprotozoal agent is Acetarsol, Azanidazole, Chloroquine, Metronidazole, Nifuratel, Nimorazole, Omidazole, Propenidazole, Secnidazole, Sineflngin, Tenonitrozole, Temidazole, or Tinidazole.

Embodiment 129: The method of any one of Embodiment 117-120, wherein the infection is a viral infection, optionally the viral infection is an infection caused by Adenovirus, Herpes, Human papillomavirus, BK virus, JC virus, Smallpox, Parvovirus, Rotavirus, Orbivirus, Coltivirus, Banna virus, Human astrovirus, Norwalk virus, Coronavirus, Hepatitis, yellow fever virus, dengue virus, West Nile virus, TBE virus, Zika virus, Rubella virus, coxsackievirus, cytomegalovirus, Epstein-Barr virus, Middle East Respiratory syndrome-related coronavirus, Severe acute respiratory syndrome coronavirus, Severe acute respiratory syndrome coronavirus 2, Varicella-zoster virus, poliovirus, rhinovirus, Lassa virus, Crimean-Congo hemorrhagic fever virus, Hantavirus, Ebola virus, Marburg virus, Influenza virus, Measles virus, Mumps virus, Parainfluenza virus, Respiratory syncytial virus, Rabies virus, Alkhurma virus, Cache Valley virus, Calcivirus, California encephalitus virus, Chapare virus, Chikunguynya virus, Eastern Equine Encephalitis virus, Enterovirus, Guanarito virus, Heartland virus, Hendra virus, Japanese encephalitis virus, Junin virus, Kyasanur Forest virus, LaCrosse encephalitis virus, Langya virus, Lujo virus, Lymphocytic choriomeningitus virus, Machupo virus, Mayoro virus, Nipah virus, O'nyong-nyong virus, Omsk hemhorragic fever virus, Oroupouche virus, Powassan/Deer tick virus, Rift Valley fever virus, St. Louis encephalitis virus, Monkeypox virus, or HIV.

Embodiment 130: The method of Embodiment 129, further comprising co-administering an antiviral agent to the subject, optionally the antiviral agent is 1-docosanol, acyclovir, brivudine, cidofovir, curcumin, daclatasvir, desciclovir, edoxudine, elbasvir, famciclovir, fiacitabine, glecaprevir, ibacitabine, imiquimod, interferon alpha-2a, interferon alpha-2b, interferon aphacon-1, lamivudine, ledipasvir/sofosbuvir, grazoprevir, pegylated interferon, pegylated interferon alpha-2b, penciclovir, pibrentasvir, ribavirin, simeprevir, sofosbuvir, telaprevir, valacyclovir, valganciclovir, velpatasvir, Entecavir, adefovir, telbivudine, ganciclovir, oseltamivir, zanamivir, nirmatrelvir, remdesivir, molnupiravir, atanzavir, cobicistat, dolutegravir, rilpivirine, enfuvirtide, etravirine, raltegravir, tenofovir, or mRNA.

Embodiment 131: A method of inhibiting cancer stem cell propagation, the method comprises: administering a compound of any one of Embodiments 1-87 to a cancer stem cell.

Embodiment 132: The method of Embodiment 131, wherein the cancer stem cell is a glioblastoma (GBM), acoustic neuroma, acute lymphoblastic leukemia (ALL), acute myeloid leukemia, adenocarcinoma, angiosarcoma, astrocytoma, basal cell carcinoma, B-cell lymphoma, bile duct carcinoma, bladder cancer, bone cancer, brain cancer, breast cancer, bronchogenic carcinoma, Burkitt's lymphoma, cancer of the peritoneum, castration-resistant prostate cancer, cervical cancer, chondrosarcoma, chordoma, choriocarcinoma, chronic leukemia (chronic myelocytic (granulocytic) leukemia and chronic lymphocytic leukemia)), colon carcinoma, colorectal cancer, craniopharyngioma, cystadenocarcinoma, diffuse large B-cell lymphoma (DLBCL), embryonal carcinoma, endometrial or uterine carcinoma, endotheliosarcoma, ependymoma, epithelial carcinoma, esophageal cancer, Ewing's tumor, fibrosarcoma, fibrotic diseases, gastric cancer, hairy cell lymphoma, head and neck cancer, heavy chain disease, hemangioblastoma, hepatocellular cancers, Hodgkins lymphoma, kidney or renal cancer, leiomyosarcoma, leukemia (e.g. acute lymphocytic leukemia, chronic lymphocytic leukemia (CLL) and acute myeloid leukemia (e.g. myeloblastic-promyelocytic-myelomonocytic-monocytic and erythroleukemia)), liposarcoma, lung cancer, lymphangioendothelial sarcoma, lymphangiosarcoma, lymphoma (Hodgkin's disease and non-Hodgkin's disease), malignant glioma, medullary carcinoma, medulloblastoma, melanoma, meningioma, mesothelioma, multiple melanoma, myelodysplastic syndrome, myeloma, myxosarcoma, neuroblastoma, non-Hodgkins lymphoma, non-small cell lung cancer, oligodendroglioma, osteogenic sarcoma, ovarian cancer, pancreatic cancer, pancreatic carcinoma, papillary adenocarcinomas, papillary carcinoma, pinealoma, polycythemia vera, prostate cancer, renal cancer, renal cell carcinoma, retinoblastoma, rhabdomyosarcoma, salivary gland carcinoma, sebaceous gland carcinoma, seminoma, small cell lung carcinoma, solid tumor, squamous cell carcinoma, sweat gland carcinoma, synovial sarcoma, synovioma, T-cell lymphoma, testicular cancer, thyroid cancer, triple-negative breast cancer, urothelial cancer, vulvar cancer, Waldenstrom macroglobulinemia, or Wilms' tumor stem cell.

Embodiment 133: The method of Embodiment 132, wherein the cancer stem cell is a GBM, DLBCL, hepatocellular cancers, acute myeloid leukemia, breast cancer, colorectal cancer, small cell lung cancer, or non-small cell lung cancer stem cell, optionally the cancer cell is a GBM cancer stem cell.

Embodiment 134: The method of any one of Embodiments 131-133, wherein the said administering is in vitro.

Embodiment 135: The method of any one of Embodiments 131-133, wherein the said administering is ex vivo.

Embodiment 136: The method of any one of Embodiments 131-133, wherein the said administering is in vivo.

Embodiment 137: The method of Embodiment 136, wherein said administering is to a subject having or diagnosed with cancer.

Embodiment 138: The method of Embodiment 137, the method further comprising co-administering an anti-cancer therapy to the subject.

Embodiment 139: The method of Embodiment 138, wherein the anti-cancer therapy is an anti-cancer agent or chemotherapeutic agent.

Embodiment 140: The method of any one of Embodiments 98-130 or 137-138, wherein the subject is a mammal.

Embodiment 141: The method of Embodiment 140, wherein the subject is a primate.

Embodiment 142: The method of Embodiments 140 or 141, wherein the subject is human.

Embodiment 143: The method of Embodiments 140 or 141, wherein the subject is a non-human primate.

Embodiment 144: A kit comprising a compound of any one of Embodiments 1-87.

Embodiment 145: The kit of Embodiment 144, further comprising instructions of use.

Embodiment 146: The kit of Embodiments 144 or 145, wherein the kit further comprises a therapeutic agent.

Embodiment 147: The kit of Embodiment 146, wherein the therapeutic agent is an anticancer agent or an antimicrobial agent.

Embodiment 148: The kit of Embodiments 144 or 145, wherein the compound and the therapeutic agent are in separate containers in the kit.

Embodiment 149: The kit of Embodiments 144 or 145, wherein the compound and the therapeutic agent are in a same container in the kit.

Embodiment 150: The kit of any one of Embodiments 144-149 further comprising instructions of use.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The embodiments will be more readily understood by reference to the following examples, which are included merely for purposes of illustration of certain aspects and embodiments of the present invention, and should not be construed as limiting. As such, it will be readily apparent that any of the disclosed specific constructs and experimental plan can be substituted within the scope of the present disclosure.

EXAMPLES

Example 1: Identification of Rocaglate Acyl Sulfamides (Roc ASFs) as Selective Inhibitors of Glioblastoma Stem Cells Metastatic spread and development of therapeutic resistance pose major challenges for the treatment of cancer.[1,2] A large body of evidence suggests that tumor initiation, progression, metastasis, and recurrence are driven by a small subpopulation (1-5%) of cells within tumors called tumor-initiating cells or cancer stem cells (CSCs). CSCs are slow-dividing, undifferentiated, self-renewing cells, which give rise to the differentiated cells comprising the bulk of the tumor (non-stem cancer cells, hereafter termed "non-CSCs"). CSCs have been identified in various types of tumors such as leukemia, breast, brain, colon, and lung, although the markers and driver pathways vary among tumor types.[3,4] In addition, CSCs interact with multiple components of the tumor microenvironment and can modulate the immune response to tumors.[5] CSCs possess a range of capabilities that confer resistance to chemo- and radiotherapies and therefore not only persist after treatment, but are often actually enriched, leading to tumor recurrence.[6,7] These capabilities include a robust DNA damage repair system, upregulated efflux pumps, activation of survival pathways, enhanced cellular plasticity, immune evasion, and the ability to adapt to hostile microenvironments.[8,9] Additionally, CSCs can undergo phenotypic changes such as epithelial-mesenchymal transition (EMT) which further enhance their resistance to treatment.[8] Thus, targeting of CSCs is crucial to prevent tumor recurrence and improve patient survival after chemotherapy. Of particular interest are compounds that specifically target and eliminate CSCs while minimizing impact on non-CSCs. Such compounds are more likely to demonstrate specific efficacy against cancers rather than acting as general cytotoxic agents.[10,11,12,13] Glioblastoma (GBM) is the most common and aggressive malignant brain tumor in adults and generally has a poor prognosis. Irrespective of treatment, which includes surgical resection, radiotherapy, and chemotherapy, almost all patients experience tumor recurrence, leading to mortality and a median survival of <15 months. Thus, targeted prevention of tumor recurrence, by specifically eradicating GBM CSCs, is a potential therapeutic strategy for glioblastoma.

Rocaglates (also known as flavaglines) are a group of natural products containing a cyclopenta[b]tetrahydrobenzofuran skeleton originally isolated from plants of the genus *Aglaia*.[14] Since the first report of rocaglamide A (RocA, FIG. 1A, 1) as an antitumor agent, there have been extensive biological studies on rocaglates.[15] Beyond RocA, other nature-produced rocaglates (FIG. 1A) include silvestrol (2), methyl rocaglate/aglafoline (3), and aglaroxin C (4). In addition, many synthetic rocaglates have been developed as molecular probes and drug candidates, including the C2-hydroxamates CR-1-31b (5), rohinitib ("RHT," 6), and SDS-1-021 (7), as well as the C2-amine eFT226 (Zotatifin, 8), a compound currently in clinical development for breast and non-small cell lung cancers. In a comprehensive study of >200 natural and synthetic rocaglates, Pelletier and coworkers showed that most rocaglates preferentially repress translation of mRNAs containing purine-rich 5' leaders by stimulating the binding of DEAD-box helicase eIF4A to these sequences, and in some cases also exerting a trans-inhibitory effect on global translation by limiting the pool of eIF4A (and parent complex eIF4F) available for ribosome recruitment.[16] Mechanistically, rocaglates bind a bimolecular cavity formed by the complexation of eIF4A onto polypurine RNA as shown in an X-ray co-crystal structure of a RocA-eIF4A1-r$(AG)_5$ complex reported by Iwasaki and coworkers.[17] The same group found that RocA could additionally clamp the related DEAD box helicase DDX3 to polypurine RNA in an ATP-independent manner, thereby expanding our understanding of the potential mechanisms underlying RocA's antiproliferative effects.[18]

In this study, the inventors probed the activity of rocaglates against glioblastoma (GBM) CSCs. Using comparative dose-response assays, the inventors found that rocaglate translation inhibitors exhibit potent, dose-dependent cytotoxic effects against GBM CSCs at concentrations that are predominantly non-lethal to non-CSC populations, prompting further study of this chemotype and the underlying mechanism. Herein, the inventors describe our results, including identification of new rocaglate congeners for use as tool compounds to explore the mechanism of action for targeted and selective killing of GBM CSCs.

Results and Discussion

Rocaglates exhibit selective, dose-dependent killing of CSCs in a patient-derived glioblastoma (GBM) cell line. The inventors first evaluated a cohort of seven rocaglate translation inhibitors (1, 3-7, and 9, FIG. 1A and Table 1, compounds 2 and 8 were not tested due to unavailability). To assay for compounds that selectively affect GBM CSCs, the inventors employed the patient-derived tumor-initiating cell (TIC) cell line 030819 that forms neurospheres (consisting exclusively of tumor-initiating cells or CSCs) when cultured in neurobasal (NBE) medium. Upon exposure to serum and growth factor withdrawal, however, the cell line differentiates, acquires a flattened morphology, and forms a non-CSC population.[20] Thus, compounds can be tested in parallel to assess their effect on GBM CSCs vs. GBM non-CSCs as separate populations with a clean and robust response. This approach has been previously used to perform RNAi-based genetic screens to identify modulators of CSCs.[20] In this study, GBM0308 cells, cultured in stem cell conditions to form CSCs or in medium containing serum to induce differentiation into a non-CSC population, were treated in parallel with compounds at varying doses. Three days post-treatment, propidium iodide (PI) and Hoechst staining were performed and quantified using a Celigo image cytometer. Hoechst dye stained all live nucleated cells, while PI exclusively stained dead cells. Cell viability and the percentage of cell death were then determined.

TABLE 1

Comparative activity of key rocaglates against GBM CSCs and non-CSCs

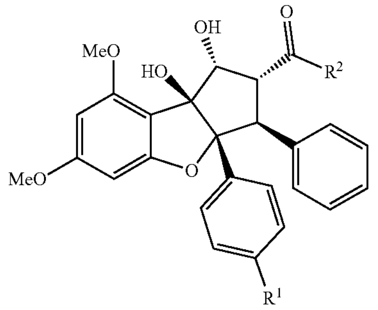

| Compound | $R^1$ | $R^2$ | CSCs $EC_{50}$ (μM)[b] | CSCs Max. observed efficacy (% dead cells) | Non-CSCs $EC_{50}$ (μM)[b] | Non-CSCs Max. observed efficacy (% dead cells) |
|---|---|---|---|---|---|---|
| (−)-1 | OMe | $N(Me)_2$ | 0.387 | 84 | nd | 31 |
| (−)-3 | OMe | OMe | 1.642 | 75 | nd | 23 |
| rac-4[a] | — | — | nd | 42 | nd | 26 |
| (−)-5 | OMe | NH(OMe) | 0.036 | 91 | nd | 22 |
| rac-6 | OMe | N(Me)OMe | 0.922 | 81 | nd | 25 |
| (−)-7 | Br | NH(OMe) | 0.007 | 92 | nd | 31 |
| (−)-9 | Br | OMe | 0.151 | 88 | nd | 25 |

[a] See Figure 1A for chemical structure.

[b] For each cell type, $EC_{50}$ values are provided for compounds causing at least 50% cell death. Values shown are relative $EC_{50}$s, obtained from a variable-slope, four-parameter nonlinear regression constrained to bottom = 0% and top <100% cell death.

Table 1 and FIG. 1B summarize the results for these experiments. Interestingly, all seven rocaglates showed specific cytotoxic activity against CSCs with lesser impact on non-CSCs (cf. FIG. 1B and FIG. 6 for dose-response curves). This selectivity manifests as a striking difference in the maximum observed percent death of the respective cell populations; in CSCs, several compounds showed dose-dependent cytotoxicity that plateaued at ≥75% cell death, whereas their dose-dependent cytotoxicity against non-CSCs, when observed, plateaued at ≤31% of cells. A notable exception was the rocaglate pyrimidinone (RP) aglaroxin C (4) (FIG. 1A) which failed to surpass >50% cell death in CSCs (Table 1, FIG. 6).

While most compounds showed CSC selectivity, there was a wide variance in their anti-CSC potency, with CSC $EC_{50}$ values ranging from ~1.6 μM to 7 nM (Table 1). The inventors also noted nascent structure-activity relationships (SAR) among the set. First, two of the more potent compounds ((−)-7 and (−)-9) bore a bromine at the B-ring C4' position, a site that is methoxy-substituted in most rocaglates found in nature. A head-to-head comparison showed that the C4'-brominated congeners 7 and 9 each exhibited a 5-to-10-fold improvement in potency over their C4'-methoxy congeners 5 and 3, respectively. In addition, the C2-hydroxamic esters (5, 7) also outperformed their C2-methyl ester counterparts 3 and 9, respectively, by >20-fold, in addition to outperforming the C2-dimethyl amide RocA (1) and N-methyl hydroxamic ester RHT (6). This preliminary SAR suggested that a protic N—H at C2 as well as a C4'-bromine were key potency drivers. Given the potential for hydroxamates such as 5 and 7 to ionize at physiological pH (pKa range 6-10), we postulated that the N—H hydroxamic esters may be behaving as carboxylic acid surrogates.[21] To further probe this hypothesis, we sought to synthesize additional analogs bearing both carboxylic acids and ionizable acid isosteres at the C2 position, while also continuing to probe the impact of C4'-bromination.

Synthesis of N-acylated Derivatives of Rocaglaic Acids. After identification of O-methyl hydroxamic esters 5 and 7 as the most potent and selective inhibitors of GBM CSCs, the inventors targeted direct replacement of the C2-hydroxamic ester with carboxylic acids and acid bioisosteres such as N-acylated sulfamides and sulfonamides, whose pKa values generally fall within the range of carboxylic acids (4-5).[21] Employing the previously established method for ESIPT-mediated [3+2] photocycloaddition to produce rocaglates,[22] the inventors subsequently transformed the derived rocaglaic acid 10/11 (obtained by hydrolysis of 3/9) to the rocaglate ß-lactone 12/13 by treatment with bis(2-oxo-3-oxazolidinyl)phosphinic chloride (BOP-Cl)/triethylamine.[23]

The inventors used ß-lactones 12/13 as lynchpin substrates to generate N-acylated congeners through ß-lactone ring-opening with various nitrogen nucleophiles (e.g. cyanamide, sulfonamide, and sulfamide, Scheme 1).

Scheme 1. (A) Synthesis of rocaglaic acids and derived N-acylated derivatives. (B) Substrate scope for β-lactone ring opening (one-step yields from precursors are denoted in parentheses).
A
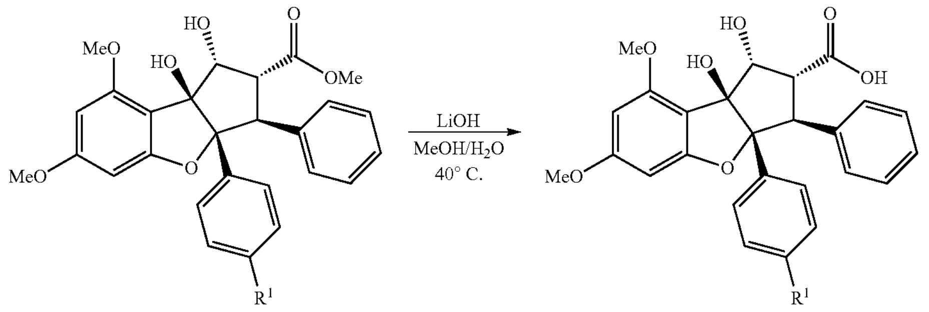
3: $R^1$ = OMe
9: $R^1$ = Br
10: $R^1$ = OMe (95%)
11: $R^1$ = Br (97%)
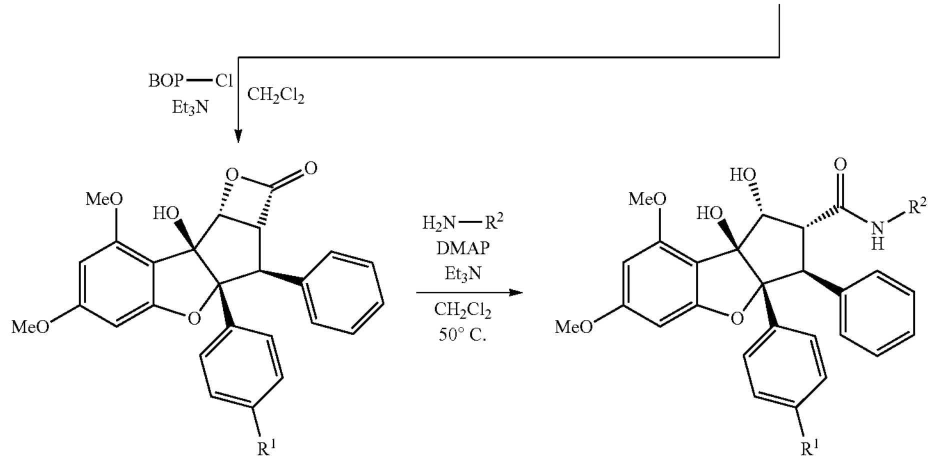
12: $R^1$ = OMe (50%)
13: $R^1$ = Br (67%)
B
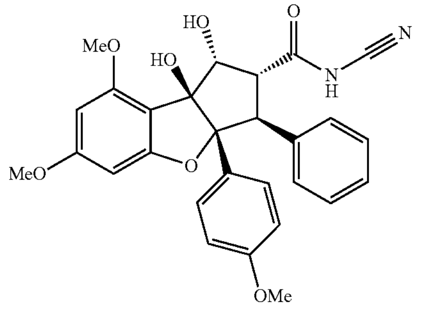
14 (75%)
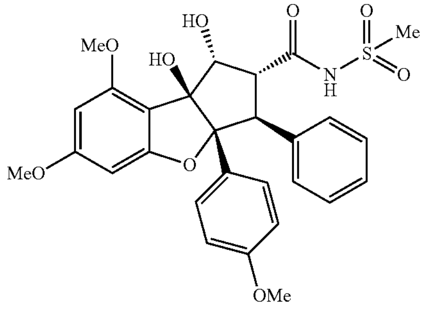
15 (72%)

-continued

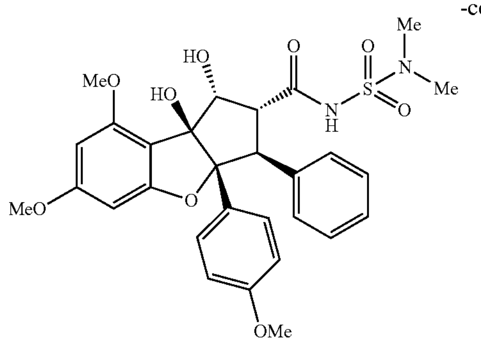

16 (40%)

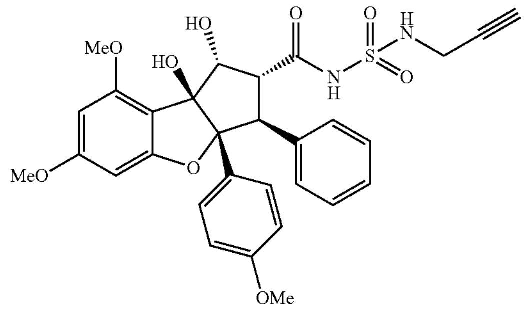

17 (40%)

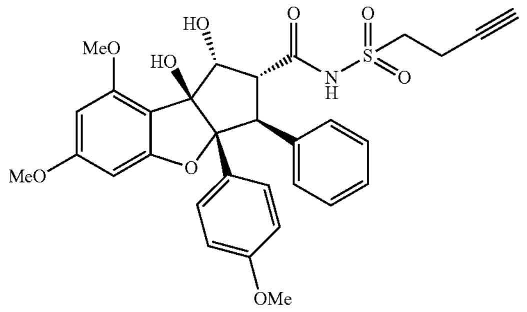

18 (67%)

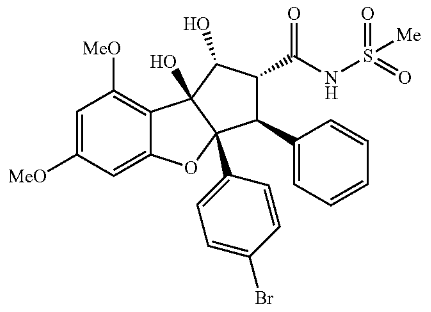

19 (60%)

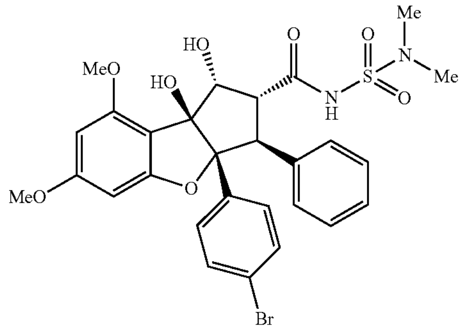

20 (56%)

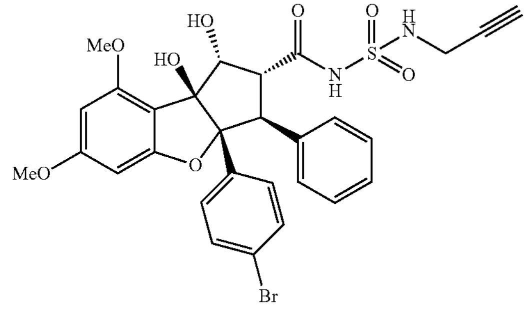

21 (47%)

A Ring-opening of 12 with cyanamide as a nucleophile afforded the corresponding rocaglate acyl cyanamide 14 in 75% yield. When methanesulfonamide was used in ring-opening with 12, a 72% yield of rocaglate acyl sulfonamide 15 was obtained. However, use of N,N-dimethylsulfamide as nucleophile with 12 afforded a lower yield (40%) of rocaglate acyl sulfamide 16. The inventors also used alkynylated reagents such as N-propargyl sulfamide and 3-butyne-1-sulfonamide for ring-opening of 12 to produce alkyne-tagged congeners such as 17 and 18, respectively (vide infra). Additionally, the inventors prepared 4'-brominated congeners 19-21 using ring-openings of ß-lactone substrate 13. Using these weak nitrogen nucleophiles, stoichiometric DMAP and mild heating (50° C.) were required for successful ß-lactone ring-opening. Conventionally, carboxylic acids such as 10/11 can be converted to amides by reacting with amines in the presence of excess N,N'-dicyclohexylcarbodiimide (DCC), but the N,N'-dicyclohexylurea byproduct generated is often difficult to remove entirely via column chromatography.[24] ß-Lactone ring-opening of 12/13 offers an alternative method to generate N-acylated rocaglate derivatives using mild conditions and comparatively facile purification.

While initial derivatization studies employed (±)-12 and (±)-13 (thus producing chiral, racemic congeners), we also sought to access key analogs in enantioenriched form. The inventors have previously reported access to enantiomerically-enriched rocaglates through reductive kinetic resolution of an aglain ketone precursor, several steps upstream from our ester starting materials 3 and 9.[25] Toward an alternative, scalable method for separation of chiral, racemic rocaglaic acids at a later stage, the inventors evaluated direct resolution of rocaglaic acids using chiral bases via formation of diastereomeric salts.[26] In these experiments, the inventors found that (±)-rocaglaic acid 10 could be resolved to its corresponding enantiomers after treatment with (−)-quinine. Specifically, the inventors treated (±)-rocaglaic acid 10 with one equivalent of (−)-quinine at 25° C. in ethanol to afford a mixture of the diastereomeric salts 22 and 23 in quantitative yield (Scheme 2).

Inventors were able to cleanly isolate 22 through recrystallization in acetone, while 23 was recovered from the mother liquor. Enantioenriched rocaglaic acids (+)-10 and (−)-10 were obtained after treatment of the respective salts 22/23 with 5% HCl (FIG. 7A). This process was repeated by resolving (+)-11 and (−)-11 from the (±)-brominated rocaglaic acid 11 (which was obtained by hydrolysis of chiral, racemic 9) via diastereomeric salts 24/25. Single-crystal X-ray diffraction analysis confirmed the absolute configuration (Flack parameter=0.002) of the (+)-rocaglaic acid (−)-quinine salt 24 (Scheme 2), which is the opposite enantiomer to naturally occurring rocaglates. Subsequently, the enantioenriched rocaglate acyl sulfonamides (−)-15/(−)-19, as well as enantioenriched acyl sulfamides (−)-16/(−)-20 were synthesized from their corresponding precursors (−)-10/(−)-11, respectively, via β-lactone formation and ring-opening (cf. Scheme 1). For comparison purposes, the enantiomeric derivatives (+)-15 and (+)-16 were also prepared from (+)-10. Our chiral resolution method using (−)-quinine offers a means to generate enantioenriched rocaglates that is more economical and scalable than our previously-established methods involving kinetic resolution of aglain precursors, or using TADDOL derivatives as chiral mediators.[25,27,28]

FIG. 2, Table 2, and FIG. 6 summarize the activity of the rocaglaic acids and N-acylated derivatives against GBM CSC and non-CSC populations.

TABLE 2

Preliminary SAR of rocaglaic acid (10) and its N-acylated derivatives against GBM CSCs and non-CSCs.

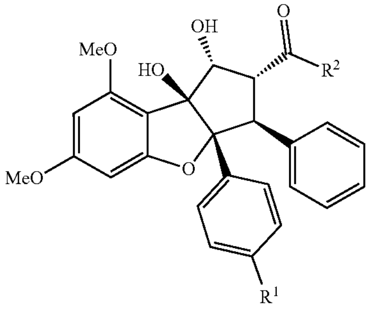

| Compound | $R^1$ | $R^2$ | CSCs: $EC_{50}$ (μM)[a] | CSCs: Max. observed efficacy (% dead cells) | Non-CSCs: $EC_{50}$ (μM)[a] | Non-CSCs: Max. observed efficacy (% dead cells) |
|---|---|---|---|---|---|---|
| (−)-10 | OMe | OH | 3.642 | 68 | nd | 27 |
| (−)-11 | Br | OH | 0.121 | 92 | nd | 25 |
| rac-14 | OMe | NHCN | nd | 44 | nd | 36 |
| (−)-15 | OMe | $NHSO_2Me$ | 0.980 | 85 | nd | 19 |
| (−)-16 | OMe | $NHSO_2N(Me)_2$ | 1.728 | 76 | nd | 23 |
| rac-17 | OMe | $NHSO_2NHCH_2CCH$ | 8.083 | 54 | nd | 24 |
| rac-18 | OMe | $NHSO_2(CH_2)_2CCH$ | nd | 40 | nd | 29 |
| (−)-19 | Br | $NHSO_2Me$ | 0.095 | 92 | nd | 20 |
| (−)-20 | Br | $NHSO_2N(Me)_2$ | 0.045 | 93 | nd | 26 |
| (−)-21 | Br | $NHSO_2NHCH_2CCH$ | 0.016 | 92 | nd | 27 |
| (+)-10 | OMe | OH | 7.085 | 58 | nd | 30 |
| (+)-15 | OMe | $NHSO_2Me$ | nd | 34 | nd | 6 |
| (+)-16 | OMe | $NHSO_2N(Me)_2$ | nd | 49 | nd | 36 |

[a]For each cell type, $EC_{50}$ values are provided for compounds causing at least 50% cell death. Values shown are relative $EC_{50}$s, obtained from a variable-slope, four-parameter nonlinear regression constrained to bottom = 0% and top <100% cell death.

Consistent with the earlier cohort, CSC-selective activity (defined as CSC maximum observed cell death: ≥75%; non-CSC maximum observed cell death: <30%) was observed for nearly all compounds synthesized, except for acyl cyanamide 14, alkynylated acyl sulfamide 17, and alkynylated acyl sulfonamide 18, which all showed <75% cell killing at the highest tested concentration (10 μM) against both CSCs and non-CSCs (FIG. 2 and FIG. 6). Also consistent with earlier results, head-to-head comparisons revealed that the C4'-brominated congeners consistently showed superior potency, with compounds (−)-11, (−)-19, (−)-20, and (−)-21 exhibiting CSC $EC_{50}$s <125 nM, while their C4'-methoxy counterparts (−)-10, (−)-15, (−)-16, and rac-17 had CSC $EC_{50}$s in the range of ~1-10 μM (FIG. 2). As the alkynylated derivative (−)-21 was also able to retain high potency (16 nM) with selectivity against GBM CSCs (CSC maximum observed cell death: 92%, non-CSC maximum observed cell death: 27%), this compound may serve as a "click"-able probe for future mechanistic investigations. For the "unnatural" enantiomers (+)-10, (+)-15, and (+)-16, the inventors observed limited activity against both CSCs and non-CSCs (FIG. 6).

To further validate the observed CSC selectivity, compound (−)-20, one of the most potent compounds identified against GBM0308 CSCs, was also evaluated against additional GBM stem-like cell lines including BT112 and BT145, both of which also showed selective susceptibility of CSCs vs. non-CSCs (FIG. 8), with CSC $EC_{50}$s of 34 nM and 93 nM against the two cell lines, respectively.

Derivatization-free target identification using a modified proteome integral solubility alteration (PISA) assay. The inventors next pursued proteome-wide target identification to better understand the target profiles of CSC-selective rocaglates. To enable cross-compound comparisons of target engagement, the inventors opted to use the Proteome Integral Solubility Alteration (PISA) assay,[29] a derivative of the mass spectrometry-based Cellular Thermal Shift Assay (MS-CETSA). In MS-CETSA,[30,31] target engagement is inferred through proteome-wide analysis of compound-induced changes to protein thermal stability; proteins with a shift in their half-maximal thermal denaturation temperature upon compound treatment are flagged as potential targets. The PISA assay obviates the need for MS-CETSA-derived thermal denaturation curves through curve integration by pooling of individual temperature points into a single "integral" sample for each treatment condition, thereby increasing throughput (FIG. 9). In contrast to MS-CETSA (which relies on curve comparisons), PISA determinations are performed by simply comparing soluble protein abundance levels between compound- and DMSO-treated samples. Importantly, protein fold-change measurements in PISA experiments generally scale with the thermal shift derived from CETSA experiments, and the magnitude of a thermal shift can inform on relative affinity between compounds and individual targets.[30,32-25] Maximal stability changes are protein-specific,[36] however, precluding estimations of preference for one target over another. Thus, PISA allows for simultaneous target profiling and comparisons of binding affinity between different compounds within a given target.

Figures 3A, 3B, 3C, 3D, 3E, 3F, 3G:
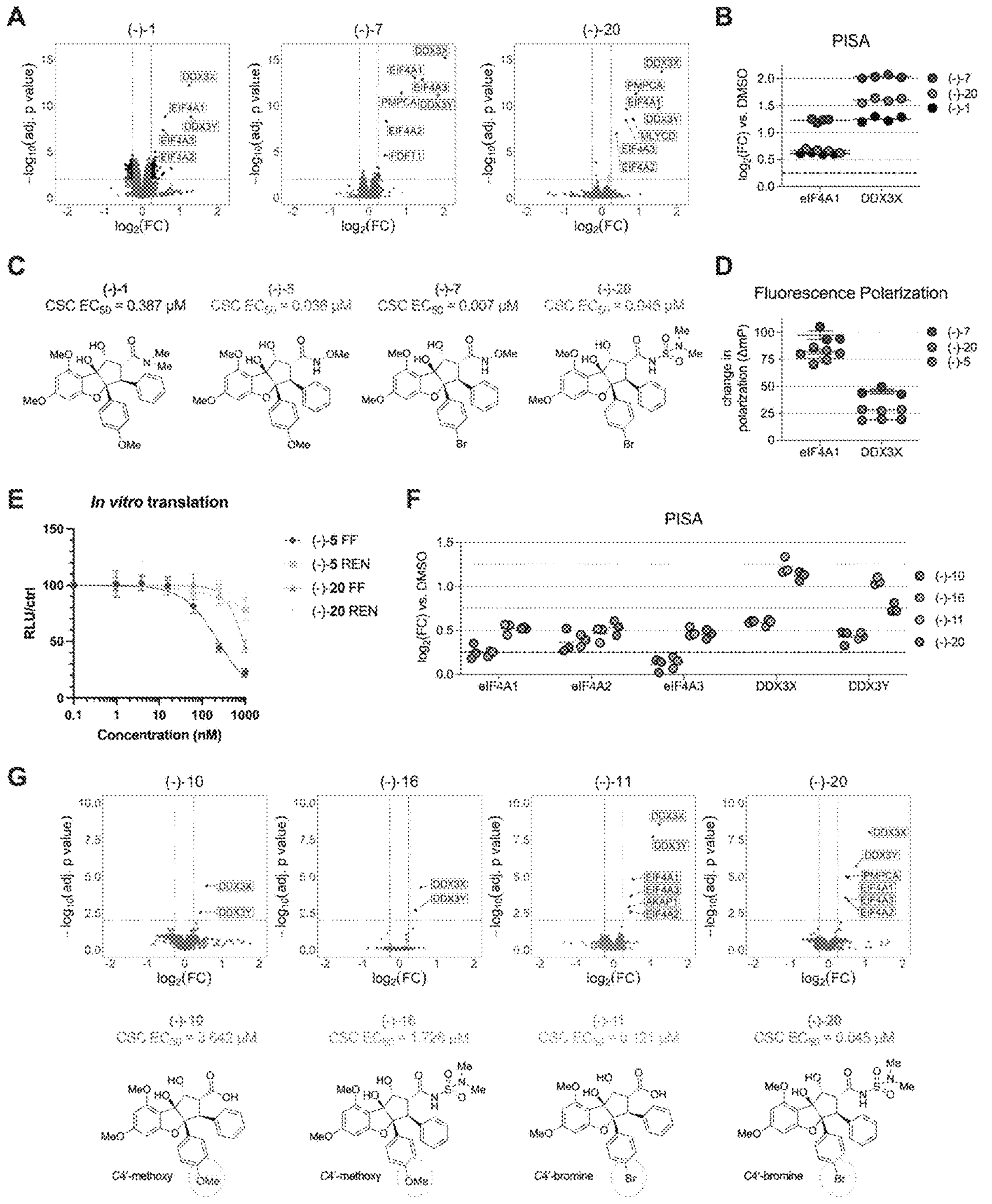
FIG. 3A shows comparative PISA profiling: volcano plots depicting differentially stabilized GBM0308 lysate proteins in the presence of the natural rocaglate (−)-1 (left), the derivative (−)-7 (middle), and (−)-20 (right). Compounds were tested at a concentration of 10 μM. Significance thresholds were set to FDR<0.01 with a |log 2(FC)|>0.25.
FIG. 3B shows extracted individual $\log_2$ (FC) (N=4) from PISA assays for DDX3X and eIF4A1 stabilization in the presence of compounds (−)-1, (−)-7, and (−)-20.
FIG. 3C shows structures of compounds (−)-1, (−)-5, (−)-7, and (−)-20 and their corresponding $EC_{50}$ against GBM CSCs.
FIG. 3D shows the change in polarization (DmP) obtained with DDX3X:FAM-labeled poly $r(AG)_8$ and eIF4A1:FAM-labeled poly $r(AG)_8$ by FP assay in the presence of (−)-5, (−)-7, and (−)-20 (10 μM). Background-subtracted values were generated using a DMSO control; (N=3; lines indicate mean±SEM).
FIG. 3E shows in vitro translation experiments testing a bicistronic mRNA reporter construct FF-HCV-Ren. The translation of the FF cistron is cap-dependent, while translation of the HCV-Ren cistron is driven off an HCV-IRES, rendering translation of this cistron cap-independent.
FIG. 3F shows the extracted individual $\log_2$ (FC) (N=3) for DDX3 and eIF4A paralog stabilization in the presence of compounds (−)-10, (−)-11, (−)-16, and (−)-20. Horizontal bars indicate mean values.
FIG. 3G shows the comparative PISA profiling of compounds (−)-10, (−)-11, (−)-16, and (−)-20 in GBM0308 cell lysate, with volcano plots depicting differentially stabilized lysate proteins in the presence of C4'-methoxy ((−)-10, (−)-16) (left) and C4'-brominated ((−)-11, (−)-20) (right) compounds tested at a concentration of 10 μM. Significance thresholds were set to FDR<. 01 with a $|\log_2 (FC)|>0.25$.

The inventors initially attempted to benchmark PISA for rocaglate target identification using CR-1-31b ((−)-5) (FIG. 1A), a well-characterized polypurine RNA-dependent inhibitor of eukaryotic translation initiation factor 4A1 (eIF4A1).[37] Using this compound, the inventors found that a standard lysate-based PISA assay was not suitable for detection of the rocaglate: protein: RNA complex. Following a detailed investigation,[38] the inventors found that the use of two key lysate additives, a polypurine $(AG)_8$ RNA probe and the non-hydrolysable ATP analog AMP-PNP satisfied the requirements for rocaglate: eIF4A1 target engagement enabling detection of compound (−)-5-induced eIF4A1 stabilization. The inventors then performed PISA in GBM0308 (CSC) lysates with compounds (−)-1, (−)-7, and (−)-20 to assess the possibility of differential targeting driven by substitutions at the rocaglate $R^1$ and $R^2$ positions as suggested by our SAR studies (Tables 1 and 2). Consistent with previous reports,[17,18,39] the inventors detected thermal stabilization of eIF4A paralogs and DDX3X by (−)-1, and confirmed that these proteins are also stabilized by (−)-7 and (−)-20 (FIG. 3A). Of note, we also detected stabilization of DDX3Y, a paralog which shares >90% sequence similarity with DDX3X. DDX3Y had been speculated, but not yet shown, to be an additional target of (−)-1 in male-derived cells.[18] The inventors then extracted the individual fold-changes for eIF4A1 and DDX3X (FIG. 3B) and noted that, interestingly, the relative stabilization of DDX3X among the three compounds ((−)-7>>(−)-20>(−)-1) more closely reflected the observed SAR differences in anti-CSC potency than did the compounds' relative stabilization of eIF4A1 ((−)-7>>(−)-20≈(−)-1).

Given these observations, the inventors next sought to interrogate the effects of compound (−)-20 in secondary assays for both eIF4A and DDX3 engagement. To directly validate our PISA findings showing stabilization of both eIF4A1 and DDX3X, we conducted fluorescence polarization (FP) assays using a fluorescein amidite (FAM)-labeled $r(AG)_8$ RNA probe developed previously.[17,40] Under these conditions, the inventors found that ATP was a necessary additive to enhance the degree of anisotropy change for both proteins as compared to $ADP+P_i$ (Figure S5). As shown in FIG. 3D, compounds (−)-5, (−)-7, and (−)-20 (10 μM concentration) all strongly stimulated the binding activity of eIF4A1 to RNA under these conditions, with the strongest clamping observed for (−)-7. For DDX3X, the C4'-brominated rocaglates (−)-7 and (−)-20 stimulated RNA binding to a greater extent than did C4'-methoxy rocaglate, (−)-5. This trend held in FP-based binding affinity experiments wherein each of the helicases was titrated against the FAM-labeled $(AG)_8$ RNA probe in the presence of 50 μM rocaglate and 1 mM ATP.[18,41] In these experiments, compounds (−)-5, (−)-7 and (−)-20 each showed similar potency and efficacy towards stimulation of eIF4A1:$(AG)_8$ complex formation (FIG. 11, top), whereas DDX3X:$(AG)_8$ complex formation was clearly favored in the presence of (−)-7, followed by (−)-20 and (−)-5, the latter of which was significantly less efficacious at stimulating binding at the tested concentrations (FIG. 11, bottom). While inherent differences between the FP assay conditions (e.g. probe affinity, protein mobility in FP buffer) preclude direct comparison of absolute AmP values across the two different proteins, the inventors noted that relative anti-CSC potencies for these compounds ((−)-7>(−)-5≈(−)-20) were similar to their relative degrees of clamping for DDX3X and eIF4A1. To follow up on these findings, the inventors performed in vitro translation experiments using a bicistronic mRNA reporter construct FF-HCV-Ren, where translation of the firefly luciferase (FF) cistron is cap-dependent, while translation of the *Renilla* luciferase (HCV-Ren) cistron is driven off an HCV-IRES, rendering translation of this cistron cap-independent. The inventors found that despite their near-equivalent CSC $EC_{50}$s, Roc ASF derivative (−)-20 was found to be a significantly less potent cap-dependent translation inhibitor in this assay than (−)-5 (937 nM vs. 215 nM $EC_{50}$s, respectively, FIG. 3E).[42]

Based on the PISA and FP results confirming eIF4A and DDX3X stabilization for the four tested CSC-selective congeners, the inventors next sought to directly interrogate the impact of C4'-bromine vs. C4'-methoxy substitutions on the relative stabilization of these helicase targets. Accordingly, the inventors performed comparative PISA profiling of two C4'-methoxy substituted compounds ((−)-10, (−)-16) against two C4'-bromine substituted congeners ((−)-11, (−)-20) in GBM0308 lysates. The inventors extracted individual fold-changes for each compound and protein of interest and found that the C4'-brominated compounds exhibited greater effect sizes and statistical significance than their C4'-methoxy congeners (FIGS. 3F and 3G) across most targets. While all compounds showed some stabilization of eIF4A, only the C4'-brominated compounds stabilized all eIF4A paralogs, especially elF4A3, beyond significance thresholds. A previous systematic study of hundreds of synthetic rocaglates from our laboratories has shown that rocaglates are generally able to induce RNA clamping of eIF4A3 to an extent that is well-correlated with their degree of eIF4A1 clamping. These studies have not, however, shown significant differences in eIF4A1 or eIF4A3 RNA clamping between C4'-bromo/methoxy-substituted matched pairs (e.g. (−)-5 and (−)-7) by FP, despite (−)-7 frequently outperforming (−)-5 in other assays such as FP clamping and translation inhibition. 43-45 Nonetheless, elF4A3 has been reported to play a role in ribosome biogenesis and may be an emerging target for cancer cells showing elevated rates of ribosome production.[46] Taken together, the results suggest the importance of the C4'-bromine substitution in both improving potency against GBM CSCs and enhancing stabilization of all DEAD-box helicases, with striking effects on the stabilization of DDX3.

Figure 4A:
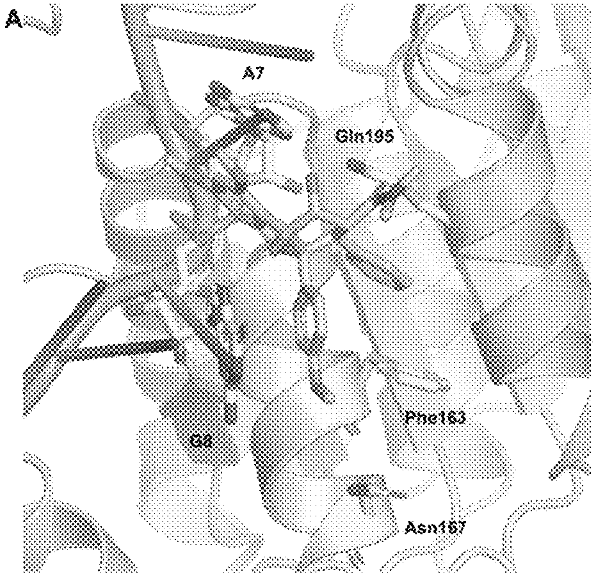
FIG. 4A shows the X-ray co-crystal structure of RocA (1)-eIF4A1-poly(AG) complex (PDB: 5ZC9).
Figure 4B:
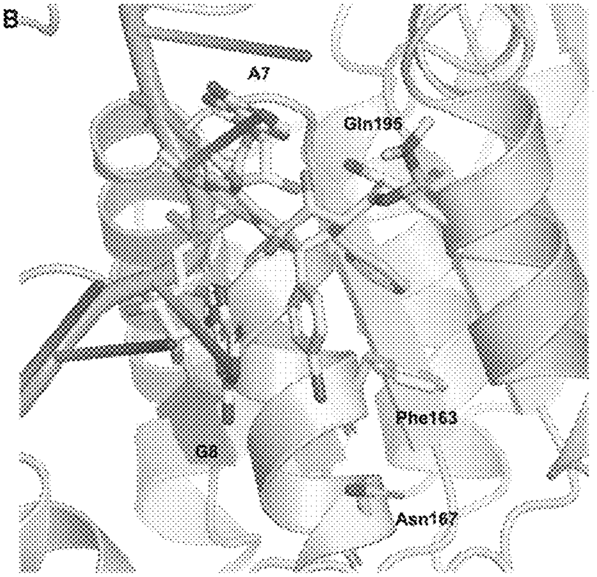
FIG. 4B shows the glide docking pose for (−)-20 into the 5ZC9 eIF4A1-poly (AG) structure (Glide $G_{score}$: −11.7 kcal/mol), showing a "canonical" rocaglate binding pose.

Modeling DEAD-box helicase engagement of the Roc ASF derivative (−)-20. The inventors next sought to use computational modeling to predict and compare how the structural features present in CSC-selective rocaglates, namely the C4'-bromo substituent and ionizable C2 substituent, may impact target engagement of eIF4A and DDX3 paralogs. An X-ray co-crystal structure of a RocA-eIF4A1- poly (AG) complex from the RIKEN group (PDB: 5ZC9) 17 shows that RocA acts as a bimodular inhibitor between eIF4A1 and RNA (FIG. 4A). Specifically, the RocA C2 carbonyl is hydrogen-bonded to eIF4A Gln195, while the A- and B-rings engage in T-x stacking interactions with A7 and G8 of RNA, respectively. Lastly, the C-ring engages in a parallel-displaced T-stacking interaction with eIF4A Phe163. Close inspection of this binding mode reveals that the C4' substituent, a methoxy group in the liganded RocA, is largely solvent-exposed, projecting toward eIF4A1 residue Asn167. A bromine substituent could be slightly preferred to methoxy at this site based on both steric and electrostatic considerations and depending on trajectory, may allow for halogen bonding of the Asn167 carbonyl. Interestingly, sequence alignments (FIG. 12) show divergence at this residue among the PISA-identified helicase targets. While this residue is conserved as Asn in eIF4A2, it is substituted in eIF4A3 as Arg172, which may also discriminate between C4'-Br and C4'-OMe based on hydrogen bonding and steric considerations. To directly probe the ability of (−)-20 to bind eIF4A1/RNA, the inventors used Glide docking (Schrödinger LLC) into the rocaglate binding site of the 5ZC9 X-ray structure. The top-scored pose (Glide $G_{score}$=−11.725 kcal/mol) was comparable to that observed in the experimentally determined RocA complex (FIG. 4B), including all expected x-stacking interactions with the A-, B-, and C-rings, and a hydrogen bond between eIF4A[1] residue Gln195 and the acyl sulfamide carbonyl, thus supporting the overall compatibility of the RocASF chemotype with eIF4A1.

The inventors next sought to evaluate docking of (−)-20 into DDX3X. Based on sequence and structural alignment between DDX3X and eIF4A1 (Figure S7), it is postulated that rocaglates may target a similar binding pocket near DDX3X residues Val328 (corresponding to eIF4A1 Phe163), Glu332, Gln360 (corresponding to eIF4A1 Gln195) and Arg363, of which Gln360 was previously shown to play a key role in binding RocA.[18] In the same study, it was also shown through computational overlays to a DDX3X structure lacking a bound oligonucleotide (PDB: 5E7M) that the phenyl "C" ring is likely sterically incompatible with DDX3X, requiring an alternate binding mode.[18] The inventors posited that sequence divergences between eIF4A1 and DDX3X at the rocaglate binding site may impact Roc ASF binding and sought to further probe this hypothesis through modeling.

For DDX3X modeling studies, the inventors used the X-ray crystal structure of DDX3X bound to an ATP analog and a remodeled RNA:DNA hybrid from Enemark and coworkers (PDB: 7LIU). The inventors selected this structure for modeling based on multiple factors. First, this structure was the only oligonucleotide-bound DDX3X structure available in a "post-unwound" conformation[47] that appeared to be rocaglate-competent (backbone r.m.s.d. from 5ZC9: 0.971 Å). In contrast, the only other oligonucleotide-bound DDX3X structure available depicts the protein in a "pre-unwound" state (PDB: 6O5F, backbone r.m.s.d. from 5ZC9: 21.917 Å). In addition, using transitive overlays of RocA from the eIF4A1 X-ray structure (5ZC9) (FIG. 13A) to DDX3X structures 7LIU (FIG. 13B) and 5E7M (FIG. 13C), the inventors observed that in the presence of the RNA:DNA hybrid, the binding site topology immediately adjacent to the RocA C-ring offers a widened binding pocket (FIG. 13B) that more closely resembles that observed for eIF4A1 (FIG. 13A), thus mitigating the clear steric clashes observed in the non-oligo-bound 5E7M structure (FIG. 13C) that were previously postulated to impact rocaglate binding.[18]

Figure 4C:
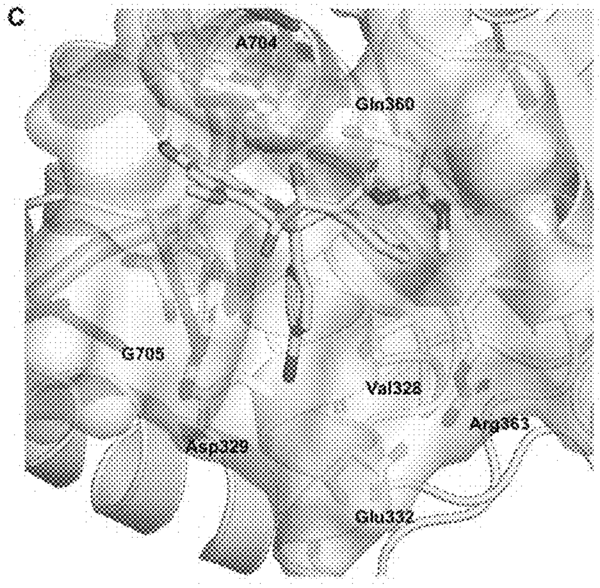
FIG. 4C shows the top-ranked induced-fit docking pose for (−)-20 ($G_{score}$ −7.0 kcal/mol), modeled from an X-ray crystal structure of DDX3X bound to a RNA:DNA hybrid (PDB: 7LIU), modified with a single (C704A) residue mutation.
Figure 4D:
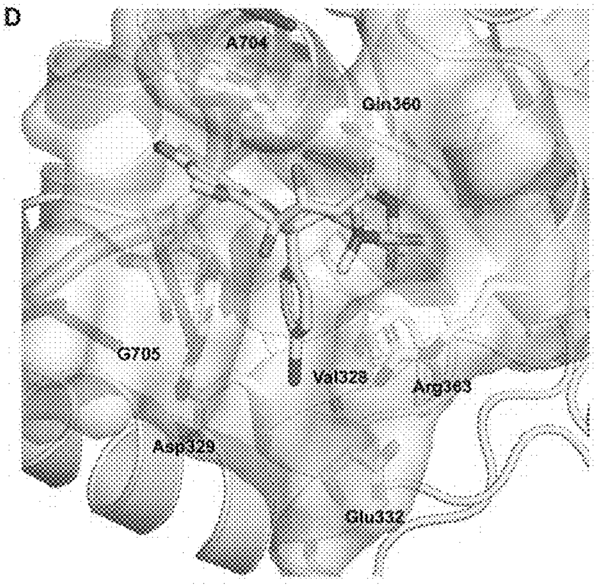
FIG. 4D shows the IFD pose ($G_{score}$: −6.1 kcal/mol) for (−)-20 and the 7LIU-C704A receptor showing interaction between the ionized rocaglate acyl sulfamide and the cationic DDX3X residue Arg363. Movement of the Arg363 sidechain creates a cleft into which the brominated "B" ring inserts.

Proceeding with the 7LIU structure, the inventors next used Pymol (Schrödinger LLC) to perform a single cytosine-to-adenine point mutation on the RNA:DNA hybrid (7LIU-C704A) based on the known preference of rocaglates to bind polypurine RNA. Accordingly, all residues within the docking grid used to define the ligand binding site are purine ribonucleotides (GGGAGGG), with all deoxyribonucleotides outside of the grid (FIG. 14A). This polypurine sequence is consistent with tetramer motifs identified by a previously reported Bind-n-Seq experiment with DDX3X and RocA. Further, the mutated GAGG RNA tetramer immediately flanking the rocaglate binding site showed excellent conformational overlay to the analogous GAGA tetramer in the 5ZC9 structure (FIG. 14B). The inventors' efforts to model compound (−)-20 at the predicted rocaglate binding site of both the 7LIU and 7LIU-C704A structures using conventional Glide docking failed to produce viable poses. Returning to the comparative overlays, the inventors noted that the 7LIU and 5E7M DDX3X structures both show a variably positioned salt bridge between key binding site residues Glu332 and Arg363 (FIGS. 13B and 13C); the inventors posited that despite a more accommodating C-ring binding pocket, clashes between Glu332 and the rocaglate B-ring may have sterically impeded our attempt at "rigid-receptor" docking into this structure (FIG. 13B). Accordingly, the inventors examined Schrödinger's Induced Fit Docking ("IFD"), an alternative Glide docking workflow that accounts for the inherent propensity of proteins to undergo sidechain conformational changes in response to ligand binding. Prior studies have established that ~90% of the rotatable sidechains on receptor amino acids undergo subtle conformational changes in response to, and to accommodate, ligand binding.[48] Thus, in IFD the receptor is treated as partially flexible; the protein backbone atoms (and in this experiment, all oligonucleotide atoms) are held rigid, while sidechain atoms are allowed to move to accommodate ligand binding. These IFD experiments produced multiple induced-fit binding poses with compound (−)-20 positioned in the "canonical" rocaglate binding mode, albeit with significantly worsened docking scores compared to the rigid-receptor docking into eIF4A1. In the top-scored IFD pose ($G_{score}$−6.986 kcal/mol, FIG. 4C), in addition to several subtle adjustments in the positioning of key binding pocket sidechains (FIG. 15A), the inventors observed a ~64° rotation of the Glu332 sidechain terminus, presumably to better accommodate the C4'-bromo substituent while retaining a salt bridge to Arg363 (FIG. 15B). Interestingly, while the second highest IFD pose ($G_{score}$ −6.131 kcal/mol, FIGS. 4D and 15C) showed a nearly identical rotation of the Glu332 sidechain, this pose also showed movement of the Arg363 sidechain to engage in a hydrogen bond interaction with the sulfonyl from the ionized acyl sulfamide of (−)-20, while still maintaining its salt bridge interaction with rotated Glu332 (FIG. 15D). Furthermore, the inventors observed that the movement of Arg363 allowed the C4'-bromine substituent to nestle in a shallow cleft lined by Arg363, Asp329, Glu332, and Val328 (FIG. 4D). Beyond these key differences, both IFD poses show the expected "canonical" rocaglate-helicase interactions, with the phenyl A- and B-rings T-T stacked to A704 and G705 of the oligonucleotide, respectively, and the expected hydrogen bonding between the acyl sulfamide carbonyl oxygen and the sidechain of Gln360. The consistent, ligand-induced rotation of the Glu332 sidechain in both structures is notable, given the previously noted steric clash of this residue with the B-ring predicted by overlay, and the clear preference for B-ring C4'-bromo (over C4'-methoxy) substitution that was illuminated in our SAR studies. Beyond the obvious steric implications of the slightly smaller bromine substituent, bromine was also found to exhibit a high propensity for interaction with arginine in a systematic study of halogenated ligands in the PDB (cf. FIG. 4D).[49]

Taken together, the modeling studies reveal putative binding modes for compound (−)-20 with both eIF4A1 and DDX3X, all of which must be validated experimentally. Given their comparatively low docking scores, our IFD-predicted DDX3X structures likely require substantial further refinement, ideally via structural biology of rocaglate-DDX3X-oligonucleotide co-complexes. Nonetheless, the unique, ligand-induced structural adjustments predicted by IFD overcome prior hurdles encountered in modeling rocaglate-DDX3 interactions and suggest a possible rationale for the experimental data clearly showing both improved CSC-selectivity and improved DDX3 target engagement for C4'-brominated rocaglates over their C4'-methoxy substituted counterparts. In addition, the IFD structure showing interaction between the acyl sulfamide sulfonyl and cationic Arg363 raises the question of whether the observed preference for ionizable C2 substituents may be reflective of an ionic engagement of Arg363.

Roc ASF (−)-20 inhibits pathways and genes required for GBM stem cell survival. Rocaglates including (−)-1 and (−)-5 have been extensively characterized by the inventors and others as potent translation inhibitors by way of stimulating the binding of DEAD box helicases eIF4A1/2, and in the case of (−)-1, DDX3X, to polypurine mRNAs.[18] When considering the potential cytotoxic impacts of helicase clamping on GBM CSCs, is important to note that despite rocaglates' strong inhibition of protein synthesis via induced clamping of these targets, the phenotypic impacts of rocaglate treatment are distinct from those arising from the loss of these helicases, or the direct inhibition of their helicase function, eIF4A-mediated RNA helicase unwinding activity is stimulated by rocaglate translation inhibitors, which show a dominant-repressive inhibitory effect on translation that is further enhanced in the presence of additional helicase target.[41] Rocaglates promote unscheduled clamping of eIF4A (and DDX3X) to purine-rich segments of mRNA, which, in the case of eIF4A, impedes recycling of the helicase through its parent elF4F complex.[16] The lack of turnover prevents eIF4A's continued participation in the initiation of eukaryotic translation, leads to stalling of ribosomes as they clamp in an unscheduled manner along the 5'-UTRs of mRNAs, and induces downstream translation repression of non-purine-rich mRNAs due to trans-inhibitory effects stemming from elF4F depletion.[16] Similarly, DDX3X has been shown to exhibit "dominant-negative" sensitivity to (−)-1,[18] and is also known to regulate RNA processing in a non-processive manner. It is reasonable to assume that unscheduled clamping of DDX3X to mRNAs would similarly impede catalytic turnover, with potential downstream impacts on multiple DDX3X-mediated processes. While the diverse functions of DDX3X include participation in both cap-dependent and cap-independent translation initiation, DDX3X has been shown to exert both stimulatory and suppressive effects on translation, depending on circumstances.[50,51] Here, the inventors observed a paradoxical reduction in translation inhibition potency for (−)-20 (~1 μM $EC_{50}$) compared to its anti-CSC potency (45 nM $EC_{50}$), that starkly contrasts to CR-1-31b (−)-5 (~200 nM translation $EC_{50}$, 36 nM CSC $EC_{50}$). These results suggest that other DDX3X-driven pathways unique to GBM CSCs may also be affected. There are also limits to our current ability to characterize the full breadth of helicase targeting for (−)-20 and other rocaglates. Given the broad and consistent stabilization of multiple helicases observed in PISA, it is possible that the clamping potentiation of (−)-20 may extend to additional helicase targets that were not detected in PISA due to confounding factors such as inadequate protein coverage, or incompatibility of the additive mRNA substrate (e.g. lack of necessary secondary structural features for helicase recognition). The inventors note that our recently reported PISA studies[38] on (−)-5 in A549 cells detected stabilization of additional DEAD box helicases (e.g. DDX21) that were not found to be stabilized in our PISA experiments in GBM CSCs by any rocaglates tested.[38] Nonetheless, the results here suggest that the potency of RocASF-mediated CSC death, which in the case of (−)-20 is ~20-fold higher than its effects on cap-dependent translation, may arise from either additive or synergistic convergence of multiple gain-of-function processes, that extend beyond the inhibition of protein synthesis. Further, these results underscore the specific utility of RocASF probes versus other CSC-selective rocaglates such as SDS-1-021 (−)-7 (which in contrast to (−)-20 is an exceptionally potent eIF4A clamper and cap-dependent translation inhibitor) in teasing out subtle mechanistic differences arising from the interplay of differential RNA helicase targeting.[16,39,43]

Figures 5A, 5B, 5C, 5D, 5E:
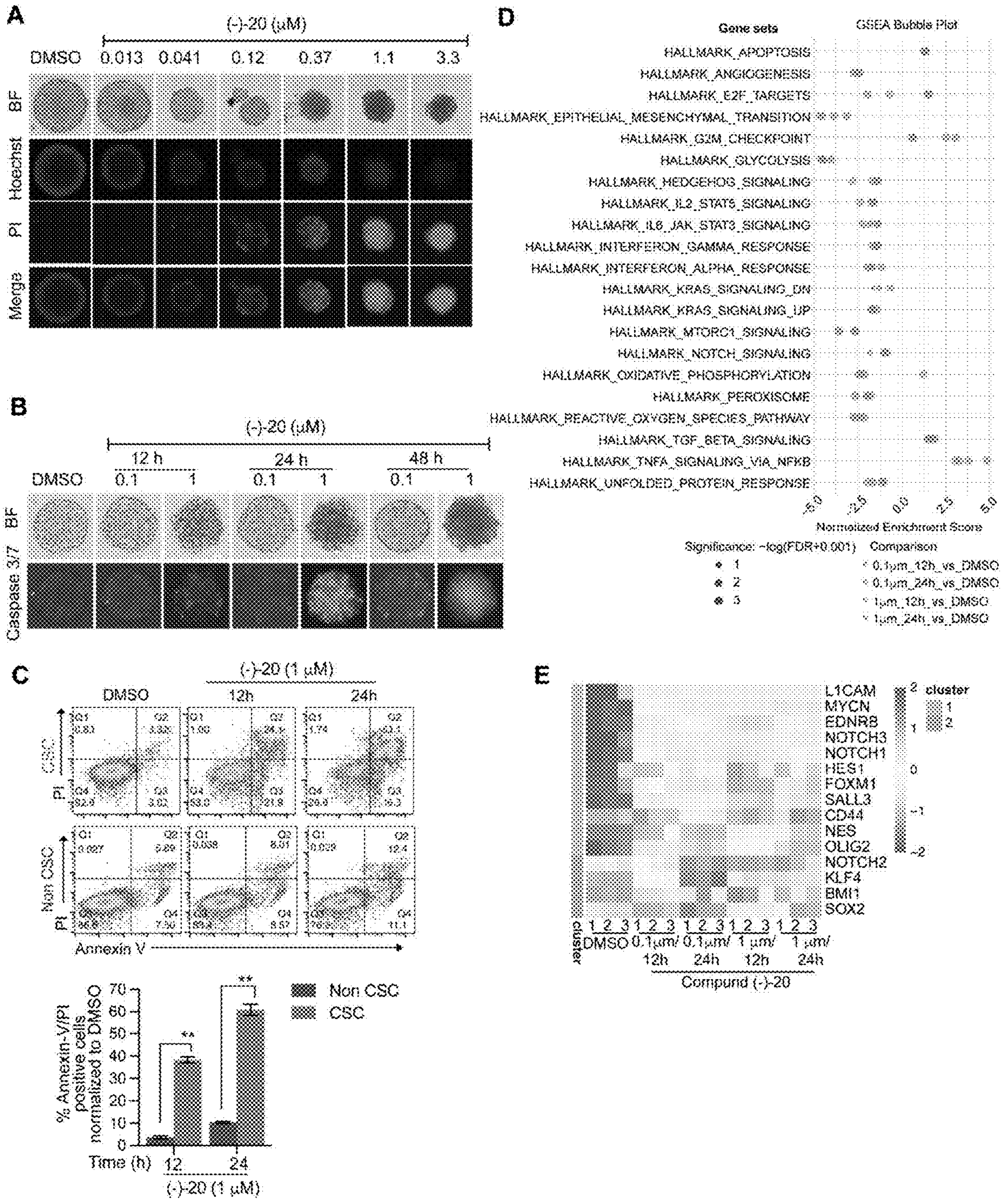
FIG. 5A shows propidium iodide (PI) and Hoechst staining of GBM neurospheres treated with either DMSO or varying doses of compound (−)-20 for 72 h and imaged using a Celigo cytometer.
FIG. 5B shows Caspase 3/7 staining of neurospheres treated with DMSO, 0.1 μM (−)-20, or 1 μM (−)-20 and imaged by Celigo cytometer at the indicated time.
FIG. 5C shows flow cytometry dot plots showing annexin-V/PI staining following treatment with either DMSO (−)-20 (1 mM) for 12 and 24 h, respectively (top). Quantification of percent annexin-V and PI-positive cells normalized to respective DMSO controls (bottom). Data are presented as mean±SD from two independent experiments. p values were calculated using a two-tailed unpaired t-test. **p<0.01.
FIG. 5D shows a GSEA multi-bubble plot: the color of the bubble represents the comparison, the size of the bubble represents the significance, and the x-axis represents the normalized enrichment score (NES). All gene sets with FDR<0.05 and |LFC|>0.585 in any of the five comparisons included here.
FIG. 5E shows a Z-score heatmap visualizing differentially expressed genes (DEGs) involved in CSC stemness. DEG signature in GBM0308 stem cells treated with either DMSO or compound (−)-20 for the indicated time and concentration are shown. Only significant genes (FDR<0.05 and |LFC|>0.585) are presented here. Hierarchical clustering was performed using the complete linkage method and 1-Pearson as the distance. The genes were then classified into two clusters based on the dendrogram.

To gain additional mechanistic insights into GBM cell death induced by (−)-20, the inventors conducted several functional assays. The inventors first derived a single neurosphere from GBM0308 cells cultured in stem cell conditions, which was treated with either DMSO or (−)-20 at varying doses for three days followed by staining with PI and Hoechst dyes and subsequent imaging. The results presented in FIG. 5A show that (−)-20 exhibits notable cytotoxic effects on CSC neurospheres, as evidenced by PI staining starting from a concentration of 0.12 μM onwards. Additionally, a significant, dose-dependent reduction in neurosphere size was observed. Notably, when treating the neurospheres with RK-33, a commercially available small molecule inhibitor of DDX3,[52] cytotoxic effects were also observed, with >3 μM concentration required to observe a noticeable effect on neurosphere size (FIG. 16). Overall, these results suggest that (−)-20 is significantly more potent in eliminating GBM CSCs than RK-33. To capture the kinetics of apoptotic events, the inventors employed caspase 3/7 staining of GBM0308 neurospheres treated with either DMSO or (−)-20 and subsequently evaluated at three timepoints over a 48-hour period. Caspases are a family of enzymes involved in apoptosis, specifically, caspase-3 and caspase-7 are key players in the execution phase.[53] The inventors observed positive staining of caspases 3/7 in cells treated with 1 μM (−)-20 at 24- and 48-hour timepoints, indicative of apoptosis. (FIG. 5B). We further performed flow cytometry-based analysis of Annexin V/PI staining in GBM0308 cells at these same timepoints, confirming that 1 μM (−)-20 treatment induced apoptosis in GBM CSCs (FIG. 5C).

Next, to further determine the role of DDX3X in GBM CSCs, we performed a knockdown experiment in GBM0308 cells. A short-hairpin (shRNA)-mediated knockdown of DDX3X reduced GBM0308 growth in culture (FIG. 17A-C), suggesting that DDX3X genetic inhibition may indeed impact the proliferation of GBM CSCs.

To understand the transcriptomic changes underlying (−)-20 effects on GBM CSCs, the inventors performed RNA sequencing experiments in these cells. Gene set enrichment analysis (GSEA) across all hallmark gene sets in the Molecular Signature Database (MSigDB) showed that the most significantly upregulated gene sets relative to controls were related to TNFα and NF-κB signaling pathways (FIG. 5D). Though NF-κB regulation is often associated with cell survival, increasing evidence suggests that TNF receptors mediate alternate cell death pathways.[55-58] Interestingly, earlier studies underscored the interplay between RNA helicase DDX3 and the NF-κB subunit p65, shedding light on DDX3 involvement in regulating transcriptional activity within the NF-κB signaling pathway.[59] It is possible that disruption of the TNF-α-NF-κB signaling cascade by compound (−)-20 may contribute to TNF-mediated induction of cell death pathways in GBM CSCs. Furthermore, upon compound treatment, the inventors observed the downregulation of several hallmark gene sets associated with critical cellular processes, including apoptosis, glycolysis, MTORC1 signaling, NOTCH signaling, epithelial-mesenchymal transition (EMT), and angiogenesis (FIGS. 5D and 18A). This data suggests that (−)-20 may inhibit multiple oncogenic pathways in GBM CSCs. This observation emphasizes the complexity of cell death mechanisms and the potential origins of selectivity of (−)-20 against CSCs. Further analysis also revealed that treatment with (−)-20 downregulated the expression of genes previously shown to be involved in stem cell maintenance and survival, notably NOTCH1, NOTCH2, NOTCH3, SALL3, and SOX2. In addition, the stem cell marker CD44 was also downregulated in (−)-20-treated CSCs. (FIG. 5E).

The expression level of DDX3X in GBM has been previously reported to be significantly higher than in normal brain tissue.[60] Through an analysis of 31 patient-derived GBM samples, Sun and coworkers reported a significant correlation between high levels of DDX3 and Snail, a transcription factor known to drive EMT and cancer metastasis.[61] Recently, Brai and coworkers identified BA103 as a micromolar $CC_{50}$ anti-GBM agent blocking the helicase activity of DDX3X, further underscoring DDX3X-targeted small molecules as promising drug leads in GBM.[62] Additionally, Kerr and coworkers reported that DDX3 was highly expressed in pluripotent stem cells such as embryonic stem cells (ESCs) and embryonal carcinoma cells (ECCs), and inhibition of DDX3 using the DDX3X inhibitor RK-33 decreased the proliferation of undifferentiated stem cells.[63] In agreement with previous literature, the inventors showed that RK-33 had effects on GBM CSC neurospheres, albeit at much higher drug concentrations than Roc ASFs. In the transcriptomic profiling experiments in GBM CSCs, the inventors also found that the expression of several genes downstream of DDX3X were affected after treatment with compound (−)-20 (FIG. 18B),[64] including FOXM1, a transcription factor downregulated by inhibition of DDX3X. Shriwas and coworkers reported that inhibition of DDX3 reduced CSC populations in oral squamous cell carcinoma with suppressed expression of FOXM1.[65] Notably, other genes that have roles in CSC maintenance and survival were also downregulated upon treatment with (−)-20, which likely also contribute to its potent anti-CSC activity.

In summary, the inventors here report the first identification of rocaglate congeners, including novel rocaglate acyl sulfamide (Roc ASF) derivatives, as selective inhibitors of glioblastoma (GBM) cancer stem cells. To access Roc ASFs, the inventors developed new synthetic methods employing rocaglate β-lactone ring-opening with nitrogen nucleophiles as a key step. A systematic dose-response study of rocaglaic acid N-acylated derivatives also established clear structure-activity relationships (SAR) for potent GBM CSC targeting. Notably, we determined that C2-acyl sulfamoylation and C4'-bromination of the rocaglate scaffold both play important roles in improving potency and selectivity of rocaglates against GBM CSCs, with compound (−)-20 showing high potency against GBM CSCs ($EC_{50}$=45 nM) with limited detectable effects on GBM non-CSCs up to 10 μM and significantly dampened cap-dependent translation inhibition. We also assessed compound (−)-20 in different GBM stem-like cell lines including BT112 and BT145, both of which showed similar selective killing towards CSCs vs. non-CSCs. The inventors' study utilized a novel adaptation of PISA involving a polypurine RNA probe and the ATP analog AMP-PNP as additives to assay for rocaglate: DEAD-box helicase target engagement. Additional mechanistic experiments and computational modeling of Roc ASFs implicate DDX3X and eIF4A paralogs as relevant targets contributing to the observed cytotoxic effects against CSCs. Using both PISA- and FP-based comparisons, the inventors found that SAR trends for CSC potency and selectivity tracked more consistently with the relative strength of DDX3X engagement than that of eIF4A1 engagement or cap-dependent translation inhibition.[18] Overall, the targeted array of derivatives and technologies used in this study have expanded the understanding of DEAD-box helicase targets for rocaglates and support the potential of designed rocaglates as cancer stem cell (CSC) agents. The mRNAs that are regulated by (−)-20 and related compounds via DDX3 in GBM stem cells can be defined using ribosome profiling, RNA Bind-n-Seq,[41] and RNA-seq,[66, 67] techniques which have been reported using rocaglates, and potentially PAR-CLIP, which has been used to identify binding between DDX3 and helix 16 on the human 40S ribosome[68] and to isolate RNA transcripts that co-purify with endogenous eIF4A1 in MYCN-amplified neuroblastoma cells in the presence of an amidino rocaglate (ADR) derivative.[69]

Methods

Cell Culture: Glioblastoma stem cell lines GBM0308, BT145, and BT112 were cultured in neurobasal (NBE medium) containing N-2 and B-27 supplements, EGF, bFGF, L-glutamine, and Penicillin-Streptomycin), as described previously.[19] Adherent GBM cells were cultured in serum-containing DMEM media (Invitrogen) supplemented with 10% fetal bovine serum (Corning Cellgro™). Cells were incubated at 37° C. and 5% $CO_2$ to allow neurosphere formation. For seeding and subculturing, the neurospheres were gently trypsinized with 0.025% trypsin to form a single-cell suspension.

Dose-Response Testing in GBM Cells: Briefly, on day 1, cells were seeded in triplicate. For CSCs, 1500 cells/well were plated in a low attachment 96-well plate with NBE media and incubated for 3 days at 37° C. and 5% $CO_2$ to allow the formation of neurospheres. For non-CSCs, 3000 cells/well were plated in a 96-well plate with DMEM media supplemented with 10% FBS. Similarly, the assay plates were also incubated for the same duration. Compound treatments started on day 4. Each compound was resuspended in DMSO and then diluted to different concentrations in media to a final concentration of DMSO less than 1%. The compounds were added at concentrations of 10, 3.3, 1.11, 0.37, 0.12, 0.041, 0.013, and 0.004 UM, respectively. DMSO-treated cells served as a control. After 72 h incubation with the compounds, fluorescent stains, propidium iodide, and Hoechst 33342 (Life Technologies, Carlsbad, CA), were used to stain the GBM cells to determine cell viability. A staining solution in 1×PBS was prepared by mixing PI and Hoechst 33342 to working concentrations of 2.5 μM and 20 μM, respectively. 20 μL of this staining solution was added per well, and plates were incubated at 37° C. and 5% $CO_2$ for 60 min. After incubation, plates were read by Celigo imaging cytometer using an inbuilt Celigo application; Cell Viability (Dead+Total). For the viability measurement, the total number of neurospheres/cells and dead neurospheres/cells in each well were counted by the cytometer. The percentage of PI+ cells was normalized to DMSO and plotted against the drug concentration to calculate the $EC_{50}$ with a four-parameter, variable-slope dose-response curve with an upper constraint of <100% dead cells and a lower constraint of =0% dead cells (GraphPad Prism v.10.0.0). For all dose response experiments, the experimental maximal efficacy (maximum observed % cell death) is reported. Relative $EC_{50}$ values are reported for all compounds killing >50% of cells.

Neurosphere Formation Assays: Single neurospheres were generated by seeding GBM0308 cells (400 cells per well) in a 384-well ultra-low attachment round bottom microplate (Nexcelom Bioscience, ULA-384 U). The plates were then centrifuged at 300×g for 10 minutes to cluster cells at the bottom of the wells, followed by incubation at 37° C. and 5% $CO_2$ for 4 days to allow the formation of single neurospheres and treated with either DMSO or drugs at concentrations of 3.3, 1.11, 0.37, 0.12, 0.041, 0.013, 0.004 μM. On Day 7, neurospheres were stained with propidium iodide and Hoechst, as described above. The "neurosphere 1+Mask" application was used to measure the fluorescent intensities of PI, using Celigo cytometer as described previously.[70]

Apoptosis Assays: For the Caspase 3/7 assay single neurospheres were generated as described above. On day four, neurospheres were treated with compound (−)-20. Apoptosis in treated tumorspheres was assessed using Nexcelom's ViaStain™ Live Caspase 3/7 Detection kit (Nexcelcom, CS1-V0002-1). The kit consists of a nucleic acid-binding dye with a fluorescent probe attached to a four-amino acid peptide sequence DEVD (Asp-Glu-Val-Asp), forming a cell membrane-permeable DEVD-DNA complex. During apoptosis, caspase 3/7 proteins cleaved the DEVD-DNA dye complex and released the high-affinity DNA binding dye, producing a bright green-fluorescent signal. After treatment, wells were stained with caspase dye (2 μM) at multiple time points, and plates were incubated for 60 minutes at 37° C. Plates were imaged using the "neurosphere 1+Mask" application to measure fluorescent intensities of the caspase dye, as described previously.[70] Apoptosis was quantified using the FITC Annexin V apoptosis detection kit II (Invitrogen). Annexin V staining was done per the manufacturer instructions. GBM0308 neurospheres were treated with (−)-20) at 1 μM concentration. At 12 h and 24 h after treatment, neurospheres were gently dissociated by using trypsin 0.025%, stained with PI and FITC and analyzed by flow cytometery using a Bio-Rad ZE5 Cell Analyzer.

REFERENCES

1. Korentzelos, D.; Clark, A. M.; Wells, A., A Perspective on Therapeutic Pan-Resistance in Metastatic Cancer. *Int. J. Mol. Med.* 2020, 21 (19), 7304.
2. Norouzi, S.; Gorgi Valokala, M.; Mosaffa, F.; Zirak, M. R.; Zamani, P.; Behravan, J., Crosstalk in cancer resistance and metastasis. *Crit. Rev. Oncol. Hematol.* 2018, 132, 145-153.
3. Desai, A.; Yan, Y.; Gerson, S. L., Concise Reviews: Cancer Stem Cell Targeted Therapies: Toward Clinical Success. *Stem. Cells Transl. Med.* 2019, 8 (1), 75-81.
4. Agliano, A.; Calvo, A.; Box, C., The challenge of targeting cancer stem cells to halt metastasis. *Semin. Cancer Biol.* 2017, 44, 25-42.
5. Wu, B.; Shi, X.; Jiang, M.; Liu, H., Cross-talk between cancer stem cells and immune cells: potential therapeutic targets in the tumor immune microenvironment. *Mol. Cancer* 2023, 22 (1), 38.
6. Kuşoğlu, A.; Biray Avci, C., Cancer stem cells: A brief review of the current status. *Gene* 2019, 681, 80-85.
7. Atashzar, M. R.; Baharlou, R.; Karami, J.; Abdollahi, H.; Rezaei, R.; Pourramezan, F.; Zoljalali Moghaddam, S. H., Cancer stem cells: A review from origin to therapeutic implications. *J. Cell Physiol.* 2020, 235 (2), 790-803.
8. Müller, L.; Tunger, A.; Plesca, I.; Wehner, R.; Temme, A.; Westphal, D.; Meier, F.; Bachmann, M.; Schmitz, M., Bidirectional Crosstalk Between Cancer Stem Cells and Immune Cell Subsets. *Front. Immunol.* 2020, 11, 140.
9. Turdo, A.; Veschi, V.; Gaggianesi, M.; Chinnici, A.; Bianca, P.; Todaro, M.; Stassi, G., Meeting the Challenge of Targeting Cancer Stem Cells. *Front. Cell Dev. Biol.* 2019, 7, 16.
10. Alves, A. L. V.; Gomes, I. N. F.; Carloni, A. C.; Rosa, M. N.; da Silva, L. S.; Evangelista, A. F.; Reis, R. M.; Silva, V. A. O., Role of glioblastoma stem cells in cancer therapeutic resistance: a perspective on antineoplastic agents from natural sources and chemical derivatives. *Stem Cell Res. Ther.* 2021, 12 (1), 206.
11. Radin, D. P.; Shifman, S.; Outhwaite, I. R.; Sharma, A.; Bases, R.; Seeliger, M. A.; Tsirka, S. E., Lucanthone, a Potential PPT1 inhibitor, Perturbs Stemness, Reduces Tumor Microtube Formation and Slows the Growth of Temozolomide-Resistant Gliomas in Vivo. *J. Pharmacol. Exp. Ther.* 2024, 2023-002021.
12. Araki, K.; Hara, M.; Hamada, S.; Matsumoto, T.; Nakamura, S., Antiproliferative Activities of Cynaropicrin and Related Compounds against Cancer Stem Cells. *Chem. Pharm. Bull.* (*Tokyo*) 2024, 72 (2), 200-208.
13. Kharkar, P. S., Cancer Stem Cell (CSC) Inhibitors in Oncology—A Promise for a Better Therapeutic Outcome: State of the Art and Future Perspectives. *J. Med. Chem.* 2020, 63 (24), 15279-15307.
14. Lu King, M.; Chiang, C.-C.; Ling, H.-C.; Fujita, E.; Ochiai, M.; McPhail, A. T., X-Ray crystal structure of rocaglamide, a novel antileulemic 1H-cyclopenta[b]benzofuran from *Aglaia elliptifolia*. *Chem. Commun.* 1982, (20), 1150-1151.
15. Schulz, G.; Victoria, C.; Kirschning, A.; Steinmann, E., Rocaglamide and silvestrol: a long story from anti-tumor to anti-coronavirus compounds. *Nat. Prod. Rep.* 2021, 38 (1), 18-23.
16. Chu, J.; Zhang, W.; Cencic, R.; O'Connor, P. B. F.; Robert, F.; Devine, W. G.; Selznick, A.; Henkel, T.; Merrick, W. C.; Brown, L. E.; Baranov, P. V.; Porco, J. A., Jr.; Pelletier, J., Rocaglates Induce Gain-of-Function Alterations to eIF4A and eIF4F. *Cell Rep.* 2020, 30 (8), 2481-2488.e5.
17. Iwasaki, S.; Iwasaki, W.; Takahashi, M.; Sakamoto, A.; Watanabe, C.; Shichino, Y.; Floor, S. N.; Fujiwara, K.; Mito, M.; Dodo, K.; Sodeoka, M.; Imataka, H.; Honma, T.; Fukuzawa, K.; Ito, T.; Ingolia, N. T., The Translation Inhibitor Rocaglamide Targets a Bimolecular Cavity between eIF4A and Polypurine RNA. *Mol. Cell* 2019, 73 (4), 738-748 e9.
18. Chen, M.; Asanuma, M.; Takahashi, M.; Shichino, Y.; Mito, M.; Fujiwara, K.; Saito, H.; Floor, S. N.; Ingolia, N. T.; Sodeoka, M.; Dodo, K.; Ito, T.; Iwasaki, S., Dual targeting of DDX3 and eIF4A by the translation inhibitor rocaglamide A. *Cell Chem. Biol.* 2021, 28 (4), 475-486.e8.

19. Lee, J.; Kotliarova, S.; Kotliarov, Y.; Li, A.; Su, Q.; Donin, N. M.; Pastorino, S.; Purow, B. W.; Christopher, N.; Zhang, W.; Park, J. K.; Fine, H. A., Tumor stem cells derived from glioblastomas cultured in bFGF and EGF more closely mirror the phenotype and genotype of primary tumors than do serum-cultured cell lines. *Cancer Cell* 2006, 9 (5), 391-403.
20. Chudnovsky, Y.; Kim, D.; Zheng, S.; Whyte, Warren A.; Bansal, M.; Bray, M.-A.; Gopal, S.; Theisen, Matthew A.; Bilodeau, S.; Thiru, P.; Muffat, J.; Yilmaz, Omer H.; Mitalipova, M.; Woolard, K.; Lee, J.; Nishimura, R.; Sakata, N.; Fine, Howard A.; Carpenter, Anne E.; Silver, Serena J.; Verhaak, Roel G. W.; Califano, A.; Young, Richard A.; Ligon, Keith L.; Mellinghoff, Ingo K.; Root, David E.; Sabatini, David M.; Hahn, William C.; Chheda, Milan G., ZFHX4 Interacts with the NuRD Core Member CHD4 and Regulates the Glioblastoma Tumor-Initiating Cell State. *Cell Rep.* 2014, 6 (2), 313-324.
21. Lassalas, P.; Gay, B.; Lasfargeas, C.; James, M. J.; Tran, V.; Vijayendran, K. G.; Brunden, K. R.; Kozlowski, M. C.; Thomas, C. J.; Smith, A. B., III; Huryn, D. M.; Ballatore, C., Structure Property Relationships of Carboxylic Acid Isosteres. *J. Med. Chem.* 2016, 59 (7), 3183-3203.
22. Roche, S. P.; Cencic, R.; Pelletier, J.; Porco Jr., J. A., Biomimetic Photocycloaddition of 3-Hydroxyflavones: Synthesis and Evaluation of Rocaglate Derivatives as Inhibitors of Eukaryotic Translation. *Angew. Chem., Int. Ed.* 2010, 49 (37), 6533-6538.
23. Lajkiewicz, N. J.; Cognetta, A. B., III; Niphakis, M. J.; Cravatt, B. F.; Porco, J. A., Jr., Remodeling Natural Products: Chemistry and Serine Hydrolase Activity of 'a Rocaglate-Derived β-Lactone. *J. Am. Chem. Soc.* 2014, 136 (6), 2659-2664.
24. Jordan, A.; Whymark, K. D.; Sydenham, J.; Sneddon, H. F., A solvent-reagent selection guide for Steglich-type esterification of carboxylic acids. *Green Chem.* 2021, 23 (17), 6405-6413.
25. Stone, S. D.; Lajkiewicz, N. J.; Whitesell, L.; Hilmy, A.; Porco, J. A., Jr., Biomimetic Kinetic Resolution: Highly Enantio- and Diastereoselective Transfer Hydrogenation of Aglain Ketones To Access Flavagline Natural Products. *J. Am. Chem. Soc.* 2015, 137 (1), 525-530.
26. Kaboudin, B.; Faghihi, M. R.; Kazemi, F.; Yokomatsu, T., Resolution of enantiomers of novel C2-symmetric aminobisphosphinic acids via diastereomeric salt formation with quinine. *Chirality* 2015, 27 (1), 71-4.
27. Gerard, B.; Sangji, S.; O'Leary, D. J.; Porco, J. A., Enantioselective Photocycloaddition Mediated by Chiral Brønsted Acids: Asymmetric Synthesis of the Rocaglamides. *J. Am. Chem. Soc.* 2006, 128 (24), 7754-7755.
28. Gerard, B.; Cencic, R.; Pelletier, J.; Porco Jr., J. A., Enantioselective Synthesis of the Complex Rocaglate (−)-Silvestrol. *Angew. Chem. Int. Ed.* 2007, 46 (41), 7831-7834.
29. Gaetani, M.; Sabatier, P.; Saei, A. A.; Beusch, C. M.; Yang, Z.; Lundström, S. L.; Zubarev, R. A., Proteome Integral Solubility Alteration: A High-Throughput Proteomics Assay for Target Deconvolution. *J. Proteome Res.* 2019, 18 (11), 4027-4037.
30. Savitski, M. M.; Reinhard, F. B. M.; Franken, H.; Werner, T.; Savitski, M. F.; Eberhard, D.; Molina, D. M.; Jafari, R.; Dovega, R. B.; Klaeger, S.; Kuster, B.; Nordlund, P.; Bantscheff, M.; Drewes, G., Tracking cancer drugs in living cells by thermal profiling of the proteome. *Science* 2014, 346 (6205), 1255784.
31. Molina, D. M.; Jafari, R.; Ignatushchenko, M.; Seki, T.; Larsson, E. A.; Dan, C.; Sreekumar, L.; Cao, Y.; Nordlund, P., Monitoring Drug Target Engagement in Cells and Tissues Using the Cellular Thermal Shift Assay. *Science* 2013, 341 (6141), 84-87.
32. Lim, Y. T.; Prabhu, N.; Dai, L.; Go, K. D.; Chen, D.; Sreekumar, L.; Egeblad, L.; Eriksson, S.; Chen, L.; Veerappan, S.; Teo, H. L.; Tan, C. S. H.; Lengqvist, J.; Larsson, A.; Sobota, R. M.; Nordlund, P., An efficient proteome-wide strategy for discovery and characterization of cellular nucleotide-protein interactions. *PLoS One* 2018, 13 (12), e0208273.
33. Dart, M. L.; Machleidt, T.; Jost, E.; Schwinn, M. K.; Robers, M. B.; Shi, C.; Kirkland, T. A.; Killoran, M. P.; Wilkinson, J. M.; Hartnett, J. R.; Zimmerman, K.; Wood, K. V., Homogeneous Assay for Target Engagement Utilizing Bioluminescent Thermal Shift. *ACS Med. Chem. Lett.* 2018, 9 (6), 546-551.
34. Lo, M.-C.; Aulabaugh, A.; Jin, G.; Cowling, R.; Bard, J.; Malamas, M.; Ellestad, G., Evaluation of fluorescence-based thermal shift assays for hit identification in drug discovery. *Anal. Biochem.* 2004, 332 (1), 153-159.
35. Molina, D. M.; Nordlund, P., The Cellular Thermal Shift Assay: A Novel Biophysical Assay for In Situ Drug Target Engagement and Mechanistic Biomarker Studies. *Annu. Rev. Pharmacol.* 2016, 56 (1), 141-161.
36. Van Vranken, J. G.; Li, J.; Mintseris, J.; Gadzuk-Shea, M.; Gygi, S. P.; Schweppe, D. K., Large-scale characterization of drug mechanism of action using proteome-wide thermal shift assays. *bioRxiv* 2024, 2024.01.26.577428.
37. Chan, K.; Robert, F.; Oertlin, C.; Kapeller-Libermann, D.; Avizonis, D.; Gutierrez, J.; Handly-Santana, A.; Doubrovin, M.; Park, J.; Schoepfer, C.; Da Silva, B.; Yao, M.; Gorton, F.; Shi, J.; Thomas, C. J.; Brown, L. E.; Porco, J. A.; Pollak, M.; Larsson, O.; Pelletier, J.; Chio, I. I. C., eIF4A supports an oncogenic translation program in pancreatic ductal adenocarcinoma. *Nat. Commun.* 2019, 10 (1), 5151.
38. Goldstein, S. I.; Fan, A. C.; Wang, Z.; Naineni, S. K.; Lengqvist, J.; Chernobrovkin, A.; Garcia-Gutierrez, S. B.; Cencic, R.; Patel, K.; Huang, S.; Brown, L. E.; Emili, A.; Porco, J. A., Proteomic Discovery of RNA-Protein Molecular Clamps Using a Thermal Shift Assay with ATP and RNA (TSAR). *bioRxiv* 2024, 2024.04.19.590252.
39. Naineni, S. K.; Cencic, R.; Robert, F.; Brown, L.; Haque, M.; Scott-Talib, J.; Senechal, P.; Schmeing, T. M.; Porco, J., Jr.; Pelletier, J., Exploring the Targeting Spectrum of Rocaglates Among eIF4A Homologs. *RNA* 2023, 29 (6), 826-835.
40. Chu, J.; Zhang, W.; Cencic, R.; Devine, W. G.; Beglov, D.; Henkel, T.; Brown, L. E.; Vajda, S.; Porco, J. A.; Pelletier, J., Amidino-Rocaglates: A Potent Class of eIF4A Inhibitors. *Cell Chem. Biol.* 2019, 26 (11), 1586-1593.e3.
41. Iwasaki, S.; Floor, S. N.; Ingolia, N. T., Rocaglates convert DEAD-box protein eIF4A into a sequence-selective translational repressor. *Nature* 2016, 534 (7608), 558-561.
42. Rodrigo, C. M.; Cencic, R.; Roche, S. P.; Pelletier, J.; Porco, J. A., Jr., Synthesis of Rocaglamide Hydroxamates and Related Compounds as Eukaryotic Translation Inhibitors: Synthetic and Biological Studies. *J. Med. Chem.* 2012, 55 (1), 558-562.

43. Chu, J.; Cencic, R.; Wang, W.; Porco, J. A., Jr; Pelletier, J., Translation Inhibition by Rocaglates Is Independent of eIF4E Phosphorylation Status. *Mol. Cancer Ther.* 2016, 15 (1), 136-141.
44. Wang, W.; Cencic, R.; Whitesell, L.; Pelletier, J.; Porco Jr., J. A., Synthesis of Aza-Rocaglates via ESIPT-Mediated (3+2) Photocycloaddition. *Chem. Eur. J.* 2016, 22 (34), 12006-12010.
45. Nalli, A. D.; Brown, L. E.; Thomas, C. L.; Sayers, T. J.; Porco, J. A.; Henrich, C. J., Sensitization of renal carcinoma cells to TRAIL-induced apoptosis by rocaglamide and analogs. *Sci. Rep.* 2018, 8 (1), 17519.
46. Kanellis, D. C.; Espinoza, J. A.; Zisi, A.; Sakkas, E.; Bartkova, J.; Katsori, A. M.; Boström, J.; Dyrskjøt, L.; Broholm, H.; Altun, M.; Elsässer, S. J.; Lindström, M. S.; Bartek, J., The exon-junction complex helicase eIF4A3 controls cell fate via coordinated regulation of ribosome biogenesis and translational output. *Sci. Adv.* 2021, 7 (32).
47. Song, H.; Ji, X., The mechanism of RNA duplex recognition and unwinding by DEAD-box helicase DDX3X. *Nat. Commun.* 2019, 10 (1), 3085.
48. Gaudreault, F.; Chartier, M.; Najmanovich, R., Side-chain rotamer changes upon ligand binding: common, crucial, correlate with entropy and rearrange hydrogen bonding. *Bioinformatics* 2012, 28 (18), i423-i430.
49. Kortagere, S.; Ekins, S.; Welsh, W. J., Halogenated ligands and their interactions with amino acids: Implications for structure-activity and structure-toxicity relationships. *J. Mol. Graph. Model.* 2008, 27 (2), 170-177.
50. Sharma, D.; Jankowsky, E., The Ded1/DDX3 subfamily of DEAD-box RNA helicases. *Crit. Rev. Biochem. Mol. Biol.* 2014, 49 (4), 343-360.
51. Park, J. T.; Oh, S., The translational landscape as regulated by the RNA helicase DDX3. *BMB Rep.* 2022, 55 (3), 125-135.
52. Bol, G. M.; Vesuna, F.; Xie, M.; Zeng, J.; Aziz, K.; Gandhi, N.; Levine, A.; Irving, A.; Korz, D.; Tantravedi, S.; Heerma van Voss, M. R.; Gabrielson, K.; Bordt, E. A.; Polster, B. M.; Cope, L.; van der Groep, P.; Kondaskar, A.; Rudek, M. A.; Hosmane, R. S.; van der Wall, E.; van Diest, P. J.; Tran, P. T.; Raman, V., Targeting DDX3 with a small molecule inhibitor for lung cancer therapy. *EMBO Mol. Med.* 2015, 7 (5), 648-669.
53. McIlwain, D. R.; Berger, T.; Mak, T. W., Caspase functions in cell death and disease. Cold *Spring Harb. Perspect. Biol.* 2013, 5 (4), a008656.
54. Oeckinghaus, A.; Ghosh, S., The NF-kappaB family of transcription factors and its regulation. *Cold Spring Harb. Perspect. Biol.* 2009, 1 (4), a000034.
55. Grootjans, S.; Vanden Berghe, T.; Vandenabeele, P., Initiation and execution mechanisms of necroptosis: an overview. *Cell Death Differ.* 2017, 24 (7), 1184-1195.
56. Webster, J. D.; Vucic, D., The Balance of TNF Mediated Pathways Regulates Inflammatory Cell Death Signaling in Healthy and Diseased Tissues. *Front. Cell Dev. Biol.* 2020, 8, 365.
57. Alvarez, S.; Blanco, A.; Fresno, M.; Muñoz-Fernández, M., TNF-α contributes to caspase-3 independent apoptosis in neuroblastoma cells: role of NFAT. *PLOS One* 2011, 6 (1), e16100.
58. Wang, L.; Du, F.; Wang, X., TNF-alpha induces two distinct caspase-8 activation pathways. *Cell* 2008, 133 (4), 693-703.
59. Xiang, N.; He, M.; Ishaq, M.; Gao, Y.; Song, F.; Guo, L.; Ma, L.; Sun, G.; Liu, D.; Guo, D.; Chen, Y., The DEAD-Box RNA Helicase DDX3 Interacts with NF-κB Subunit p65 and Suppresses p65-Mediated Transcription. *PLoS One* 2016, 11 (10), e0164471.
60. Hueng, D.-Y.; Tsai, W.-C.; Chiou, H.-Y. C.; Feng, S.-W.; Lin, C.; Li, Y.-F.; Huang, L.-C.; Lin, M.-H., DDX3X Biomarker Correlates with Poor Survival in Human Gliomas. *Int. J. Mol. Sci.* 2015, 16 (7), 15578-15591.
61. Sun, M.; Song, L.; Zhou, T.; Gillespie, G. Y.; Jope, R. S., The role of DDX3 in regulating Snail. *Biochim. Biophys. Acta, Mol. Cell Res.* 2011, 1813 (3), 438-447.
62. Brai, A.; Riva, V.; Clementi, L.; Falsitta, L.; Zamperini, C.; Sinigiani, V.; Festuccia, C.; Sabetta, S.; Aiello, D.; Roselli, C.; Garbelli, A.; Trivisani, C. I.; Maccari, L.; Bugli, F.; Sanguinetti, M.; Calandro, P.; Chiariello, M.; Quaranta, P.; Botta, L.; Angelucci, A.; Maga, G.; Botta, M., Targeting DDX3X Helicase Activity with BA103 Shows Promising Therapeutic Effects in Preclinical Glioblastoma Models. *Cancers* 2021, 13 (21), 5569.
63. Kerr, C. L.; Bol, G. M.; Vesuna, F.; Raman, V., Targeting RNA helicase DDX3 in stem cell maintenance and teratoma formation. *Genes Cancer* 2019, 10 (1-2), 11-20.
64. Mo, J.; Liang, H.; Su, C.; Li, P.; Chen, J.; Zhang, B., DDX3X: structure, physiologic functions and cancer. *Mol. Cancer* 2021, 20 (1), 38.
65. Shriwas, O.; Priyadarshini, M.; Samal, S. K.; Rath, R.; Panda, S.; Das Majumdar, S. K.; Muduly, D. K.; Botlagunta, M.; Dash, R., DDX3 modulates cisplatin resistance in OSCC through ALKBH5-mediated m6A-demethylation of FOXM1 and NANOG. *Apoptosis* 2020, 25 (3), 233-246.
66. Wolfe, A. L.; Singh, K.; Zhong, Y.; Drewe, P.; Rajasekhar, V. K.; Sanghvi, V. R.; Mavrakis, K. J.; Jiang, M.; Roderick, J. E.; Van der Meulen, J.; Schatz, J. H.; Rodrigo, C. M.; Zhao, C.; Rondou, P.; de Stanchina, E.; Teruya-Feldstein, J.; Kelliher, M. A.; Speleman, F.; Porco, J. A.; Pelletier, J.; Rätsch, G.; Wendel, H.-G., RNA G-quadruplexes cause eIF4A-dependent oncogene translation in cancer. *Nature* 2014, 513 (7516), 65-70.
67. Rubio, C. A.; Weisburd, B.; Holderfield, M.; Arias, C.; Fang, E.; DeRisi, J. L.; Fanidi, A., Transcriptome-wide characterization of the eIF4A signature highlights plasticity in translation regulation. *Genome Biol.* 2014, 15 (10), 476.
68. Calviello, L.; Venkataramanan, S.; Rogowski, K. J.; Wyler, E.; Wilkins, K.; Tejura, M.; Thai, B.; Krol, J.; Filipowicz, W.; Landthaler, M.; Floor, Stephen N., DDX3 depletion represses translation of mRNAs with complex 5' UTRs. *Nucleic Acids Res.* 2021, 49 (9), 5336-5350.
69. Volegova, M. P.; Brown, L. E.; Banerjee, U.; Dries, R.; Sharma, B.; Kennedy, A.; Porco, J. A.; George, R. E., The MYCN 5' UTR as a therapeutic target in neuroblastoma. *Cell Rep.* 2024, 43 (5), 114134.
70. Kessel, S.; Cribbes, S.; Bonasu, S.; Rice, W.; Qiu, J.; Chan, L. L.-Y., Real-time viability and apoptosis kinetic detection method of 3D multicellular tumor spheroids using the Celigo Image Cytometer. *Cytom. Part A* 2017, 91 (9), 883-892.

SUPPLEMENTARY MATERIALS FOR EXAMPLE 1

I. Methods Biology and Proteomics

PISA assay in GBM0308 cell lysates: The PISA assay was performed in lysates as described by Gaetani and coworkers[S2] with slight modification. Pelleted GBM0308 cells were resuspended in ice-cold lysis buffer (1×PBS pH 7.4, 2 mM $MgCl_2$, 0.5 mM AMP-PNP, 1 μM $(AG)_8$ RNA, HALT protease inhibitor cocktail EDTA-free) and subjected to three freeze-thaw cycles with liquid nitrogen to extract lysate proteins. Thawing was performed at room temperature until ~80% thawed, then completed on ice. Lysate was clarified by centrifugation for 10 minutes at 20,000 RCF and 4° C., transferred to a fresh Eppendorf tube, then centrifuged again for 10 minutes at 20,000 RCF and 4° C. to ensure removal of debris. Lysate concentration was determined using a Pierce BCA Protein Assay Kit and adjusted to 2.0 mg/mL in lysis buffer. Lysate was mixed 1:1 with a 2× solution of test compound or DMSO in lysis buffer, gently aspirated to ensure proper mixing, and incubated at room temperature for 10 minutes. After incubation, lysate was aliquoted across a 96-well PCR plate (25 μL per well) and heated for 3 minutes in an Applied Biosystems ProFlex PCR System with six temperature zones (52, 54.4, 56.8, 59.2, 61.6, 64° C.). After heating, the PCR plate was placed on ice and an equal volume of lysate (20 μL) was used to pool lysate from each of six temperature points back into one "integrated" sample per replicate. Precipitated protein aggregates were pelleted by centrifugation at 30,000 RCF and 4° C. for 30 minutes. 20 μL of supernatant (~10 μg protein) was transferred to fresh tubes containing 2 μL of Benzonase solution (~30 units) and incubated on ice for 30 minutes. Finally, samples were mixed with 11 μL of 3×SP3 sample preparation buffer (600 mM HEPES pH 8.5, 1.5% SDS, 30 mM TCEP, 120 mM chloroacetamide) and heated to 95° C. for 10 minutes to denature, reduce, and alkylate proteins. Samples were then processed using solid-phase-enhanced sample-preparation (SP3).Proteomics Sample Preparation: For SP3-based sample cleanup,[S3, 4] samples were mixed with Sera-Mag carboxylate-modified magnetic beads (10:1 bead to protein ratio by mass) and proteins precipitated onto beads with a 4× volume of ethanol. After 20 minutes of incubation in a ThermoMixer (24° C., 1000 RPM), samples were centrifuged for 1 minute at 500 RCF and beads pelleted against a magnet for 2 minutes. Upon removal of liquid, beads were washed 3× with 80% ethanol and 1X with 100% acetonitrile, briefly dried by SpeedVac, and resuspended in 50 μL of digestion buffer (100 mM HEPES pH 8.5, 1 mM $CaCl_2$), 0.01 μg/μL Trypsin/Lys-C mix). Proteins were digested on-bead in a ThermoMixer set to 37° C. for 18 h with shaking. After digestion, samples containing beads were evaporated to dryness, resuspended in LC-MS grade water, then reacted with ~65 μg of TMTpro reagents (final reaction volume 20 μL, 30% acetonitrile) for 1 h. Samples were quenched with hydroxylamine, pooled, and evaporated to dryness in a SpeedVac. The pooled sample was resuspended in 2% acetonitrile, acidified with formic acid, and desalted using a Pierce Peptide Desalting Spin Column. The eluate was again evaporated to dryness in a SpeedVac prior to high pH reversed-phase peptide fractionation.

High pH Reversed-Phase Peptide Fractionation: TMTpro-labeled peptides were fractionated using high pH reversed-phase chromatography on an Agilent 1260 Infinity Capillary LC equipped with an XBridge Peptide BEH C18 column (300 Å, 3.5 μm, 1 mm×150 mm, Waters Corporation). Prior to fractionation, the column was flushed with 100% methanol containing 0.1% formic acid for 1 hour. Peptides were resuspended in 2% acetonitrile, 0.1% $NH_4OH$ in water, injected manually, and separated using a gradient of mobile phase A (2% acetonitrile, 0.1% $NH_4OH$ in water) to mobile phase B (2% water, 0.1% $NH_4OH$ in acetonitrile) at a flow rate of 75 μL/min. Separation conditions were 100% mobile phase A for 5 minutes, a linear gradient to 12% mobile phase B for 5 minutes, a linear gradient to 32% mobile phase B for 35 minutes, a linear gradient to 45% mobile phase B for 8 minutes, a linear gradient to 70% mobile phase B for 1 minute, and a wash with 70% mobile phase B for 16 minutes (70 minutes total). Eluate fractions were collected from 19 to 67 minutes in 30 second time slices for a total of 96 fractions. Fractions were then concatenated into 24 pooled fractions and evaporated to dryness in a SpeedVac.

LC-MS/MS Data Acquisition and Database Searching: Pooled fractions were resuspended in 2% acetonitrile, 0.1% formic acid in water at ~0.1 μg/μL, and ~0.5 μg of peptides were separated on an Easy-nLC 1200 system connected to an Orbitrap Eclipse mass spectrometer equipped with a FAIMS Pro Interface. Mobile phase A consisted of 2% acetonitrile, 0.1% formic acid in water, and mobile phase B consisted of 80% acetonitrile, 0.1% formic acid in water. Peptides were first loaded onto an Acclaim PepMap C18 nano-trap column (100 Å, 3 μm, 75 μm×2 cm, Thermo Scientific) in mobile phase A, then separated on an EASY-Spray column (100 Å, 2 μm, 75 μm×500 mm, Thermo ES903, Scientific). Flow rate was set to 250 nL/min. Separation conditions were a linear gradient from 2% to 6% mobile phase B over five minutes, a linear gradient to 30% mobile phase B for 112 minutes, a linear gradient to 40% mobile phase B for seven minutes, a linear gradient to 100% mobile phase B for four minutes, and a hold at 100% mobile phase B for six minutes before re-equilibration. The mass spectrometer was operated in positive ion mode with a spray voltage of 2500V and a capillary temperature of 275° C. Data dependent acquisition was performed in cycle time mode with 3 FAIMS compensation voltages (−35, −50, −65) and a cycle time of 1 second per compensation voltage. Precursor ion scans were acquired in the Orbitrap with a resolution of 60,000, a normalized AGC target of 100%, maximum injection time set to automatic (50 ms), and a scan range of 400-1600 m/z. Additional filters included MIPS mode, a 60 second dynamic exclusion window, an intensity threshold of $4e^4$, and charge states of 2-6 for MS2. For MS2 scans, data were acquired in the Orbitrap with a resolution of 50,000, a normalized AGC target of 200%, maximum injection time set to automatic (86 ms), and HCD collision energy set to 35%.

MS/MS spectra were searched using the *Andromeda* search engine[S5] in MaxQuant software (version 2.0.3.0)[S6] against the UniProt Human complete FASTA database (downloaded Feb. 8, 2023) and the MaxQuant contaminants database. Searches were performed using default MaxQuant settings with minor modification. Briefly, reporter ion MS2 mode was used with internal and terminal TMTpro 16plex labels corrected according to manufacturer-supplied correction values. Searches allowed for methionine oxidation and N-terminal protein acetylation as variable modifications, while cysteine carbamidomethylation was set as a fixed modification. Enzyme specificity was set to Trypsin/P with a maximum of two missed cleavages allowed. Precursor ions were searched with a mass tolerance set to 4.5 ppm and fragment ions were searched with a mass tolerance set to 20 ppm. Peptide spectrum match and protein FDRs were set at 0.01 using the target-decoy database search strategy.[S7] The minimum score for modified peptides was left at 40. Only unique peptides were used for quantification.

Proteomics Data Analysis: Additional data filtering and statistical analysis were conducted using R: *A language and environment for Statistical Computing* (R Foundation for Statistical Computing, http://www.R-project.org) using the Omics Notebook analysis pipeline.[S8] The MaxQuant output file designated "proteinGroups" provided a table of protein intensities that, after removal of contaminants and reverse hits, was log transformed and normalized. Group comparisons were conducted using moderated t-tests with a Benjamini-Hochberg correction to contain the false discovery rate at 1%. Only proteins that were quantified with at least 2 unique peptides were included in analyses. Volcano plots were built using the R package ggplot2 and dot plots were generated in Prism (version 9.3.1).

Fluorescence Polarization (FP) Assays: Recombinant DDX3X or eIF4A1 (1.5 μM) were incubated with 10 nM FAM-labelled RNA probe and test compounds for 10 min in FP buffer (14.4 mM HEPES-KOH (pH 8), 108 mM NaCl, 1 mM $MgCl_2$, 14.4% glycerol, 0.1% DMSO, 2 mM DTT, 1 mM ATP) at room temperature in black, low-volume 384 well plates (Corning 3820). FP readings were performed using a Pherastar FS microplate reader (BMG Labtech). Compounds were tested at a final concentration of 10 μM.[S9] For ADP+$P_i$ conditions, ATP was substituted with 1 mM ADP and 1 mM $Na_2HPO_4$. To assess potency of complex formation, proteins were titrated in the presence of 10 nM probe, 50 μM compounds and 1 mM ATP. Experiments were run in three replicates, with each replicate employing the same master mix of protein, probe and buffer split across the four test conditions (DMSO+three test compounds). Within each replicate, data was normalized such that the highest response across the four tested conditions (as raw AmP counts) was used as 100% relative change in polarization, and the lowest response across the four tested conditions was used as 0% relative change in polarization. Data was analyzed using GraphPad Prism 8.4.0, with a "[Agonist] vs. normalized response" nonlinear regression model used to determine the $EC_{50}$ for stimulation of helicase-RNA probe binding in the presence of test compound.

In vitro translation assays: In vitro translations were performed using 4 ng/μL of bicistronic FF-HCV-Ren/pA51 reporter mRNA and the indicated compound concentrations in Krebs-2 extracts at 30° C. for 1 h as described previously.[S10] Cap-dependent FLuc and cap-independent RLuc activities were assessed on a Berthold Lumat LB 9507 luminometer (Berthold Technologies). Curves were determined using a non-linear regression model on GraphPad Prism 8.4.0.

Lentivirus packaging, transduction, and shRNA knockdown: All shRNA clones were obtained from Open Biosystems/Thermo Scientific through the UMMS RNAi Core Facility. For packaging lentiviral shRNAs, $1\times10^6$ HEK293T cells were transfected with shRNA vectors expressing non-silencing (NS) or DDX3X shRNAs (shRNA1: TRCN0000000003 shRNA2: TRCN0000000004) along with packaging plasmids psPAX2 and pMD2.G in a 2:2:1 ratio using Effectene transfection reagent (QIAGEN, cat #301425). The next day, the medium was replaced to remove DNA complexes, and a fresh NBE medium was added. Forty-eight hours post-transfection, medium containing lentiviral particles were collected and filtered through a 0.45 μm filter. For shRNA knockdown, $2\times10^6$ GBM0308 cells per well were seeded in 6-well plates and transduced with 750 μL lentivirus particles in a total volume of 1 mL of NBE medium supplemented with 8 μg/mL polybrene (Sigma, Cat #1003). The medium was replaced after overnight incubation to remove polybrene and viral particles, and cells were then subjected to puromycin selection (1 μg/mL) for 2 days. The knockdown of DDX3X was confirmed by qRT-PCR, and immunoblotting with DDX3X antibody.

Quantitative RT-PCR: Total RNA was extracted from cells using Trizol (Invitrogen, Cat #15596). cDNA was synthesized using Proto Script II reverse transcription kit (NEB, Cat #E6560) and real-time PCR reactions were performed using Quant Studio 3 (Applied Biosystems by Thermo Scientific) using primer sequences given below. Expression of DDX3X was normalized to that of GAPDH.

```
DDX3-Forward:
                                    (SEQ ID NO: 4)
5'-AGCAGTTTTGGATCTCGTAGTG-3'

DDX3-Reverse:
                                    (SEQ ID NO: 5)
5'-ACTGTTTCCACCACGTTCAAAT-3'

GAPDH-Forward:
                                    (SEQ ID NO: 6)
5'-GTCTCCTCTGACTTCAACAGCG-3'

GAPDH-Reverse:
                                    (SEQ ID NO: 7)
5'-ACCACCCTGTTGCTGTAGCCAA-3'
```

Immunoblot Analysis: GBM0308 cells were lysed in RIPA buffer (50 mM Tris-HCl pH 7.4, 1% NP-40, 0.25% sodium deoxycholate, 150 mM NaCl, 1 mM EDTA) containing 1X protease inhibitor cocktail (Roche) and 1 mM PMSF. Total cell lysates (50 μg) were subjected to SDS-PAGE and transferred to nitrocellulose membrane, which were blocked with 5% non-fat dry milk, and incubated with anti-DDX3 (1:1000 dilution; Cell Signaling, Cat #2635), or anti-β-actin (1:2000 dilution; Sigma) antibodies overnight at 4° C. Rabbit and mouse HRP-conjugated secondary antibodies (Jackson Laboratories) were used for detection with ECL western blotting substrate (Thermofisher Scientific). Protein bands were detected and analyzed using ChemiDoc image analyzer (Bio-Rad).

Cell Proliferation Assay: GBM0308 cells were transduced with a lentivirus expressing non-silencing (NS) or DDX3X shRNA, cells were selected with puromycin for 2 days. The selected DDX3X KD cells and NS cells were seeded at a density of 3000 cells per well in 96 well plates. Cell proliferation was monitored for 7 days. Cell viability was assessed using PrestoBlue Cell Viability Reagent (Invitrogen™, Cat #A13261) as per the manufacturer's instructions.

RNA Sequencing and Analysis: GBM0308 cells cultured in NBE medium were treated with compound (−)-20 at concentrations of 0.1 μM, 1 μM and DMSO. At 12 h and 24 h timepoints, total RNA was extracted using RNeasy mini kit (Qiagen) as per the manufacturer's instruction. Preparation of the RNA library and transcriptome sequencing were conducted by Novogene. RNASeq data analysis was performed with OneStopRNAseq.[S11] Paired-end reads were aligned to human genome hg38, with star_2.5.3a,[S12] annotated with GENCODE GRCh38.p12 annotation release 34.[S13] Aligned exon fragments with mapping quality higher than 20 were counted toward gene expression with featureCounts_1.5.2.[S14] Differential expression (DE) analysis was performed with DESeq2_1.20.0.[S15] Within DE analysis, 'ashr' was used to create log 2 Fold Change (LFC) shrinkage for each comparison.$16 Gene set enrichment analysis were performed with GSEA.[S17] GSEA analysis were performed on ranked gene list based on both LFC and p-value from the DE analysis (LFC-GSEA and pvalue-GSEA).

II. Computational Methods

Ligand Preparation: Compound (−)-20 was prepared for docking using Schrödinger's LigPrep in the Maestro software environment (Version 14.0.134, Release 2024-2). During ligand preparation, Epik was used to predict possible protonation states in the pH range of 7.4+/−2.0. LigPrep produced two predicted protonation states for docking: the neutral species, and C2 acylsulfamide anion negatively charged at the amide oxygen.

DDX3X Receptor Preparation: The "7LIU-C704A" receptor was prepared from PDB X-ray structure 7LIU, point mutated to adenosine at residue C704 using Pymol (Version 2.4.0, Schrödinger LLC). The resulting structure was prepared for docking using the default Protein Preparation Workflow in the Maestro Software environment (Version 14.0.134, Release 2024-2), which involved structure pre-processing, hydrogen-bond optimization, restrained minimization (S-OPLS force field, hydrogen atoms freely minimized and heavy atoms minimized to r.m.s.d. 0.3), and removal of waters >4 Å from heteroatoms.

Glide Rigid Receptor Docking: Glide rigid receptor docking was performed in Schrödinger's Maestro software environment (Version 14.0.134, Release 2024-2). EIF4A1 X-ray structure (PDB: 5ZC9) was prepared for use as the docking receptor through default Protein Preparation Workflow, which involved structure preprocessing, hydrogen-bond optimization, restrained minimization (S-OPLS force field, hydrogen atoms freely minimized and heavy atoms minimized to r.m.s.d. 0.3), and removing water >4 Å from heteroatoms. To define the binding site, compound (−)-20 was confined to the centroid of Workspace ligand (i.e. RocA) during receptor grid generation. The highest-scored docking pose was selected for further analysis.

Induced Fit Docking (IFD): Induced Fit Docking was performed in Schrödinger's Maestro software environment (Version 14.0.134, Release 2024-2). To define the binding site, the center-of-mass of each docked ligand was restrained to a 10 Å box positioned at the centroid of the following residues: Val328, Glu332, Gln360, Arg363 (from DDX3X), A704 and G705 (from the DNA-RNA hybrid oligonucleotide). During Induced Fit Docking, all protein sidechains within 5 Å of the docked ligand were designated flexible, while all oligonucleotide sidechains were designated as rigid. Of note, the oxygen-anion input ligand produced by LigPrep exclusively produced output IFD poses bearing a negative charge at nitrogen. The top-scored and the second-scored IFD poses were both obtained for the compound (−)-20 nitrogen anion (docking score-6.986 kcal/mol and -6.131, respectively) and were selected for analysis.

III. General Methods for Chemical Synthesis

Unless otherwise stated, $^{1}H$ NMR and $^{13}C$ NMR spectra were obtained in $CDCl_3$, $CD_3OD$ (Cambridge Isotope Laboratories, Inc.) using a Varian Innova-400 MHZ 500 MHz spectrometer. Chemical shifts are reported in parts per million relative to the internal solvent peak ($CDCl_3$: δ 7.26 for $^{1}H$; δ 77.16 for $^{13}C$. $CD_3OD$: δ 3.31 for $^{1}H$; δ 49.00 for $^{13}C$). Data for $^{1}H$ NMR are reported as follows: chemical shift, multiplicity (br=broad, s=singlet, d=doublet, t=triplet, q=quartet, m=multiplet), coupling constants, and integration. All $^{13}C$ NMR spectra were recorded with complete proton decoupling. Infrared (IR) spectra were recorded on a Bruker ALPHA P FT-IR spectrometer equipped with a diamond ATR module. High resolution mass spectra (HRMS) (ESI) were obtained using a Waters Q-TOF mass spectrometer at the Boston University Chemical Instrumentation Center, or by DART at the Boston College Mass Spectrometry Center. Melting points were recorded on a Mel-temp apparatus (Laboratory Devices) and are uncorrected. Analytical LC-MS and chiral HPLC analysis was performed on a Waters Acquity UPC$^{2}$ system (Waters MassLynx Version 4.2) with a binary solvent manager (Supercritical $CO_2$ and MeOH), a QDa mass spectrometer, a Waters PDA (PhotoDiode Array) detector, and an ELSD (Evaporative Light Scattering Detector). Optical rotations were measured on Rudolph Autopol II at 589 nm, and specific rotations are given $[\alpha]_D$. All reactions were carried out in oven-dried glassware under an argon/nitrogen atmosphere unless otherwise noted. Analytical thin layer chromatography (TLC) was conducted using 0.25 mm silica gel F-254 plates (SiliCycle). Flash chromatography was conducted using silica gel (SiliaFlash P60, particle size 40-63 μm) purchased from SiliCycle.

Materials: Chemicals were purchased from Sigma-Aldrich, Fisher, Alfa Aesar, TCI, Oakwood, Enamine, and ChemScene and were used without further purification.

IV. Chemical Synthesis Procedures and Compound Characterization

General Method for Synthesis of Rocaglate ß-Lactones

Synthesis of Rocaglate ß-Lactones Using Previously Reported Conditions

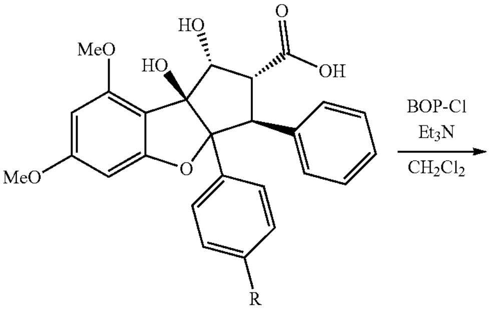

10: R = OMe
11: R = Br

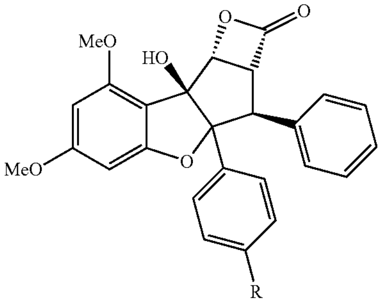

12: R = OMe
13: R = Br

To a dry 4 mL vial was added rocaglaic acid 10 or 11, a stir bar and dry dichloromethane under argon, and the resulting solution was cooled to 0° C. before adding triethylamine (3.0 equiv.) and bis(2-oxo-3-oxazolidinyl) phosphinic chloride (BOP-Cl, 1.3 equiv.). The reaction mixture was warmed to room temperature while stirring for 3 h. Water (2 mL) and $CH_2Cl_2$ (2 mL) were added after the reaction was complete and the aqueous layer was further extracted with $CH_2Cl_2$ (3×10 mL). The combined organic layers were washed with water and brine before being dried over sodium sulfate, filtered, and concentrated in vacuo to afford a yellow foam. The crude yellow solid was purified using silica gel column chromatography (35:65 EtOAc/ hexanes) to afford ß-lactone 12 or 13 (50%, 67%, respectively) as a white solid. Characterization data for 12 agreed with the literature report. S18

(2aR,3S,3aR,8bS,8cR)-3a-(4-bromophenyl)-8b-hydroxy-6,8-dimethoxy-3-phenyl-3,3a,8b,8c-tetrahydrooxeto[2',3':3,4] cyclopenta[1,2-b]benzofuran-2 (2aH)-one (13)

13

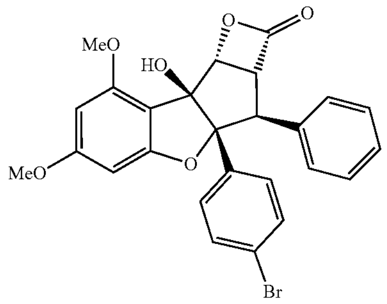

$^{1}H$ NMR (500 MHZ, $CDCl_3$) δ 7.21 (d, J=1.9 Hz, 1H), 7.20 (d, J=1.9 Hz, 1H), 7.17 (dd, J=4.9, 1.8 Hz, 3H), 7.00 (d, J=1.9 Hz, 1H), 6.99 (d, J=1.9 Hz, 1H), 6.96-6.92 (m, 2H), 6.23 (d, J=1.9 Hz, 1H), 6.08 (d, J=1.9 Hz, 1H), 5.40 (d, J=5.0 Hz, 1H), 4.57 (t, J=4.9 Hz, 1H), 4.13-4.10 (m, 1H), 3.81 (s, 3H), 3.80 (s, 3H) ppm. $^{13}C$ NMR (126 MHZ, $CDCl_3$) δ 169.0, 164.1, 159.6, 157.3, 136.7, 134.1, 130.4, 129.3, 128.7, 128.3, 127.5, 122.1, 107.5, 106.4, 93.0, 89.9, 89.8, 82.9, 60.7, 55.7, 55.6, 54.6 ppm. IR $v_{max}$: 3498, 2927, 2847, 1832, 1601, 1501, 1454, 1218, 1200, 1148, 1126, 1073, 817, 735 $cm^{-1}$. M.p.: 140-145° C. (EtOAc: hexanes). TLC $R_f$=0.3 (Eluent: EtOAc:hexanes=35:65). HRMS (DART): m/z calculated for $[C_{25}H_{21}BrO_6+H]^+$ 509.0594, found 509.0590.

General Method for the Synthesis of Rocaglaic Acid Derivatives Through Ring-Opening of Rocaglate ß-Lactones:

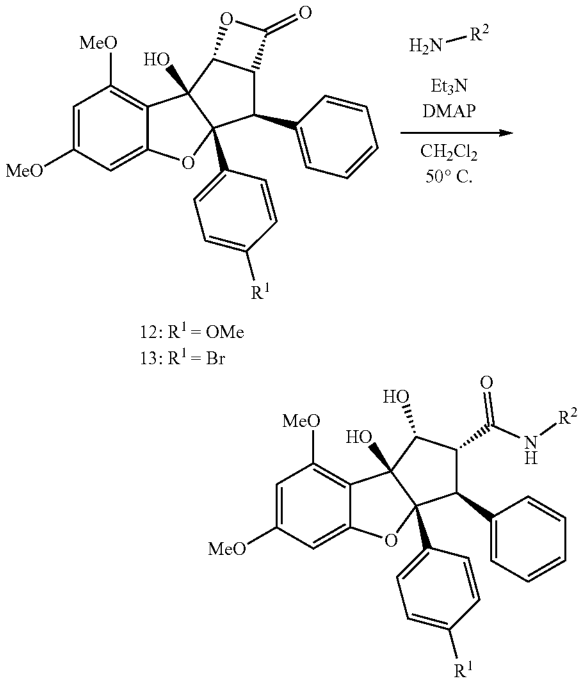

12: $R^1$ = OMe
13: $R^1$ = Br

To an oven-dried reaction vessel was added rocaglate ß-lactone 12 or 13, a stir bar, anhydrous $CH_2Cl_2$ (0.1 M), triethylamine (3 equiv.), primary amine (2 equiv.), and 4-dimethylaminopyridine (DMAP, 1 equiv.) at room temperature. After stirring the reaction mixture at 50° C. for 18 h, 1M HCl was added to the solution until the aqueous layer reached a pH of ~2. The organic phase was separated before the aqueous layer was further extracted with $CH_2Cl_2$ (3×10 mL). The combined organic layers were washed sequentially with water and brine, dried over sodium sulfate, filtered, and concentrated in vacuo to afford the crude product mixture as a yellow foam. Flash chromatography or preparative TLC was utilized to obtain pure rocaglate derivatives as white solids (note: the corresponding yields employing various amines are shown in Scheme 1).

Chiral Resolution of (±)-Rocaglaic Acids Using (−)-Quinine:

To a 20 mL vial was added (±)-rocaglaic acid, a stir bar, and ethanol (0.2 M), and to the resulting solution was added (−)-quinine (1 equiv.). The reaction was stirred at room temperature for 18 h. The solvent was removed in vacuo to afford a white solid before conducting recrystallization to separate the diastereomeric salts using acetone. The precipitated white solid (diastereomeric salts 22 or 24) was collected by filtration, and the mother liquor was dried under vacuum to afford the diastereomeric salts 23 or 25. The separated salts were suspended in ethyl acetate before adding 5% HCl and the biphasic mixture was stirred for 0.5 h at room temperature. The aqueous layer was further extracted with ethyl acetate and the combined organic fractions were washed with water and brine, dried over sodium sulfate, filtered, and concentrated in vacuo to afford the enantioenriched rocaglaic acid derivative.

(1R,2R,3S,3aR,8bS)—N-cyano-1,8b-dihydroxy-6,8-dimethoxy-3a-(4-methoxyphenyl)-3-phenyl-2,3,3a,8b-tetrahydro-1H-cyclopenta[b]benzofuran-2-carboxamide (14)

14

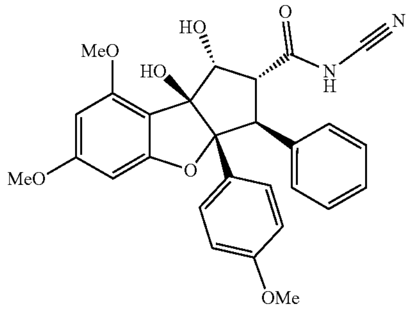

$^{1}H$ NMR (500 MHZ, $CDCl_3$) δ 7.11-7.06 (m, 5H), 6.88 (t, J=4.1 Hz, 2H), 6.67 (d, J=8.2 Hz, 2H), 6.29 (d, J=1.7 Hz, 1H), 6.15 (d, J=1.8 Hz, 1H), 5.11-5.06 (m, 1H), 4.18 (d, J=13.1 Hz, 1H), 4.13-3.93 (m, 1H), 3.89 (s, 3H), 3.84 (s, 3H), 3.71 (s, 3H) ppm. $^{13}C$ NMR (126 MHz, $CDCl_3$) δ 169.9, 164.4, 160.9, 159.0, 156.9, 135.0, 129.0, 128.2, 127.9, 127.2, 125.0, 112.8, 106.9, 106.6, 101.2, 93.4, 92.9, 89.6, 78.5, 56.4, 55.9, 55.8, 55.1, 50.8 ppm. IR $v_{max}$: 3447, 3059, 2928, 2843, 2260, 1735, 1598, 1440, 1147, 1030, 869 $cm^{-1}$. M.p.: 170-175° C. ($MeOH:CH_2Cl_2$). TLC $R_f$=0.1 (Eluent: $MeOH:CH_2Cl_2$=5:95). HRMS (ESI): m/z calculated for $[C_{28}H_{26}N_2O_7+Na]^+$ 525.1638, found 525.1624.

(1R,2R,3S,3aR,8bS)-1,8b-dihydroxy-6,8-dimethoxy-3a-(4-methoxyphenyl)-N-(methylsulfonyl)-3-phenyl-2,3,3a,8b-tetrahydro-1H-cyclopenta[b]benzofuran-2-carboxamide (15)

15

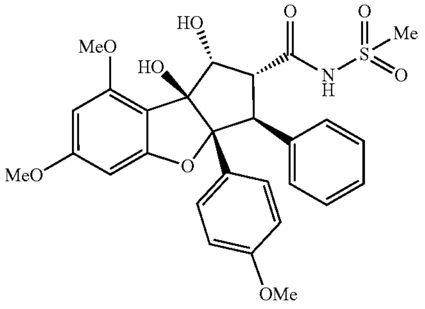

$^1$H NMR (500 MHZ, $CDCl_3$) δ 7.11-7.04 (m, 5H), 6.90 (dd, J=6.7, 3.0 Hz, 2H), 6.29 (d, J=1.9 Hz, 1H), 6.14 (d, J=2.0 Hz, 1H), 5.04 (d, J=6.3 Hz, 1H), 4.18 (d, J=13.2 Hz, 1H), 3.88 (s, 3H), 3.84 (s, 3H), 3.81 (dd, J=13.6, 6.0 Hz, 1H), 3.70 (s, 3H), 3.02 (s, 3H) ppm. $^{13}$C NMR (126 MHz, $CDCl_3$) δ 164.4, 160.9, 158.9, 156.9, 135.3, 129.0, 128.2, 127.9, 126.6, 125.8, 112.4, 106.7, 101.3, 93.4, 92.8, 89.5, 78.8, 77.2, 56.1, 55.9, 55.8, 55.1, 52.0, 43.4, 40.9 ppm. IR $\nu_{max}$: 3520, 3254, 2957, 2932, 2845, 1719, 1600, 1514, 1453, 1440, 1274, 1200, 1172, 1031, 869 $cm^{-1}$. M.p.: 135-140° C. ($MeOH:CH_2Cl_2$). TLC $R_f$=0.2 (Eluent: MeOH: $CH_2Cl_2$=5:95). HRMS (ESI): m/z calculated for $[C_{28}H_{29}NO_9S+Na]^+$ 598.1461, found 598.1441.

(1R,2R,3S,3aR,8bS)—N—(N,N-dimethylsulfamoyl)-1,8b-dihydroxy-6,8-dimethoxy-3a-(4-methoxyphenyl)-3-phenyl-2,3,3a,8b-tetrahydro-1H-cyclopenta[b]benzofuran-2-carboxamide (16)

16

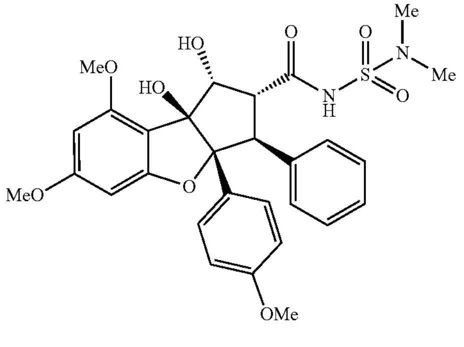

$^1$H NMR (500 MHZ, $CDCl_3$) δ 8.59 (s, 1H), 7.14-7.06 (m, 5H), 6.93 (dd, J=6.9, 2.8 Hz, 2H), 6.69-6.65 (m, 2H), 6.30 (d, J=1.9 Hz, 1H), 6.15 (d, J=1.9 Hz, 1H), 4.97 (dd, J=5.8, 1.7 Hz, 1H), 4.11 (d, J=14.2 Hz, 1H), 3.90 (s, 3H), 3.85 (s, 3H), 3.78 (dd, J=14.0, 5.1 Hz, 1H), 3.71 (s, 3H), 2.59 (s, 6H) ppm. $^{13}$C NMR (126 MHz, $CDCl_3$) δ 168.6, 164.4, 160.8, 158.9, 156.9, 135.2, 129.1, 128.3, 127.9, 127.2, 125.7, 112.8, 106.8, 101.1, 93.6, 92.8, 89.5, 78.4, 56.8, 55.9, 55.8, 55.1, 52.4, 38.0 ppm. IR $\nu_{max}$: 3481, 3251, 3059, 2960, 2924, 2850, 1724, 1623, 1514, 1454, 1199, 1147, 1015, 800 $cm^{-1}$. M.p.: 120-125° C. ($MeOH:CH_2Cl_2$). TLC $R_f$=0.2 (Eluent: $MeOH:CH_2Cl_2$=5:95). HRMS (ESI): m/z calculated for $[C_{29}H_{32}N_2O_9S+H]^+$ 585.1907, found 585.1927.

(1R,2R,3S,3aR,8bS)-1,8b-dihydroxy-6,8-dimethoxy-3a-(4-methoxyphenyl)-3-phenyl-N—(N-(prop-2-yn-1-yl)sulfamoyl)-2,3,3a,8b-tetrahydro-1H-cyclopenta[b]benzofuran-2-carboxamide (17)

17

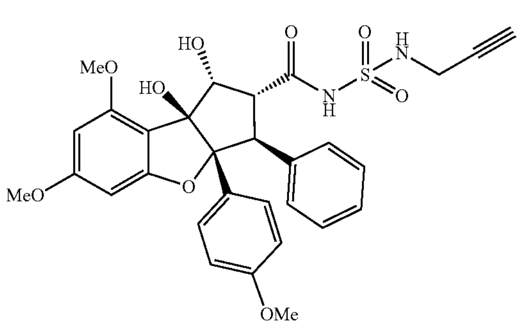

$^1$H NMR (500 MHZ, $CD_3OD$) δ 7.15-7.08 (m, 2H), 7.06-6.98 (m, 3H), 6.90-6.87 (m, 2H), 6.66-6.61 (m, 2H), 6.29 (d, J=1.9 Hz, 1H), 6.18 (d, J=2.0 Hz, 1H), 4.89 (s, 1H), 4.26 (d, J=14.0 Hz, 1H), 3.90-3.86 (m, 1H), 3.85 (s, 3H), 3.82 (s, 3H), 3.73-3.68 (m, 1H), 3.66 (s, 4H), 3.66-3.62 (m, 1H), 2.54 (t, J=2.6 Hz, 1H) ppm. $^{13}$C NMR (126 MHZ, $CD_3OD$) δ 168.9, 163.9, 160.7, 158.5, 157.8, 137.5, 128.8, 127.8, 127.7, 127.1, 125.9, 111.8, 107.9, 101.1, 93.8, 91.7, 79.0, 78.1, 72.1, 54.7, 54.6, 54.6, 54.0, 51.4, 32.1 ppm. IR $\nu_{max}$: 3485, 3279, 2928, 2843, 1712, 1600, 1513, 1453, 1200, 1146, 1032, 827, 643 $cm^{-1}$. M.p.: 175-180° C. ($MeOH:CH_2Cl_2$). TLC $R_f$=0.1 (Eluent: $MeOH:CH_2Cl_2$=10:90). HRMS (ESI): m/z calculated for $[C_{30}H_{30}N_2O_9S+H]^+$ 595.1750 found 595.1750.

(1R,2R,3S,3aR,8bS)—N-(but-3-yn-1-ylsulfonyl)-1,8b-dihydroxy-6,8-dimethoxy-3a-(4-methoxyphenyl)-3-phenyl-2,3,3a,8b-tetrahydro-1H-cyclopenta[b]benzofuran-2-carboxamide (18)

18

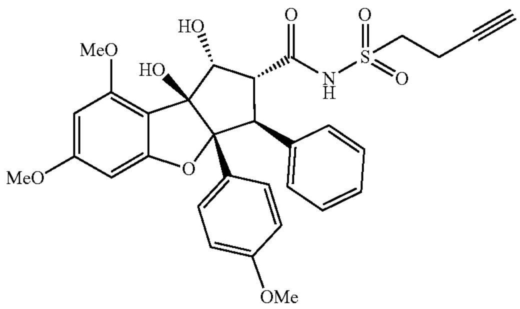

$^1$H NMR (500 MHZ, $CDCl_3$) δ 7.09 (dt, J=7.0, 2.7 Hz, 5H), 6.92-6.85 (m, 2H), 6.71-6.64 (m, 2H), 6.30 (d, J=1.9 Hz, 1H), 6.16 (d, J=1.9 Hz, 1H), 5.03 (d, J=6.2 Hz, 1H), 4.14 (d, J=13.5 Hz, 1H), 3.80 (dd, J=13.5, 6.2 Hz, 1H), 3.41 (t, J=7.8 Hz, 2H), 2.53-2.31 (m, 2H), 1.94 (t, J=2.7 Hz, 1H) ppm. $^{13}$C NMR (126 MHz, $CDCl_3$) δ 169.2, 164.5, 160.8, 159.0, 156.8, 135.0, 129.0, 128.2, 128.0, 127.3, 125.6, 112.8, 106.7, 101.1, 93.4, 92.9, 89.6, 79.1, 78.7, 70.5, 56.3, 56.0, 55.8, 55.1, 52.2, 51.1, 13.4 ppm. IR $\nu_{max}$: 3489, 3288, 3057, 2960, 2924, 2850, 1726, 1623, 1514, 1439, 1120, 1146, 1029, 869, 641 $cm^{-1}$. M.p.: 160-165° C. (MeOH:$CH_2Cl_2$). TLC $R_f$=0.1 (Eluent: MeOH:$CH_2Cl_2$=5:95). HRMS (ESI): m/z calculated for $[C_{31}H_{31}NO_9S+H]^+$ 594.1798, found 594.1788.

(1R,2R,3S,3aR,8bS)-3a-(4-bromophenyl)-1,8b-dihydroxy-6,8-dimethoxy-N-(methylsulfonyl)-3-phenyl-2,3,3a,8b-tetrahydro-1H-cyclopenta[b]benzofuran-2-carboxamide (19)

19

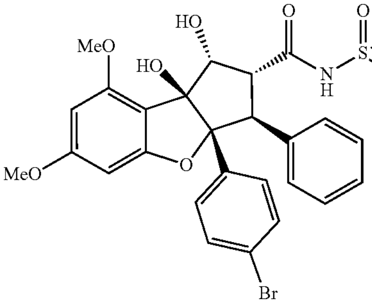

$^1$H NMR (500 MHZ, $CD_3OD$) δ 7.20 (dd, J=8.8, 2.3 Hz, 2H), 7.12 (dd, J=8.8, 2.2 Hz, 2H), 7.04 (dtt, J=13.8, 7.2, 3.5 Hz, 3H), 6.94 (d, J=7.6 Hz, 2H), 6.29 (d, J=2.1 Hz, 1H), 6.18 (d, J=2.2 Hz, 1H), 4.60 (s, 1H), 4.35 (dd, J=14.1, 2.2 Hz, 1H), 3.92 (ddd, J=14.0, 6.3, 2.2 Hz, 1H), 3.84 (s, 3H), 3.82 (s, 3H), 3.09 (s, 3H) ppm. $^{13}$C NMR (126 MHz, $CD_3OD$) δ 163.9, 160.6, 157.9, 137.3, 135.5, 129.5, 129.4, 127.6, 127.3, 126.1, 120.4, 107.5, 101.1, 93.9, 91.8, 88.5, 79.1, 70.1, 54.7, 54.6, 52.0, 39.5 ppm. IR $\nu_{max}$: 3484, 3200, 2961, 2923, 2853, 1721, 1604, 1501, 1455, 1440, 1257, 1218, 1185, 1038, 869 $cm^{-1}$. M.p.: >200° C. (MeOH:$CH_2Cl_2$). TLC $R_f$=0.1 (Eluent: MeOH:$CH_2Cl_2$=10:90). HRMS (DART): m/z calculated for $[C27H26BrNO_8S+H]^+$ 604.0635, found 604.0631.

(1R,2R,3S,3aR,8bS)-3a-(4-bromophenyl)-N—(N,N-dimethylsulfamoyl)-1,8b-dihydroxy-6,8-dimethoxy-3-phenyl-2,3,3a,8b-tetrahydro-1H-cyclopenta[b]benzofuran-2-carboxamide (20)

20

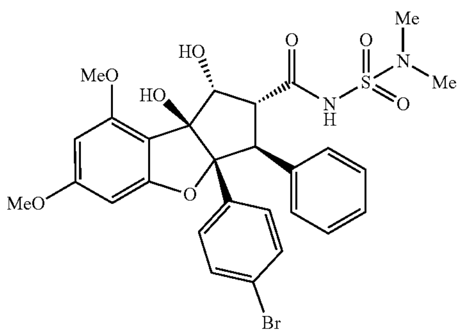

$^1$H NMR (500 MHZ, $CD_3OD$) δ 7.23-7.19 (m, 2H), 7.14-7.11 (m, 2H), 7.08-7.01 (m, 3H), 6.96-6.91 (m, 2H), 6.30 (d, J=2.0 Hz, 1H), 6.18 (d, J=1.9 Hz, 1H), 4.85 (d, J=6.2 Hz, 1H), 4.33 (d, J=14.1 Hz, 1H), 3.90 (dd, J=14.1, 6.2 Hz, 1H), 3.84 (s, 3H), 3.82 (s, 3H), 2.76 (s, 6H) ppm. $^{13}$C NMR (126 MHz, $CD_3OD$) δ 169.3, 163.9, 160.6, 157.9, 137.2, 135.4, 129.6, 129.4, 127.6, 127.3, 126.2, 120.4, 107.5, 101.0, 94.0, 91.8, 88.6, 78.9, 70.1, 54.8, 54.7, 54.6, 51.5, 37.2 ppm. IR $\nu_{max}$: 3486, 3236, 2917, 2800, 1732, 1628, 1596, 1466, 1151, 1137, 1057, 808 $cm^{-1}$. M.p.: >200° C. (MeOH:$CH_2Cl_2$). TLC $R_f$=0.2 (Eluent: MeOH:$CH_2Cl_2$=10:90). HRMS (DART): m/z calculated for $[C_{28}H_{29}BrN_2O_8S+H]^+$ 633.0901, found 633.0905.

(1R,2R,3S,3aR,8bS)-3a-(4-bromophenyl)-1,8b-dihydroxy-6,8-dimethoxy-3-phenyl-N—(N-(prop-2-yn-1-yl)sulfamoyl)-2,3,3a,8b-tetrahydro-1H-cyclopenta[b]benzofuran-2-carboxamide (21)

21

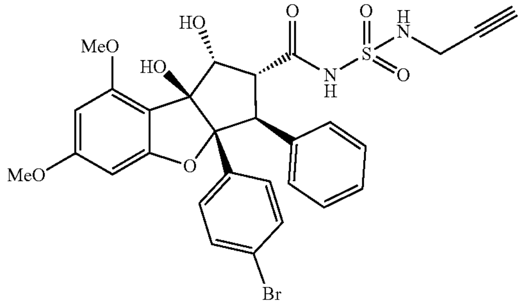

$^1$H NMR (500 MHZ, $CD_3OD$) δ 7.22-7.18 (m, 2H), 7.14-7.10 (m, 2H), 7.08-6.99 (m, 3H), 6.96-6.92 (m, 2H), 6.29 (d, J=1.9 Hz, 1H), 6.18 (d, J=2.0 Hz, 1H), 4.85 (d, J=6.1 Hz, 1H), 4.61 (s, 1H), 4.35 (d, J=14.0 Hz, 1H), 3.89 (dd, J=14.0, 6.2 Hz, 1H), 3.84 (s, 3H), 3.82 (s, 3H), 3.73-3.63 (m, 2H), 2.56 (t, J=2.5 Hz, 1H) ppm. $^{13}$C NMR (126 MHz, $CD_3OD$) δ 168.1, 163.9, 160.7, 157.9, 137.3, 135.5, 129.6, 129.3, 127.8, 127.3, 126.1, 120.4, 107.5, 101.1, 93.9, 91.8, 88.5, 79.0, 78.3, 72.0, 54.9, 54.7, 54.6, 51.8, 32.2 ppm. IR $\nu_{max}$: 3501, 3287, 2934, 2810, 1708, 1626, 1601, 1500, 1491, 1201, 1148, 1037, 816, 620 $cm^{-1}$. M.p.: 185-190° C. (MeOH:$CH_2Cl_2$). TLC $R_f$=0.2 (Eluent: MeOH:$CH_2Cl_2$=10:90). HRMS (DART): m/z calculated for $[C_{29}H_{27}BrN_2O_8S+H]^+$ 643.0744, found 643.0758.

(1S,2S,4S,5R)-2-((R)-hydroxy (6-methoxyquinolin-4-yl)methyl)-5-vinylquinuclidin-1-ium (1S,2S,3R,3aS,8bR)-1,8b-dihydroxy-6,8-dimethoxy-3a-(4-methoxyphenyl)-3-phenyl-2,3,3a,8b-tetrahydro-1H-cyclopenta[b]benzofuran-2-carboxylate (22)

22

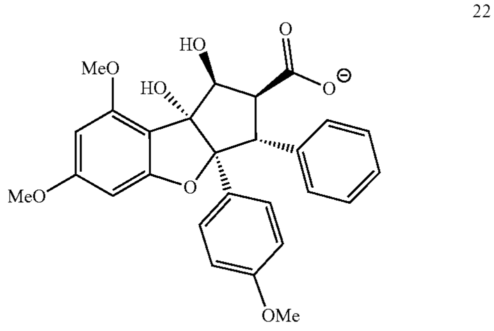

-continued

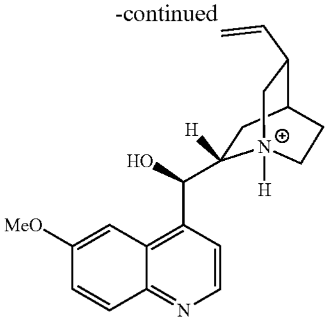

$^1$H NMR (500 MHZ, $CD_3OD$) δ 8.60 (d, J=4.6 Hz, 1H), 7.87 (d, J=9.2 Hz, 1H), 7.69 (dd, J=4.6, 0.8 Hz, 1H), 7.35 (dd, J=9.2, 2.6 Hz, 1H), 7.30 (d, J=2.7 Hz, 1H), 7.16-7.11 (m, 2H), 7.07-7.04 (m, 2H), 6.99-6.89 (m, 3H), 6.61-6.57 (m, 2H), 6.25 (d, J=2.0 Hz, 1H), 6.09 (d, J=2.0 Hz, 1H), 6.08 (s, 1H), 5.64 (ddd, J=17.2, 10.4, 6.9 Hz, 1H), 5.00 (dt, J=17.2, 1.3 Hz, 2H), 4.87 (d, J=6.1 Hz, 1H), 4.25 (d, J=14.2 Hz, 1H), 4.01 (tdd, J=10.8, 4.9, 2.5 Hz, 1H), 3.86 (dd, J=14.2, 6.1 Hz, 1H), 3.79 (s, 3H), 3.75 (s, 3H), 3.74 (s, 3H), 3.62 (s, 3H), 3.40 (ddd, J=12.1, 6.0, 4.3 Hz, 1H), 3.22 (dd, J=13.4, 10.6 Hz, 1H), 3.02 (ddd, J=13.3, 5.3, 2.6 Hz, 1H), 2.95-2.86 (m, 1H), 2.58 (dtt, J=12.1, 6.7, 2.1 Hz, 1H), 2.14-1.98 (m, 1H), 1.95 (q, J=3.0 Hz, 1H), 1.75 (m, 1H), 1.35 (tt, J=13.5, 3.3 Hz, 1H) ppm. $^{13}$C NMR (126 MHz, $CD_3OD$) δ 177.6, 163.6, 160.9, 158.6, 158.3, 157.9, 146.5, 146.3, 143.1, 138.8, 138.4, 129.9, 128.8, 128.4, 128.1, 127.1, 126.1, 125.6, 122.2, 118.9, 115.2, 111.7, 108.4, 101.9, 100.9, 93.8, 91.5, 88.5, 79.5, 66.8, 59.5, 57.0, 55.5, 54.7, 54.5, 54.0, 53.9, 52.9, 43.4, 37.3, 27.0, 24.1, 18.0 ppm. M.p.: 175-180° C. ($MeOH:CH_2Cl_2$). $\alpha_D^{19}$=−9.94 (c=0.1, MeOH).

(1S,2S,4S,5R)-2-((R)-hydroxy (6-methoxyquinolin-4-yl)methyl)-5-vinylquinuclidin-1-ium (1R,2R,3S,3aR,8bS)-1,8b-dihydroxy-6,8-dimethoxy-3a-(4-methoxyphenyl)-3-phenyl-2,3,3a,8b-tetrahydro-1H-cyclopenta[b]benzofuran-2-carboxylate (23)

23

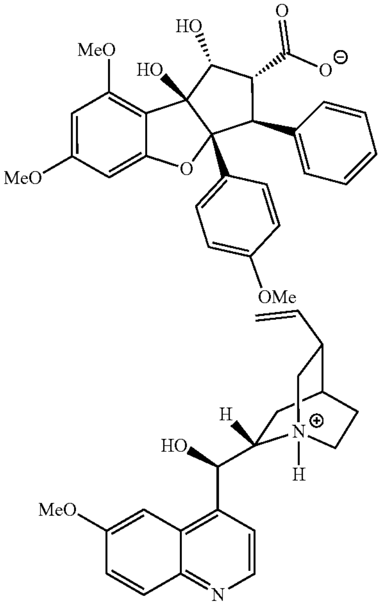

$^1$H NMR (500 MHZ, $CD_3OD$) δ 8.58 (d, J=4.6 Hz, 2H), 7.86 (d, J=9.2 Hz, 1H), 7.68 (d, J=4.6 Hz, 2H), 7.36 (d, J=2.7 Hz, 2H), 7.32 (dd, J=9.2, 2.6 Hz, 1H), 7.18-7.12 (m, 2H), 7.09-7.05 (m, 2H), 7.00-6.89 (m, 3H), 6.61-6.57 (m, 2H), 6.27 (d, J=2.0 Hz, 1H), 6.16 (d, J=2.0 Hz, 1H), 6.00-5.97 (m, 1H), 5.65 (ddd, J=17.3, 10.4, 7.0 Hz, 1H), 5.01 (t, J=1.4 Hz, 1H), 4.94-4.90 (m, 1H), 4.88 (d, J=6.1 Hz, 1H), 4.27 (d, J=14.1 Hz, 1H), 3.98 (tt, J=10.8, 8.3, 3.6 Hz, 1H), 3.87 (dd, J=14.2, 6.1 Hz, 1H), 3.80 (s, 3H), 3.78 (s, 3H), 3.75 (s, 4H), 3.61 (s, 3H), 3.30 (m, 1H), 3.16 (dd, J=13.3, 10.5 Hz, 2H), 2.96 (ddd, J=13.4, 5.3, 2.5 Hz, 2H), 2.88 (td, J=11.8, 5.1 Hz, 1H), 2.53-2.47 (m, 2H), 2.01 (dddd, J=16.1, 10.8, 5.5, 2.9 Hz, 3H), 1.74-1.66 (m, 2H), 1.36 (tt, J=13.5, 3.2 Hz, 1H) ppm. $^{13}$C NMR (126 MHz, $CD_3OD$) δ 178.0, 163.6, 161.0, 158.5, 158.3, 158.1, 147.0, 146.6, 143.2, 139.0, 138.8, 130.0, 128.8, 128.4, 128.2, 127.1, 126.2, 125.7, 122.2, 118.9, 115.0, 111.7, 108.6, 102.0, 100.9, 93.8, 91.5, 88.5, 67.6, 59.5, 57.2, 55.3, 54.7, 54.7, 54.4, 54.1, 53.0, 43.3, 37.8, 27.2, 24.7, 18.5 ppm. M.p.: 165-170° C. ($MeOH:CH_2Cl_2$). $\alpha_D^{19}$=−82.247 (c=0.1, MeOH).

(1S,2S,4S,5R)-2-((R)-hydroxy (6-methoxyquinolin-4-yl)methyl)-5-vinylquinuclidin-1-ium (1S,2S,3R,3aS,8bR)-3a-(4-bromophenyl)-1,8b-dihydroxy-6,8-dimethoxy-3-phenyl-2,3,3a,8b-tetrahydro-1H-cyclopenta[b]benzofuran-2-carboxylate (24)

24

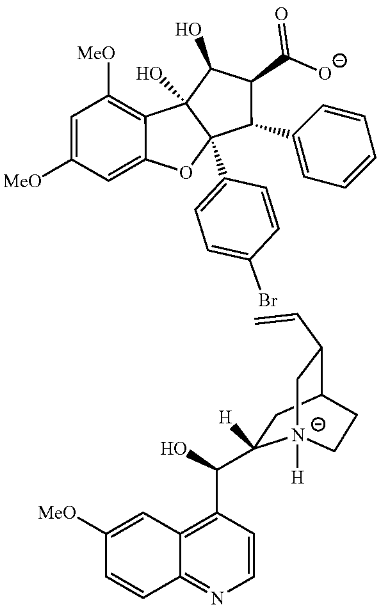

$^1$H NMR (500 MHZ, $CD_3OD$) δ 8.64 (d, J=4.6 Hz, 1H), 7.91 (d, J=9.2 Hz, 1H), 7.71 (d, J=4.6 Hz, 1H), 7.38 (dd, J=9.2, 2.4 Hz, 1H), 7.33 (d, J=2.6 Hz, 1H), 7.18-7.06 (m, 6H), 7.01-6.92 (m, 3H), 6.25 (d, J=2.0 Hz, 1H), 6.11 (d, J=2.0 Hz, 1H), 6.04 (s, 1H), 5.68 (ddd, J=17.3, 10.4, 6.9 Hz, 1H), 5.05-4.94 (m, 2H), 4.82 (d, J=5.8 Hz, 1H), 4.32 (d, J=14.2 Hz, 1H), 4.08-3.98 (m, 1H), 3.86 (dd, J=14.2, 5.8 Hz, 1H), 3.82-3.78 (m, 6H), 3.75 (s, 3H), 3.43 (t, J=8.9 Hz, 1H), 3.28-3.24 (m, 1H), 3.05 (ddd, J=13.3, 5.4, 2.4 Hz, 1H), 2.96 (td, J=12.1, 5.0 Hz, 1H), 2.61 (t, J=6.9 Hz, 1H), 2.12-2.07 (m, 1H), 1.97 (q, J=3.2 Hz, 1H), 1.82-1.72 (m, 1H), 1.40 (ddt, J=13.6, 10.4, 3.2 Hz, 1H) ppm. $^{13}$C NMR (126 MHz, $CD_3OD$) δ 177.4, 163.6, 160.8, 158.6, 157.9, 146.6, 146.4, 143.2, 138.5, 138.4, 136.0, 130.0, 129.6, 129.2, 128.0, 127.2, 126.1, 125.8, 122.2, 120.2, 118.9, 115.2, 108.0, 101.7, 101.0, 93.9, 91.6, 88.4, 79.4, 67.1, 59.6, 57.0, 55.4, 54.7, 54.5, 54.1, 53.0, 43.4, 37.4, 27.0, 24.2, 18.2 ppm. M.p.: 175-180° C. ($MeOH:CH_2Cl_2$). $\alpha_D^{30}$=−18.00 (c=0.1, MeOH).

(1S,2S,4S,5R)-2-((R)-hydroxy (6-methoxyquinolin-4-yl)methyl)-5-vinylquinuclidin-1-ium (1R,2R,3S, 3aR,8bS)-3a-(4-bromophenyl)-1,8b-dihydroxy-6,8-dimethoxy-3-phenyl-2,3,3a,8b-tetrahydro-1H-cyclopenta[b]benzofuran-2-carboxylate (25)

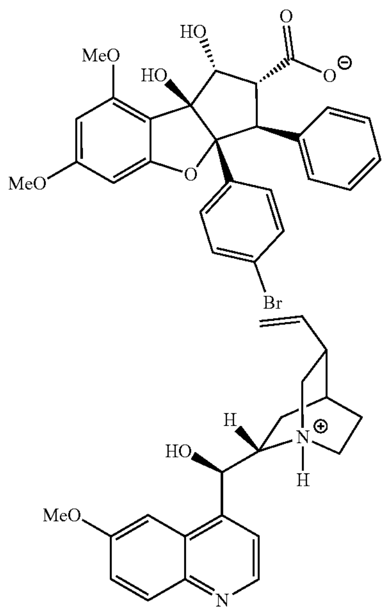

$^1H$ NMR (500 MHZ, $CD_3OD$) δ 8.65 (d, J=4.6 Hz, 1H), 7.93 (d, J=9.1 Hz, 2H), 7.72 (d, J=4.6 Hz, 1H), 7.40 (d, J=9.2 Hz, 3H), 7.18-7.06 (m, 5H), 7.03-6.92 (m, 3H), 6.27 (d, J=2.0 Hz, 1H), 6.16 (d, J=2.0 Hz, 1H), 5.97 (s, 1H), 5.71 (ddd, J=17.3, 10.4, 7.0 Hz, 1H), 5.04 (d, J=17.1 Hz, 1H), 4.97 (d, J=10.4 Hz, 1H), 4.80 (d, J=5.8 Hz, 1H), 4.33 (d, J=14.2 Hz, 1H), 4.02 (s, 1H), 3.87-3.83 (m, 1H), 3.82-3.80 (m, 9H), 3.47-3.41 (m, 2H), 3.25 (d, J=11.9 Hz, 1H), 3.06 (d, J=12.7 Hz, 1H), 2.97 (s, 1H), 2.60 (s, 1H), 2.08 (d, J=7.7 Hz, 1H), 1.98 (d, J=3.2 Hz, 1H), 1.43 (tt, J=10.4, 3.1 Hz, 1H) ppm. $^{13}C$ NMR (126 MHz, $CD_3OD$) δ 179.3, 164.3, 160.8, 158.6, 157.7, 146.6, 143.3, 139.1, 138.0, 136.0, 130.0, 129.6, 129.2, 128.0, 127.2, 126.2, 125.8, 122.1, 120.2, 118.9, 115.1, 108.1, 101.8, 101.0, 93.9, 91.6, 88.2, 79.3, 67.5, 59.6, 57.1, 55.3, 54.7, 54.5, 54.3, 43.4, 37.6, 27.1, 24.4, 18.4 ppm. M.p.: 170-175° C. ($MeOH:CH_2Cl_2$). $\alpha_D^{31}$=−77.52 (c=0.1, MeOH).

TABLE 3

| Additional optical rotations for compounds in this study: |
|---|
| (−)-10, $\alpha_D^{31}$ = −46.32 (c = 0.1, $CHCl_3$) |
| (+)-10, $\alpha_D^{24}$ = +45.14 (c = 0.1, $CHCl_3$) |
| (−)-11, $\alpha_D^{20}$ = −25.924 (c = 0.1, $CHCl_3$) |
| (+)-11, $\alpha_D^{21}$ = +28.523 (c = 0.1, $CHCl_3$) |
| (−)-13, $\alpha_D^{21}$ = −141.32 (c = 0.1, $CHCl_3$) |
| (−)-15, $\alpha_D^{21}$ = −40.22 (c = 0.1, $CHCl_3$) |
| (+)-15, $\alpha_D^{23}$ = +39.48 (c = 0.1, $CHCl_3$) |
| (−)-16, $\alpha_D^{22}$ = −27.60 (c = 0.1, $CHCl_3$) |
| (+)-16, $\alpha_D^{23}$ = +28.44 (c = 0.1, $CHCl_3$) |
| (−)-19, $\alpha_D^{21}$ = −20.88 (c = 0.1, $CHCl_3$) |
| (−)-20, $\alpha_D^{22}$ = −20.49 (c = 0.1, $CHCl_3$) |

V. X-Ray Crystallographic Data for Compound 24

X-ray crystal diffraction data for (+)-rocaglaic acid-(−)-quinine salt 24. Crystals of compound 24 suitable for X-ray analysis were obtained by slow evaporation from methanol.

Results are summarized in Tables 4-6.

TABLE 4

| Crystal data | |
|---|---|
| $C_{26}H_{22}BrO_7$•$C_{20}H_{25}N_2O_2$•$H_2O$ | $D_x$ = 1.366 Mg $m^{-3}$ |
| $M_r$ = 869.78 | Cu Ka radiation, l = 1.54184 Å |
| Orthorhombic, $P2_12_12_1$ | Cell parameters from 46591 reflections |
| a = 7.0577 (1) Å | q = 2.4-75.6° |
| b = 18.6325 (3) Å | m = 1.83 $mm^{-1}$ |
| c = 32.1571 (4) Å | T = 100 K |
| V = 4228.74 (10) $Å^3$ | Plank, white |
| Z = 4 | 0.28 × 0.09 × 0.08 mm |
| F(000) = 1816 | |

TABLE 5

| Data collection | |
|---|---|
| Saxi-CrysAlisPro-abstract goniometer imported SAXI images diffractometer | 8364 independent reflections |
| Radiation source: fine-focus sealed X-ray tube, Enhance (Cu) X-ray Source | 8251 reflections with I > 2s(I) |
| Graphite monochromator | $R_{int}$ = 0.099 |
| w and f scans | $q_{max}$ = 75.6°, $q_{min}$ = 2.8° |
| Absorption correction: multi-scan CrysAlis PRO 1.171.42.49 (Rigaku Oxford Diffraction, 2022) Empirical absorption correction using spherical harmonics, implemented in SCALE3 ABSPACK scaling algorithm. | h = −8 → 8 |
| $T_{min}$ = 0.816, $T_{max}$ = 1.000 | k = −22 → 21 |
| 140268 measured reflections | l = −38 → 39 |

TABLE 6

| Refinement | |
|---|---|
| Refinement on $F^2$ | H atoms treated by a mixture of independent and constrained refinement |
| Least-squares matrix: full | $w = 1/[s^2(F_o^2) + (0.0335P)^2 + 2.8976P]$ where $P = (F_o^2 + 2F_c^2)/3$ |
| $R[F^2 > 2s(F^2)] = 0.035$ | $(D/s)_{max} = 0.001$ |
| $wR(F^2) = 0.084$ | $D\rho_{max} = 0.62$ e Å$^{-3}$ |
| S = 1.09 | $D\rho_{min} = -0.41$ e Å$^{-3}$ |
| 8364 reflections | Extinction correction: SHELXL2018/3 (Sheldrick 2018), $Fc^* = kFc[1 + 0.001 \times Fc^2l^3/\sin(2g)]^{-1/4}$ |
| 570 parameters | Extinction coefficient: 0.00085 (10) |
| 19 restraints | Absolute structure: Flack x determined using 3281 quotients [(I+) − (I−)]/[(I+) + (I−)] (Parsons, Flack and Wagner, Acta Cryst. B69 (2013) 249-259). |
| Primary atom site location: dual | Absolute structure (Flack) parameter: 0.002 (5) |
| Hydrogen site location: mixed | |

References for the Supplementary Materials

S1. Chen, M.; Asanuma, M.; Takahashi, M.; Shichino, Y.; Mito, M.; Fujiwara, K.; Saito, H.; Floor, S. N.; Ingolia, N. T.; Sodeoka, M.; Dodo, K.; Ito, T.; Iwasaki, S., Dual targeting of DDX3 and eIF4A by the translation inhibitor rocaglamide A. *Cell Chem. Biol.* 2021, 28 (4), 475-486.e8.

S2. Gaetani, M.; Sabatier, P.; Saei, A. A.; Beusch, C. M.; Yang, Z.; Lundström, S. L.; Zubarev, R. A., Proteome Integral Solubility Alteration: A High-Throughput Proteomics Assay for Target Deconvolution. *J. Proteome Res.* 2019, 18 (11), 4027-4037.

S3. Moggridge, S.; Sorensen, P. H.; Morin, G. B.; Hughes, C. S., Extending the Compatibility of the SP3 Paramagnetic Bead Processing Approach for Proteomics. *J. Proteome Res.* 2018, 17 (4), 1730-1740.

S4. Hughes, C. S.; Moggridge, S.; Müller, T.; Sorensen, P. H.; Morin, G. B.; Krijgsveld, J., Single-pot, solid-phase-enhanced sample preparation for proteomics experiments. *Nat. Protoc.* 2019, 14 (1), 68-85.

S5. Cox, J.; Neuhauser, N.; Michalski, A.; Scheltema, R. A.; Olsen, J. V.; Mann, M., *Andromeda*: A Peptide Search Engine Integrated into the MaxQuant Environment. *J.* Proteome Res. 2011, 10 (4), 1794-1805.

S6. Cox, J.; Mann, M., MaxQuant enables high peptide identification rates, individualized p.p.b.-range mass accuracies and proteome-wide protein quantification. *Nat. Biotechnol.* 2008, 26 (12), 1367-1372.

S7. Elias, J. E.; Gygi, S. P., Target-decoy search strategy for increased confidence in large-scale protein identifications by mass spectrometry. *Nat. Methods* 2007, 4 (3), 207-214.

S8. Blum, B. C.; Emili, A., Omics Notebook: robust, reproducible and flexible automated multiomics exploratory analysis and reporting. *Bioinform. Adv.* 2021, 1 (1), vbab024.

S9. Chu, J.; Zhang, W.; Cencic, R.; Devine, W. G.; Beglov, D.; Henkel, T.; Brown, L. E.; Vajda, S.; Porco, J. A.; Pelletier, J., Amidino-Rocaglates: A Potent Class of eIF4A Inhibitors. *Cell Chem. Biol.* 2019, 26 (11), 1586-1593.e3.

S10. Novac, O.; Guenier, A. S.; Pelletier, J., Inhibitors of protein synthesis identified by a high throughput multiplexed translation screen. *Nucleic Acids Res.* 2004, 32 (3), 902-915.

S11. Li, R.; Hu, K.; Liu, H.; Green, M. R.; Zhu, L. J., OneStopRNAseq: A Web Application for Comprehensive and Efficient Analyses of RNA-Seq Data. *Genes* 2020, 11 (10), 1165.

S12. Dobin, A.; Davis, C. A.; Schlesinger, F.; Drenkow, J.; Zaleski, C.; Jha, S.; Batut, P.; Chaisson, M.; Gingeras, T. R., STAR: ultrafast universal RNA-seq aligner. *Bioinformatics* 2012, 29 (1), 15-21.

S13. Harrow, J.; Frankish, A.; Gonzalez, J. M.; Tapanari, E.; Diekhans, M.; Kokocinski, F.; Aken, B. L.; Barrell, D.; Zadissa, A.; Searle, S.; Barnes, I.; Bignell, A.; Boychenko, V.; Hunt, T.; Kay, M.; Mukherjee, G.; Rajan, J.; Despacio-Reyes, G.; Saunders, G.; Steward, C.; Harte, R.; Lin, M.; Howald, C.; Tanzer, A.; Derrien, T.; Chrast, J.; Walters, N.; Balasubramanian, S.; Pei, B.; Tress, M.; Rodriguez, J. M.; Ezkurdia, I.; van Baren, J.; Brent, M.; Haussler, D.; Kellis, M.; Valencia, A.; Reymond, A.; Gerstein, M.; Guigo, R.; Hubbard, T. J., GENCODE: the reference human genome annotation for The ENCODE Project. *Genome Res.* 2012, 22 (9), 1760-74.

S14. Liao, Y.; Smyth, G. K.; Shi, W., featureCounts: an efficient general purpose program for assigning sequence reads to genomic features. *Bioinformatics* 2013, 30 (7), 923-930.

S15. Love, M. I.; Huber, W.; Anders, S., Moderated estimation of fold change and dispersion for RNA-seq data with DESeq2. *Genome Biol.* 2014, 15 (12), 550.

S16. Stephens, M., False discovery rates: a new deal. *Biostatistics* 2016, 18 (2), 275-294.

S17. Subramanian, A.; Tamayo, P.; Mootha, V. K.; Mukherjee, S.; Ebert, B. L.; Gillette, M. A.; Paulovich, A.; Pomeroy, S. L.; Golub, T. R.; Lander, E. S.; Mesirov, J. P., Gene set enrichment analysis: A knowledge-based approach for interpreting genome-wide expression profiles. *Proc. Natl. Acad. Sci. U.S.A.* 2005, 102 (43), 15545-15550.

S18. Lajkiewicz, N. J.; Cognetta, A. B., III; Niphakis, M. J.; Cravatt, B. F.; Porco, J. A., Jr., Remodeling Natural Products: Chemistry and Serine Hydrolase Activity of a Rocaglate-Derived β-Lactone. *J. Am. Chem. Soc.* 2014, 136 (6), 2659-2664.

Example 2: Additional Exemplary Compounds

General Methods for Chemical Synthesis

General Procedure for Diazonium Coupling of 3-Hydroxyflavone Synthesis

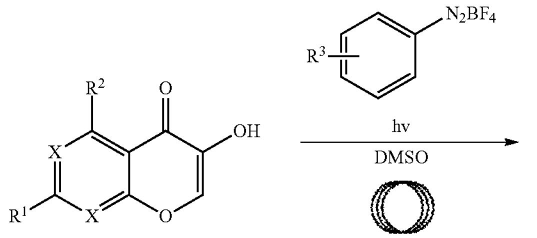

A

-continued

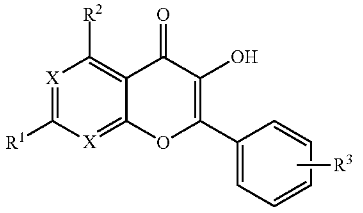

B

To an oven-dried reaction vessel was added 3-hydroxychromone A, diazonium salt B (1.1 equiv.), and DMSO (0.2 M). After degassing with argon for 10 min, the mixture was injected to a flow reactor and irradiated (λ=440 nm) at rt for 30 min. The resulting reaction mixture was poured into ice water, and the solid was collected as the desired 3-hydroxyflavone product.

Representative Procedure: Synthesis of Rocaglate Acyl Sulfamide 5.

Scheme 3
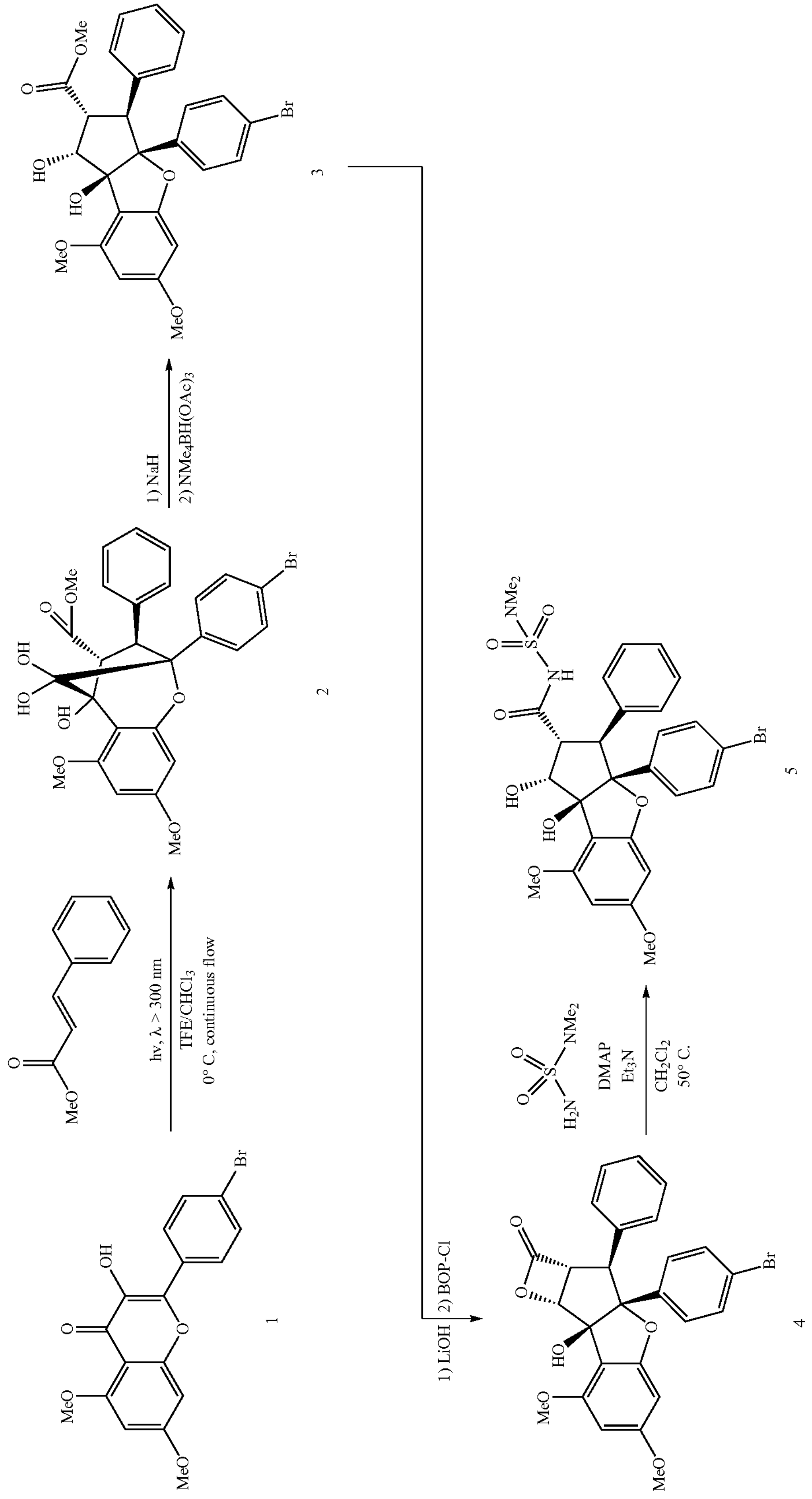
1 2 3 4 5

An oven-dried reaction vessel was charged with 3-hydroxyflavone 1, methyl cinnamate (10 equiv.) in the solvent mixture $CHCl_3$—TFE (7:3; 0.13 M). After degassing with argon for 10 min, the mixture was injected to the flow reactor and irradiated (λ>330 nm) at 0° C. The solution was concentrated in vacuo to afford a brown oil containing aglain 2. Purification via flash chromatography using a gradient of hexanes/EtOAc (8:2 to 3:7) afforded product 2 as a mixture of isomers. This mixture of isomers was transformed into the same ketone intermediate through ketol shift rearrangement under basic conditions using NaH (2.1 equiv.) in THF (0.035 M), which subsequently reduced into the methyl rocaglate product 3 through Saksena-Evans reduction with $(Me_4N)BH(OAc)_3$ (6 equiv.) and acetic acid (10 equiv.) in acetonitrile (0.03 M). The endo methyl rocaglate 3 was purified via flash chromatography before hydrolysis with LiOH (20 equiv.) in a solvent mixture of $CH_3OH$—$H_2O$ (75:25). The resulting crude product was used in the next step after aqueous water work-up and transformed into rocaglate β-lactone 4 by treating with triethylamine (3 equiv.) and bis(2-oxo-3-oxazolidinyl)phosphinic chloride (BOP-Cl, 1.3 equiv.) in dichloromethane (0.1 M). Rocaglate β-lactone 4 was purified through column chromatography using a solvent mixture of hexanes/EtOAc (65:35). Subsequently, to an oven-dried reaction vessel was added rocaglate β-lactone 4 (50 mg, 0.1 mM), a stir bar, anhydrous $CH_2Cl_2$ (0.1 M), triethylamine (41 μL, 0.3 mM, 3 equiv.), N,N-dimethylsulfamide (24 mg, 0.2 mM, 2 equiv.), and 4-dimethylaminopyridine (DMAP, 12 mg, 0.1 mM, 1 equiv.) at room temperature. After stirring the reaction mixture at 50° C. for 18 h, 1M HCl was added to the solution until the aqueous layer reached a pH of ~2. The organic phase was separated before the aqueous layer was further extracted with $CH_2Cl_2$ (3×10 mL). The combined organic layers were washed sequentially with water and brine, dried over sodium sulfate, filtered, and concentrated in vacuo to afford the crude product mixture as a yellow foam. Flash chromatography was utilized to obtain pure rocaglate acyl sulfamide 5 (35 mg, 0.056 mM, 56%) as a white solid.

(1R,2R,3S,3aR,8bS)-3a-(4-bromophenyl)-N—(N,N-dimethylsulfamoyl)-1,8b-dihydroxy-6,8-dimethoxy-3-phenyl-2,3,3a,8b-tetrahydro-1H-cyclopenta[b]benzofuran-2-carboxamide (5)

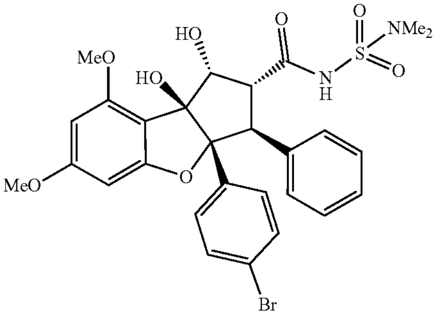

$^1H$ NMR (500 MHZ, $CD_3OD$) δ 7.23-7.19 (m, 2H), 7.14-7.11 (m, 2H), 7.08-7.01 (m, 3H), 6.96-6.91 (m, 2H), 6.30 (d, J=2.0 Hz, 1H), 6.18 (d, J=1.9 Hz, 1H), 4.85 (d, J=6.2 Hz, 1H), 4.33 (d, J=14.1 Hz, 1H), 3.90 (dd, J=14.1, 6.2 Hz, 1H), 3.84 (s, 3H), 3.82 (s, 3H), 2.76 (s, 6H) ppm. $^{13}C$ NMR (126 MHz, $CD_3OD$) δ 169.3, 163.9, 160.6, 157.9, 137.2, 135.4, 129.6, 129.4, 127.6, 127.3, 126.2, 120.4, 107.5, 101.0, 94.0, 91.8, 88.6, 78.9, 70.1, 54.8, 54.7, 54.6, 51.5, 37.2 ppm. IR $\nu_{max}$: 3486, 3236, 2917, 2800, 1732, 1628, 1596, 1466, 1151, 1137, 1057, 808 $cm^{-1}$. M.p.: >200° C. ($MeOH:CH_2Cl_2$). TLC $R_f$=0.2 (Eluent: $MeOH:CH_2Cl_2$=10:90). HRMS (DART): m/z calculated for $[C_{28}H_{29}BrN_2O_8S+H]^+$ 633.0901, found 633.0905.

General Method for the Synthesis of Roc ASFs Using Previously Reported Conditions:

Scheme 4
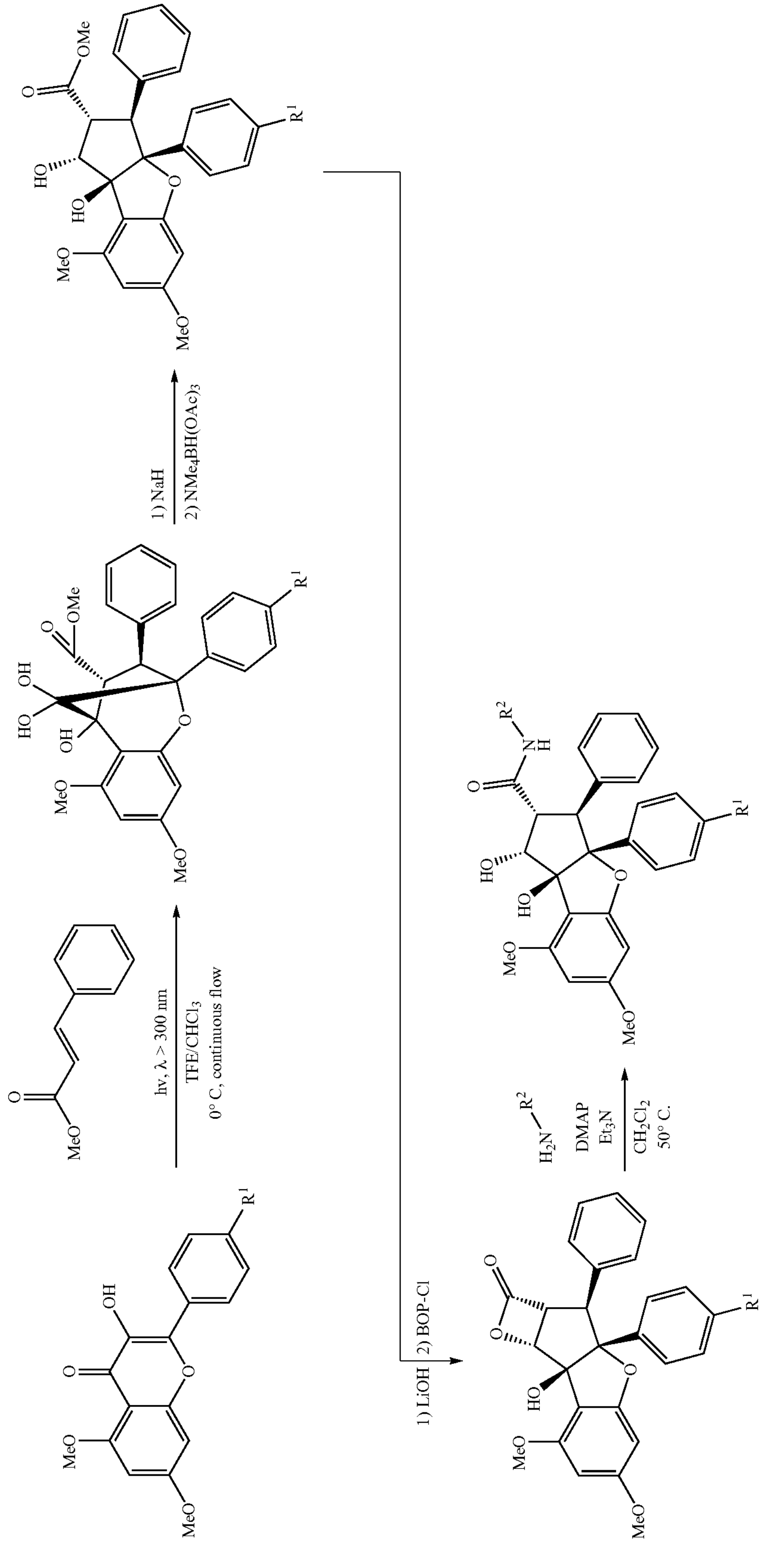

ADDITIONAL REFERENCES

71. "Identification of Rocaglate Acyl Sulfamides as Selective Inhibitors of Glioblastoma Stem Cells" Wang, Z.; Thakare, R. P.; Chitale, S.; Mishra, A. K.; Goldstein, S. I.; Fan, A. C.; Li, R.; Zhu, L. J.; Brown, L. E.; Cencic, R.; Huang, S.; Green, M. R.; Pelletier, J.; Malonia, S. K.; Porco, J. A., Jr. *ACS Cent. Sci.* 2024 ASAP.
72. "Biomimetic Photocycloaddition of 3-Hydroxyflavones: Synthesis and Evaluation of Rocaglate Derivatives as Inhibitors of Eukaryotic Translation", Roche, S. P.; Cencic, R.; Pelletier, J.; and Porco, J. A., Jr. *Angew. Chem. Int. Ed.* 2010, 49, 6533-6538.

Compound Characterization for Additional Roc ASFs (1R,2R,3S,3aR,8bS)—N—(N,N-dimethylsulfamoyl)-1,8b-dihydroxy-6,8-dimethoxy-3-phenyl-3a-(4-(trifluoromethyl)phenyl)-2,3,3a,8b-tetrahydro-1H-cyclopenta[b]benzofuran-2-carboxamide (ZW-12-29)

ZW-12-29

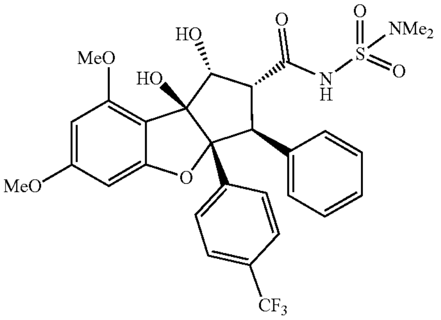

$^1$H NMR (500 MHZ, $CD_3OD$): δ 7.42-7.33 (m, 5H), 7.05-7.01 (m, 2H), 6.94-6.91 (m, 2H), 6.32 (d, J=2.0 Hz, 1H), 6.20 (d, J=2.0 Hz, 1H), 4.89 (d, J=6.2 Hz, 1H), 4.39 (d, J=14.1 Hz, 1H), 4.00-3.95 (m, 1H), 3.85 (s, 3H), 3.83 (s, 3H), 2.78 (s, 6H). MS: m/z calculated for $[C_{29}H_{29}F_3N_2O_8S+H]^+$ 623.159, found 622.912.

(1R,2R,3S,3aR,8bS)-3a-(4-cyanophenyl)-N—(N,N-dimethylsulfamoyl)-1,8b-dihydroxy-6,8-dimethoxy-3-phenyl-2,3,3a,8b-tetrahydro-1H-cyclopenta[b]benzofuran-2-carboxamide (ZW-12-30)

ZW-12-30

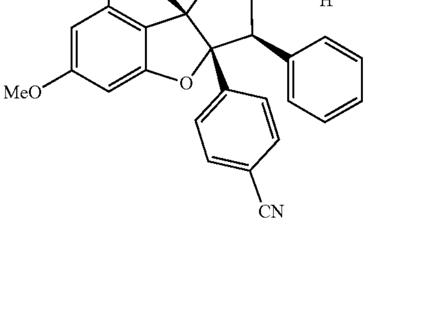

$^1$H NMR (500 MHZ, $CD_3OD$) δ 7.42-7.36 (m, 4H), 7.09-7.02 (m, 3H), 6.97-6.93 (m, 2H), 6.31 (d, J=2.0 Hz, 1H), 6.19 (d, J=2.0 Hz, 1H), 4.44 (d, J=14.0 Hz, 1H), 3.99-3.95 (m, 1H), 3.84 (s, 3H), 3.82 (s, 3H), 2.78 (s, 6H). MS: m/z calculated for $[C_{29}H_{29}N_3O_8S+H]^+$ 580.167, found 580.142.

(1R,2R,3S,3aR,8bS)-3a-(4-chlorophenyl)-N—(N,N-dimethylsulfamoyl)-1,8b-dihydroxy-6,8-dimethoxy-3-phenyl-2,3,3a,8b-tetrahydro-1H-cyclopenta[b]benzofuran-2-carboxamide (ZW-12-31)

ZW-12-31

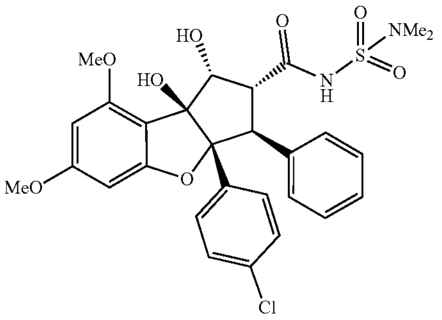

$^1$H NMR (500 MHZ, $CD_3OD$) δ 7.21-7.16 (m, 2H), 7.08-7.02 (m, 5H), 6.94-6.90 (m, 2H), 6.30 (d, J=2.0 Hz, 1H), 6.19 (d, J=2.0 Hz, 1H), 4.87 (s, 1H), 4.33 (d, J=14.0 Hz, 1H), 3.91 (dd, J=14.2, 6.3 Hz, 1H), 3.85 (s, 3H), 3.82 (s, 3H), 2.77 (s, 6H). MS: m/z calculated for $[C_{28}H_{29}ClN_2O_8S+H]^+$ 589.133, found 589.093.

(1R,2R,3S,3aR,8bS)-3a-(4-bromophenyl)-1,8b-dihydroxy-N—(N-isopropyl-N-methylsulfamoyl)-6,8-dimethoxy-3-phenyl-2, 3,3a,8b-tetrahydro-1H-cyclopenta[b]benzofuran-2-carboxamide (ZW-12-34)

ZW-12-34

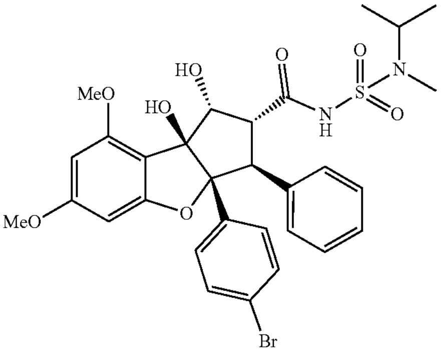

$^1$H NMR (500 MHZ, $CD_3OD$) δ 7.24-7.20 (m, 2H), 7.15-7.12 (m, 2H), 7.07-7.02 (m, 3H), 6.93-6.90 (m, 2H), 6.30 (d, J=2.0 Hz, 1H), 6.19 (d, J=2.0 Hz, 1H), 4.85 (d, J=6.3 Hz, 1H), 4.34 (d, J=14.1 Hz, 1H), 4.11-4.03 (m, 1H), 3.91-3.89 (m, 1H), 3.85 (s, 3H), 3.83 (s, 3H), 2.69 (s, 3H), 1.00-0.95 (m, 6H). MS: m/z calculated for $[C_{30}H_{33}BrN_2O_8S+H]^+$ 661.114, found 661.105.

(1R,2R,3S,3aR,8bS)-3a-(4-bromophenyl)-N—(N,N-diethylsulfamoyl)-1,8b-dihydroxy-6,8-dimethoxy-3-phenyl-2,3,3a,8b-tetrahydro-1H-cyclopenta[b]benzofuran-2-carboxamide (ZW-12-35)

ZW-12-35

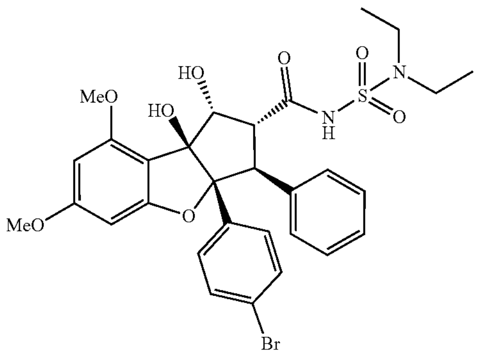

$^1$H NMR (500 MHZ, $CD_3OD$) δ 7.21-7.12 (m, 4H), 7.04 (d, J=5.2 Hz, 3H), 6.72 (d, J=6.1 Hz, 2H), 6.27 (d, J=2.0 Hz, 1H), 6.16 (d, J=2.0 Hz, 1H), 4.76 (d, J=5.4 Hz, 1H), 4.38 (d, J=14.1 Hz, 1H), 3.83 (s, 3H), 3.82 (s, 3H), 3.22-3.13 (m, 4H), 1.05 (t, J=7.1 Hz, 6H). MS: m/z calculated for $[C_{30}H_{33}BrN_2O_8S+H]^+$ 661.114, found 661.105.

(1R,2R,3S,3aR,8bS)-3a-(4-bromophenyl)-1,8b-dihydroxy-6,8-dimethoxy-N-((3-methylazetidin-1-yl)sulfonyl)-3-phenyl-2,3,3a,8b-tetrahydro-1H-cyclopenta[b]benzofuran-2-carboxamide (ZW-12-36)

ZW-12-36

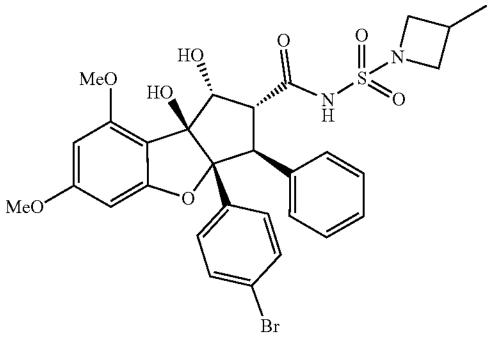

$^1$H NMR (500 MHZ, $CD_3OD$) δ 7.17 (d, J=6.0 Hz, 2H), 7.12 (d, J=7.2 Hz, 2H), 7.06-6.97 (m, 3H), 6.80 (d, J=6.4 Hz, 2H), 6.27 (d, J=2.0 Hz, 1H), 6.16 (d, J=2.0 Hz, 1H), 4.79 (d, J=5.3 Hz, 1H), 4.42 (d, J=14.2 Hz, 1H), 3.94 (dd, J=14.2, 5.4 Hz, 1H), 3.83 (s, 6H), 3.12-3.07 (m, 4H), 2.46-2.34 (m, 1H), 1.03 (d, J=6.8 Hz, 3H). MS: m/z calculated for $[C_{30}H_{31}BrN_2O_8S+H]^+$ 659.098, found 659.080.

(1R,2R,3S,3aR,8bS)-3a-(4-bromophenyl)-1,8b-dihydroxy-6,8-dimethoxy-3-phenyl-N-(pyrrolidin-1-ylsulfonyl)-2,3,3a,8b-tetrahydro-1H-cyclopenta[b]benzofuran-2-carboxamide (ZW-12-37)

ZW-12-37

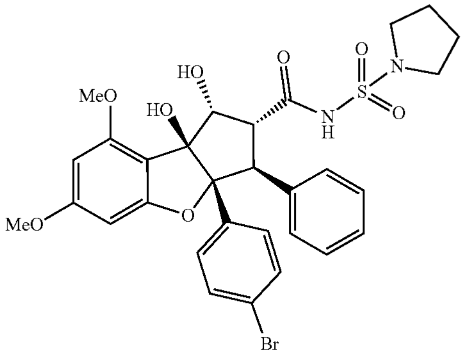

$^1$H NMR (500 MHZ, $CD_3OD$) δ 7.20-7.14 (m, 4H), 7.05 (d, J=5.3 Hz, 3H), 6.73 (d, J=7.1 Hz, 2H), 6.27 (d, J=2.0 Hz, 1H), 6.16 (d, J=2.0 Hz, 1H), 4.77 (d, J=5.5 Hz, 1H), 4.38 (d, J=14.2 Hz, 1H), 3.89 (dd, J=14.2, 5.5 Hz, 1H), 3.83 (s, 3H), 3.82 (s, 3H), 3.27-3.22 (m, 4H), 1.66-1.60 (m, 4H). MS: m/z calculated for $[C_{30}H_{31}BrN_2O_8S+H]^+$ 659.098, found 659.120.

(1R,2R,3S,3aR,8bS)-3a-(4-bromophenyl)-1,8b-dihydroxy-6,8-dimethoxy-N-(morpholinosulfonyl)-3-phenyl-2,3,3a,8b-tetrahydro-1H-cyclopenta[b]benzofuran-2-carboxamide (ZW-12-38)

ZW-12-38

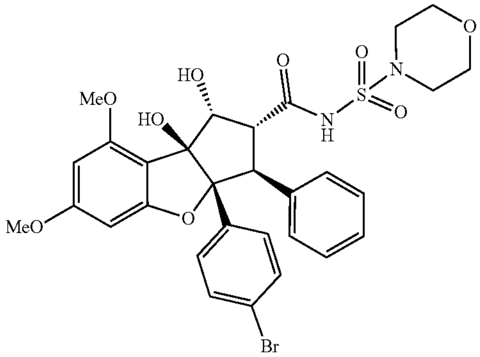

$^1$H NMR (500 MHZ, $CD_3OD$) δ 7.16 (d, J=2.6 Hz, 3H), 7.12 (d, J=7.1 Hz, 2H), 7.04 (t, J-7.5 Hz, 2H), 6.75 (d, J=6.2 Hz, 2H), 6.26 (d, J=2.0 Hz, 1H), 6.15 (d, J=2.0 Hz, 1H), 4.74 (d, J=5.2 Hz, 1H), 4.39 (d, J=14.2 Hz, 1H), 3.88 (dd, J=14.2, 5.2 Hz, 1H), 3.82 (s, 6H), 3.57-3.53 (m, 4H), 3.09-3.00 (m, 4H). MS: m/z calculated for $[C_{30}H_{31}BrN_2O_9S+H]^+$ 675.093, found 675.118.

TABLE 7

| compound | CSC EC$_{50}$ (μM) | CSC Max. observed efficacy (% dead cells) | Non-CSC EC$_{50}$ (μM) | Non-CSC Max. observed efficacy (% dead cells) |
|---|---|---|---|---|
| BUCMD747 (rac) | 0.453 | 89 | nd | 27 |
| BUCMD790 (—) | 0.045 | 93 | nd | 26 |
| ZW-12-29 | 5.63 | 57 | nd | 26 |
| ZW-12-30 | 0.632 | 94 | nd | 21 |
| ZW-12-31 | 0.693 | 72 | nd | 25 |
| ZW-12-34 | 1.854 | 79 | nd | 18 |
| ZW-12-35 | 1.175 | 92 | nd | 16 |
| ZW-12-36 | 0.804 | 96 | nd | 11 |
| ZW-12-37 | 0.7 | 95 | 0.401 | 25 |
| ZW-12-38 | 0.7 | 95 | 0.463 | 19 |

All patents and other publications identified are expressly incorporated herein by reference for the purpose of describing and disclosing, for example, the methodologies described in such publications that might be used in connection with the present disclosure. These publications are provided solely for their disclosure prior to the filing date of the present application. Nothing in this regard should be construed as an admission that the inventors are not entitled to antedate such disclosure by virtue of prior disclosure or for any other reason. All statements as to the date or representation as to the contents of these documents are based on the information available to the applicants and do not constitute any admission as to the correctness of the dates or contents of these documents.

What is claimed is:

1. A compound of Formula (I):

(Formula I)

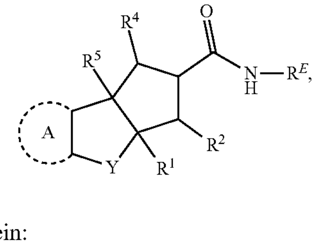

wherein:

Ring A is aryl or heteroaryl;

Y is O, S, $NR^{YA}$, $CR^{YA}R^{YB}$, $C{=}CR^{YA}R^{YB}$, SO or $SO_2$, where $R^{YA}$ and $R^{YB}$ are independently aryl, heteroaryl, cycloalkyl, heterocyclyl, H, halogen, cyano (CN), alkyl, haloalkyl, alkenyl, alkynyl, $OR^A$, $NR^AR^B$, —$C(O)R^A$, $C(O)NHR^A$, $C(O)NR^AR^B$, C(O)[alkylene]$NHR^A$, C(O)[alkylene]$NR^AR^B$, $CO_2R^A$, $C(S)NHR^A$, $C(S)NR^AR^B$, $SR^A$, $S(O)R^A$, $SO_2R^A$, $SO_2NHR^A$, $SO_2NR^AR^B$, $NHC(O)R^A$, $NR^AC(O)R^B$, $NHC(O)NHR^A$, $NHC(O)NR^AR^B$, $NR^AC(O)NHR^B$, $NR^AC(O)NR^BR^C$, $P(O)(OH)(OR^A)$, or $P(O)(OR^A)(OR^B)$;

$R^1$ is aryl, heteroaryl, cycloalkyl, heterocyclyl, H, halogen, CN, alkyl, haloalkyl, alkenyl, alkynyl, $OR^A$, $NR^AR^B$, —$C(O)R^A$, $C(O)NHR^A$, $C(O)NR^AR^B$, C(O)[alkylene]$NHR^A$, C(O)[alkylene]$NR^AR^B$, $CO_2R^A$, $C(S)NHR^A$, $C(S)NR^AR^B$, $SR^A$, $S(O)R^A$, $SO_2R^A$, $SO_2NHR^A$, $SO_2NR^AR^B$, $NHC(O)R^A$, $NR^AC(O)R^B$, $NHC(O)NHR^A$, $NHC(O)NR^AR^B$, $NR^AC(O)NHR^B$, $NR^AC(O)NR^BR^C$, $P(O)(OH)(OR^A)$, or $P(O)(OR^A)(OR^B)$;

$R^2$ is aryl, heteroaryl, alkyl, alkenyl, alkynyl, cycloalkyl, heterocyclyl, H, halogen, CN, haloalkyl, $OR^A$, $NR^AR^B$, —$C(O)R^A$, $C(O)NHR^A$, $C(O)NR^AR^B$, C(O)[alkylene]$NHR^A$, C(O)[alkylene]$NR^AR^B$, $CO_2R^A$, $C(S)NHR^A$, $C(S)NR^AR^B$, $SR^A$, $S(O)R^A$, $SO_2R^A$, $SO_2NHR^A$, $SO_2NR^AR^B$, $NHC(O)R^A$, $NR^AC(O)R^B$, $NHC(O)NHR^A$, $NHC(O)NR^AR^B$, $NR^AC(O)NHR^B$, $NR^AC(O)NR^BR^C$, $P(O)(OH)(OR^A)$, or $P(O)(OR^A)(OR^B)$;

$R^E$ is —$SO_2$—$R^3$ or CN;

$R^3$ is $NR^{N1}R^{N2}$, alkyl, alkenyl, alkynyl, aryl, heteroaryl, cycloalkyl, heterocyclyl, H, halogen, CN, haloalkyl, $OR^A$, —$C(O)R^A$, $C(O)NHR^A$, $C(O)NR^AR^B$, C(O)[alkylene]$NHR^A$, C(O)[alkylene]$NR^AR^B$, $CO_2R^A$, $C(S)NHR^A$, $C(S)NR^AR^B$, $SR^A$, $S(O)R^A$, $SO_2R^A$, $SO_2NHR^A$, $SO_2NR^AR^B$, $NHC(O)R^A$, $NR^AC(O)R^B$, $NHC(O)NHR^A$, $NHC(O)NR^AR^B$, $NR^AC(O)NHR^B$, $NR^AC(O)NR^BR^C$, $P(O)(OH)(OR^A)$, or $P(O)(OR^A)(OR^B)$; wherein $R^{N1}$ and $R^{N2}$ are independently H, alkyl, alkenyl, cycloalkyl, heterocyclyl, H, halogen, CN, haloalkyl, $OR^A$, —$C(O)R^A$, $C(O)NHR^A$, $C(O)NR^AR^B$, C(O)[alkylene]$NHR^A$, C(O)[alkylene]$NR^AR^B$, $CO_2R^A$, $C(S)NHR^A$, $C(S)NR^AR^B$, $SR^A$, $S(O)R^A$, $SO_2R^A$, $SO_2NHR^A$, $SO_2NR^AR^B$, $NHC(O)R^A$, $NR^AC(O)R^B$, $NHC(O)NHR^A$, $NHC(O)NR^AR^B$, $NR^AC(O)NHR^B$, $NR^AC(O)NR^BR^C$, $P(O)(OH)(OR^A)$, or $P(O)(OR^A)(OR^B)$; or $R^{N1}$ and $R^{N2}$ together with the nitrogen they are attached to form a heterocyclyl or heteroaryl;

$R^4$ is $OR^{4A}$, H, halogen, CN, alkyl, haloalkyl, alkenyl, alkynyl, aryl, heteroaryl, cycloalkyl, heterocyclyl, $NR^AR^B$, —$C(O)R^A$, $C(O)NHR^A$, $C(O)NR^AR^B$, C(O)[alkylene]$NHR^A$, C(O)[alkylene]$NR^AR^B$, $CO_2R^A$, $C(S)NHR^A$, $C(S)NR^AR^B$, $SR^A$, $S(O)R^A$, $SO_2R^A$, $SO_2NHR^A$, $SO_2NR^AR^B$, $NHC(O)R^A$, $NR^AC(O)R^B$, $NHC(O)NHR^A$, $NHC(O)NR^AR^B$, $NR^AC(O)NHR^B$, $NR^AC(O)NR^BR^C$, $P(O)(OH)(OR^A)$, or $P(O)(OR^A)(OR^B)$;

$R^5$ is $OR^{5A}$, H, halogen, CN, alkyl, haloalkyl, alkenyl, alkynyl, aryl, heteroaryl, cycloalkyl, heterocyclyl, $NR^AR^B$, —$C(O)R^A$, $C(O)NHR^A$, $C(O)NR^AR^B$, C(O)[alkylene]$NHR^A$, C(O)[alkylene]$NR^AR^B$, $CO_2R^A$, $C(S)NHR^A$, $C(S)NR^AR^B$, $SR^A$, $S(O)R^A$, $SO_2R^A$, $SO_2NHR^A$, $SO_2NR^AR^B$, $NHC(O)R^A$, $NR^AC(O)R^B$, $NHC(O)NHR^A$, $NHC(O)NR^AR^B$, $NR^AC(O)NHR^B$, $NR^AC(O)NR^BR^C$, $P(O)(OH)(OR^A)$, or $P(O)(OR^A)(OR^B)$; or $R^5$ together with the carbon $R^4$ is attached to forms a heterocyclyl;

and $R^A$, $R^B$, $R^{4A}$ and $R^{5A}$ are independently H, substituted or unsubstituted ($C_1$-$C_8$) alkyl, ($C_1$-$C_8$) haloalkyl, ($C_1$-$C_8$) branched alkyl, ($C_1$-$C_8$) linear alkyl, ($C_1$-$C_8$) cycloalkyl, ($C_1$-$C_8$) aryl or phenyl, ($C_1$-$C_8$) alkenyl, or ($C_1$-$C_8$)alkynyl;

or a solvate, stereoisomer, or pharmaceutical acceptable salt thereof, and wherein any alkyl, alkenyl, cycloalkyl, heterocyclyl, heteroaryl or aryl is optionally substituted with 1, 2, 3, 4 or more substituents selected independently from the group consisting of heterocycle, OH, oxo (=O), CN, SH, $SO_2NH_2$, $SO_2$($C_1$-$C_4$)alkyl, $SO_2NH$($C_1$-$C_4$)alkyl, halogen, $NH_2$, NH($C_1$-$C_4$)alkyl, N[($C_1$-$C_4$)alkyl]$_2$, C(O)$NH_2$, COOH, COOMe, acetyl, ($C_1$-$C_8$)alkyl, O($C_1$-$C_8$)alkyl, O($C_1$-$C_8$)haloalkyl, ($C_2$-$C_8$)alkenyl, ($C_2$-$C_8$)alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ and $CH_2$-aryl-alkoxy, where "m" and "p" are independently 1, 2, 3, 4, 5 or 6.

2. The compound of claim 1, wherein $R^1$ is a 3-12 membered heteroaryl comprising 1, 2 or 3 independently selected heteroatoms, or $R^1$ is a 3-12 membered aryl, wherein the 3-12 membered heteroaryl or 3-12 membered aryl is optionally substituted with 1, 2, 3, 4 or more substituents selected independently from the group consisting of OH, oxo (=O), CN, SH, $SO_2NH_2$, $SO_2$($C_1$-$C_4$)alkyl, $SO_2NH$($C_1$-$C_4$)alkyl, halogen, $NH_2$, NH($C_1$-$C_4$)alkyl, N[($C_1$-$C_4$)alkyl]$_2$, C(O)$NH_2$, COOH, COOMe, acetyl, ($C_1$-$C_8$)alkyl, O($C_1$-$C_8$)alkyl, —O-heterocyclyl, heterocyclyl, O($C_1$-$C_8$)haloalkyl, ($C_2$-$C_8$)alkenyl, ($C_2$-$C_8$)alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—[CH(OH)]

$_m$—$(CH_2)_p$—OH, $CH_2$—[CH(OH)]$_m$—$(CH_2)_p$—$NH_2$ and $CH_2$-aryl-alkoxy, where "m" and "p" are independently 1, 2, 3, 4, 5 or 6.

3. The compound of claim 2, wherein $R^1$ is

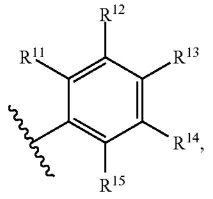

wherein $R^{11}$, $R^{12}$, $R^{13}$, $R^{14}$ and $R^{15}$ are independently H, OH, CN, SH, $SO_2NH_2$, $SO_2(C_1\text{-}C_4)$alkyl, $SO_2NH(C_1\text{-}C_4)$ alkyl, halogen, $NH_2$, $NH(C_1\text{-}C_4)$alkyl, $N[(C_1\text{-}C_4)alkyl]_2$, $C(O)NH_2$, COOH, COOMe, acetyl, $(C_1\text{-}C_8)$alkyl, $O(C_1\text{-}C_8)$ alkyl, —O-heterocyclyl, heterocyclyl, $O(C_1\text{-}C_8)$haloalkyl, $(C_2\text{-}C_8)$alkenyl, $(C_2\text{-}C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—[CH(OH)]$_m$—$(CH_2)_p$—OH, $CH_2$—[CH(OH)]$_m$—$(CH_2)_p$—$NH_2$ or $CH_2$-aryl-alkoxy, where "m" and "p" are independently 1, 2, 3, 4, 5 or 6; and optionally any two vicinal $R^{11}$, $R^{12}$, $R^{13}$, $R^{14}$, and $R^{15}$ together with the carbons they are attached to can form a 3-12 membered aryl, 3-12 membered heteroaryl, 3-12 membered cycloalkyl or 3-12 membered heterocyclyl, each of which can be optionally substituted with 1, 2, 3, 4 or more substituents selected independently from the group consisting of OH, oxo (═O), CN, SH, $SO_2NH_2$, $SO_2(C_1\text{-}C_4)$alkyl, $SO_2NH(C_1\text{-}C_4)$alkyl, halogen, $NH_2$, $NH(C_1\text{-}C_4)$alkyl, $N[(C_1\text{-}C_4)alkyl]_2$, C(O) $NH_2$, COOH, COOMe, acetyl, $(C_1\text{-}C_8)$alkyl, O $(C_1\text{-}C_8)$ alkyl, $O(C_1\text{-}C_8)$haloalkyl, $(C_2\text{-}C_8)$alkenyl, $(C_2\text{-}C_8)$ alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—[CH(OH)]$_m$—$(CH_2)_p$—OH, $CH_2$—[CH(OH)]$_m$—$(CH_2)_p$—$NH_2$ and $CH_2$-aryl-alkoxy, where "m" and "p" are independently 1, 2, 3, 4, 5 or 6.

4. The compound of claim 3, wherein $R^1$ is phenyl, 4-bromophenyl, 4-cyanophenyl, 4-methoxyphenyl, 4-fluorophenyl, 4-chlorophenyl, 4-iodophenyl, 4-trifluoromethylphenyl, 3-trifluoromethylphenyl, 4-trifluoromethylphenyl, 4-cyanophenyl, benzothiazol-6-yl, benzothiazole-5-yl, 2-benzoxazolinon-6-yl, 2-benzoxazolinon-5-yl, 4-ethynylphenyl, 3,4,5-trimethylphenyl, 5-carboxythiophen-2-yl, 5-carboxythiophen-3-yl, 5-carboxythiophen-4-yl, 4-difluoromethoxyphenyl, 4-(azetidin-3-yl)phenyl, 4-(2-hydroxymethylazetidin-3-yl)phenyl, 4-(2-(2-hydroxyethyl) azetidine-3-yl)phenyl, 4-(azetidine-3-ylmethyl)phenyl, 4-(azetidine-3-yl-hydroxy)phenyl, 4-(pyrrolidine-3-yl)phenyl, 4-piperidin-4-yl)phenyl, or benzimidazol-6-yl, optionally $R^1$-bromophenyl, 4-methoxyphenyl, 4-cyanophenyl, 4-trifluoromethylphenyl, 4-(azetidin-3-yl)phenyl, 4-(2-hydroxymethylazetidin-3-yl)phenyl, 4-(2-(2-hydroxyethyl) azetidine-3-yl)phenyl, 4-(azetidine-3-ylmethyl)phenyl, 4-(azetidine-3-yl-hydroxy)phenyl, 4-(pyrrolidine-3-yl)phenyl, 4-piperidin-4-yl)phenyl, or benzimidazol-6-yl.

5. The compound of claim 1, wherein $R^2$ is a 3-12 membered heteroaryl comprising 1, 2 or 3 independently selected heteroatoms, or $R^2$ is a 3-12 membered aryl, or $R^2$ is a 3-12 membered heterocyclyl comprising 1, 2 or 3 independently selected heteroatoms, 3-12 membered cycloalkyl, $(C_1\text{-}C_8)$alkyl, $(C_1\text{-}C_8)$haloalkyl, $(C_2\text{-}C_8)$alkenyl, or $(C_2\text{-}C_8)$alkynyl, and wherein the 3-12 membered heteroaryl, 3-12 membered aryl, 3-12 membered heterocyclyl, 3-12 membered cycloalkyl, $(C_1\text{-}C_8)$alkyl, $(C_1\text{-}C_8)$haloalkyl, $(C_2\text{-}C_8)$alkenyl, or $(C_2\text{-}C_8)$alkynyl is optionally substituted with 1, 2, 3, 4 or more substituents selected independently from the group consisting of OH, oxo (═O), CN, SH, $SO_2NH_2$, $SO_2(C_1\text{-}C_4)$alkyl, $SO_2NH(C_1\text{-}C_4)$alkyl, halogen, $NH_2$, $NH(C_1\text{-}C_4)$alkyl, $N[(C_1\text{-}C_4)alkyl]_2$, $C(O)NH_2$, COOH, COOMe, acetyl, $(C_1\text{-}C_8)$alkyl, $O(C_1\text{-}C_8)$alkyl, $O(C_1\text{-}C_8)$haloalkyl, $(C_2\text{-}C_8)$alkenyl, $(C_2\text{-}C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—[CH(OH)]$_m$—$(CH_2)_p$—OH, $CH_2$—[CH(OH)]$_m$—$(CH_2)_p$—$NH_2$ and $CH_2$-aryl-alkoxy, where "m" and "p" are independently 1, 2, 3, 4, 5 or 6.

6. The compound of claim 5, wherein $R^2$ is

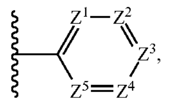

where $Z^1$, $Z^2$, $Z^3$, $Z^4$ and $Z^5$ are independently $CR^{21}$ or N, where each $R^{21}$ is independently H, OH, CN, SH, $SO_2NH_2$, $SO_2(C_1\text{-}C_4)$alkyl, $SO_2NH(C_1\text{-}C_4)$alkyl, halogen, $NH_2$, $NH(C_1\text{-}C_4)$alkyl, $N[(C_1\text{-}C_4)alkyl]_2$, $C(O)NH_2$, COOH, COOMe, acetyl, $(C_1\text{-}C_8)$alkyl, $O(C_1\text{-}C_8)$alkyl, $O(C_1\text{-}C_8)$haloalkyl, $(C_2\text{-}C_8)$alkenyl, $(C_2\text{-}C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—[CH(OH)]$_m$—$(CH_2)_p$—OH, $CH_2$—[CH(OH)]$_m$—$(CH_2)_p$—$NH_2$ or $CH_2$-aryl-alkoxy, where "m" and "p" are independently 1, 2, 3, 4, 5 or 6;

and optionally any two vicinal $R^{11}$, $R^{12}$, $R^{13}$, $R^{14}$, and $R^{15}$ together with the carbons they are attached to can form a 5-8 membered aryl, heteroaryl, cycloalkyl or heterocyclyl, each of which can be optionally substituted with 1, 2, 3, 4 or more substituents selected independently from OH, oxo (═O), CN, SH, $SO_2NH_2$, $SO_2(C_1\text{-}C_4)$ alkyl, $SO_2NH(C_1\text{-}C_4)$alkyl, halogen, $NH_2$, $NH(C_1\text{-}C_4)$ alkyl, $N[(C_1\text{-}C_4)alkyl]_2$, $C(O)NH_2$, COOH, COOMe, acetyl, $(C_1\text{-}C_8)$alkyl, $O(C_1\text{-}C_8)$alkyl, $O(C_1\text{-}C_8)$haloalkyl, $(C_2\text{-}C_8)$alkenyl, $(C_2\text{-}C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—[CH(OH)]$_m$—$(CH_2)_p$—OH, $CH_2$—[CH(OH)]$_m$—$(CH_2)_p$—$NH_2$ or $CH_2$-aryl-alkoxy, where "m" and "p" are independently 1, 2, 3, 4, 5 or 6, and provided that only 0, 1, 2, 3 or 4 of $Z^1$, $Z^2$, $Z^3$, $Z^4$ and $Z^5$ are N.

7. The compound of claim 1, wherein $R^2$ is $(C_1\text{-}C_8)$alkyl, $(C_1\text{-}C_8)$haloalkyl, $(C_2\text{-}C_8)$alkenyl), or $(C_2\text{-}C_8)$alkynyl, and wherein the $(C_1\text{-}C_8)$alkyl, $(C_1\text{-}C_8)$haloalkyl, $(C_2\text{-}C_8)$alkenyl), or $(C_2\text{-}C_8)$alkynyl is optionally substituted with 1, 2, 3, 4 or more substituents selected independently from the group consisting of heterocycle, OH, oxo (═O), CN, SH, $SO_2NH_2$, $SO_2(C_1\text{-}C_4)$alkyl, $SO_2NH(C_1\text{-}C_4)$alkyl, halogen, $NH_2$, $NH(C_1\text{-}C_4)$alkyl, $N[(C_1\text{-}C_4)alkyl]_2$, $C(O)NH_2$, COOH, COOMe, acetyl, $(C_1\text{-}C_8)$alkyl, $O(C_1\text{-}C_5)$alkyl, $O(C_1\text{-}C_8)$haloalkyl, $(C_2\text{-}C_8)$alkenyl, $(C_2\text{-}C_8)$alkynyl, haloalkyl, thioalkyl, cyanomethylene, alkylaminyl, $NH_2$—C(O)- alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ and $CH_2$-aryl-alkoxy, where "m" and "p" are independently 1, 2, 3, 4, 5 or 6.

8. The compound of claim 7, wherein $R^2$ is methyl, ethyl, propyl, propenyl, propynyl, isopropyl, butyl, isobutenyl, butan-2-yl, 2-methylpropyl, tert-butyl, pentyl, 2-methylbutan-2-yl, pentan-2-yl, pentan-3-yl, 3-methylbutan-2-yl, each of which can be optionally substituted with 1, 2, 3, 4 or more substituents selected independently from the group consisting of heterocycle, H, oxo (=O), CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)alkyl]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ and $CH_2$-aryl-alkoxy, where "m" and "p" are independently 1, 2, 3, 4, 5 or 6.

9. The compound of claim 7, wherein $R^2$ is —$CH_2$L, wherein L is alkoxy, alkylamino, or heterocycle.

10. The compound of claim 1, wherein $R^2$ is phenyl, 4-trifluoromethylphenyl, 2-bromo-5-fluoropheyl, 2-chloro-6-fluorohenyl, 3,5-dichlorophenyl, pentafluorophenyl, 2-fluoro-3-trifluoromethyl-5-methoxyphenyl, 4-trifluoromethylphenyl, 2-pyridinyl, 3-pyridinyl, 4-pyrimidinyl, methyl, ethyl, propyl, propenyl, propynyl, isopropyl, butyl, isobutenyl, butan-2-yl, 2-methylpropyl, tert-butyl, pentyl, 2-methylbutan-2-yl, pentan-2-yl, pentan-3-yl, 3-methylbutan-2-yl, 1,4-diazinylmethyl, N-methyl-1,4-diazinzylmethyl or N-methyl-morpholinylmethyl.

11. The compound of claim 1, wherein $R^E$ is —$SO_2$—$R^3$ and the compound is of Formula (Ia):

(Formula Ia)

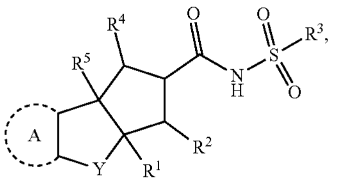

or a solvate, stereoisomer, or pharmaceutical acceptable salt thereof.

12. The compound of claim 11, wherein $R^{N1}$ and $R^{N2}$ are independently H, $(C_1-C_8)$alkyl, $(C_1-C_8)$haloalkyl, $(C_2-C_8)$ alkenyl), or $(C_2-C_8)$alkynyl; or $R^{N1}$ and $R^{N2}$ together with the nitrogen they are attached to form a 3-12 membered heterocyclyl, and wherein the $(C_1-C_8)$alkyl, $(C_1-C_8)$haloalkyl, $(C_2-C_8)$alkenyl), $(C_2-C_8)$alkynyl, or 3-12 membered heterocyclyl is optionally substituted with 1, 2, 3, 4 or more substituents selected independently from the group consisting of OH, oxo (=O), CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)alkyl]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ and $CH_2$-aryl-alkoxy, where "m" and "p" are independently 1, 2, 3, 4, 5 or 6.

13. The compound of claim 11, wherein $R^{N1}$ and $R^{N2}$ together with the nitrogen they are attached to attached to form 3-12 membered heterocycle comprising 1, 2, or 3 heteroatoms selected independently from the group consisting of O, S, and N, or $R^{N1}$ and $R^{N2}$ together with the nitrogen they are attached to attached to form a 3-12 membered heteroaryl comprising 1, 2, or 3 heteroatoms selected independently from the group consisting of O, S, and N, and wherein the 3-12 membered heteroaryl or 3-12 membered aryl is optionally substituted with 1, 2, 3, 4 or more substituents selected independently from OH, oxo (=O), CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)alkyl]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy, where "m" and "p" are independently 1, 2, 3, 4, 5 or 6.

14. The compound of claim 11, wherein: (i) $R^3$ is azirdinyl, azetidinyl, piperdinyl, or morpholinyl, each of which can be optionally substituted with 1, 2, 3, 4 or more substituents selected independently from OH, oxo (=O), CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)alkyl]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy, where "m" and "p" are independently 1, 2, 3, 4, 5 or 6; or (ii) $R^3$ is $(C_1-C_8)$alkyl, $(C_1-C_8)$haloalkyl, $(C_2-C_8)$alkenyl, or $(C_2-C_8)$alkynyl, each of which can be optionally substituted with 1, 2, 3, 4 or more substituents selected independently from OH, oxo (=O), CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)alkyl]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy, where "m" and "p" are independently 1, 2, 3, 4, 5 or 6.

15. The compound of claim 11, wherein $R^3$ is N-isopropyl-N-methylamino, diethylamino, N-2-hydoxyethyl-N-methylamino, 2-hydroxyethylamino, 3-hydroxypropylamino, 2-hydroxy-2,2-dimethylamino, 2-dimethylaminoethylamino, 3-dimethylaminopropylamino, di(2-dimethylaminoethyl)amino, azetidinyl, 4-methylazetidinyl, 4-hydroxyazetidinyl, pyrrolidinyl, 2-(trifluoromethyl)pyrrolidinyl, morpholinyl, piperidinyl or 4-hydroxypiperdinyl.

16. The compound of claim 1, wherein $R^4$ is $OR^{4A}$, halogen, CN, alkyl, alkenyl, alkynyl, or haloalkyl, and wherein alkyl, alkenyl, or alkynyl, is optionally substituted with 1, 2, 3, 4 or more substituents selected independently from OH, oxo (=O), CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)alkyl]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy, where "m" and "p" are independently 1, 2, 3, 4, 5 or 6.

17. The compound of claim 16, wherein $R^4$ is $OR^{4A}$, halogen or CN, and where $R^{4A}$ is H, $(C_1$-$C_8)$alkyl, $(C_1$-$C_8)$haloalkyl, $(C_2$-$C_8)$alkenyl, or $(C_2$-$C_8)$alkynyl.

18. The compound of claim 1, wherein $R^5$ is $OR^{5A}$, halogen, CN, alkyl, alkenyl, alknyl, or haloalkyl, and wherein alkyl, alkenyl, or alkynyl, is optionally substituted with 1, 2, 3, 4 or more substituents selected independently from OH, oxo (═O), CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)alkyl]_2$, $C(O)NH_2$, COOH, COOMe, acetyl, $(C_1$-$C_8)$alkyl, $O(C_1$-$C_8)$alkyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy, where "m" and "p" are independently 1, 2, 3, 4, 5 or 6.

19. The compound of claim 18, wherein $R^5$ is $OR^{5A}$, halogen or CN, and where $R^{5A}$ is H, $(C_1$-$C_8)$alkyl, $(C_1$-$C_8)$haloalkyl, $(C_2$-$C_8)$alkenyl, or $(C_2$-$C_8)$alkynyl.

20. The compound of claim 1, wherein Ring A is a 3-12 membered aryl, 3-12 membered heteroaryl, 3-12 membered cycloalkyl, or 3-12 membered heterocycle, each of which can be optionally substituted with 1, 2, 3, 4 or more substituents selected independently from OH, oxo (═O), CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)alkyl]_2$, $C(O)NH_2$, COOH, COOMe, acetyl, $(C_1$-$C_8)$alkyl, $O(C_1$-$C_8)$alkyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy, where "m" and "p" are independently 1, 2, 3, 4, 5 or 6.

21. The compound of claim 1, wherein: (i) Ring A has the structure

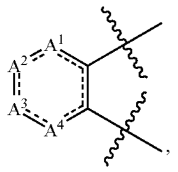

where $A^1$ is N, C(O), NH or $CR^{120}$; $A^2$ is N, C(O), NH or $CR^{121}$; $A^3$ is N, C(O), NH or $CR^{122}$; $A^4$ is N, C(O), NH or $CR^{123}$, $R^{120}$, $R^{121}$, $R^{122}$ and $R^{123}$ are independently are H, halogen, CN, $C_1$-$C_8$(alkyl), $(C_1$-$C_8)$haloalkyl, $(C_2$-$C_8)$alkenyl, $(C_2$-$C_8)$alkynyl, $OR^O$, $NR^OR^P$, $[(C_1$-$C_8)alkylene]OR^O$, $[(C_1$-$C_8)alkylene]NHR^A$, $[(C_1$-$C_8)alkylene]NR^OR^P$, $C(O)R^O$, $C(O)NHR^O$, $C(O)NR^OR^P$, $C(O)[(C_1$-$C_8)alkylene]NHR^O$, $C(O)[(C_1$-$C_8)alkylene]NR^OR^P$, $CO_2R^O$, $C(S)NHR^O$, $C(S)NR^OR^P$, $SR^O$, $S(O)R^O$, $SO_2R^O$, $SO_2NHR^O$, $SO_2NR^OR^P$, $NHC(O)R^O$, $NR^OC(O)R^P$, $NHC(O)NHR^O$, $NHC(O)NR^OR^P$, $NR^OC(O)NHR^P$, $NR^OC(O)NR^PR^Q$, $P(O)(OH)(OR^O)$, $P(O)(OR^O)(OR^P)$, tosylate, aryl, heteroaryl, cycloalkyl or heterocyclyl, $R^O$, $R^P$ and $R^Q$ independently are H, —OH, aryl, $(C_1$-$C_8)$alkyl, $[(C_1$-$C_8)alkyl]aryl$ (C1-$C_5$) alkoxy, $(C_1$-$C_8)$haloalkyl, cycloalkyl, heterocyclyl, $[(C_1$-$C_8)alkylene]heterocyclyl$, $[(C_1$-$C_8)alkylene]aryl$ or heteroaryl; or $R^O$ and $R^P$ together with the nitrogen atom to which they are attached form a heterocyclyl ring; or (ii) Ring A has the structure

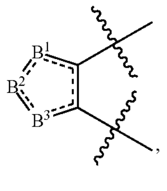

where any two of $B^1$, $B^2$ and $B^3$ are $CR^{130}$ and N and the remaining ring atom is $N(R^{131})$ or S, wherein $R^{130}$ is H, CN, halogen, $OR^R$, $SR^R$, $(C_1$-$C_8)$alkyl, C (O) $O(C_1$-$C_8)$alkyl, $C(O)(C_1$-$C_8)$alkyl, $SO_2(C_1$-$C_8)$alkyl, $SO_2NR^RR^S$, $C(O)NR^RR^S$, $NR^RR^S$ or $NR^RC(O)R^S$, and $R^{131}$ is H or $(C_1$-$C_8)$alkyl, $R^R$ and $R^S$, independently are H, —OH, aryl, $(C_1$-$C_8)$alkyl, $[(C_1$-$C_8)alkyl]aryl$ $(C_1$-$C_8)$alkoxy, $(C_1$-$C_8)$haloalkyl, cycloalkyl, heterocyclyl, $[(C_1$-$C_8)alkylene]heterocyclyl$, $[(C_1$-$C_8)alkylene]aryl$ or heteroaryl; or the $R^R$ and $R^S$ together with the nitrogen atom to which they are attached to form a heterocyclyl ring.

22. The compound of claim 21, wherein: (i) $A^1$ is $CR^{120}$; $A^2$ is $CR^{121}$; $A^3$ is $CR^{122}$; $A^4$ is $CR^{123}$; and $R^{120}$, $R^{121}$, $R^{122}$ and $^{123}$ independently are H or $OR^O$ and at least one of $R^{120}$, $R^{121}$, $R^{122}$ and $R^{123}$ are $OR^O$; (ii) $A^1CR^{120}$ where $R^{120}$ is methoxy, $A^3$ is methoxy is $CR^{122}$ where $R^{122}$ is methoxy, $A^2$ is $CR^{121}$ where $R^{121}$ is H, and $A^4$ is $CR^{123}$ where $R^{123}$ is H; (iii) $A^1$ is $CR^{120}$ where $R^{120}$ is a halide, $A^3$ is methoxy where is $CR^{122}$ where $R^{122}$ is methoxy, $A^2$ is N, and $A^4$ is $CR^{123}$ where $R^{123}$ is H, $A^1CR^{120}$ where $R^{120}$ is methoxy, $A^3$ is $CR^{122}$ where $R^{122}$ is methoxy, $A^2$ is N, and $A^4$ is $CR^{123}$ where $R^{123}$ is H; (iv) $A^1$ is N, $A^3$ is methoxy is $CR^{122}$ where $R^{122}$ is methoxy, $A^2$ is $CR^{121}$ where $R^{121}$ is H, and $A^4$ is $CR^{123}$ where $R^{123}$ is H; (v) $A^1$ is C(C═O) or NH, $A^4$ is C(C═O) or NH, $A^2$ is $CR^{121}$, and $A^3$ is $CR^{123}$; (vi) $A^1$ is C(C═O), $A^4$ is NH, $A^2$ is $CR^{121}$, and $A^3$ is $CR^{123}$; (vii) $A^1$ is C(C═O), $A^4$ is NH, $A^2$ is $CR^{121}$, and $A^3$ is $CR^{123}$ wherein $R^{123}$ is methoxy; (viii) $A^1$ is C(C═O), $A^4$ is N, and $A^3$ is $CR^{123}$ wherein $R^{123}$ is methoxy; (ix) $A^1$ is $CR^{120}$ where $R^{120}$ is H, $A^3$ is $CR^{122}$ where $R^{120}$ is H, $A^2$ is $CR^{121}$ and $A^4$ is $CR^{123}$; where at least one of $R^{121}$ or $R^{123}$ are $NR^OR^P$ and $R^{121}$ and $R^{123}$ together with the carbon to which they are attached for a heterocycle; (x) $A^1$ is $CR^{120}$ and $R^{120}$, $R^{121}$, $R^{122}$ and $R^{123}$ independently are H or $OR^O$ and at least one of $R^{120}$, $R^{121}$, $R^{122}$ and $R^{123}$ are $OR^O$; (xi) $B^1$ is N or S, $B^3$ is N or S, and $B^2$ is $CR^{130}$ wherein $R^{130}$ is a methoxy; (xii) $B^1$ is N, $B^3$ is S, and $B^2$ is $CR^{130}$ wherein $R^{130}$ is a methoxy; (xiii) $B^1$ is $CR^{130}$ where $R^{130}$ is H, $B^2$ is S or N, and $B^3$ is S or N; or (xiv) $B^1$ is $CR^{130}$ where $R^{130}$ is H, $B^2$ is S, and $B^3$ is N.

23. The compound of claim 1, wherein Ring A is:

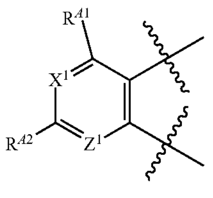

(i)

wherein $X^1$ is CH or N; $Z^1$ is CH or N; and $R^{A1}$ and $R^{A2}$ are selected independently from the group consisting of H, alkyl, alkoxy, alkylamino, acyloxy, fluorine, chlorine, bromine, $OCF_3$, and nitrile;

(ii)

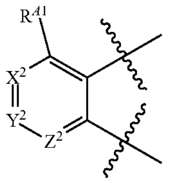

wherein $X^2$ is CH or N; $Y^2$ is CH or N; $Z^2$ is CH or N; and RAI is selected independently from the group consisting of H, alkyl, alkoxy, alkylamino, acyloxy, fluorine, chlorine, bromine, $OCF_3$, and nitrile;

(iii)

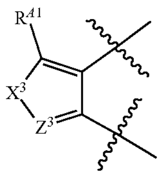

wherein $X^3$ is NH, O or S; $Z^3$ is CH or N; and $R^{A1}$ is selected independently from the group consisting of H, alkyl, alkoxy, alkylamino, acyloxy, fluorine, chlorine, bromine, $OCH_3$, and nitrile;

(iv)

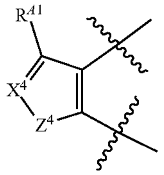

wherein $X^4$ is NH, O or S; $Z^4$ is CH or N; and $R^{A1}$ is selected independently from the group consisting of H, alkyl, alkoxy, alkylamino, acyloxy, fluorine, chlorine, bromine, $OCF_3$, and nitrile;

(v)

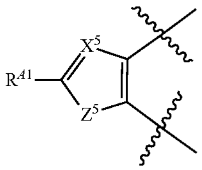

wherein $X^5$ is NH, O or S; $Z^5$ is CH or N; and $R^{A1}$ is selected independently from the group consisting of H, alkyl, alkoxy, alkylamino, acyloxy, fluorine, chlorine, bromine, $OCF_3$, and nitrile;

(vi)

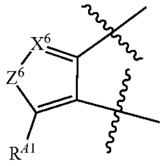

wherein $X^6$ is NH, O or S; $Z^6$ is CH or N; and $R^{A1}$ is selected independently from the group consisting of H, alkyl, alkoxy, alkylamino, acyloxy, fluorine, chlorine, bromine, $OCF_3$, and nitrile;

(vii)

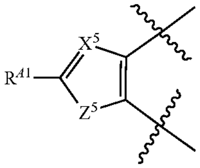

wherein $X^7$ is NH, O or S; $Z^7$ is CH or N; and $R^{A1}$ is selected independently from the group consisting of H, alkyl, alkoxy, alkylamino, acyloxy, fluorine, chlorine, bromine, $OCF_3$, and nitrile; or (viii)

(viii)

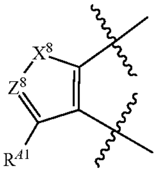

wherein $X^8$ is NH, O or S; $Z^8$ is CH or N; and $R^{A1}$ is selected independently from the group consisting of H, alkyl, alkoxy, alkylamino, acyloxy, fluorine, chlorine, bromine, $OCF_3$, and nitrile.

24. The compound of claim 23, wherein Ring A is

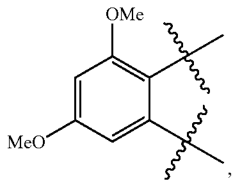
,
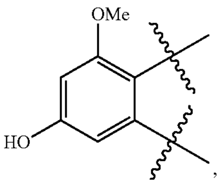
,
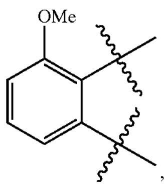
,
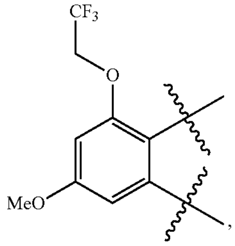
,

-continued

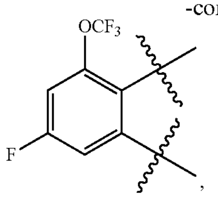

,

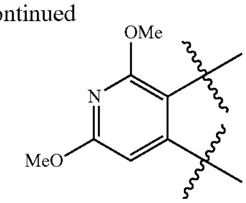

,

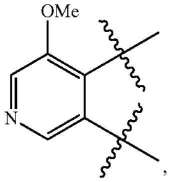

,

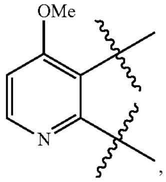

,

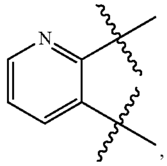

,

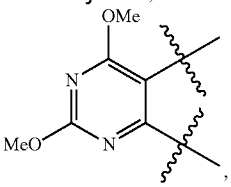

, or

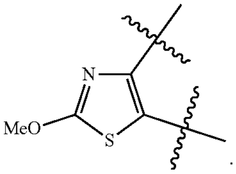

.

25. The compound of claim 1, wherein the compound is of structure:

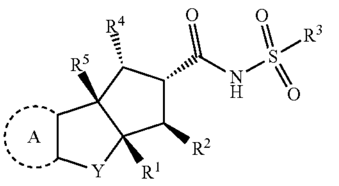

or

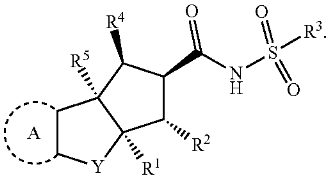

26. The compound of claim 1, wherein:

(i) the compound is of structure:

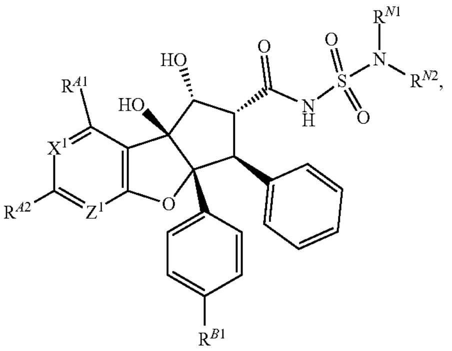

wherein: $X^1$ is CH or N; $Z^1$ is CH or N; $R^{A1}$ and $R^{A2}$ are independently H, alkyl, alkoxy, alkylamino, acyloxy, fluorine, chlorine, bromine, $OCF_3$, or nitrile; $R^{N1}$ and $R^{N2}$ are independently linear or branched alkyl or cyclic alkyl; $R^{B1}$ is methoxy, fluorine, bromine, chlorine, iodine, trifluoromethyl, nitrile, acetylene, $OCF_2H$, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached to, form imidazole; or (ii) the compound is of structure:

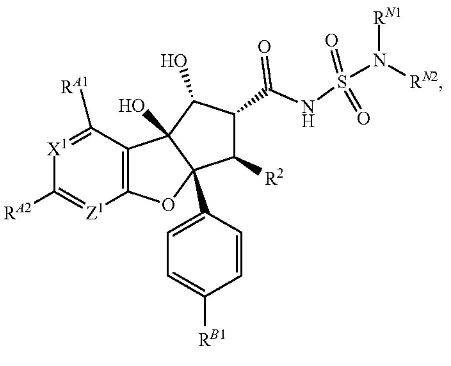

wherein: $X^1$ is CH or N; $Z^1$ is CH or N; $R^{A1}$ and $R^{A2}$ are independently H, alkyl, alkoxy, alkylamino, acyloxy, fluorine, chlorine, bromine, $OCF_3$, or nitrile; $R^{N1}$ and $R^{N2}$ are independently linear or branched alkyl or cyclic alkyl; $R^{B1}$ is methoxy, fluorine, bromine, chlorine, iodine, trifluoromethyl, nitrile, acetylene, $OCF_2H$, alkyl, alkoxy, alkylamine, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached to, form imidazole; and $R^2$ is alkyl, alkenyl, alkynyl, substituted aryl, substituted heteroaryl, or $CH_2L$, where L is selected independently from the group consisting of alkoxy, alkylamino, and heterocyclyl; or (iii) the compound is of structure:

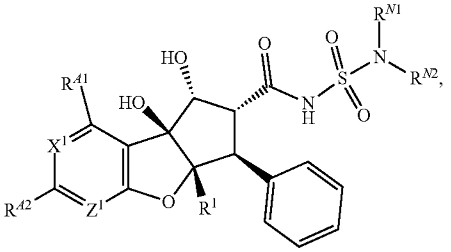

$X^1$ is CH or N; $Z^1$ is CH or N; $R^{A1}$ and $R^{A2}$ are independently H, alkyl, alkoxy, alkylamino, acyloxy, fluorine, chlorine, bromine, $OCF_3$, or nitrile; $R^{N1}$ and $R^{N2}$ are independently linear or branched alkyl or cyclic alkyl; and $R^1$ is substituted aryl, heteroaryl, and substituted heteroaryl, optionally $R^1$ is 4-bromophenyl, 4-methoxyphenyl, 4-cyanophenyl, 4-trifluoromethylphenyl, 4-(azetidin-3-yl)phenyl, 4-(2-hydroxymethylazetidin-3-yl)phenyl, 4-(2-(2-hydroxyethyl) azetidine-3-yl)phenyl, 4-(azetidine-3-ylmethyl)phenyl, 4-(azetidine-3-yl-hydroxy)phenyl, 4-(pyrrolidine-3-yl)phenyl, 4-piperidin-4-yl)phenyl, or benzimidazol-6-yl; or (iv) the compound is of structure:

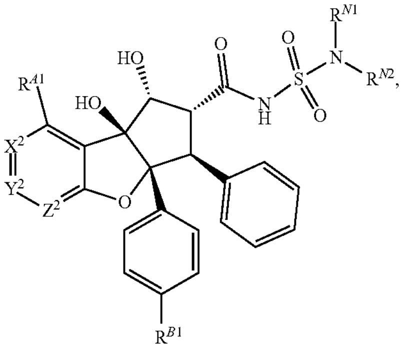

wherein: $X^2$ is CH or N; $Z^2$ is CH or N; $Y^2$ is CH or N; $R^{A1}$ is selected independently from the group consisting of H, alkyl, alkoxy, alkylamino, acyloxy, fluorine, chlorine, bromine, $OCF_3$, and nitrile; $R^{N1}$ and $R^{N2}$ are independently linear or branched alkyl or cyclic alkyl; $R^{B1}$ is methoxy, fluorine, bromine, chlorine, iodine, trifluoromethyl, nitrile, acetylene, $OCF_2H$, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached to, form imidazole; or (v) the compound is of structure:

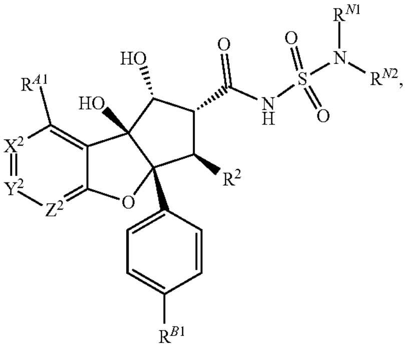

$X^2$ is CH or N; $Z^2$ is CH or N; $Y^2$ is CH or N; $R^{A1}$ is selected independently from the group consisting of H, alkyl, alkoxy, alkylamino, acyloxy, fluorine, chlorine, bromine, $OCF_3$, and nitrile; $R^{N1}$ and $R^{N2}$ are independently linear or branched alkyl or cyclic alkyl; $R^{B1}$ is methoxy, fluorine, bromine, chlorine, iodine, trifluoromethyl, nitrile, acetylene, $OCF_2H$, alkyl, alkoxy, alkylamine, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached to, form imidazole; and $R^2$ is alkyl, alkenyl, alkynyl, substituted aryl, substituted heteroaryl, and $CH_2L$ where L is selected independently from the group consisting of alkoxy, alkylamino, or heterocyclyl; or (vi) the compound is of structure:

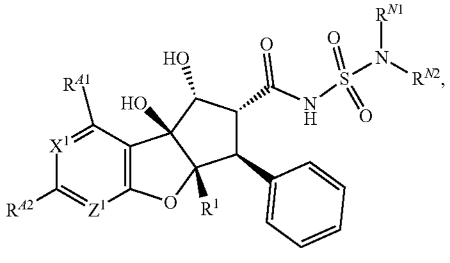

wherein: $X^2$ is CH or N; $Z^2$ is CH or N; $Y^2$ is CH or N; $R^{A1}$ and $R^{A2}$ are selected independently from the group consisting of H, alkyl, alkoxy, alkylamino, acyloxy, fluorine, chlorine, bromine, $OCF_3$, and nitrile; $R^{N1}$ and $R^{N2}$ are independently linear or branched alkyl or cyclic alkyl; and $R^1$ is substituted aryl, heteroaryl, and substituted heteroaryl, optionally $R^1$ is 4-bromophenyl, 4-methoxyphenyl, 4-cyanophenyl, 4-trifluoromethylphenyl, 4-(azetidin-3-yl)phenyl, 4-(2-hydroxymethylazetidin-3-yl)phenyl, 4-(2-(2-hydroxyethyl) azetidine-3-yl)phenyl, 4-(azetidine-3-ylmethyl)phenyl, 4-(azetidine-3-yl-hydroxy)phenyl, 4-(pyrrolidine-3-yl) phenyl, 4-piperidin-4-yl)phenyl, or benzimidazol-6-yl;

(vii) the compound is of structure:

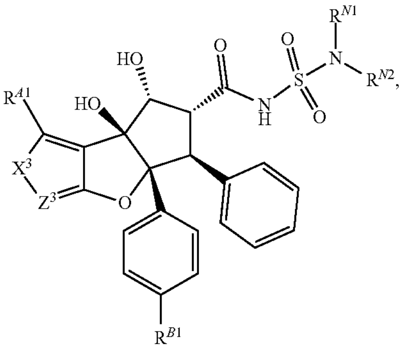

wherein: $X^3$ is CH or N; $Z^3$ is CH or N; $R^{A1}$ is H, alkyl, alkoxy, alkylamino, acyloxy, fluorine, chlorine, bromine, $OCF_3$, or nitrile; $R^{N1}$ and $R^{N2}$ are independently linear or branched alkyl or cyclic alkyl; and $R^{B1}$ is selected independently from the group consisting of methoxy, fluorine, bromine, chlorine, iodine, trifluoromethyl, nitrile, acetylene, $OCF_2H$, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached to, form imidazole; or (viii) the compound is of structure:

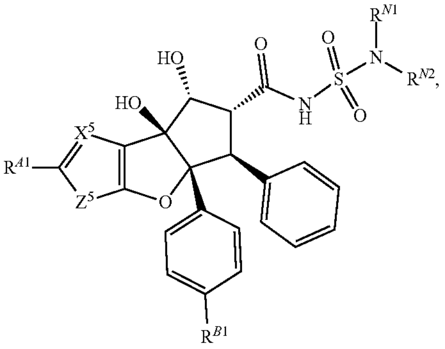

wherein: $X^5$ is CH or N; $Z^5$ is CH or N; $R^{A1}$ is H, alkyl, alkoxy, alkylamino, acyloxy, fluorine, chlorine, bromine, $OCF_3$, and nitrile; $R^{N1}$ and $R^{N2}$ are independently linear or branched alkyl or cyclic alkyl; and $R^{B1}$ is selected independently from the group consisting of: methoxy, fluorine, bromine, chlorine, iodine, trifluoromethyl, nitrile, acetylene, $OCF_2H$, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached to, form imidazole; or (ix) the compound is of structure:

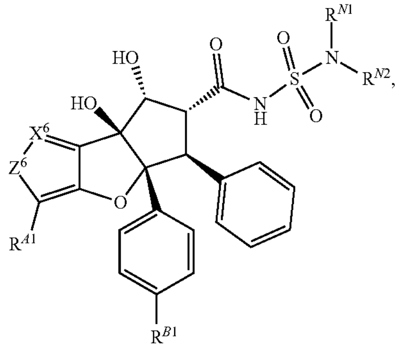

wherein: $X^6$ is CH or N; $Z^6$ is CH or N; $R^{A1}$ is selected independently from the group consisting of H, alkyl, alkoxy, alkylamino, acyloxy, fluorine, chlorine, bromine, $OCF_3$, and nitrile; $R^{N1}$ and $R^{N2}$ are independently linear or branched alkyl or cyclic alkyl; and $R^{B1}$ is methoxy, fluorine, bromine, chlorine, iodine, trifluoromethyl, nitrile, acetylene, $OCF_2H$, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached to, form imidazole; or (x) the compound is of structure:

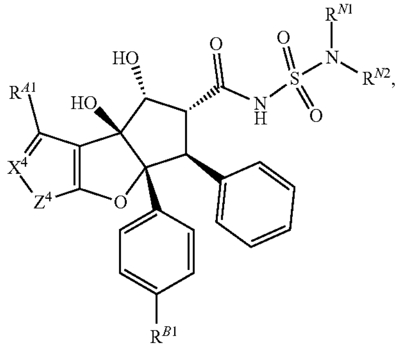

wherein: $X^4$ is CH or N; $Z^4$ is CH or N; $R^{A1}$ is selected from the group consisting of H, alkyl, alkoxy, alkylamino, acyloxy, fluorine, chlorine, bromine, $OCF_3$, and nitrile; $R^{N1}$ and $R^{N2}$ are independently linear or branched alkyl or cyclic alkyl; and $R^{B1}$ is methoxy, fluorine, bromine, chlorine, iodine, trifluoromethyl, nitrile, acetylene, $OCF_2H$, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached to, form imidazole; or (xi) the compound is of structure:

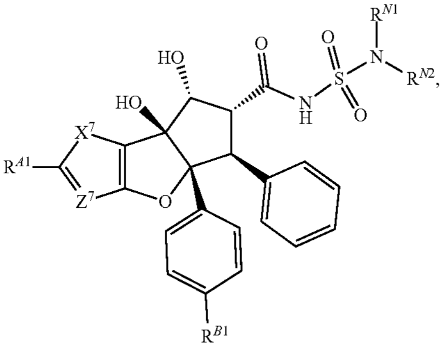

wherein: $X^7$ is CH or N; $Z^7$ is CH or N; $R^{A1}$ H, alkyl, alkoxy, alkylamino, acyloxy, fluorine, chlorine, bromine, $OCF_3$, and nitrile; $R^{N1}$ and $R^{N2}$ are independently linear or branched alkyl or cyclic alkyl; and $R^{B1}$ is selected independently from the group consisting of: methoxy, fluorine, bromine, chlorine, iodine, trifluoromethyl, nitrile, acetylene, $OCF_2H$, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached to, form imidazole; or (xii) the compound is of structure:

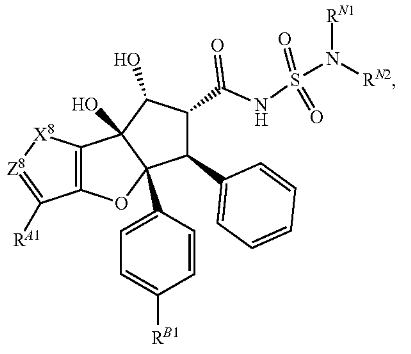

wherein $X^8$ is CH or N; $Z^8$ is CH or N; $R^{A1}$ is H, alkyl, alkoxy, alkylamino, acyloxy, fluorine, chlorine, bromine, $OCF_3$, and nitrile; $R^{N1}$ and $R^{N2}$ are independently linear or branched alkyl or cyclic alkyl; and $R^{B1}$ is methoxy, fluorine, bromine, chlorine, iodine, trifluoromethyl, nitrile, acetylene, —$OCF_2H$, azetidinyl, 2-hydroxymethylazetidinyl, 2-(2-hydroxyethyl) azetidinyl, azetidinylmethyl, azetidinyl-hydroxy, pyrrolidinyl, or piperidinyl, or $R^{B1}$ and a vicinal hydrogen, together with the carbon atoms they are attached to, form imidazole.

27. The compound of claim 1, wherein the compound is selected from the group consisting of:

BUCMD00773

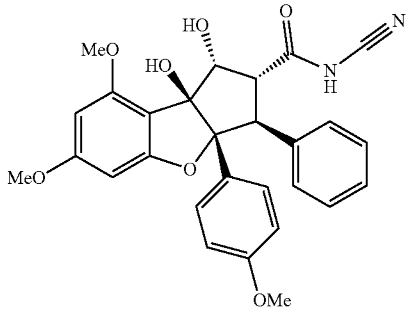

BUCMD00705

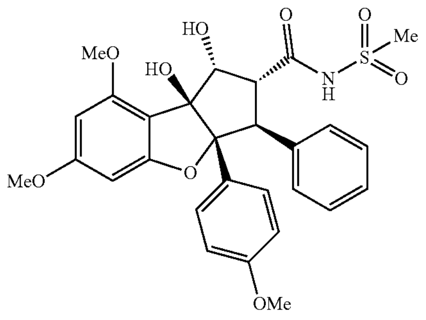

-continued

BUCMD00707

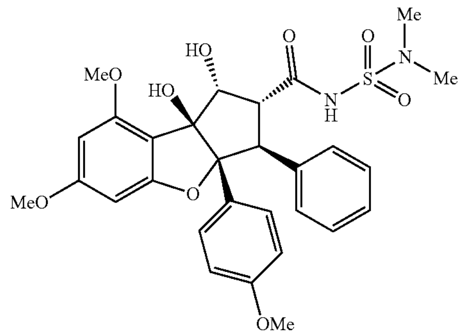

BUCMD00736

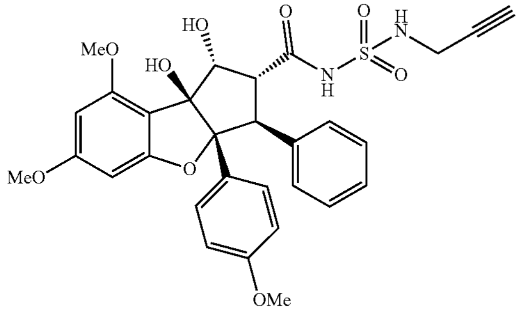

BUCMD00735

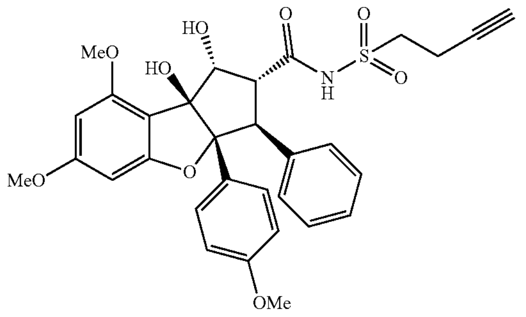

BUCMD00789

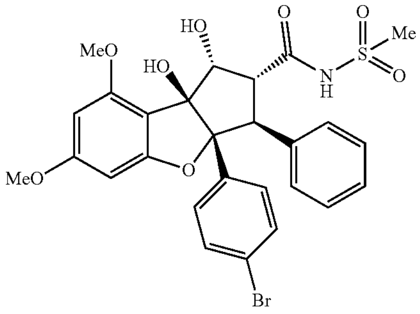

-continued
BUCMD00790
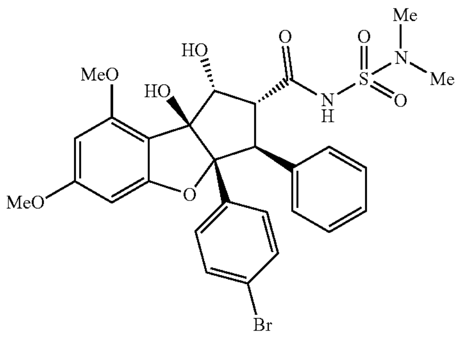
BUCMD00836
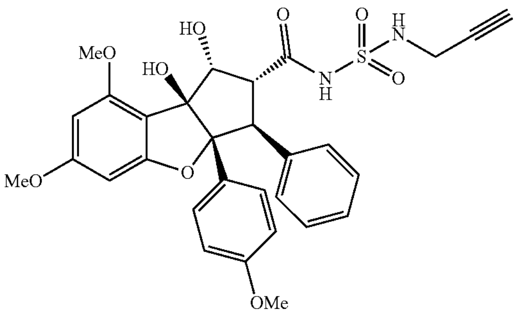
ZW-12-29
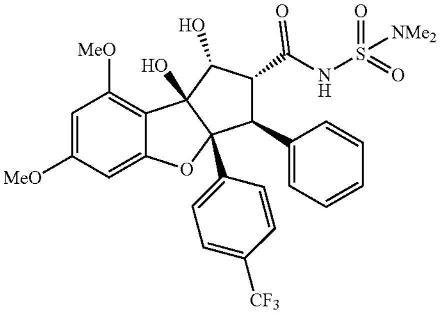
ZW-12-30
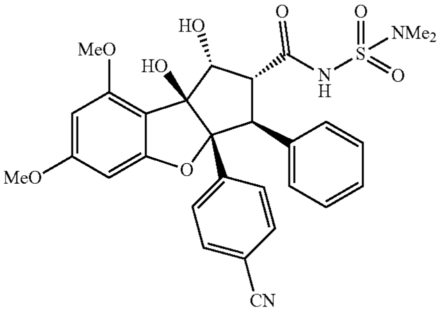
-continued
ZW-12-31
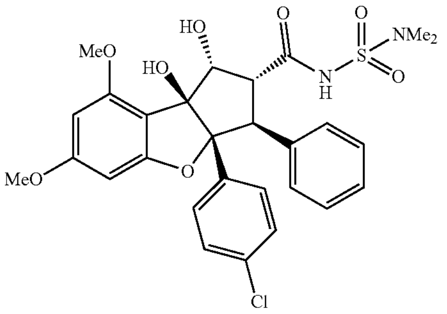
ZW-12-34
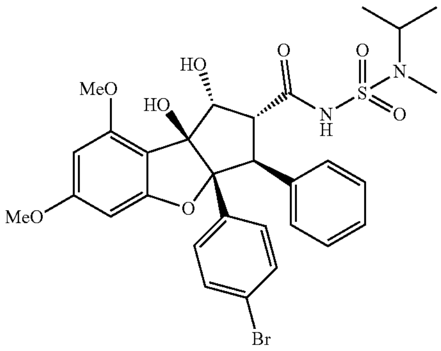
ZW-12-35
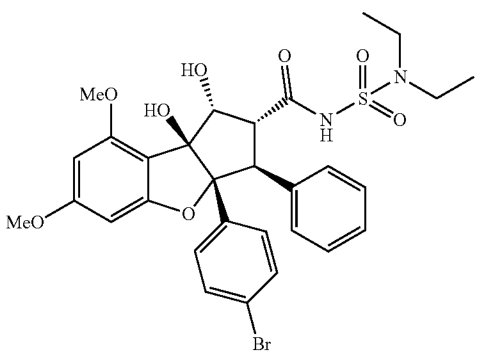
ZW-12-36
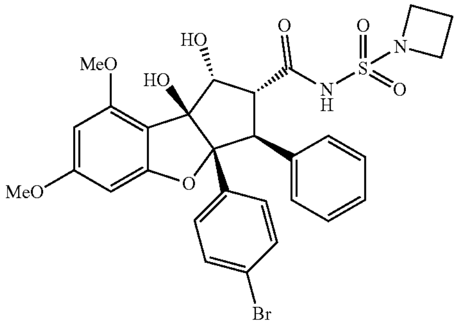

-continued
ZW-12-37
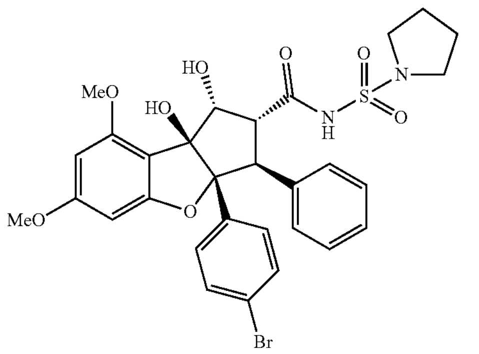
ZW-12-38
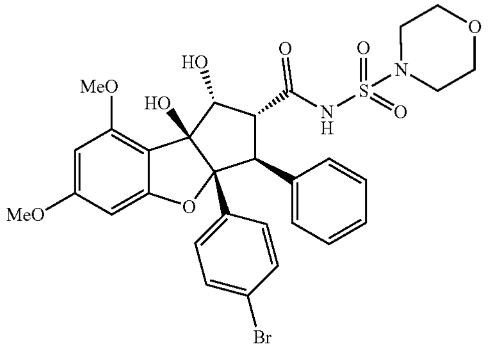
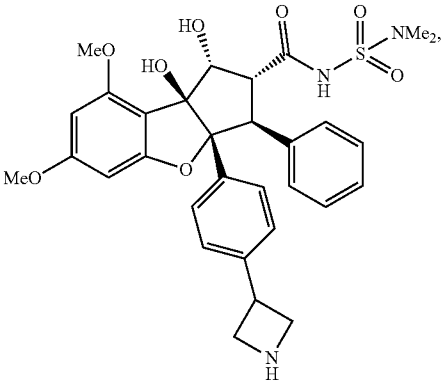
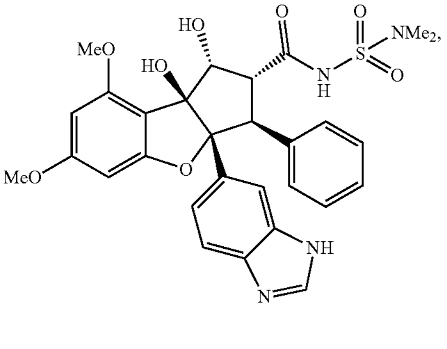
-continued
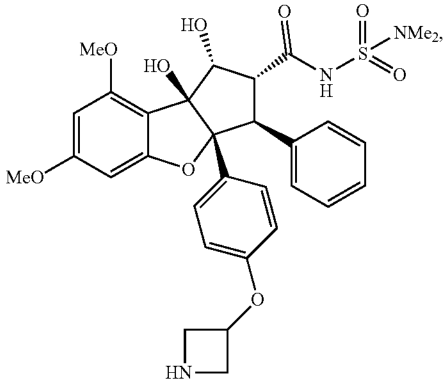
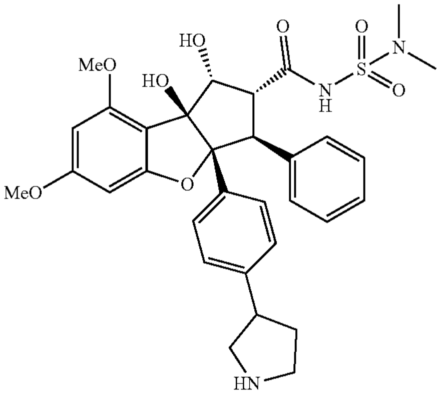
,
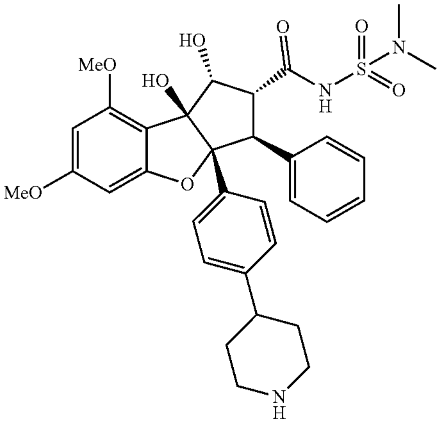
,
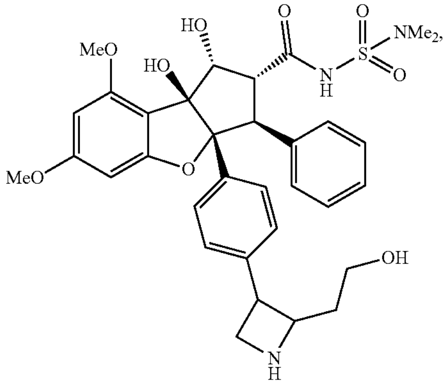

-continued

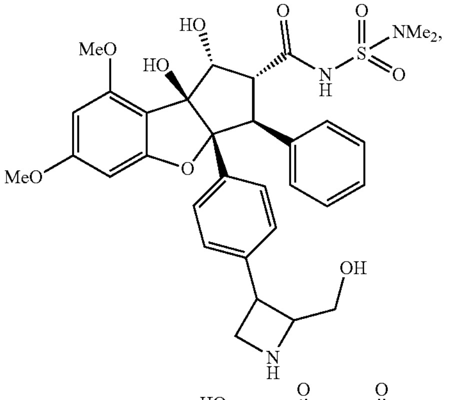

and

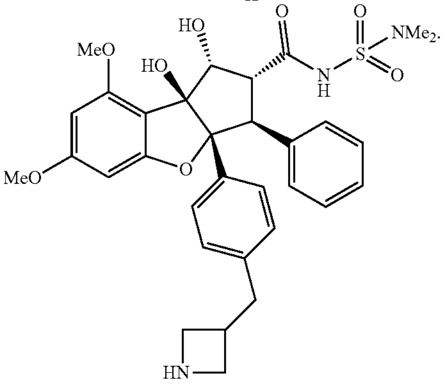

.

28. A composition comprising a compound of claim 1 and a pharmaceutically acceptable carrier, diluent, or excipient.

29. A method for treating a eukaryotic initiation factor 4A (eIF4A)-dependent condition, the method comprising administering a therapeutically effective amount of a compound of claim 1 to a subject in need thereof.

30. A method for treating cancer, the method comprising administering a therapeutically effective amount of a compound of claim 1 to a subject in need thereof.

31. The composition of claim 28, wherein the composition further comprises a therapeutic agent.

32. The composition of claim 31, wherein the therapeutic agent is an anticancer agent or an antimicrobial agent.

33. The compound of claim 26, wherein $R^1$ is 4-bromophenyl, 4-methoxyphenyl, 4-cyanophenyl, 4-trifluoromethylphenyl, 4-(azetidin-3-yl)phenyl, 4-(2-hydroxymethyl-azetidin-3-yl)phenyl, 4-(2-(2-hydroxyethyl)azetidine-3-yl) phenyl, 4-(azetidine-3-ylmethyl)phenyl, 4-(azetidine-3-yl-hydroxy)phenyl, 4-(pyrrolidine-3-yl)phenyl, 4-piperidin-4-yl)phenyl, or benzimidazol-6-yl.

34. The compound of claim 24, wherein Ring A is

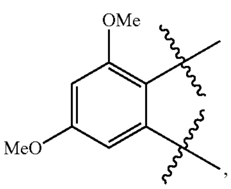

, or

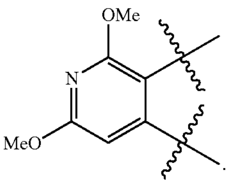 [SMILES: *c1cc(OC)cc(OC)c1*]

.

35. The compound of claim 19, wherein $R^5$ is $OR^{5A}$, where $R^{5A}$ is H, methyl, ethyl, propyl, isopropyl, or butyl.

36. The compound of claim 35, wherein $R^5$ is OH.

37. The compound of claim 17, wherein $R^4$ is $OR^{4A}$, where $R^{4A}$ is H, methyl, ethyl, propyl, isopropyl, or butyl.

38. The compound of claim 37, wherein $R^4$ is OH.

39. The compound of claim 14, wherein $R^3$ is $(C_1\text{-}C_8)$ alkyl.

40. The compound of claim 39, wherein $R^3$ is methyl.

41. The compound of claim 12, wherein $R^{N1}$ and $R^{N2}$ are independently H, methyl, ethyl, propyl, isopropyl, butyl, butan-2-yl, 2-methylpropyl, tert-butyl, pentyl, 2-methylbutan-2-yl, 2,2-dimethylpropyl, 3-methylbutyl, pentan-2-yl, pentan-3-yl, 3-methylbutan-2-yl, 2-methylbutyl, 2-methylpentyl, 3-methylpentyl, 2,3-dimethylbutyl, 2,2-dimethylbutyl, linear or branched hexyl, heptyl, or octyl, vinyl, allyl, acetylenyl, propylenyl, 1-butynl, 2-butynl, 1-pentynyl, 2-pentynyl, 3-methyl-1-butynl, 1-hexynyl, 2-hexynl, 3-hexynl, 4-methyl-1-pentynl, 4-methyl-2-pentynl, or 3-methyl-1-pentynl, 3,3-dimethyl-1-butynl, each of which can be optionally substituted with 1, 2, 3, 4 or more substituents selected independently from the group consisting of OH, oxo (=O), CN, SH, $SO_2NH_2$, $SO_2(C_1\text{-}C_4)$alkyl, $SO_2NH(C_1\text{-}C_4)$alkyl, halogen, $NH_2$, $NH(C_1\text{-}C_4)$alkyl, $N[(C_1\text{-}C_4)alkyl]_2$, $C(O)NH_2$, COOH, COOMe, acetyl, $(C_1\text{-}C_8)$alkyl, $O(C_1\text{-}C_8)$alkyl, $O(C_1\text{-}C_8)$haloalkyl, $(C_2\text{-}C_8)$alkenyl, $(C_2\text{-}C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ and $CH_2$-aryl-alkoxy, where "m" and "p" are independently 1, 2, 3, 4, 5 or 6.

42. The compound of claim 41, wherein $R^{N1}$ and $R^{N2}$ are independently H, methyl, ethyl, 2-hydroxyethyl, 2-dimetylaminoethyl, 2-hydroxy-1,1-dimethylethyl, propyl, isopropyl, 3-hyroxypropyl, 3-dimetylaminopropyl, butyl, butan-2-yl, 2-methylpropyl, tert-butyl, pentyl, 2-methylbutan-2-yl, 2,2-dimethylpropyl, 3-methylbutyl, pentan-2-yl, pentan-3-yl, 3-methylbutan-2-yl, 2-methylbutyl, 2-methylpentyl, 3-methylpentyl, 2,3-dimethylbutyl, 2,2-dimethylbutyl, vinyl, allyl, acetylenyl, or propylenyl, more optionally, $R^{N1}$ and $R^{N2}$ are independently H, methyl, ethyl, 2-hydroxyethyl, 2-dimetylaminoethyl, 2-hydroxy-1,1-dimethylethyl, propyl, isopropyl, 3-hyroxypropyl, or 3-dimetylaminopropyl.

43. The compound of claim 10, wherein $R^2$ is phenyl.

44. The compound of claim 9, wherein L is heterocycle.

45. The compound of claim 44, wherein L is diazinanyl, 1,4-diazinyl, N-methyl-1,4-diazinzyl, morpholinyl or N-methyl-morpholinyl.

* * * * *

SEQUENCE LISTING

```
Sequence total quantity: 7
SEQ ID NO: 1           moltype = AA  length = 58
FEATURE                Location/Qualifiers
source                 1..58
                       mol_type = protein
                       organism = synthetic construct
SEQUENCE: 1
TPGRVFDMLN RRYLSPKYIK MFVLDEADEM LSRGFKDQIY DIFQKLNSNT QVVLLSAT    58

SEQ ID NO: 2           moltype = AA  length = 58
FEATURE                Location/Qualifiers
source                 1..58
                       mol_type = protein
                       organism = synthetic construct
SEQUENCE: 2
TPGRVFDMIR RRSLRTRAIK MLVLDEADEM LNKGFKEQIY DVYRYLPPAT QVVLISAT    58

SEQ ID NO: 3           moltype = AA  length = 62
FEATURE                Location/Qualifiers
source                 1..62
                       mol_type = protein
                       organism = synthetic construct
SEQUENCE: 3
TPGRLVDMME RGKIGLDFCK YLVLDEADRM LDMGFEPQIR RIVEQDTMPP KGVRHTMMFS  60
AT                                                                 62

SEQ ID NO: 4           moltype = DNA  length = 22
FEATURE                Location/Qualifiers
source                 1..22
                       mol_type = other DNA
                       organism = synthetic construct
SEQUENCE: 4
agcagttttg gatctcgtag tg                                           22

SEQ ID NO: 5           moltype = DNA  length = 22
FEATURE                Location/Qualifiers
source                 1..22
                       mol_type = other DNA
                       organism = synthetic construct
SEQUENCE: 5
actgtttcca ccacgttcaa at                                           22

SEQ ID NO: 6           moltype = DNA  length = 22
FEATURE                Location/Qualifiers
source                 1..22
                       mol_type = other DNA
                       organism = synthetic construct
SEQUENCE: 6
gtctcctctg acttcaacag cg                                           22

SEQ ID NO: 7           moltype = DNA  length = 22
FEATURE                Location/Qualifiers
source                 1..22
                       mol_type = other DNA
                       organism = synthetic construct
```

-continued

```
SEQUENCE: 7
accaccctgt tgctgtagcc aa                                                22
```